US012780930B2

(12) United States Patent
Ioan et al.

(10) Patent No.: US 12,780,930 B2
(45) Date of Patent: Nov. 3, 2026

(54) ANTIBODIES CAPABLE OF BINDING TO CD27, VARIANTS THEREOF AND USES THEREOF

(71) Applicant: Genmab A/S, Valby (DK)

(72) Inventors: Andreea Ioan, Utrecht (NL); Frank Beurskens, Utrecht (NL); Rob N. de Jong, Utrecht (NL); Janine Schuurman, Utrecht (NL); Esther C. W. Breij, Utrecht (NL); Isil Altintas, Utrecht (NL); Pauline L. de Goeje, Utrecht (NL); David Satijn, Utrecht (NL); Peter Boross, Utrecht (NL); Ugur Sahin, Mainz (DE); Friederike Gieseke, Mainz (DE); Alexander Muik, Mainz (DE); Kristina Schödel, Mainz (DE)

(73) Assignee: GENMAB A/S, Valby (DK)

( * ) Notice: Subject to any disclaimer, the term of this patent is extended or adjusted under 35 U.S.C. 154(b) by 815 days.

(21) Appl. No.: 17/929,799

(22) Filed: Sep. 6, 2022

(65) Prior Publication Data

US 2023/0109496 A1 Apr. 6, 2023

(30) Foreign Application Priority Data

May 12, 2022 (EP) .................................... 22173126

(51) Int. Cl.
*C07K 16/28* (2006.01)
*A61K 39/00* (2006.01)
(Continued)

(52) U.S. Cl.
CPC .......... *C07K 16/2878* (2013.01); *A61P 35/00* (2018.01); *C07K 16/4208* (2013.01); *A61K 2039/505* (2013.01); *C07K 2317/565* (2013.01)

(58) Field of Classification Search
CPC ........ A61K 2039/505; C07K 2317/565; C07K 2317/524; C07K 2317/526; C07K 2317/732
See application file for complete search history.

(56) References Cited

U.S. PATENT DOCUMENTS 4,699,880 A 10/1987 Goldstein
5,589,466 A 12/1996 Felgner et al.
(Continued)

FOREIGN PATENT DOCUMENTS

AU 2004279877 B2 4/2005
CN 102250246 A 11/2011
(Continued)

OTHER PUBLICATIONS

Thomas et al. Targeting human CD27 with an agonist antibody stimulates T-cell activation and antitumor immunity. Oncoimmunology. Jan. 1, 2014;3(1): e27255.*
(Continued)

*Primary Examiner* — Vanessa L. Ford
(74) *Attorney, Agent, or Firm* — LATHROP GPM LLP; James H. Velema, Esq.

(57) ABSTRACT

The present invention relates to antibodies capable of binding to human CD27 and to variants thereof comprising a modified Fc region comprising one or more mutations that enhances the Fc-Fc interaction of the antibody. The invention further provides pharmaceutical compositions comprising the antibodies and use of the antibodies for therapeutic and diagnostic procedures, in particular in cancer therapy.

15 Claims, 27 Drawing Sheets

Figure 1:
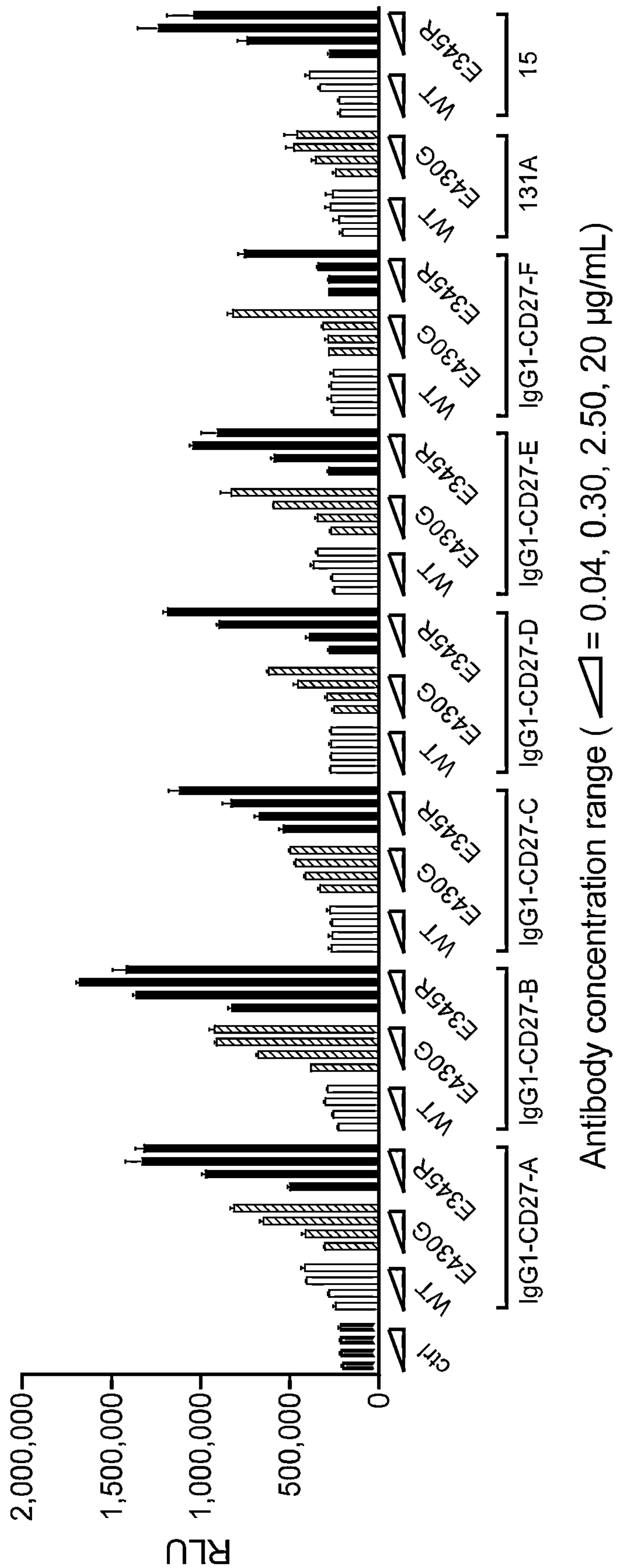

Specification includes a Sequence Listing.

(51) Int. Cl.
*A61P 35/00* (2006.01)
*C07K 16/42* (2006.01)

(56) References Cited

U.S. PATENT DOCUMENTS

| | | | |
|---|---|---|---|
| 5,973,972 | A | 10/1999 | Kwon et al. |
| 6,077,835 | A | 6/2000 | Hanson et al. |
| 6,602,684 | B1 | 8/2003 | Umana et al. |
| 6,808,710 | B1 | 10/2004 | Wood et al. |
| 7,262,028 | B2 | 8/2007 | Van Berkel et al. |
| 7,488,802 | B2 | 2/2009 | Collins et al. |
| 7,612,181 | B2 | 11/2009 | Wu et al. |
| 7,951,918 | B2 | 5/2011 | Glaser et al. |
| 8,008,449 | B2 | 8/2011 | Korman et al. |
| 8,168,757 | B2 | 5/2012 | Finnefrock et al. |
| 8,354,509 | B2 | 1/2013 | Carven et al. |
| 8,735,553 | B1 | 5/2014 | Li et al. |
| 8,779,105 | B2 | 7/2014 | Korman et al. |
| 8,779,108 | B2 | 7/2014 | Queva |
| 9,221,891 | B2 | 12/2015 | Bancel et al. |
| 9,254,311 | B2 | 2/2016 | Bancel et al. |
| 9,527,916 | B2 | 12/2016 | Van Eenennaam |
| 9,611,327 | B2 | 4/2017 | Vermot-Desroches |
| 9,834,606 | B2 | 12/2017 | Li et al. |
| 10,195,156 | B2 | 2/2019 | Benenato et al. |
| 10,590,206 | B2 | 3/2020 | Labrijn et al. |
| 10,647,774 | B2 | 5/2020 | Vermot-Desroches |
| 10,668,152 | B2 | 6/2020 | Coric et al. |
| 10,759,867 | B2 | 9/2020 | Parren |
| 10,882,913 | B2 | 1/2021 | Overdijk |
| 10,968,280 | B2 | 4/2021 | Altintas |
| 11,084,882 | B2 | 8/2021 | Altintas |
| 11,091,557 | B2 | 8/2021 | Altintas |
| 11,440,966 | B2 | 9/2022 | Altintas |
| 11,549,395 | B2 | 1/2023 | Nayak et al. |
| 12,110,337 | B2 * | 10/2024 | Lu .......................... A61P 35/00 |
| 2002/0028178 | A1 | 3/2002 | Hanna et al. |
| 2003/0115614 | A1 | 6/2003 | Kanda et al. |
| 2003/0118588 | A1 | 6/2003 | Diehl et al. |
| 2003/0223989 | A1 | 12/2003 | Pluenneke |
| 2009/0074711 | A1 | 3/2009 | Martin |
| 2010/0155133 | A1 | 6/2010 | Makwinski et al. |
| 2010/0226923 | A1 | 9/2010 | Rao et al. |
| 2011/0223188 | A1 | 9/2011 | Langermann |
| 2011/0311550 | A1 | 12/2011 | Law |
| 2013/0039911 | A1 | 2/2013 | Bedi |
| 2013/0243795 | A1 | 9/2013 | Chen |
| 2014/0099254 | A1 | 4/2014 | Chang |
| 2014/0170148 | A1 | 6/2014 | De Goeij |
| 2014/0348839 | A1 | 11/2014 | Chowdhury et al. |
| 2015/0079109 | A1 | 3/2015 | Li et al. |
| 2015/0139997 | A1 | 5/2015 | Vermot-Desroches |
| 2015/0175707 | A1 | 6/2015 | De Jong |
| 2015/0203578 | A1 * | 7/2015 | Bebbington ....... C07K 16/2803 424/139.1 |
| 2015/0203579 | A1 | 7/2015 | Papadopoulos et al. |
| 2016/0185840 | A1 | 6/2016 | Hoerr et al. |
| 2016/0256527 | A1 | 9/2016 | Gurney |
| 2016/0272708 | A1 | 9/2016 | Chen |
| 2016/0376367 | A1 | 12/2016 | Yuan et al. |
| 2017/0190763 | A1 * | 7/2017 | Balakrishnan .......... A61P 31/18 |
| 2017/0210806 | A1 | 7/2017 | Liu |
| 2017/0226217 | A1 | 8/2017 | Ellmark |
| 2017/0260281 | A1 | 9/2017 | Vermot-Desroches |
| 2017/0334995 | A1 | 11/2017 | Zettl et al. |
| 2018/0044427 | A1 | 2/2018 | Armstrong et al. |
| 2018/0170866 | A1 | 6/2018 | Payne et al. |
| 2018/0185482 | A1 | 7/2018 | Sheng et al. |
| 2019/0022247 | A1 | 1/2019 | Ansell et al. |
| 2019/0276549 | A1 | 9/2019 | De Jong et al. |
| 2020/0062853 | A1 | 2/2020 | Altintas |
| 2020/0165349 | A1 | 5/2020 | Altintas |
| 2020/0239579 | A1 | 7/2020 | Altintas |
| 2020/0247899 | A1 | 8/2020 | Altintas |
| 2020/0332016 | A1 | 10/2020 | Vermot-Desroches |
| 2021/0163616 | A1 | 6/2021 | Altintas |
| 2021/0269541 | A1 | 9/2021 | Altintas |
| 2021/0277133 | A1 | 9/2021 | Altintas |
| 2021/0317225 | A1 | 10/2021 | Altintas |
| 2021/0369842 | A1 | 12/2021 | Altintas |
| 2022/0033510 | A1 | 2/2022 | Altintas |
| 2022/0064317 | A1 | 3/2022 | Altintas |
| 2023/0087164 | A1 | 3/2023 | Sahin |
| 2023/0087745 | A1 | 3/2023 | Altintas |
| 2023/0089969 | A1 | 3/2023 | Altintas |
| 2023/0109496 | A1 | 4/2023 | Ioan |
| 2023/0212301 | A1 | 7/2023 | Ioan |

FOREIGN PATENT DOCUMENTS

| | | | |
|---|---|---|---|
| CN | 107840887 | A | 3/2018 |
| EP | 0629240 | A1 | 12/1994 |
| EP | 1176195 | A1 | 1/2002 |
| EP | 1870459 | A1 | 12/2007 |
| EP | 1975182 | A1 | 10/2008 |
| EP | 2391343 | A2 | 12/2011 |
| EP | 2972360 | A1 | 1/2016 |
| EP | 3118224 | | 1/2017 |
| JP | 2009-542202 | A | 12/2009 |
| WO | WO 1992/022653 | A1 | 12/1992 |
| WO | WO 1998/050431 | A2 | 11/1998 |
| WO | WO 1999/036093 | A1 | 7/1999 |
| WO | WO 1999/054342 | A1 | 10/1999 |
| WO | WO 2000/046147 | A2 | 8/2000 |
| WO | WO 2000/061739 | A1 | 10/2000 |
| WO | WO 2000/070087 | A1 | 11/2000 |
| WO | WO 2001/029246 | A1 | 4/2001 |
| WO | WO 2002/020039 | A2 | 3/2002 |
| WO | WO 2002/028481 | A2 | 4/2002 |
| WO | WO 2002/030954 | A1 | 4/2002 |
| WO | WO 2002/031140 | A1 | 4/2002 |
| WO | WO 2003/035835 | A2 | 5/2003 |
| WO | WO 2003/040170 | A2 | 5/2003 |
| WO | WO 2003/042402 | A2 | 5/2003 |
| WO | WO 2003/099196 | A2 | 12/2003 |
| WO | WO 2004/004771 | A1 | 1/2004 |
| WO | WO 2005/035584 | A1 | 4/2005 |
| WO | WO 2005/044307 | A2 | 5/2005 |
| WO | WO 2005/044854 | A2 | 5/2005 |
| WO | WO 2005/044855 | A2 | 5/2005 |
| WO | WO 2005/092927 | A1 | 10/2005 |
| WO | WO 2006/121168 | A1 | 11/2006 |
| WO | WO 2007/053767 | A1 | 5/2007 |
| WO | WO 2007/059782 | A1 | 5/2007 |
| WO | WO 2007/110205 | A2 | 10/2007 |
| WO | WO 2007/005874 | A2 | 11/2007 |
| WO | WO 2008/003116 | A2 | 1/2008 |
| WO | WO 2008/004760 | A1 | 1/2008 |
| WO | WO 2008/051424 | A2 | 5/2008 |
| WO | WO 2008/119353 | A1 | 10/2008 |
| WO | WO 2008/156712 | A1 | 12/2008 |
| WO | WO 2008/157379 | A2 | 12/2008 |
| WO | WO 2009/014708 | A2 | 1/2009 |
| WO | WO 2009/034172 | A1 | 3/2009 |
| WO | WO 2009/089004 | A1 | 7/2009 |
| WO | WO 2009/101611 | A1 | 8/2009 |
| WO | WO 2009/114335 | A2 | 9/2009 |
| WO | WO 2010/027827 | A2 | 3/2010 |
| WO | WO 2010/036959 | A2 | 4/2010 |
| WO | WO 2010/077634 | A1 | 7/2010 |
| WO | WO 2010/080538 | A1 | 7/2010 |
| WO | WO 2010/089411 | A2 | 8/2010 |
| WO | WO 2010/129304 | A2 | 11/2010 |
| WO | WO 2010/151792 | A1 | 12/2010 |
| WO | WO 2011/028952 | A1 | 3/2011 |
| WO | WO 2011/066342 | A2 | 6/2011 |
| WO | WO 2011/066389 | A1 | 6/2011 |
| WO | WO 2011/069104 | A2 | 6/2011 |
| WO | WO 2011/082400 | A2 | 7/2011 |
| WO | WO 2011/104558 | A1 | 9/2011 |
| WO | WO 2011/117329 | A1 | 9/2011 |
| WO | WO 2011/130434 | A2 | 10/2011 |
| WO | WO 2011/131746 | A2 | 10/2011 |
| WO | WO 2011/143545 | A1 | 11/2011 |

(56) References Cited

FOREIGN PATENT DOCUMENTS

| | | | | |
|---|---|---|---|---|
| WO | WO 2011/159877 | A2 | 12/2011 | |
| WO | WO 2011/161699 | A2 | 12/2011 | |
| WO | WO 2012/004367 | A1 | 1/2012 | |
| WO | WO 2012/023053 | A2 | 2/2012 | |
| WO | WO 2012/025525 | A1 | 3/2012 | |
| WO | WO 2012/025530 | A1 | 3/2012 | |
| WO | WO 2012/032433 | A1 | 3/2012 | |
| WO | WO 2012/058768 | A1 | 5/2012 | |
| WO | WO 2012/145493 | A1 | 10/2012 | |
| WO | WO 2012/149356 | A2 | 11/2012 | |
| WO | WO 2013/004842 | A2 | 1/2013 | |
| WO | WO 2013/060867 | A2 | 5/2013 | |
| WO | WO 2013/079174 | A1 | 6/2013 | |
| WO | WO 2013/157953 | A1 | 10/2013 | |
| WO | WO 2013/164694 | A1 | 11/2013 | |
| WO | WO 2013/173223 | A1 | 11/2013 | |
| WO | WO 2014/006217 | A1 | 1/2014 | |
| WO | WO 2014/022758 | A1 | 2/2014 | |
| WO | WO 2014/031646 | A2 | 2/2014 | |
| WO | WO 2014/055648 | A1 | 4/2014 | |
| WO | WO 2014/070934 | A1 | 5/2014 | |
| WO | WO 2014/108198 | A1 | 7/2014 | |
| WO | WO 2014/108483 | A1 | 7/2014 | |
| WO | WO 2014/152774 | A1 | 9/2014 | |
| WO | WO 2014/179664 | A2 | 11/2014 | |
| WO | WO 2014/194302 | A2 | 12/2014 | |
| WO | WO 2015/001085 | A1 | 1/2015 | |
| WO | WO 2017/009442 | A1 | 1/2015 | |
| WO | WO 2015/016718 | A1 | 2/2015 | |
| WO | WO 2015/035606 | A1 | 3/2015 | |
| WO | WO 2015/085847 | A1 | 6/2015 | |
| WO | WO 2015/112800 | A1 | 7/2015 | |
| WO | WO 2015/112900 | A1 | 7/2015 | |
| WO | WO 2015/143079 | A1 | 9/2015 | |
| WO | WO 2015/150327 | A1 | 10/2015 | |
| WO | WO 2015/156268 | A1 | 10/2015 | |
| WO | WO 2015/158867 | A1 | 10/2015 | |
| WO | WO 2016/100882 | A1 | 6/2016 | |
| WO | WO 2016/110576 | A1 | 7/2016 | |
| WO | WO 2016/110584 | A1 | 7/2016 | |
| WO | WO 2016/134358 | A1 | 8/2016 | |
| WO | WO 2016/145085 | A2 | 9/2016 | |
| WO | WO 2021/046445 | A1 | 9/2016 | |
| WO | WO 2016/185016 | A1 | 11/2016 | |
| WO | WO 2017/019846 | A1 | 2/2017 | |
| WO | WO 2017/024465 | A1 | 2/2017 | |
| WO | WO 2017/025016 | A1 | 2/2017 | |
| WO | WO 2017/025051 | A1 | 2/2017 | |
| WO | WO 2017/040790 | A1 | 3/2017 | |
| WO | WO 2017/049452 | A1 | 3/2017 | |
| WO | WO 2017/055398 | A2 | 4/2017 | |
| WO | WO 2017/055547 | A1 | 4/2017 | |
| WO | WO 2017/060144 | A1 | 4/2017 | |
| WO | WO 2017/071625 | A1 | 5/2017 | |
| WO | WO 2017/077085 | A2 | 5/2017 | |
| WO | WO 2017/106656 | A1 | 6/2017 | |
| WO | WO 2017/123650 | A2 | 7/2017 | |
| WO | WO 2017/132825 | A1 | 8/2017 | |
| WO | WO 2017/133540 | A1 | 8/2017 | |
| WO | WO 2017/166804 | A1 | 10/2017 | |
| WO | WO 2017/182672 | A1 | 10/2017 | |
| WO | WO 2017/201281 | A1 | 11/2017 | |
| WO | WO 2017/205738 | A1 | 11/2017 | |
| WO | WO 2017/214092 | A1 | 12/2017 | |
| WO | WO 2017/218707 | A2 | 12/2017 | |
| WO | WO 2018/006052 | A1 | 1/2018 | |
| WO | WO 2018/011421 | A1 | 1/2018 | |
| WO | WO 2018/014260 | A1 | 1/2018 | |
| WO | WO 2018/017761 | A1 | 1/2018 | |
| WO | WO 2018/022831 | A1 | 2/2018 | |
| WO | WO 2018/031258 | A1 | 2/2018 | |
| WO | WO 2018/036472 | A1 | 3/2018 | |
| WO | WO 2018/056821 | A1 | 3/2018 | |
| WO | WO 2018/058022 | A1 | 3/2018 | |
| WO | WO 2018/083126 | A1 | 5/2018 | |
| WO | WO 2018/098370 | A1 | 5/2018 | |
| WO | WO 2018/103017 | A1 | 6/2018 | |
| WO | WO 2018/103501 | A1 | 6/2018 | |
| WO | WO 2018/114877 | A1 | 6/2018 | |
| WO | WO 2018/114878 | A1 | 6/2018 | |
| WO | WO 2018/114879 | A1 | 6/2018 | |
| WO | WO 2018/127916 | A1 | 7/2018 | |
| WO | WO 2018/146317 | A1 | 8/2018 | |
| WO | WO 2018/162749 | A1 | 9/2018 | |
| WO | WO 2018/187215 | A1 | 10/2018 | |
| WO | WO 2018/213747 | A1 | 11/2018 | |
| WO | WO 2018/222711 | A2 | 12/2018 | |
| WO | WO 2019/000146 | A1 | 1/2019 | |
| WO | WO 2019/025545 | A1 | 2/2019 | |
| WO | WO 2019/040808 | A1 | 2/2019 | |
| WO | WO 2019/145455 | A1 | 8/2019 | |
| WO | WO 2019/204462 | A2 | 10/2019 | |
| WO | WO-2019195452 | A1 * | 10/2019 | .............. A61P 35/00 |
| WO | WO 2019/243636 | A1 | 12/2019 | |
| WO | WO 2021/156326 | A1 | 8/2021 | |
| WO | WO 2022/089377 | A1 | 5/2022 | |
| WO | WO 2022/189498 | A1 | 9/2022 | |
| WO | WO 2023/285552 | A1 | 1/2023 | |
| WO | WO 2023/031473 | A1 | 3/2023 | |
| WO | WO 2023/217987 | A1 | 11/2023 | |
| WO | WO 2023/218051 | A1 | 11/2023 | |

OTHER PUBLICATIONS

Barthelemy, "Comprehensive analysis of the factors contributing to the stability and solubility of autonomous human VH domains", Journal of Biological Chemistry, 2008, 283:3639-3654.

Beiboer et al., "Guided selection of a pan carcinoma specific antibody reveals similar binding characteristics yet structural divergence between the original murine antibody and its human equivalent", Journal of Molecular Biology, 2000, 296:833-849.

Bretz et al. (2002) "Inflammatory cytokine regulation of TRAIL-mediated apoptosis in thyroid epithelial cells," Cell Death Diff 9:274-286.

Canfield et al., "The Binding Affinity of Human IgG for its High Affinity Fc Receptor Is Determined by Multiple Amino Acids in the CH2 Domain and Is Modulated by the Hinge Region", J. Exp. Med., 1991, (173): 1483-1491.

Chen et al., "Enhancement and destruction of antibody function by somatic mutation: unequal occurrence is controlled by V gene combinatorial associations", The EMBO Journal, 1995, 14(12): 2784-2794.

Chen et al., Phase 1b/3 study of avelumab-based combination regimens in patients with relapsed or refractory diffuse large B-cell lymphoma (R/R DLBCL), J Clin Oncol, 2017, 35(15 suppl): abstr TPS7575.

Choi et al., "Predicting antibody complementarity determining region structures without classification", Molecular Biosystems, 2011, 7:3327-334.

Christiansen et al., (2011) "Eradication of solid tumors using histone deacetylase inhibitors combined with immune-stimulating antibodies", Proceedings of the National Academy of Sciences, 108(10):4141-4146.

ClinicalTrials.gov, Clinical Trial NCT02554812, "A Study of Avelumab in Combination With Other Cancer Immunotherapies in Advanced Malignancies (Javelin Medley)", Sep. 18, 2015.

Colman et al., "Effects of amino acid sequence changes on antibody-antigen interactions", Research in Immunology, 1994, 145: 33-36.

D'Angelo et al., "Many Routes to an Antibody Heavy-Chain CDR3: Necessary, Yet Insufficient, for Specific Binding," Frontiers in Immunology, vol. 9, Article 395 Mar. 2018; (Year: 2018).

Dall'Acqua et al., "Modulation of the Effector Functions of a Human IgG1 through Engineering of Its Hinge Region", J Immunol., 2006, 177(2): 1129-1138.

De Genst et al., "Antibody repertoire development in camelids", Developmental and Comparative Immunology, 30 (2006); 187-198.

Dondelinger et al., "Understanding the significance and Implications of Antibody Numbering and Antigen-Binding Surface/Residue Definition", Frontiers in Immunology, Oct. 16, 2018, vol. 9, Article 2278, pp. 1-15.

(56) References Cited

OTHER PUBLICATIONS

Duncan et al., "The Binding Site for Clq on IgG", Nature, 1988 (332): 738-740.
European Search Report corresponding to European Patent Application No. 12305821, completed Dec. 4, 2012.
Fisher et al., "Targeting of 4-1BB by monoclonal antibody PF-05082566 enhances T-cell function and promotes anti-tumor activity", 2012 61: 1721-17333.
Gershoni et al, "Epitope mapping—The first step in developing epitope-based vaccines", BIOD, Jan. 2007, 21(3): 145-156.
Gray et al., "Optimising anti-tumor CD8 T-cell responses using . . . ". European Journal of Immunology. vol 38 (9), 2008. p. 2499-2511.
Griffiths et al., "Human anti-self antibodies with high specificity from phage display libraries", The EMBO Journal, 1993, 12:725-734.
Gros et al., PD-1 identifies the patient-specific CD8+ tumor reactive repertoire infiltrating human tumors J. Clin Invest 2014;124(5):2246-59.
Haynes et al., (2008) "Immunogenic anti-cancer chemotherapy as an emerging concept", Current Opinion in Immunology, 20(5):545-557.
Hezareh et al., "Effector Function Activities of a Panel of Mutant of a Broadly Neutralizing Antibody against Human Immunodeficiency Virus Type 1", J Virol., 2001, 75(24): 12161-12168.
Horn et al., "CD3xPDL1 bi-specific T cell engager (BiTE) simultaneously activates T cells and NKT cells, kills PDL1<sup>+</sup> tumor cells, and extends the survival of tumor-bearing humanized mice", Oncotarget, Aug. 29, 2017, 8(35): 57964-57980.
Horton et al., "Agonist anti-4-1BB plus neutralizing anti-CTLA-4 or -PD-L1 synergize to promote tumor regression by rescuing dying dysfunctional CD8+ T cells within the tumor microenvironment", J Immunother Cancer, 2015, 3(Suppl 2): O10.
Ichikawa et al. (2003) "TRAIL-R2 (DR5) mediates apoptosis of synovial fibroblasts in rheumatoid arthritis," J. Immunol. 171:1061-1069.
Idusogie et al., "Mapping of the C1q Binding Site on Rituxan, a Chimeric Antibody with a Human IgG1 Fc", J Immunol., 2000, 164: 4178-4184.
International Search Report and Written Opinion for PCT Application No. PCT/EP2018/071002, mailed Jan. 4, 2019.
International Search Report and Written Opinion for PCT International Patent Application No. PCT/EP2017/067924, mailed Dec. 21, 2017.
International Search Report and Written Opinion for PCT International Patent Application No. PCT/EP2018/055977, mailed Jul. 4, 2018.
International Search Report and Written Opinion in related PCT Application No. PCT/EP2019/080445, mailed Jan. 30, 2020.
International Search Report and Written Opinion in related PCT Application No. PCT/EP2022/074696, mailed Nov. 30, 2022.
International Search Report corresponding to International Patent Application No. PCT/EP2013/064466, mailed Sep. 30, 2013.
Kaufman et al., "Avelumab in patients with chemotherapy-refractory metastatic Merkel cell carcinoma: a multicentre, single-group, open-label, phase 2 trial", Lancet Oncol., Oct. 2016, 17(10): 1374-1385.
Klimka et al., "Human anti-CD30 recombinant antibodies by guided phage antibody selection using cell panning", British Journal of Cancer, 2000, 83:252-260.
Kranz et al., "Restricted reassociation of heavy and light chains from hapten-specific monoclonal antibodies", Proc. National Acad. Sci. USA, Sep. 1981, vol. 78, No. 9, pp. 5807-5811.
Krupka et al., "Blockade of the PD-1/PD-L1 axis augments lysis of AML cells by the CD33/CD3 BiTE antibody construct AMG 330: reversing a T-cell-induced immune escape mechanism", Leukemia, Aug. 4, 2015, 30(2): 484-491.
Kussie et al., "A single engineered amino acid substitution changes antibody fine specificity," J. Immunol., 152:146-152, (Year: 1994).
Lamminmaki et al., "Crystal structure of a recombinant anti-estradiol Fab fragment in complex with the 17beta-estradiol", Journal of Biol. Chem., 2001, vol. 276, pp. 36687-36694.
Latchman et al., "PD-L1-deficient mice show that PD-L1 on T cells, antigen-presenting cells, and host tissues negatively regulates T cells", PNAS USA, Jul. 2004, 101(29): 10691-10696.
Leabman et al., "Effects of Altered FcγR binding on antibody pharmacokinetics in cynomolgus monkeys", MAbs, 2013, 5(6): 896-903.
Malia et al., "Epitope mapping and structural basis for the recognition of phosphorylated tau by the anti-tau antibody AT8", Proteins, 2016, 84: 427-434.
Massard et al., "Safety and Efficacy of Durvalumab (MEDI4736), an Anti-Programmed Cell Death Ligand-1 Immune Checkpoint Inhibitor, in Patients With Advanced Urothelial Bladder Cancer", J Clin Oncol., Sep. 10, 2016, 34(26): 3119-3125.
Mundt et al. (2003) "Involvement of TRAIL and its receptors in viral hepatits," Faseb J. 17:94-96.
Murillo et al., Therapeutic Antitumor Efficacy of Anti-CD137 Agonistic Monoclonal Antibody in Mouse Models of Myeloma. Clin cancer res. 2008;14(21):6895-906.
Nagane et al. (2010) "Predominant antitumor effects by fully human anti-TRAIL-receptor2 (DR5) monoclonal antibodies in human glioma cells in vitro and in vivo," Neuro. Oncology. 12(7):687-700.
Oganesyan et al., "Structural characterization of a human Fc fragment engineered for lack of effector functions", Acta Cryst., 2008, (D64): 700-704.
Osada et al., "CEA/CD3-bispecific T cell-engaging (BiTE) antibody-mediated T lymphocyte cytotoxicity maximized by inhibition of both PD1 and PD-L1", Cancer Immunology Immunotherapy, Jun. 2015, 64(6): 677-688.
Ramelet et al., "Beneficial outcome of combination therapy with 4-1BB targeting antibody", European Journal of Cancer, vol. 69, Nov. 29, 2016.
Rittmeyer et al., "Atezolizumab versus docetaxel in patients with previously treated non-small-cell lung cancer (OAK): a phase 3, open-label, multicentre randomised controlled trial", Lancet, Jan. 21, 2017, 389(10066): 255-265.
Rudikoff et al., "Single amino acid substitution altering antigen-binding specificity", Proc. Natl Acad. Sci. USA, 1982, 79: 1979-1983, Immunology.
Shields et al., "High Resolution Mapping of the Binding Site on Human OgG1 for FcγRI, FcγRII, FcγRIII, and FcRn and Design of IgG1 Variants with Improved Binding to the FcγR*", J. Biol. Chem., 2001, 276(9): 6591-6604.
Shindo et al., "Combination immunotherapy with 4-1BB activation and PD-1 blockade enhances antitumor efficacy in a mouse model of subcutaneous tumor", Anticancer Research—International Journal of Cancer Research and Treatment, vol. 35, No. 1, Jan. 1, 2015, pp. 129-136.
Storz, "Intellectual property issues of immune checkpoint inhibitors", mAbs, 2016, 8(1): 10-26.
UniProtKB Results for RTS Search [Online], Retrieved from the Internet <URL:http://www.uniprot.org/uniprot/?query=rts&sort=score>. [retrieved on Jun. 27, 2016].
Uno et al., (2006) "Eradication of established tumors in mice by a combination antibody-based therapy", Nature Medicine, 12(6):693-698.
Vermot-Desroches et al. (2005) "Characterization of monoclonal antibodies directed against trail or trail receptors," Cell Immunol. 236(1-2):86-91.
Wang et al. (2008) "Characterization of a novel anti-DR5 monoclonal antibody WD1 with the potential to induce tumor cell apoptosis," Cell Mol. Immunol. 5(1):55-60.
Ward et al., Binding activities of a repertoire of single immunoglobin variable domains secreted from *Escherichia coli*, Nature, 1989, 341: 544-546.
Westwood et al., (2014) "Combination anti-CD137 and anti-CD40 antibody therapy in murine myc-driven hematological cancers", Leukemia Research, 38(8):948-954.
Wu et al. (Nov. 2015) "Increased serum TRAIL and DR5 levels correlated with lung function and inflammation in stable COPD patients," Intl. J. COPD. 10:2405-2412.

(56) References Cited

OTHER PUBLICATIONS

Xu et al., "In Vitro Characterization of Five Humanized OKT3 Effector Function Variant Antibodies", Cell Immunol., 2000, 200: 16-26.
Yao et al. (2006) "Intra-articular injection of recombinant TRAIL induces synovial apoptosis and reduces inflammation in a rabbit knee model of arthritis," Arthritis Res. Ther. 8(1):R16. pp. 1-8.
Yonezawa et al., (2015) "Boosting Cancer Immunotherapy with Anti-CD137 Antibody Therapy", Clinical Cancer Research, 21(14):3113-3120.
Piche-Nicolas et al., Changes in complementarity-determining regions significantly alter IgG binding to the neonatal Fc receptor (FcRN) and pharmacokinetics; MABS, 2018, 10(1): 81-94.
Azpilikueta et al., Successful Immunotherapy against a Transplantable Mouse Squamous Lung Carcinoma with Anti-PD-1 and Anti-CD137 Monoclonal Antibodies, vol. 11, No. 4, pp. 524-536, Feb. 1, 2016, Journal of Thoracic Oncology.
Barbas et al., Molecular Profile of an Antibody Response to HIV-1 as Probed by Combinatorial Libraries, 230(3), pp. 812-823, Apr. 5, 1993, Academic Press.
Bebbington, R.C et al., High-level expression of a recombinant antibody from myeloma cells using a glutamine synthetase gene as an amplifiable selectable marker, vol. 10 issue 2, pp. 169-175, 1992, Biotechnology.
Benvenisty, N. et al., Direct introduction of genes into rats and expression of the genes,, vol. 83, pp. 9551-9555, 1986, PNAS.
Berenbaum, M.C, What is synergy?, 41(2), pp. 93-141, Jun. 1989, Pharmacol. Rev.
Beurskens, F. J. et al., Exhaustion of cytotoxic effector systems may limit monoclonal antibody-based immunotherapy in cancer patients, vol. 188, 3532-3541, 2012, J Immunol.
Bitter, G.A. et al., Expression and secretion vectors for yeast, 153, pp. 516-544, 1987, Methods in Enzymol.
Bleeker, W.K. et al., Accelerated autoantibody clearance by intravenous immunoglobulin therapy: studies in experimental models to determine the magnitude and time course of the effect, 98(10), pp. 3131-3141, Nov. 15, 2001, Blood.
Bliss, C.I., the Toxicity of Poisons Applied Jointly, 26, pp. 585-615, 1939, Annals of Applied Biology.
Brezski, R. et al., Immunoglobulin isotype knowledge and application to Fc engineering, vol. 40, 62-69, 2016.
Brochet X, et al., IMGT/V-QUEST: the highly customized and integrated system for IG and TR standardized V-J and V-D-J sequence analysis, vol. 36, W503-W508, 2008, Nucleic Acid Research.
Buchan et al., "PD-1 Blockade and CD27 Stimulation Activate Distinct Transcriptional Programs That Synergize for CD8+ T-Cell-Driven Antitumor Immunity", Clinical Cancer Research, Mar. 7, 2018: 24(10): 2383-2394,.
Calvo et al., Interim results of a phase 1/2 study of JNJ-63723283, an anti-PD-1 monoclonal antibody, in patients with advanced cancers., 36 (Suppl. 5), Abstract 58, 2018, Journal of Clinical Oncology.
Carr et al, CD27 mediates interleukin-2-independent clonal expansion of the CD8plus T cell without effect or differentiation, 103, No. 51, pp. 19454-19459, Dec. 19, 2006, PNAS.
Chiu, M. et al., Antibody Structure and Function: The Basis for Engineering Therapeutics, vol. 8 (55), 80 pages, 2019.
Corsaro, CM, et al., Enhancing the efficiency of DNA-mediated gene transfer in mammalian cells, vol. 7(5), 603-611, 1981.
Crowe, J. et al., Humanized monoclonal antibody CAMPATH-1H: myeloma cell expression of genomic constructs, nucleotide sequence of cDNA constructs and comparison of effector mechanisms of myeloma and Chinese hamster ovary cell-derived material, 87(1), pp. 105-110, 1992, Oxford University Press.
Dacres et al., Comparison of enhanced bioluminescence energy transfer donors for protease biosensors, May 15, 2012, pp. 206210, May 15, 2012, Analytical Biochemistry.
Davies, J. et al., Expression of GnTIll in a recombinant anti-CD20 CHO production cell line: Expression of antibodies with altered glycoforms leads to an increase in ADCC through higher affinity for Fc RIII, 74(4), pp. 288-294, Aug. 20, 2001, John Wiley & Sons, Inc.
De Jong, R. et al., A Novel Platform for the Potentiation of Therapeutic Antibodies Based on AntigenDependent Formation of IgG Hexamers at the Cell Surface, vol. 14(1), 24 pages, 2016, PLOS Biol.
Desjarlais, J.R. et al., Modulation of antibody effector function, vol. 317(9), 1278-1285, 2011.
Dick, L. et al., C-terminal lysine variants in fully human monoclonal antibodies: investigation of test methods and possible causes, vol. 100(6), 1132-1143, 2008.
Diebolder, C.A. et al., Complement is activated by IgG hexamers assembled at the cell surface, vol. 343(6176), pp. 1260-1263, 2014, Science.
Diggs et al., CD40-mediated immune cell activation enhances response to anti-PD-1 in murine intrahepatic cholangiocarcinoma, 74, pp. 1145-1154, Dec. 1, 2020, Journal of Hepatology.
Dimasi, N. et al., The Design and Characterization of Oligospecific Antibodies for Simultaneous Targeting of Multiple Disease Mediators, vol. 393(3), 672-692, 2009, Journal Molecular Biology.
Engelberts, P. et al., DuoBody-CD3xCD20 induces potent T-cell-mediated killing of malignant B cells in preclinical models and provides opportunities for subcutaneous dosing, vol. 52, 102625, 2020.
Garber et al., Immune agonist antibodies face critical test, vol. 19, pp. 3-5, Jan. 2020, Nature Reviews, Drug Discovery.
Hamers-Casterman et al., Naturally occurring antibodies devoid of light chains, 363(6428), pp. 446-448, Jun. 3, 1993, Nature Publishing Group UK.
Hardy et al., A Monoclonal Antibody against a Human B Lymphoblastoid Cell Line Induces Tumor Regression in Mice, 54(22), pp. 5793-5796, Nov. 15, 1994, Cancer Research.
Hayes et al., Fc gamma receptors: glycobiology and therapeutic prospects, 9, pp. 209-219, 2016, Journal of Inflammation Research.
He et al, Agonist anti-human CD27 monoclonal antibody induces T cell activation and tumor immunity in human CD27-transgenic mice, vol. 191 (8), pp. 4174-4183., 2013, J. Immunol.
Huang, J. et al., Safety, Activity, and Biomarkers of SHR-1210, an Anti-PD-1 Antibody, for Patients with Advanced Esophageal Carcinoma, 24(6), pp. 1296-1304, Mar. 15, 2018, Clinical Cancer Research.
International Search Report and Written Opinion for PCT International Patent Application No. PCT/EP2023/062793, dated Aug. 9, 2023.
International Search Report and Written Opinion for PCT International Patent Application No. PCT/EP2023/062798, dated Jul. 19, 2023.
Jefferis and Lefranc, Human immunoglobulin allotypes, 1(4), pp. 1-7, 2009, Taylor & Francis.
Johnson, M.L. et al., Phase I trial of the programmed death receptor 1 (PD-1) inhibitor, BI 754091, in patients (pts) with advanced solid tumors, 36(5), Abstract 212, 2018, Journal of Clinical Oncology.
Kaneko et al., Optimizing Therapeutic Antibody Function: Progress with Fc domain Engineering, 25(1), 1-11, 2011.
Labrijn, A. F. et al., Controlled Fab-arm exchange for the generation of stable bispecific IgG1, 9(10), 2450-2463, Oct. 2014, Nature Protocols.
Labrijn, A.F. et al., Efficient Generation of Bispecific Murine Antibodies for Pre-Clinical Investigations in Syngeneic Rodent Models, 7, pp. 2476, May 30, 2017, Scientific Reports.
Lefranc MP . et al., IMGT, the international ImMunoGeneTics database, 27, 209-212, 1999, Nucleic Acids Research.
Lefranc, M-P. et al., IMGT, the international ImMunoGene Tics information system, 33, pp. D593-D597, 2005, Nucleic Acids Research.
Lefranc, M-P. et al., Unique database number system for immunogenetic analysis, 18(11), p. 509, Nov. 1997, Immunology Today.
Li et al., A Mini-Review for Cancer Immunotherapy: Molecular Understanding of PD-1/PD-L1 Pathway & Translational Blockade of Immune Checkpoints, 17, 1151, pp. 1-22, 2016, Int. J. Mol. Sci.

(56) References Cited

OTHER PUBLICATIONS

Lindhofer, H. et al., Preferential species-restricted heavy/light chain pairing in rat/mouse quadromas. Implications for a single-step purification of bispecific antibodies, 155(1), 219-225, 1995, J Immunology.
Liu et al., "Fc-Engineering for Modulated Effector Functions-Improving Antibodies for Cancer Treatment", Antibodies, Dec. 17, 2020, 9(4): 64.
Liu, H. et al., Heterogeneity of monoclonal antibodies, 97, 2426-2447, 2008.
Liu, S-Y. and Wu, Y-L., Ongoing clinical trials of PD-1 and PD-L1 inhibitors for lung cancer in China Si-Yang, 10(136), 8 pages, 2017, J Hematology and Oncology.
Moore, G.L. et al., Engineered Fc variant antibodies with enhanced ability to recruit complement and mediate effector functions, 2(2), 181-189, 2010.
Naing, A et al., A first-in-human phase I study of the anti-PD-1 antibody PDR001 in patients with advanced solid tumors, 34 (Suppl 15), pp. 3060 (Abstract 3060), 2016, Journal of Clinical Oncology.
Nakajima et al., Critical role of the CD44lowCD62Llow CD8+ T cell subset in restoring antitumor immunity in aged mice, 118, 23, pp. 1-10, 2021, PNAS.
Needleman et al., A general method applicable to the search for similarities in the amino acid sequence of two proteins, 48(3), pp. 443-453, Mar. 1970, J Mol Biol.
Okazaki et al., Fucose depletion from human IgG1 oligosaccharide enhances binding enthalpy and association rate between IgG1 and FcgammaRllla, 336(5), pp. 1239-1249, Mar. 5, 2004, JMB.
Oostindie et al., CD20 and CD37 antibodies synergize to activate complement by Fc-mediated clustering, 104(9), pp. 1841-1852, 2019, Haematologica.
Overdijk et al., Dual Epitope Targeting and Enhanced Hexamerization by DR5 Antibodies as a Novel Approach to Induce Potent Antitumor Activity Through DR5 Agonism, 19(10), pp. 2126-2138, Oct. 2020, Molecular Cancer Therapeutics.
Overdijk et al., Improving therapeutic activity of agonistic DR5 antibodies by inducing target binding-dependent hexamer formation, Cancer Res., Jul. 2016, Poster, 76(14 Suppl.): Abstract 592.
Patel et al., In Vivo Delivery of Synthetic Human DNA-Encoded Monoclonal Antibodies Protect against Ebolavirus Infection in a Mouse Model, 25(7), pp. 1982-1993, Nov. 2018, Cell Press.
Patel, P. et al., P242—A phase 1 multicenter, dose escalation study of CBT-501, a novel anti-PD-1 inhibitor in subjects with select advanced or relapsed recurrent solid tumors, 5 (Suppl. 2), P242 SITC 2017, 2017, Journal for Immuno Therapy of Cancer.
Rice et al., EMBOSS: The European Molecular Biology Open Software Suite, 16(6), pp. 276-277, Jun. 1, 2000, Elsevier Current Trends.
Roberts et al, Control of Established Melanoma by CD27 Stimulation Is Associated With Enhanced Effector Function and Persistence, and Reduced PD-1 Expression of Tumor Infiltrating CD8+ T Cells, vol. 33, No. 8, J Immunother • vol. 33, No. 8, Oct. 2010, Oct. 2010, J Immunother.
Sasikumar, P.G. et al., Small-Molecule Immune Checkpoint Inhibitors Targeting PD1/PDL1 and Other Emerging Checkpoint Pathways, 32, pp. 481-497, 2018, BioDrugs.
Schakowski et al., A novel minimal-size vector (MIDGE) improves transgene expression in colon carcinoma cells and avoids transfection of undesired DNA, 3(5), 793-800, May 2001, Molecular Therapy.
Schlake et al., mRNA: A Novel Avenue to Antibody Therapy?, 27, 4, pp. 773-784, Apr. 2019, Molecular Therapy.
Schlothauer et al., Novel human IgG1 and IgG4 Fc-engineered antibodies with completely abolished immune effector functions, vol. 29 issue 10, pp. 457-466, 2016, Protein Eng. Design and Selection.
Shaabani et al., A patent review on PD-1/PD-L1 antagonists: small molecules, peptides, and macrocycles (2015-2018), 28(9), pp. 665-678, Sep. 2, 2018, Taylor & Francis.
Shen, J. et al., Single variable domain antibody as a versatile building block for the construction of IgG-like bispecific antibodies, 318(1-2), pp. 65-74, Oct. 1, 2007, J Immunol Methods.
Shields et al., Lack of Fucose on Human IgG1 N-Linked Oligosaccharide Improves Binding to Human FcRlll and Antibody-dependent Cellular Toxicity*, 277(30), pp. 26733-26740, 2002, J. Biol. Chem.
Shinkawa et al., The Absence of Fucose but Not the Presence of Galactose or Bisecting N-Acetylglucosamine of Human IgG1 Complex-type Oligosaccharides Shows the Critical Role of Enhancing Antibody-dependent Cellular Cytotoxicity*, 278(5), pp. 3466-3473, Jan. 31, 2003, American Society for Biochemistry and Molecular Biology.
Sondermann, P. et al., Harnessing Fc receptor biology in the design of therapeutic antibodies, 40, 78-87, 2016.
Song et al., Evaluation of a fully human monoclonal antibody against multiple influenza A viral strains in mice and a pandemic H1N1 strain in nonhuman primates, 111, 60-68, 2014, Antiviral Research.
Sykes, K, et al, Linear expression elements: a rapid, in vivo, method to screen for gene functions, 17, 355-359, 1999, Nature Biotechnology.
The Human Protein Atlas, TNFRSF10B, Tissue and Pathology, 2022, Retrieved online from url: <https://www.proteinatlas.org/ENSG00000120889-TNFRSF10B>.
The Merck Manuals Online Medical Library [online], Merck Research Laboratories, 2006-2007, Cellular and Molecular Basis of Cancer, 2020, Retrieved from url: <https://www.merckmanuals.com/professional/hematology-and-oncology/overview-of-cancer/cellular-and-molecular-basis-of-cancer>.
Umana, P. et al., Engineered glycoforms of an antineuroblastoma IgG1 with optimized antibody-dependent cellular cytotoxic activity, 17(2), pp. 176-180, Feb. 1999, Nature Publishing Group.
Vafa et al., An engineered Fc variant of an IgG eliminates all immune effector functions via structural perturbations, 65, pp. 114-126, 2014, Methods.
Van De Ven et al., Targeting the T-Cell Co-stimulatory CD27, CD70 Pathway in Cancer Immunotherapy, Rationale and Potential, 7(6), pp. 655-667, 2015, Immunotherapy.
Van Heeke, G et al., Expression of human asparagine synthetase in *Escherichia coli*, 264(10), 5503-5509, 1989, Journ of Biological Chemistry.
Van Ostervijk et al, CD27-CD70 interactions sensitise naive CD4plus T cells for IL-12-induced Th1 cell development, vol. 19, No. 6, pp. 713-718, International Immunology.
Vitale et al, Development of a Human Monoclonal Antibody for Potential Therapy of CD27-Expressing Lymphoma and Leukemia, 18(14), pp. 3812-3821, Jul. 15, 2012, Clinical Cancer Research.
Vitale et al., Development of CDX527: a bispecifc antibody combining PD1 blockade and CD27 costimulation for cancer immunotherapy, 69, pp. 2125-2137, 2020, Cancer Immunology, Immunotherapy.
Wang et al., First-in-Human DRS PET reveals insufficient DR5 expression in patients with gastrointestinal cancer, J. Immunother. Canc, 2021, 9: e002926, pp. 1-11.
Wang et al., Molecular Basis of Assembly and Activation of Complement Component C1 in Complex with immunoglobulin G1 and antigen, 63, pp. 135-145, Jul. 7, 2016, Molecular Cell.
Wang, J. et al., Characterization of a novel anti-DR5 monoclonal antibody WD1 with the potential to induce tumor cell apoptosis, 5(1), 55-60, 2008, Cellular & Molecular Immunology.
Wigler, M. et al., Biochemical transfer of single-copy eucaryotic genes using total cellular DNA as donor, 14(3), 725-731, 1978, Cell.
Wu et al., Increased serum TRAIL and DR5 levels correlated with lung function and inflammation in stable COPD patients, vol. 10, pp. 2405-2412, Nov. 2015, International Journal of COPD.
Wu et al., Resonance Energy Transfer: Methods and Applications, vol. 218, 1, pp. 1-13, Apr. 1994, Analytical Biochemistry.
Youssef et al., Abstract 2667: In vitro properties and pre-clinical activity of PF-06801591, a high-affinity engineered anti-human PD-1, 33 (Suppl 13), pp. 2667, 2017, Cancer research.
Zhang et al., Functional optimization of agonistic antibodies to OX40 receptor with novel Fc mutations to promote antibody multimerization, 9(7), 1129-1142, 2017.

(56) References Cited

OTHER PUBLICATIONS

Zheng et al., SynergyFinder Plus: Toward Better Interpretation and Annotation of Drug Combination Screening Datasets, 20, pp. 587-596, 2022, Genomics Proteomics Bioinformatica.
Wang et al., "IgG Fc engineering to modulate antibody effector functions", Protein and Cell, Jan. 2018, 9(1): 63-73.
U.S. Appl. No. 14/413,194 2015/0139997 U.S. Pat. No. 9,611,327, Jan. 6, 2015 May 21, 2015 Apr. 4, 2017, Claudine Brigitte Fernande Vermot-Desroches, Anti-DRS Family Antibodies, Bispecific or Multivalent Anti-DRS Family Antibodies and Methods of Use Thereof.
U.S. Appl. No. 15/436,583 2017/0260281 U.S. Pat. No. 10,647,774, Feb. 17, 2017 Sep. 14, 2017 May 12, 2020, Claudine Brigitte Fernande Vermot-Desroches, Anti-DRS Family Antibodies, Bispecific or Multivalent Anti-DRS Family Antibodies and Methods of Use Thereof.
U.S. Appl. No. 16/841,306 2020/0332016, Apr. 6, 2020 Oct. 22, 2020, Claudine Brigitte Fernande Vermot-Desroches, Anti-DRS Family Antibodies, Bispecific or Multivalent Anti-DRS Family Antibodies and Methods of Use Thereof.
U.S. Appl. No. 16/316,534 2020/0062853 U.S. Pat. No. 11,091,557, Jul. 14, 2017 Feb. 27, 2020 Aug. 17, 2021, Isil Altintas, Methods of Producing Multispecific Antibodies Against CD40 and CD137.
U.S. Appl. No. 16/855,703 2020/0247899 U.S. Pat. No. 11,084,882, Apr. 22, 2020 Aug. 6, 2020 Aug. 10, 2021, Isil Altintas, Multispecific Antibodies Against CD40 and CD137.
U.S. Appl. No. 17/360,437 2022/0064317, Jun. 28, 2021 Mar. 3, 2022, Isil Altintas, Multispecific Antibodies Against CD40 and CD137.
U.S. Appl. No. 17/360,438 2022/0033510, Jun. 28, 2021 Feb. 3, 2022, Isil Altintas, Multispecific Antibodies Against CD40 and CD137.
U.S. Appl. No. 17/345,628 2021/0317225 U.S. Pat. No. 11,440,966, Jun. 11, 2021 Oct. 14, 2021 Sep. 13, 2022, Isil Altintas, Multispecific Antibodies Against CD40 and CD137.
U.S. Appl. No. 17/817,033 2023/0089969, Aug. 3, 2022 Mar. 23, 2023, Isil Altintas, Multispecific Antibodies Against CD40 and CD137.
U.S. Appl. No. 16/491,464 2020/0239579, Sep. 5, 2019 Jul. 30, 2020, Isil Altintas, Multispecific Antibodies Against PD-L1.
U.S. Appl. No. 16/779,011 2020/0165349 U.S. Pat. No. 10,968,280, Jan. 31, 2020 May 28, 2020 Apr. 6, 2021, Isil Altintas, Binding Agents Binding to PD-L1 and CD137 and Use Thereof.
U.S. Appl. No. 17/172,694 2021/0163616 U.S. Pat. No. 11,459,395, Feb. 10, 2021 Jun. 3, 2021 Sep. 14, 2022, Isil Altintas, Binding Agents Binding to PD-L1 and CD137 and Use Thereof.
U.S. Appl. No. 17/821,837 2023/0087745, Aug. 24, 2022 Mar. 23, 2023, Isil Altintas, Binding Agents Binding to PD-L1 and CD137 and Use Thereof.
U.S. Appl. No. 17/172,698 2021/0269541, Feb. 10, 2021 Sep. 2, 2021, Isil Altintas, Binding Agents Binding to PD-L1 and CD137 and Use Thereof.
U.S. Appl. No. 17/172,700 2021/0277133, Feb. 10, 2021 Sep. 9, 2021, Isil Altintas, Binding Agents Binding to PD-L1 and CD137 and Use Thereof.
U.S. Appl. No. 17/289,602 2021/0369847, Apr. 28, 2021 Dec. 2, 2021, Isil Altintas, Antibody Formulation.
U.S. Appl. No. 17/795,318 2023/0087164, Jul. 26, 2022 Mar. 23, 2023, Ugur Sahin, Antibodies for Use in Therapy.
U.S. Appl. No. 18/055,362, filed Nov. 14, 2022, Andreea Ioan, Antibodies Capable of Binding to CD27, Variants Thereof and Uses Thereof.
U.S. Appl. No. 18/861,665, filed Oct. 30, 2024, Esther C. W. Breij, Binding Agents Capable of Binding to CD27 in Combination Therapy.
U.S. Appl. No. 18/861,928, filed May 12, 2023, Esther C. W. Breij, Binding Agents Capable of Binding to CD27 in Combination Therapy.
U.S. Appl. No. 18/055,362 2023/0212301, Nov. 14, 2022 Jul. 6, 2023, Andreea Ioan, Antibodies Capable of Binding to CD27, Variants Thereof and Uses Thereof.
U.S. Appl. No. 14/413,194 2015/0139997 U.S. Pat. No. 9,611,327, Jan. 6, 2015 May 21, 2015 Apr. 4, 2017, Claudine Brigitte Fernande Vermot-Desroches, Anti-DR5 Family Antibodies, Bispecific or Multivalent Anti-DR5 Family Antibodies and Methods of Use Thereof.
U.S. Appl. No. 15/436,583 2017/0260281 U.S. Pat. No. 10,647,774, Feb. 17, 2017 Sep. 19, 2017 May 12, 2020, Claudine Brigitte Fernande Vermot-Desroches, Anti-DR5 Family Antibodies, Bispecific or Multivalent Anti-DR5 Family Antibodies and Methods of Use Thereof.
U.S. Appl. No. 16/841,306, filed Apr. 6, 2020, Claudine Brigitte Fernande Vermot-Desroches, Anti-DR5 Family Antibodies, Bispecific or Multivalent Anti-DR5 Family Antibodies and Methods of Use Thereof.
U.S. Appl. No. 17/817,033, filed Aug. 3, 2022, Isil Altintas, Multispecific Antibodies Against CD40 and CD137.
U.S. Appl. No. 16/491,464 2020/0239579, Sep. 5, 2019 Jul. 30, 2020, Isil Altintas, Antibodies Against PD-L1.
U.S. Appl. No. 17/821,837, filed Aug. 24, 2022, Isil Altintas, Binding Agents Binding to PD-L1 and CD137 and Use Thereof.
U.S. Appl. No. 17/289,602 2021/0369842, Apr. 28, 2021 Dec. 2, 2021, Isil Altintas, Antibody Formulation.
U.S. Appl. No. 17/795,318, filed Jul. 26, 2022, Ugur Sahin, Antibodies for Use in Therapy.

* cited by examiner

A: CD8+ T cells, 4 different donors

CD4+ T cells, 4 different donors

Figure 9:
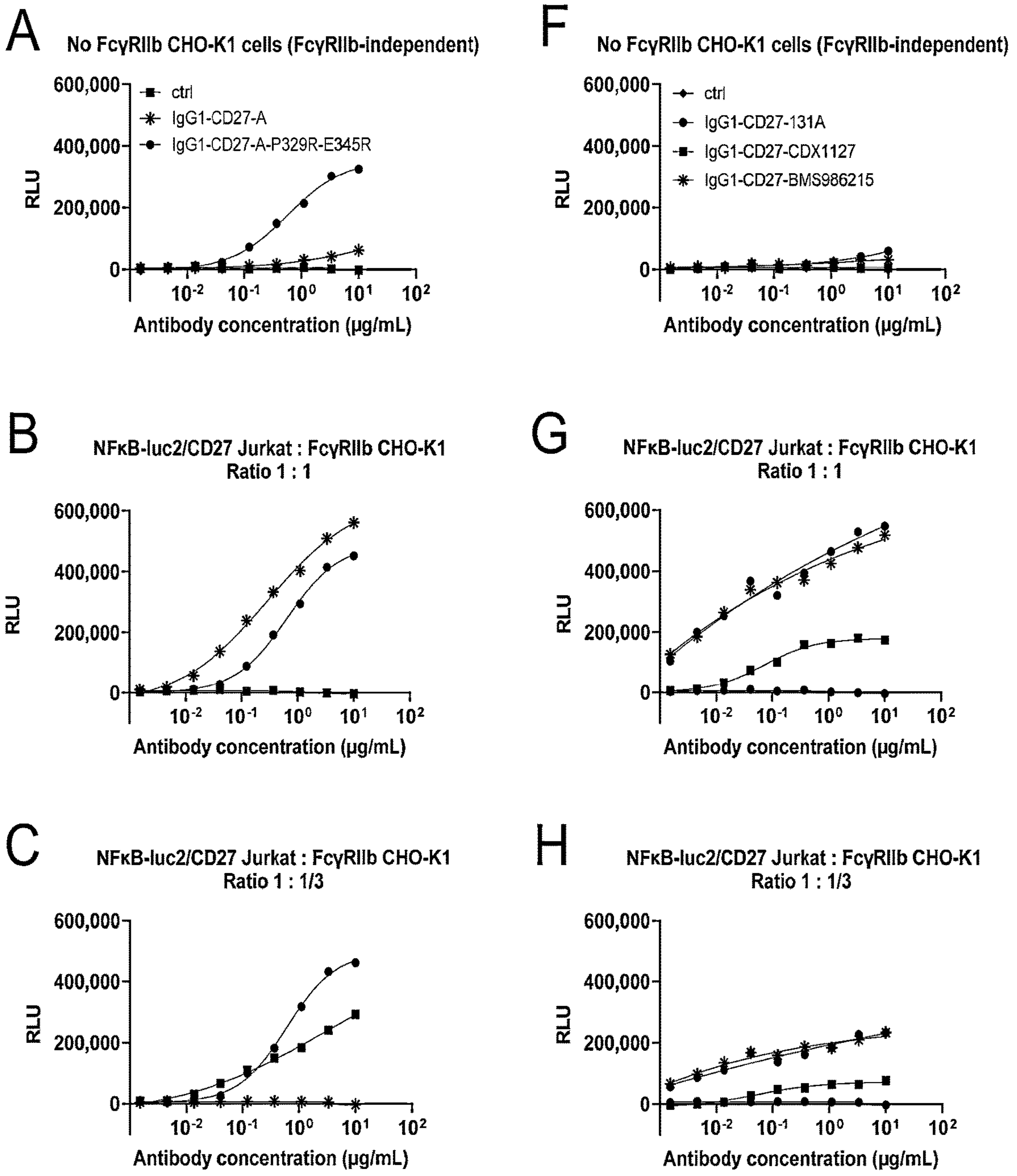

Figure 9 - continued
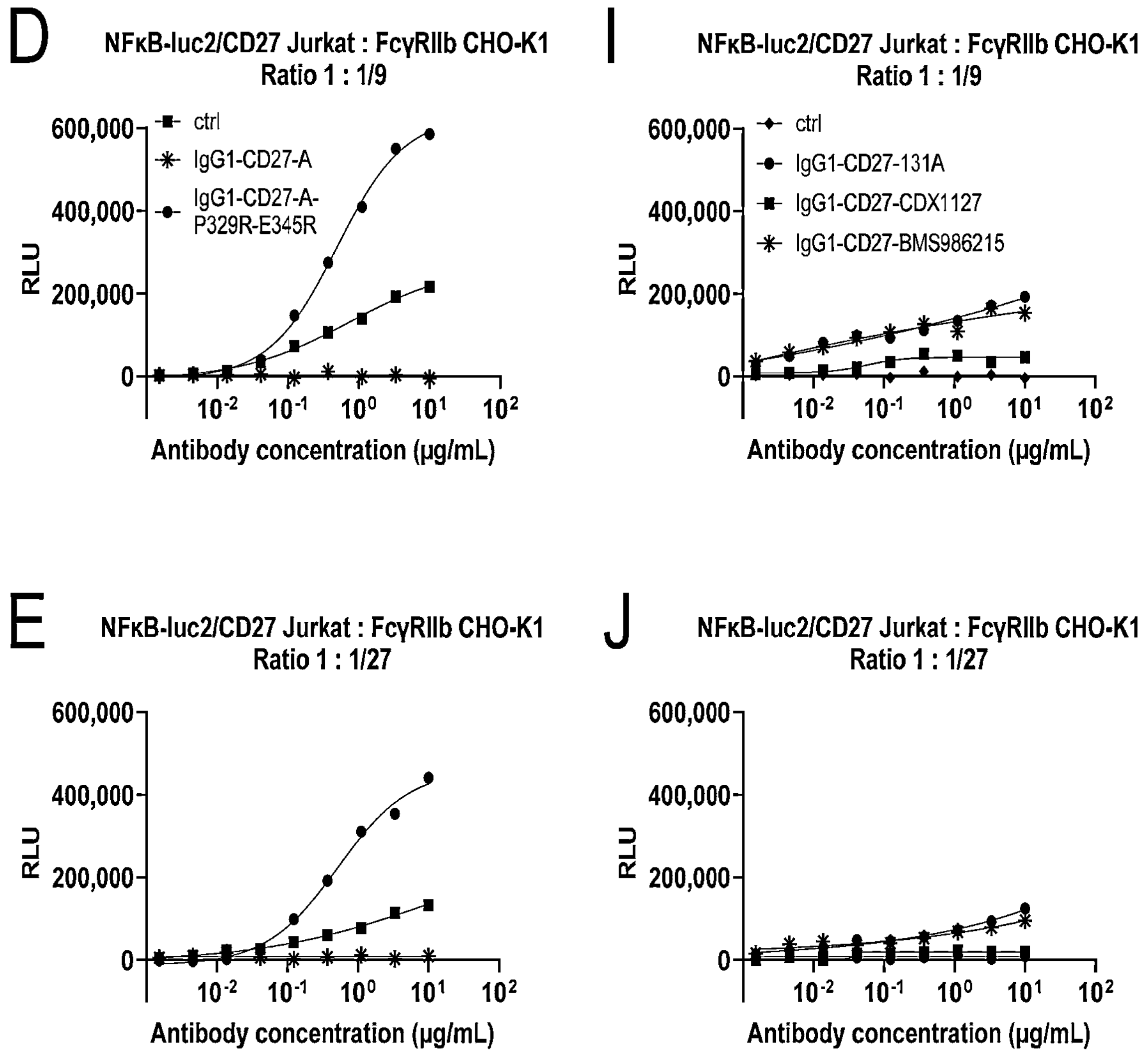

A

Figure 14A – *continued*
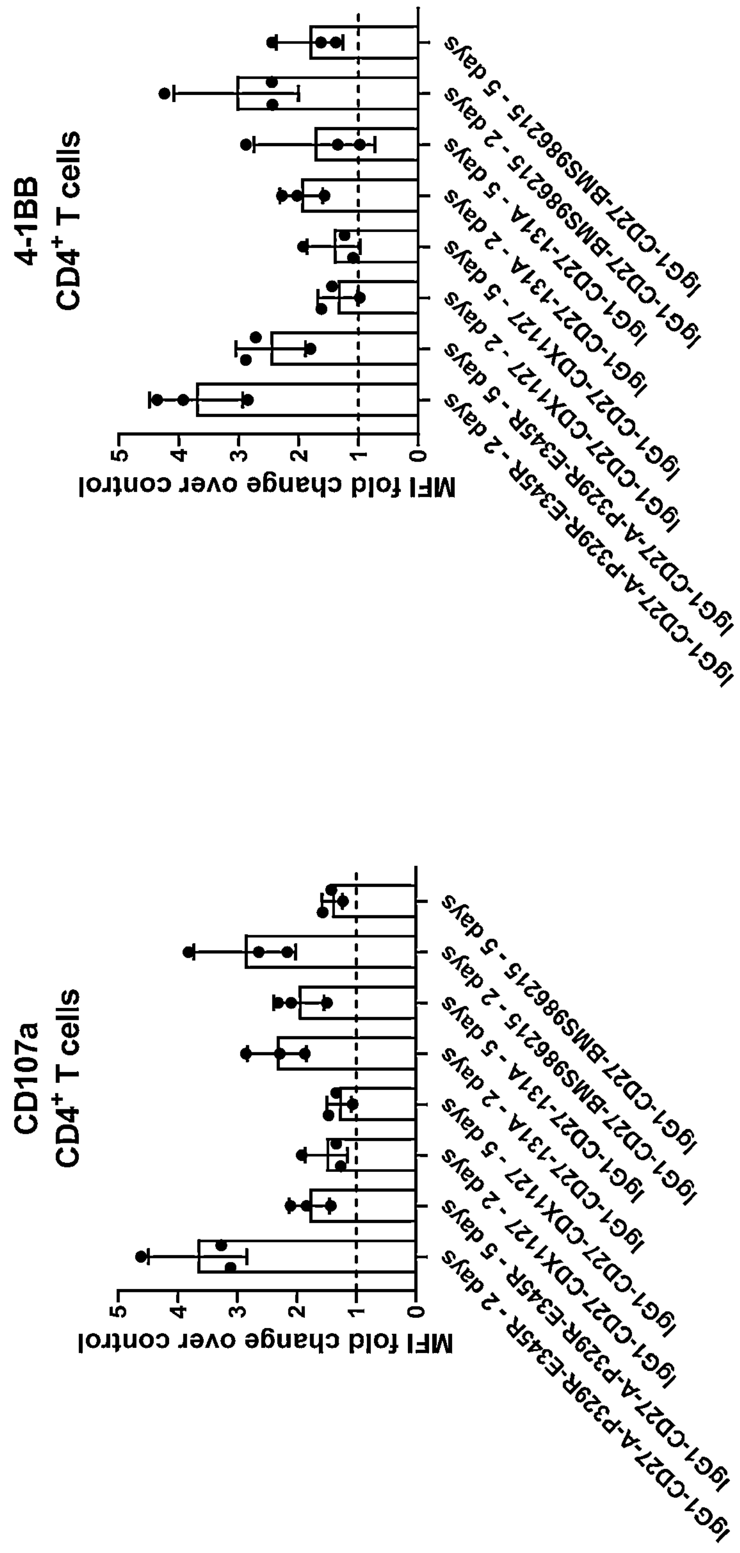

Figure 14:
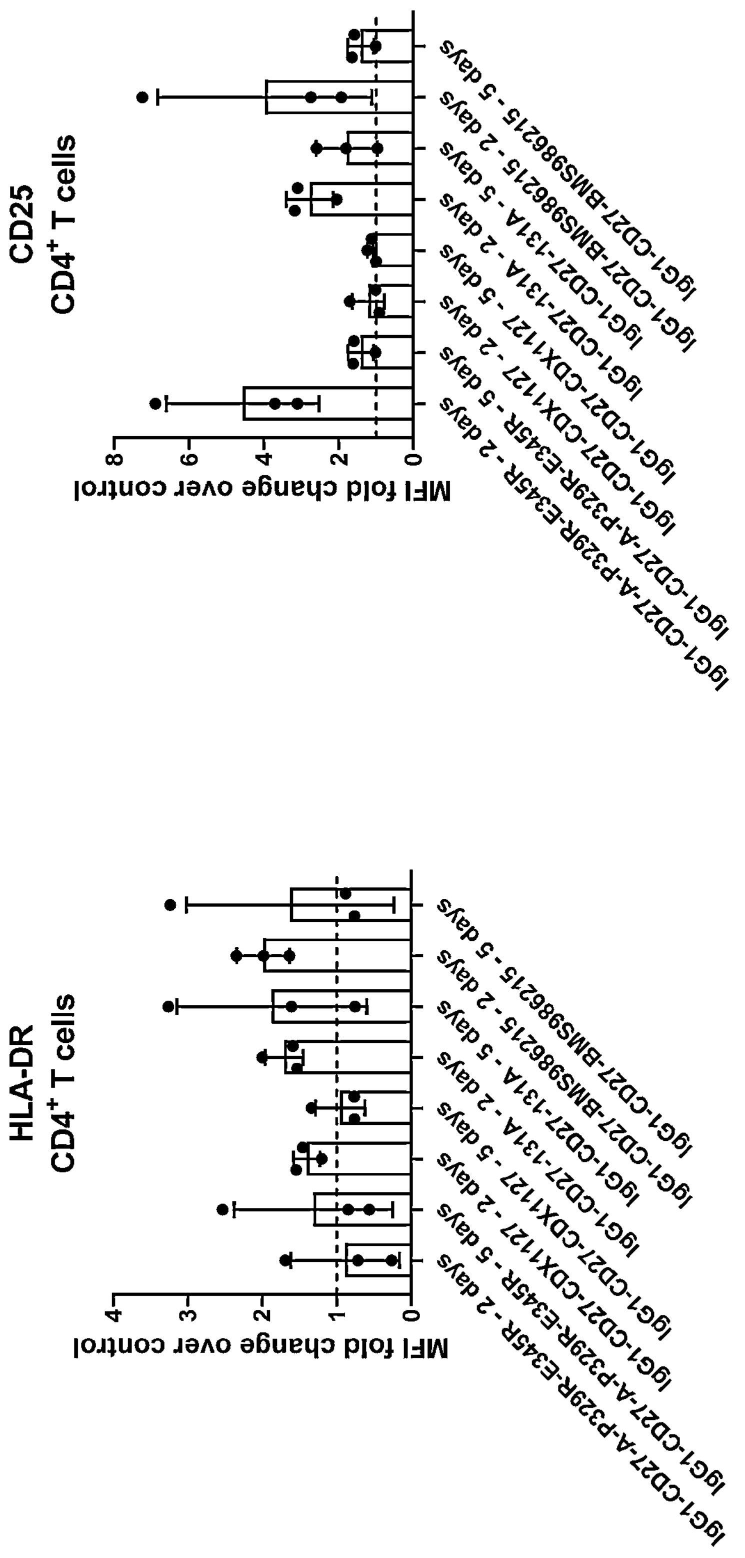
Figure 14B:
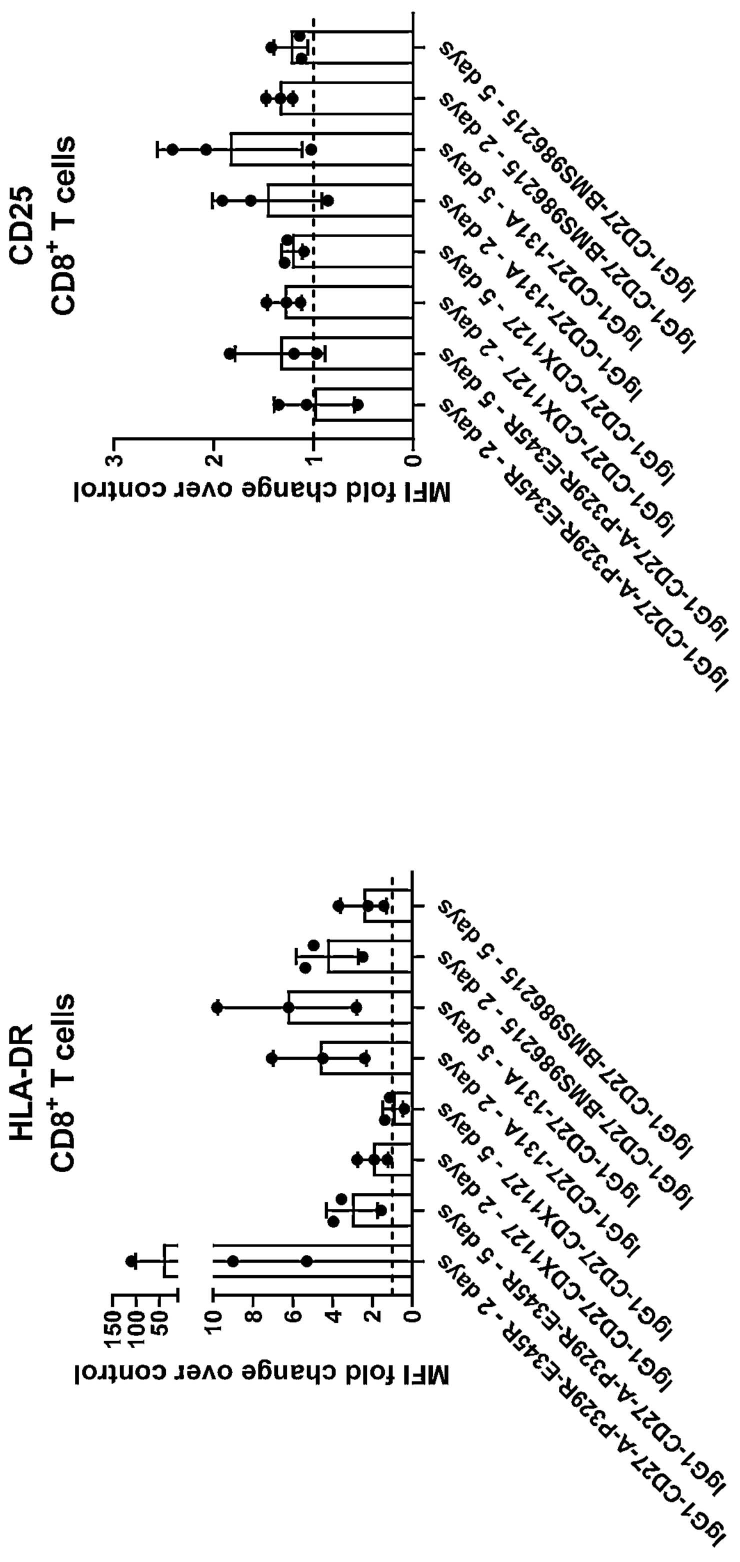

Figure 14B – continued
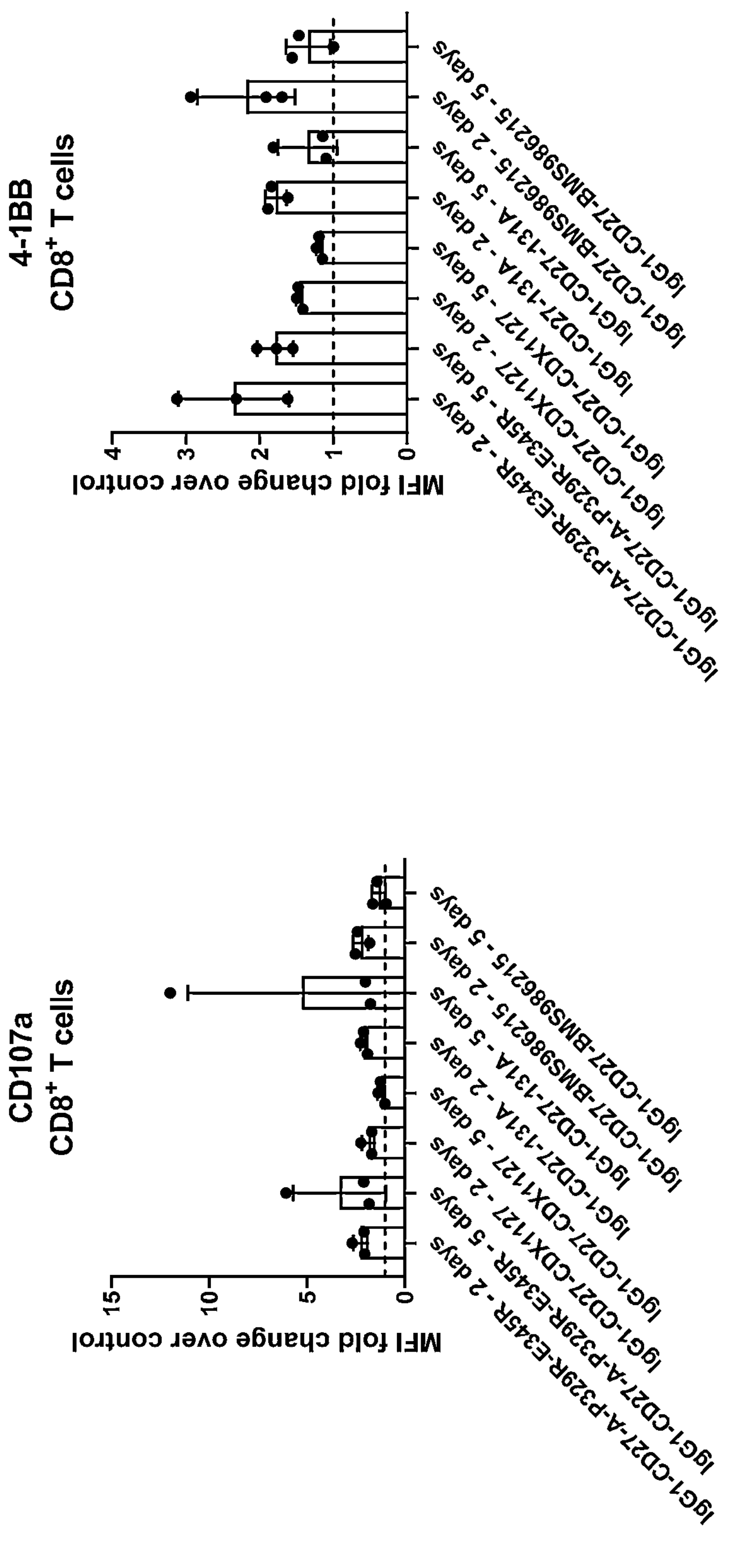

SEQUENCE LISTING

```
Sequence total quantity: 44
SEQ ID NO: 1            moltype = AA  length = 260
FEATURE                 Location/Qualifiers
source                  1..260
                        mol_type = protein
                        organism = Homo sapiens
SEQUENCE: 1
MARPHPWWLC VLGTLVGLSA TPAPKSCPER HYWAQGKLCC QMCEPGTFLV KDCDQHRKAA  60
QCDPCIPGVS FSPDHHTRPH CESCRHCNSG LLVRNCTITA NAECACRNGW QCRDKECTEC  120
DPLPNPSLTA RSSQALSPHP QPTHLPYVSE MLEARTAGHM QTLADFRQLP ARTLSTHWPP  180
QRSLCSSDFI RILVIFSGMF LVFTLAGALF LHQRRKYRSN KGESPVEPAE PCHYSCPREE  240
EGSTIPIQED YRKPEPACSP                                              260

SEQ ID NO: 2            moltype = AA  length = 260
FEATURE                 Location/Qualifiers
source                  1..260
                        mol_type = protein
                        organism = Homo sapiens
SEQUENCE: 2
MARPHPWWLC VLGTLVGLSA TPAPKSCPER HYWAQGKLCC QMCEPGTFLV KDCDQHRKTA  60
QCDPCIPGVS FSPDHHTRPH CESCRHCNSG LLVRNCTITA NAECACRNGW QCRDKECTEC  120
DPLPNPSLTA RSSQALSPHP QPTHLPYVSE MLEARTAGHM QTLADFRQLP ARTLSTHWPP  180
QRSLCSSDFI RILVIFSGMF LVFTLAGALF LHQRRKYRSN KGESPVEPAE PCHYSCPREE  240
EGSTIPIQED YRKPEPACSP                                              260

SEQ ID NO: 3            moltype = AA  length = 260
FEATURE                 Location/Qualifiers
source                  1..260
                        mol_type = protein
                        organism = Macaca fascicularis
SEQUENCE: 3
MARPHPWWLC FLGTLVGLSA TPAPKSCPER HYWAQGKLCC QMCEPGTFLV KDCDQHRKAA  60
QCHPCIPGVS FSPDHHTRPH CESCRHCNSG LLIRNCTITA NAVCACRNGW QCRDKECTEC  120
DPPPNPSLTT WPSQALGPHP QPTHLPYVNE MLEARTAGHM QTLADFRHLP ARTLSTHWPP  180
QRSLCSSDFI RILVIFSGMF LVFTLAGTLF LHQQRKYRSN KGESPMEPAE PCPYSCPREE  240
EGSTIPIQED YRKPEPASSP                                              260

SEQ ID NO: 4            moltype = AA  length = 116
FEATURE                 Location/Qualifiers
source                  1..116
                        mol_type = protein
                        organism = synthetic construct
SEQUENCE: 4
QVQLMQSGSE LKKPGASVKV SCRASGYTFT TYAMNWVRQA PGQGPEWMGW INTNTGNPTY  60
AQGFTGRFVF SLDTTVTTTY LQISSLKAED TAVYFCAREA GSFDYWGQGT LVTVSS      116
```

-continued

```
SEQ ID NO: 5           moltype = AA  length = 8
FEATURE                Location/Qualifiers
source                 1..8
                       mol_type = protein
                       organism = synthetic construct
SEQUENCE: 5
GYTFTTYA                                                           8

SEQ ID NO: 6           moltype = AA  length = 8
FEATURE                Location/Qualifiers
source                 1..8
                       mol_type = protein
                       organism = synthetic construct
SEQUENCE: 6
INTNTGNP                                                           8

SEQ ID NO: 7           moltype = AA  length = 9
FEATURE                Location/Qualifiers
source                 1..9
                       mol_type = protein
                       organism = synthetic construct
SEQUENCE: 7
AREAGSFDY                                                          9

SEQ ID NO: 8           moltype = AA  length = 110
FEATURE                Location/Qualifiers
source                 1..110
                       mol_type = protein
                       organism = synthetic construct
SEQUENCE: 8
QSALTQPASV SGSPGQSITI SCTGTSSDVY YYNYVSWYQQ HPGRAPKLVI YDVSNRPSGV  60
SNRFSGSKSG NTASLTISGL RAEDEADYYC SSYTVNRVWV FGGGTKLTVL             110

SEQ ID NO: 9           moltype = AA  length = 9
FEATURE                Location/Qualifiers
source                 1..9
                       mol_type = protein
                       organism = synthetic construct
SEQUENCE: 9
SSDVYYYNY                                                          9

SEQ ID NO: 10          moltype =   length =
SEQUENCE: 10
000

SEQ ID NO: 11          moltype = AA  length = 10
FEATURE                Location/Qualifiers
source                 1..10
                       mol_type = protein
                       organism = synthetic construct
SEQUENCE: 11
SSYTVNRVWV                                                         10

SEQ ID NO: 12          moltype = AA  length = 330
FEATURE                Location/Qualifiers
source                 1..330
                       mol_type = protein
                       organism = synthetic construct
SEQUENCE: 12
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKRVEP KSCDKTHTCP PCPAPELLGG  120
PSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LPAPIEKTIS KAKGQPREPQ VYTLPPSREE  240
MTKNQVSLTC LVKGFYPSDI AVEWESNGQP ENNYKTTPPV LDSDGSFFLY SKLTVDKSRW  300
QQGNVFSCSV MHEALHNHYT QKSLSLSPGK                                   330

SEQ ID NO: 13          moltype = AA  length = 330
FEATURE                Location/Qualifiers
source                 1..330
                       mol_type = protein
                       organism = synthetic construct
SEQUENCE: 13
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKRVEP KSCDKTHTCP PCPAPELLGG  120
PSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LPAPIEKTIS KAKGQPRRPQ VYTLPPSREE  240
MTKNQVSLTC LVKGFYPSDI AVEWESNGQP ENNYKTTPPV LDSDGSFFLY SKLTVDKSRW  300
QQGNVFSCSV MHEALHNHYT QKSLSLSPGK                                   330
```

```
SEQ ID NO: 14          moltype = AA  length = 330
FEATURE                Location/Qualifiers
source                 1..330
                       mol_type = protein
                       organism = synthetic construct
SEQUENCE: 14
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKRVEP KSCDKTHTCP PCPAPELLGG  120
PSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LRAPIEKTIS KAKGQPREPQ VYTLPPSREE  240
MTKNQVSLTC LVKGFYPSDI AVEWESNGQP ENNYKTTPPV LDSDGSFFLY SKLTVDKSRW  300
QQGNVFSCSV MHEALHNHYT QKSLSLSPGK                                  330

SEQ ID NO: 15          moltype = AA  length = 329
FEATURE                Location/Qualifiers
source                 1..329
                       mol_type = protein
                       organism = synthetic construct
SEQUENCE: 15
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKRVEP KSCDKTHTCP PCPAPELLGG  120
PSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LRAPIEKTIS KAKGQPRRPQ VYTLPPSREE  240
MTKNQVSLTC LVKGFYPSDI AVEWESNGQP ENNYKTTPPV LDSDGSFFLY SKLTVDKSRW  300
QQGNVFSCSV MHEALHNHYT QKSLSLSPG                                   329

SEQ ID NO: 16          moltype = AA  length = 107
FEATURE                Location/Qualifiers
source                 1..107
                       mol_type = protein
                       organism = synthetic construct
SEQUENCE: 16
RTVAAPSVFI FPPSDEQLKS GTASVVCLLN NFYPREAKVQ WKVDNALQSG NSQESVTEQD  60
SKDSTYSLSS TLTLSKADYE KHKVYACEVT HQGLSSPVTK SFNRGEC                107

SEQ ID NO: 17          moltype = AA  length = 106
FEATURE                Location/Qualifiers
source                 1..106
                       mol_type = protein
                       organism = synthetic construct
SEQUENCE: 17
GQPKAAPSVT LFPPSSEELQ ANKATLVCLI SDFYPGAVTV AWKADSSPVK AGVETTTPSK  60
QSNNKYAASS YLSLTPEQWK SHRSYSCQVT HEGSTVEKTV APTECS                 106

SEQ ID NO: 18          moltype = AA  length = 329
FEATURE                Location/Qualifiers
source                 1..329
                       mol_type = protein
                       organism = synthetic construct
SEQUENCE: 18
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKRVEP KSCDKTHTCP PCPAPELLGG  120
PSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LPAPIEKTIS KAKGQPREPQ VYTLPPSREE  240
MTKNQVSLTC LVKGFYPSDI AVEWESNGQP ENNYKTTPPV LDSDGSFFLY SKLTVDKSRW  300
QQGNVFSCSV MHEALHNHYT QKSLSLSPG                                   329

SEQ ID NO: 19          moltype = AA  length = 330
FEATURE                Location/Qualifiers
source                 1..330
                       mol_type = protein
                       organism = synthetic construct
SEQUENCE: 19
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKPVEP KSCDKTHTCP PCPAPELLGG  120
PSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV MHEALHNHYT QKSLSLSPGK                                  330

SEQ ID NO: 20          moltype = AA  length = 330
FEATURE                Location/Qualifiers
source                 1..330
                       mol_type = protein
                       organism = synthetic construct
SEQUENCE: 20
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKPVEP KSCDKTHTCP PCPAPELLGG  120
PSVFLFPPKP KDTLMISRTP EVTCVVVDVS HEDPEVKFNW YVDGVEVHNA KTKPREEQYN  180
```

```
STYRVVSVLT VLHQDWLNGK EYKCKVSNKA LPAPIEKTIS KAKGQPREPQ VYTLPPSREE  240
MTKNQVSLTC LVKGFYPSDI AVEWESNGQP ENNYKTTPPV LDSDGSFFLY SKLTVDKSRW  300
QQGNVFSCSV MHEGLHNHYT QKSLSLSPGK                                  330

SEQ ID NO: 21          moltype = AA  length = 326
FEATURE                Location/Qualifiers
source                 1..326
                       mol_type = protein
                       organism = synthetic construct
SEQUENCE: 21
ASTKGPSVFP LAPCSRSTSE STAALGCLVK DYFPEPVTVS WNSGALTSGV HTFPAVLQSS  60
GLYSLSSVVT VPSSNFGTQT YTCNVDHKPS NTKVDKTVER KCCVECPPCP APPVAGPSVF  120
LFPPKPKDTL MISRTPEVTC VVVDVSHEDP EVQFNWYVDG VEVHNAKTKP REEQFNSTFR  180
VVSVLTVVHQ DWLNGKEYKC KVSNKGLPAP IEKTISKTKG QPREPQVYTL PPSREEMTKN  240
QVSLTCLVKG FYPSDIAVEW ESNGQPENNY KTTPPMLDSD GSFFLYSKLT VDKSRWQQGN  300
VFSCSVMHEA LHNHYTQKSL SLSPGK                                      326

SEQ ID NO: 22          moltype = AA  length = 377
FEATURE                Location/Qualifiers
source                 1..377
                       mol_type = protein
                       organism = synthetic construct
SEQUENCE: 22
ASTKGPSVFP LAPCSRSTSG GTAALGCLVK DYFPEPVTVS WNSGALTSGV HTFPAVLQSS  60
GLYSLSSVVT VPSSSLGTQT YTCNVNHKPS NTKVDKRVEL KTPLGDTTHT CPRCPEPKSC  120
DTPPPCPRCP EPKSCDTPPP CPRCPEPKSC DTPPPCPRCP APELLGGPSV FLFPPKPKDT  180
LMISRTPEVT CVVVDVSHED PEVQFKWYVD GVEVHNAKTK PREEQYNSTF RVVSVLTVLH  240
QDWLNGKEYK CKVSNKALPA PIEKTISKTK GQPREPQVYT LPPSREEMTK NQVSLTCLVK  300
GFYPSDIAVE WESSGQPENN YNTTPPMLDS DGSFFLYSKL TVDKSRWQQG NIFSCSVMHE  360
ALHNRFTQKS LSLSPGK                                                377

SEQ ID NO: 23          moltype = AA  length = 327
FEATURE                Location/Qualifiers
source                 1..327
                       mol_type = protein
                       organism = synthetic construct
SEQUENCE: 23
ASTKGPSVFP LAPCSRSTSE STAALGCLVK DYFPEPVTVS WNSGALTSGV HTFPAVLQSS  60
GLYSLSSVVT VPSSSLGTKT YTCNVDHKPS NTKVDKRVES KYGPPCPSCP APEFLGGPSV  120
FLFPPKPKDT LMISRTPEVT CVVVDVSQED PEVQFNWYVD GVEVHNAKTK PREEQFNSTY  180
RVVSVLTVLH QDWLNGKEYK CKVSNKGLPS SIEKTISKAK GQPREPQVYT LPPSQEEMTK  240
NQVSLTCLVK GFYPSDIAVE WESNGQPENN YKTTPPVLDS DGSFFLYSRL TVDKSRWQEG  300
NVFSCSVMHE ALHNHYTQKS LSLSLGK                                     327

SEQ ID NO: 24          moltype = AA  length = 446
FEATURE                Location/Qualifiers
source                 1..446
                       mol_type = protein
                       organism = synthetic construct
SEQUENCE: 24
QVQLMQSGSE LKKPGASVKV SCRASGYTFT TYAMNWVRQA PGQGPEWMGW INTNTGNPTY  60
AQGFTGRFVF SLDTTVTTTY LQISSLKAED TAVYFCAREA GSFDYWGQGT LVTVSSASTK  120
GPSVFPLAPS SKSTSGGTAA LGCLVKDYFP EPVTVSWNSG ALTSGVHTFP AVLQSSGLYS  180
LSSVVTVPSS SLGTQTYICN VNHKPSNTKV DKRVEPKSCD KTHTCPPCPA PELLGGPSVF  240
LFPPKPKDTL MISRTPEVTC VVVDVSHEDP EVKFNWYVDG VEVHNAKTKP REEQYNSTYR  300
VVSVLTVLHQ DWLNGKEYKC KVSNKALRAP IEKTISKAKG QPRRPQVYTL PPSREEMTKN  360
QVSLTCLVKG FYPSDIAVEW ESNGQPENNY KTTPPVLDSD GSFFLYSKLT VDKSRWQQGN  420
VFSCSVMHEA LHNHYTQKSL SLSPGK                                      446

SEQ ID NO: 25          moltype = AA  length = 216
FEATURE                Location/Qualifiers
source                 1..216
                       mol_type = protein
                       organism = synthetic construct
SEQUENCE: 25
QSALTQPASV SGSPGQSITI SCTGTSSDVY YYNYVSWYQQ HPGRAPKLVI YDVSNRPSGV  60
SNRFSGSKSG NTASLTISGL RAEDEADYYC SSYTVNRVWV FGGGTKLTVL GQPKAAPSVT  120
LFPPSSEELQ ANKATLVCLI SDFYPGAVTV AWKADSSPVK AGVETTTPSK QSNNKYAASS  180
YLSLTPEQWK SHRSYSCQVT HEGSTVEKTV APTECS                           216

SEQ ID NO: 26          moltype = AA  length = 250
FEATURE                Location/Qualifiers
source                 1..250
                       mol_type = protein
                       organism = Mus musculus
SEQUENCE: 26
MAWPPPYWLC MLGTLVGLSA TLAPNSCPDK HYWTGGGLCC RMCEPGTFFV KDCEQDRTAA  60
QCDPCIPGTS FSPDYHTRPH CESCRHCNSG FLIRNCTVTA NAECSCSKNW QCRDQECTEC  120
DPPLNPALTR QPSETPSPQP PPTHLPHGTE KPSWPLHRQL PNSTVYSQRS SHRPLCSSDC  180
```

```
IRIFVTFSSM FLIFVLGAIL FFHQRRNHGP NEDRQAVPEE PCPYSCPREE EGSAIPIQED  240
YRKPEPAFYP                                                         250

SEQ ID NO: 27          moltype = AA  length = 330
FEATURE                Location/Qualifiers
source                 1..330
                       mol_type = protein
                       organism = synthetic construct
SEQUENCE: 27
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKRVEP KSCDKTHTCP PCPAPELLGG  120
PSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LRAPIEKTIS KAKGQPRRPQ VYTLPPSREE  240
MTKNQVSLTC LVKGFYPSDI AVEWESNGQP ENNYKTTPPV LDSDGSFFLY SKLTVDKSRW  300
QQGNVFSCSV MHEALHNHYT QKSLSLSPGK                                   330

SEQ ID NO: 28          moltype = AA  length = 329
FEATURE                Location/Qualifiers
source                 1..329
                       mol_type = protein
                       organism = synthetic construct
SEQUENCE: 28
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKRVEP KSCDKTHTCP PCPAPELLGG  120
PSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LPAPIEKTIS KAKGQPREPQ VYTLPPSREE  240
MTKNQVSLTC LVKGFYPSDI AVEWESNGQP ENNYKTTPPV LDSDGSFFLY SKLTVDKSRW  300
QQGNVFSCSV MHEALHNHYT QKSLSLSPG                                    329

SEQ ID NO: 29          moltype = AA  length = 329
FEATURE                Location/Qualifiers
source                 1..329
                       mol_type = protein
                       organism = synthetic construct
SEQUENCE: 29
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKRVEP KSCDKTHTCP PCPAPELLGG  120
PSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LPAPIEKTIS KAKGQPRRPQ VYTLPPSREE  240
MTKNQVSLTC LVKGFYPSDI AVEWESNGQP ENNYKTTPPV LDSDGSFFLY SKLTVDKSRW  300
QQGNVFSCSV MHEALHNHYT QKSLSLSPG                                    329

SEQ ID NO: 30          moltype = AA  length = 329
FEATURE                Location/Qualifiers
source                 1..329
                       mol_type = protein
                       organism = synthetic construct
SEQUENCE: 30
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKRVEP KSCDKTHTCP PCPAPELLGG  120
PSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LRAPIEKTIS KAKGQPREPQ VYTLPPSREE  240
MTKNQVSLTC LVKGFYPSDI AVEWESNGQP ENNYKTTPPV LDSDGSFFLY SKLTVDKSRW  300
QQGNVFSCSV MHEALHNHYT QKSLSLSPG                                    329

SEQ ID NO: 31          moltype = AA  length = 329
FEATURE                Location/Qualifiers
source                 1..329
                       mol_type = protein
                       organism = synthetic construct
SEQUENCE: 31
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKPVEP KSCDKTHTCP PCPAPELLGG  120
PSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV MHEALHNHYT QKSLSLSPG                                    329

SEQ ID NO: 32          moltype = AA  length = 329
FEATURE                Location/Qualifiers
source                 1..329
                       mol_type = protein
                       organism = synthetic construct
SEQUENCE: 32
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKPVEP KSCDKTHTCP PCPAPELLGG  120
PSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LPAPIEKTIS KAKGQPREPQ VYTLPPSREE  240
MTKNQVSLTC LVKGFYPSDI AVEWESNGQP ENNYKTTPPV LDSDGSFFLY SKLTVDKSRW  300
```

```
QQGNVFSCSV MHEGLHNHYT QKSLSLSPG                                   329

SEQ ID NO: 33           moltype = AA  length = 325
FEATURE                 Location/Qualifiers
source                  1..325
                        mol_type = protein
                        organism = synthetic construct
SEQUENCE: 33
ASTKGPSVFP LAPCSRSTSE STAALGCLVK DYFPEPVTVS WNSGALTSGV HTFPAVLQSS  60
GLYSLSSVVT VPSSNFGTQT YTCNVDHKPS NTKVDKTVER KCCVECPPCP APPVAGPSVF  120
LFPPKPKDTL MISRTPEVTC VVVDVSHEDP EVQFNWYVDG VEVHNAKTKP REEQFNSTFR  180
VVSVLTVVHQ DWLNGKEYKC KVSNKGLPAP IEKTISKTKG QPREPQVYTL PPSREEMTKN  240
QVSLTCLVKG FYPSDIAVEW ESNGQPENNY KTTPPMLDSD GSFFLYSKLT VDKSRWQQGN  300
VFSCSVMHEA LHNHYTQKSL SLSPG                                       325

SEQ ID NO: 34           moltype = AA  length = 376
FEATURE                 Location/Qualifiers
source                  1..376
                        mol_type = protein
                        organism = synthetic construct
SEQUENCE: 34
ASTKGPSVFP LAPCSRSTSG GTAALGCLVK DYFPEPVTVS WNSGALTSGV HTFPAVLQSS  60
GLYSLSSVVT VPSSSLGTQT YTCNVNHKPS NTKVDKRVEL KTPLGDTTHT CPRCPEPKSC  120
DTPPPCPRCP EPKSCDTPPP CPRCPEPKSC DTPPPCPRCP APELLGGPSV FLFPPKPKDT  180
LMISRTPEVT CVVVDVSHED PEVQFKWYVD GVEVHNAKTK PREEQYNSTF RVVSVLTVLH  240
QDWLNGKEYK CKVSNKALPA PIEKTISKTK GQPREPQVYT LPPSREEMTK NQVSLTCLVK  300
GFYPSDIAVE WESSGQPENN YNTTPPMLDS DGSFFLYSKL TVDKSRWQQG NIFSCSVMHE  360
ALHNRFTQKS LSLSPG                                                 376

SEQ ID NO: 35           moltype = AA  length = 445
FEATURE                 Location/Qualifiers
source                  1..445
                        mol_type = protein
                        organism = synthetic construct
SEQUENCE: 35
QVQLMQSGSE LKKPGASVKV SCRASGYTFT TYAMNWVRQA PGQGPEWMGW INTNTGNPTY  60
AQGFTGRFVF SLDTTVTTTY LQISSLKAED TAVYFCAREA GSFDYWGQGT LVTVSSASTK  120
GPSVFPLAPS SKSTSGGTAA LGCLVKDYFP EPVTVSWNSG ALTSGVHTFP AVLQSSGLYS  180
LSSVVTVPSS SLGTQTYICN VNHKPSNTKV DKRVEPKSCD KTHTCPPCPA PELLGGPSVF  240
LFPPKPKDTL MISRTPEVTC VVVDVSHEDP EVKFNWYVDG VEVHNAKTKP REEQYNSTYR  300
VVSVLTVLHQ DWLNGKEYKC KVSNKALRAP IEKTISKAKG QPRRPQVYTL PPSREEMTKN  360
QVSLTCLVKG FYPSDIAVEW ESNGQPENNY KTTPPVLDSD GSFFLYSKLT VDKSRWQQGN  420
VFSCSVMHEA LHNHYTQKSL SLSPG                                       445

SEQ ID NO: 36           moltype = AA  length = 329
FEATURE                 Location/Qualifiers
source                  1..329
                        mol_type = protein
                        organism = synthetic construct
SEQUENCE: 36
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKRVEP KSCDKTHTCP PCPAPELLGG  120
PSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LRAPIEKTIS KAKGQPRRPQ VYTLPPSREE  240
MTKNQVSLTC LVKGFYPSDI AVEWESNGQP ENNYKTTPPV LDSDGSFFLY SKLTVDKSRW  300
QQGNVFSCSV MHEALHNHYT QKSLSLSPG                                   329

SEQ ID NO: 37           moltype = AA  length = 392
FEATURE                 Location/Qualifiers
source                  1..392
                        mol_type = protein
                        organism = synthetic construct
SEQUENCE: 37
QSALTQPASV SGSPGQSITI SCTGTSSDVY YYNYVSWYQQ HPGRAPKLVI YDVSNRPSGV  60
SNRFSGSKSG NTASLTISGL RAEDEADYYC SSYTVNRVWV FGGGTKLTVL GQPKAAPSVT  120
LFPPSSEELQ ANKATLVCLI SDFYPGAVTV AWKADSSPVK AGVETTTPSK QSNNKYAASS  180
YLSLTPEQWK SHRSYSCQVT HEGSTVEKTV APTECSSLGS SGVFTLEDFV GDWRQTAGYN  240
LDQVLEQGGV SSLFQNLGVS VTPIQRIVLS GENGLKIDIH VIIPYEGLSG DQMGQIEKIF  300
KVVYPVDDHH FKVILHYGTL VIDGVTPNMI DYFGRPYEGI AVFDGKKITV TGTLWNGNKI  360
IDERLINPDG SLLFRVTING VTGWRLCERI LA                               392

SEQ ID NO: 38           moltype = AA  length = 529
FEATURE                 Location/Qualifiers
source                  1..529
                        mol_type = protein
                        organism = synthetic construct
SEQUENCE: 38
QSALTQPASV SGSPGQSITI SCTGTSSDVY YYNYVSWYQQ HPGRAPKLVI YDVSNRPSGV  60
SNRFSGSKSG NTASLTISGL RAEDEADYYC SSYTVNRVWV FGGGTKLTVL GQPKAAPSVT  120
```

```
LFPPSSEELQ ANKATLVCLI SDFYPGAVTV AWKADSSPVK AGVETTTPSK QSNNKYAASS  180
YLSLTPEQWK SHRSYSCQVT HEGSTVEKTV APTECSSLEP TTEDLYFQSD NDGSEIGTGF  240
PFDPHYVEVL GERMHYVDVG PRDGTPVLFL HGNPTSSYVW RNIIPHVAPT HRCIAPDLIG  300
MGKSDKPDLG YFFDDHVRFM DAFIEALGLE EVVLVIHDWG SALGFHWAKR NPERVKGIAF  360
MEFIRPIPTW DEWPEFARET FQAFRTTDVG RKLIIDQNVF IEGTLPMGVV RPLTEVEMDH  420
YREPFLNPVD REPLWRFPNE LPIAGEPANI VALVEEYMDW LHQSPVPKLL FWGTPGVLIP  480
PAEAARLAKS LPNCKAVDIG PGLNLLQEDN PDLIGSEIAR WLSTLEISG               529

SEQ ID NO: 39           moltype = AA  length = 391
FEATURE                 Location/Qualifiers
source                  1..391
                        mol_type = protein
                        organism = synthetic construct
SEQUENCE: 39
EIVLTQSPGT LSLSPGERAT FSCRSSHSIR SRRVAWYQHK PGQAPRLVIH GVSNRASGIS  60
DRFSGSGSGT DFTLTITRVE PEDFALYYCQ VYGASSYTFG QGTKLERKRT VAAPSVFIFP  120
PSDEQLKSGT ASVVCLLNNF YPREAKVQWK VDNALQSGNS QESVTEQDSK DSTYSLSSTL  180
TLSKADYEKH KVYACEVTHQ GLSSPVTKSF NRGECSLGSS GVFTLEDFVG DWRQTAGYNL  240
DQVLEQGGVS SLFQNLGVSV TPIQRIVLSG ENGLKIDIHV IIPYEGLSGD QMGQIEKIFK  300
VVYPVDDHHF KVILHYGTLV IDGVTPNMID YFGRPYEGIA VFDGKKITVT GTLWNGNKII  360
DERLINPDGS LLFRVTINGV TGWRLCERIL A                                391

SEQ ID NO: 40           moltype = AA  length = 528
FEATURE                 Location/Qualifiers
source                  1..528
                        mol_type = protein
                        organism = synthetic construct
SEQUENCE: 40
EIVLTQSPGT LSLSPGERAT FSCRSSHSIR SRRVAWYQHK PGQAPRLVIH GVSNRASGIS  60
DRFSGSGSGT DFTLTITRVE PEDFALYYCQ VYGASSYTFG QGTKLERKRT VAAPSVFIFP  120
PSDEQLKSGT ASVVCLLNNF YPREAKVQWK VDNALQSGNS QESVTEQDSK DSTYSLSSTL  180
TLSKADYEKH KVYACEVTHQ GLSSPVTKSF NRGECSLEPT TEDLYFQSDN DGSEIGTGFP  240
FDPHYVEVLG ERMHYVDVGP RDGTPVLFLH GNPTSSYVWR NIIPHVAPTH RCIAPDLIGM  300
GKSDKPDLGY FFDDHVRFMD AFIEALGLEE VVLVIHDWGS ALGFHWAKRN PERVKGIAFM  360
EFIRPIPTWD EWPEFARETF QAFRTTDVGR KLIIDQNVFI EGTLPMGVVR PLTEVEMDHY  420
REPFLNPVDR EPLWRFPNEL PIAGEPANIV ALVEEYMDWL HQSPVPKLLF WGTPGVLIPP  480
AEAARLAKSL PNCKAVDIGP GLNLLQEDNP DLIGSEIARW LSTLEISG              528

SEQ ID NO: 41           moltype = AA  length = 392
FEATURE                 Location/Qualifiers
source                  1..392
                        mol_type = protein
                        organism = synthetic construct
SEQUENCE: 41
QSALTQPASV SGSPGQSITI SCTGTSSDVY YYNYVSWYQQ HPGRAPKLVI YDVSNRPSGV  60
SNRFSGSKSG NTASLTISGL RAEDEADYYC SSYTVNRVWV FGGGTKLTVL GQPKAAPSVT  120
LFPPSSEELQ ANKATLVCLI SDFYPGAVTV AWKADSSPVK AGVETTTPSK QSNNKYAASS  180
YLSLTPEQWK SHRSYSCQVT HEGSTVEKTV APTECSSLGS SGVFTLEDFV GDWRQTAGYN  240
LDQVLEQGGV SSLFQNLGVS VTPIQRIVLS GENGLKIDIH VIIPYEGLSG DQMGQIEKIF  300
KVVYPVDDHH FKVILHYGTL VIDGVTPNMI DYFGRPYEGI AVFDGKKITV TGTLWNGNKI  360
IDERLINPDG SLLFRVTING VTGWRLCERI LA                               392

SEQ ID NO: 42           moltype = AA  length = 529
FEATURE                 Location/Qualifiers
source                  1..529
                        mol_type = protein
                        organism = synthetic construct
SEQUENCE: 42
QSALTQPASV SGSPGQSITI SCTGTSSDVY YYNYVSWYQQ HPGRAPKLVI YDVSNRPSGV  60
SNRFSGSKSG NTASLTISGL RAEDEADYYC SSYTVNRVWV FGGGTKLTVL GQPKAAPSVT  120
LFPPSSEELQ ANKATLVCLI SDFYPGAVTV AWKADSSPVK AGVETTTPSK QSNNKYAASS  180
YLSLTPEQWK SHRSYSCQVT HEGSTVEKTV APTECSSLEP TTEDLYFQSD NDGSEIGTGF  240
PFDPHYVEVL GERMHYVDVG PRDGTPVLFL HGNPTSSYVW RNIIPHVAPT HRCIAPDLIG  300
MGKSDKPDLG YFFDDHVRFM DAFIEALGLE EVVLVIHDWG SALGFHWAKR NPERVKGIAF  360
MEFIRPIPTW DEWPEFARET FQAFRTTDVG RKLIIDQNVF IEGTLPMGVV RPLTEVEMDH  420
YREPFLNPVD REPLWRFPNE LPIAGEPANI VALVEEYMDW LHQSPVPKLL FWGTPGVLIP  480
PAEAARLAKS LPNCKAVDIG PGLNLLQEDN PDLIGSEIAR WLSTLEISG               529

SEQ ID NO: 43           moltype = AA  length = 390
FEATURE                 Location/Qualifiers
source                  1..390
                        mol_type = protein
                        organism = synthetic construct
SEQUENCE: 43
EIVLTQSPAT LSLSPGERAT LSCRASQSVS SYLAWYQQKP GQAPRLLIYD ASNRATGIPA  60
RFSGSGSGTD FTLTISSLEP EDFAVYYCQQ RSDWPLTFGG GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGECSLGSSG VFTLEDFVGD WRQTAGYNLD  240
QVLEQGGVSS LFQNLGVSVT PIQRIVLSGE NGLKIDIHVI IPYEGLSGDQ MGQIEKIFKV  300
```

-continued

```
VYPVDDHHFK VILHYGTLVI DGVTPNMIDY FGRPYEGIAV FDGKKITVTG TLWNGNKIID  360
ERLINPDGSL LFRVTINGVT GWRLCERILA                                   390

SEQ ID NO: 44          moltype = AA  length = 527
FEATURE                Location/Qualifiers
source                 1..527
                       mol_type = protein
                       organism = synthetic construct
SEQUENCE: 44
DIQMTQSPAS LSVSVGETVT ITCRASENIR SNLAWYQQKQ GKSPQLLVNV ATNLADGVPS  60
RFSGSGSGTQ YSLKINSLQS EDFGTYYCQH YWGTTWTFGG GTKLEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGECSLEPTT EDLYFQSDND GSEIGTGFPF  240
DPHYVEVLGE RMHYVDVGPR DGTPVLFLHG NPTSSYVWRN IIPHVAPTHR CIAPDLIGMG  300
KSDKPDLGYF FDDHVRFMDA FIEALGLEEV VLVIHDWGSA LGFHWAKRNP ERVKGIAFME  360
FIRPIPTWDE WPEFARETFQ AFRTTDVGRK LIIDQNVFIE GTLPMGVVRP LTEVEMDHYR  420
EPFLNPVDRE PLWRFPNELP IAGEPANIVA LVEEYMDWLH QSPVPKLLFW GTPGVLIPPA  480
EAARLAKSLP NCKAVDIGPG LNLLQEDNPD LIGSEIARWL STLEISG                527
```

ANTIBODIES CAPABLE OF BINDING TO CD27, VARIANTS THEREOF AND USES THEREOF

RELATED APPLICATIONS

This application claims priority to European Patent Application Nos. 22173126.8, filed May 12, 2022, and 21195118.1, filed Sep. 6, 2021, the entire disclosures of which are hereby incorporated herein by reference.

SEQUENCE LISTING

The instant application contains a Sequence Listing which has been submitted electronically in XML format and is hereby incorporated by reference in its entirety. Said XML copy, created on Sep. 6, 2022, is named 733398_GMB9-019_ST26.xml and is 50,782 bytes in size.

FIELD OF THE INVENTION

The present invention relates to antibodies capable of binding to CD27 and to antibody variants thereof comprising one or more mutations in the Fc region and to the use of such antibodies and Fc variants.

BACKGROUND OF THE INVENTION

CD27 (TNFRSF7) is a 55 kDa type I transmembrane protein member of the tumor necrosis factor (TNF) receptor superfamily (TNFRSF) which co-stimulates T-cell activation after binding to its ligand CD70. It is expressed in humans on the cell membrane of T, B, NK cells, and their immediate precursors, all of them part of the lymphoid lineage. On human T cells, CD27 is expressed on resting αβ $CD4^+$ (Treg and conventional T cells), $CD8^+$ T cells, stem-cell memory cells, and central-memory-like cells. On human B cells, CD27 is a memory B cell marker and CD27 signaling promotes differentiation of B cells into plasma cells.

The only known ligand for CD27 is the type II transmembrane protein CD70 (Tumor Necrosis Factor Superfamily member 7, TNFSF7; CD27 ligand, CD27L), which is quite restrictively and only transiently expressed on activated immune cells, including T, B, NK, and dendritic cells (DCs).

Upon binding of CD27 to CD70, a truncated 32 kDa form of CD27 can be released (known as soluble CD27, sCD27) through the action of matrix metalloproteinases.

CD27 plays a role in early generation of a primary immune response and is required for generation and long-term maintenance of T cell immunity. CD27-CD70 binding leads to activation of NF-KB and MAPK8/JNK pathways. Adaptor proteins TRAF2 and TRAF5 have been shown to mediate the signaling resulting from CD27 engagement.

To unlock their effector functions, T cells require T-cell antigen receptor-mediated recognition of their cognate antigen in the context of major histocompatibility complex (MHC) molecules on the surface of antigen presenting cells (APCs), and activation of costimulatory receptors. CD27 and CD28 are considered the most important costimulatory receptors expressed on T cells.

In mice, CD27 stimulation during the priming phase of T-cell activation, has been found to promote clonal expansion of antigen-specific $CD4^+$ and $CD8^+$ T cells by IL-2-independent survival signaling (Carr J M et al, Proc Natl Acad Sci USA 2006 Dec. 19; 130(51):19454-9). CD27 also counteracts apoptosis of activated T cells throughout successive divisions and was also shown to play an important role in memory differentiation of mouse $CD8^+$ T cells. (van de Ven K, Borst J. Immunotherapy 2015; 7(6):655-67). As a result, CD27 stimulation promotes the generation of effector T cells in lymphoid organs and broadens the responder T-cell repertoire. In human naïve T cells, CD27 stimulation promotes T helper-1 (Th1) differentiation of $CD4^+$ T cells and supports effector differentiation of cytotoxic T-lymphocytes (Oosterwijk et al, Int Immunol. 2007 June; 19(6):713-8).

Contrarily to its presence on tumor cells in some hematological malignancies, CD27 expression has not been detected on tumor cells in solid malignancies. However, CD27-expressing lymphoid cells have been described in the tumor microenvironment of both hematological malignancies and solid cancers.

In the treatment of cancer, engagement and stimulation of the immune response has been shown to induce and/or enhance anti-tumor immunity resulting in clinical responses, as exemplified by the clinical success of immune checkpoint inhibitors. An active immune response and/or existing anti-tumor immunity can be increased by providing co-stimulatory signaling, for example CD27 co-stimulatory signaling.

In mouse tumor models, T-cell functions and therefore antitumor immunity can be enhanced by agonistic CD27 antibodies. In hCD27-transgenic lymphoma mouse models, CD27 activation using agonistic antibodies showed potent antitumor activity and induction of protective immunity, which is dependent on $CD4^+$ and $CD8^+$ T cells (He L Z et al., J Immunol. 2013 Oct. 15; 191(8):4174-83). Furthermore, CD27 activation using monoclonal antibodies prevented tumor growth in mouse xenografts, including models derived from leukemia (Vitale et al, Keler T. Clin Cancer Res. 2012 Jul. 15; 18(14):3812-21), melanoma (Roberts D J, et al., J Immunother. 2010 October; 33(8):769-79), colon carcinoma, and thymoma (He L Z, et al., J Immunol. 2013 Oct. 15; 191(8):4174-83), among others.

Monoclonal IgG1 agonistic antibodies against human CD27 have been disclosed in the prior art.

WO2008/051424 relates to CD27 agonists, preferably an agonistic CD27 antibody, alone or in association with another moiety such as immune stimulant or immune modulator for treatment of cancer, infection, inflammation, allergy, and autoimmunity and for enhancing the efficacy of vaccines but does not disclose the sequence of any CD27 antibodies.

In WO2012/004367 a humanized anti-human CD27 agonistic antibody (designated hCD27.15) is described. It is reported that hCD27.15 does not require crosslinking by FcyR expressing cells to activate CD27-mediated co-stimulation of the immune response. However, this antibody does not bind to a frequently occurring SNP in hCD27 (A59T) and does not bind to cynomolgus CD27.

WO2011/130434 discloses a human agonistic anti-human CD27 antibody designated 1F5, which activates CD27 upon crosslinking by FcyR expressing cells and further is ligand (sCD70) blocking. 1F5 is reported to have CDC and ADCC activity on target cells and to enhance the immune response and to have anti-tumor activity in mouse models.

WO2018/058022 discloses the agonistic murine anti-human CD27 antibody 131A and humanized versions thereof. It is disclosed that 131A binds the frequent occurring SNP in hCD27 (A59T) and to cynomolgus CD27. WO2018/058022 further discloses that antibody 131A had greater anti-tumor response compared to the antibody 1F5 in a mouse tumor model.

WO2019/195452 discloses the non-ligand blocking agonistic anti-human CD27 antibody designated BMS-986215 which is reported to have a higher affinity for human and cynomolgus CD27 than the CD27-antibody 1F5 mentioned above. It is disclosed that CD27 co-stimulation of T cells by binding to its ligand CD70 occurs in the presence of BMS-986215. It is further disclosed that BMS-986215 reduces the suppression of $CD4^+$ responder T cells by regulatory T-cells (Tregs) and that BMS-986215 induces modest ADCC and low levels of ADCP, CDC and binds C1q. It is further disclosed that BMS-986215 only has weak agonist activity in the absence of FcyR and in the absence of soluble CD70.

Anti-CD27 antibodies must induce clustering of CD27 on the plasma membrane to induce CD27 agonism. In the case of wild type IgG1 antibodies, clustering of CD27 may be achieved through interaction of membrane-bound CD27 antibodies with FcyR-bearing cells, such as monocytes, macrophages, B cells and other immune cells. As a consequence, anti-CD27 IgG1 molecules may be less efficient when the number of FcyR-expressing cells is limited. In addition, FcyR engagement may also result in undesired effector functions, such as activation of antibody-dependent cellular cytotoxicity (ADCC), antibody-dependent cellular phagocytosis (ADCP), and complement-dependent cytotoxicity (CDC), which may cause unwanted depletion of CD27-positive T cells.

Optimization of the effector functions by modifications of the Fc region of the antibody may improve the effectivity of therapeutic antibodies for treating cancer or other diseases, e.g., to improve the ability of an antibody to elicit an immune response to antigen-expressing cells. Such efforts are described in, e.g., WO 2013/004842 A2; WO 2014/108198 A1; WO2018/146317; WO2018/083126; WO 2018/031258 A1; Dall'Acqua, Cook et al. J Immunol 2006, 177(2): 1129-1138; Moore, Chen et al. MAbs 2010 2(2): 181-189; Desjarlais and Lazar, Exp Cell Res 2011, 317(9): 1278-1285; Kaneko and Niwa, BioDrugs 2011, 25(1): 1-11; Song, Myojo et al., Antiviral Res 2014, 111: 60-68; Brezski and Georgiou, Curr Opin Immunol 2016, 40: 62-69; Sondermann and Szymkowski, Curr Opin Immunol 2016, 40: 78-87; Zhang, Armstrong et al. MAbs 2017, 9(7): 1129-1142; Wang, Mathieu et al. Protein & Cell 2018, 9(1): 63-73; Beurskens F J et al., Science. 2014 Mar. 14; 343(6176): 1260-3).

Despite these and other efforts in the art, however, there is a need for agonistic CD27 therapeutic antibodies with increased agonism and/or increased potency and/or which are efficacious even when the number of FcyR-expressing cells is limited. It is thus an object of the present invention to provide an anti-CD27 antibody having high potency and agonism and which induces higher activation of T-cell proliferation independently of the number of FcgR-expressing cells providing the secondary crosslinking for the clustering of CD27 on cell membrane. Thus, it is a further object to provide an anti-CD27 antibody which does not require crosslinking by FcyR expressing cells to activate CD27-mediated co-stimulation of the immune response. It is a further object to provide an anti-CD27 antibody which binds to human CD27 and which further binds to the frequently occurring SNP in hCD27 (A59T) and which also binds to cynomolgus CD27. It is a further object of the present invention to provide CD27 agonist antibodies that induce CD27 agonism through enhanced IgG hexamer formation, independent of secondary crosslinking by C1q or in an FcyR-independent manner. In the context of cancer, such antibodies may increase antitumor immunity. There remains a need for anti-CD27 antibodies exhibiting potent agonistic activities that enhance antitumor immune responses.

SUMMARY OF THE INVENTION

The present invention concerns CD27 binding antibodies and Fc variants thereof.

So, in one aspect, the invention relates to an antibody comprising at least one antigen-binding region capable of binding to human CD27 wherein said antibody comprises a heavy chain variable (VH) region CDR1, CDR2, and CDR3 comprising the sequences as set forth in SEQ ID NOs: 5, 6, and 7, respectively, and a light chain variable (VL) region CDR1, CDR2, and CDR3 comprising the sequences as set forth in SEQ ID NO: 9, 10 and 11, respectively.

In one aspect the invention relates to an antibody comprising the VH and VL regions comprising the sequences as set forth in SEQ ID NO: 4 and SEQ ID NO: 8, respectively.

In one aspect the invention relates to an antibody comprising the VH and VL regions comprising the sequences as set forth in SEQ ID NO: 4 and SEQ ID NO: 8, respectively and further comprising a light chain constant region (CL) and a heavy chain constant region (CH).

In one aspect the invention relates to an antibody comprising the VH and VL regions comprising the sequences as set forth in SEQ ID NO: 4 and SEQ ID NO: 8, respectively and further comprising a light chain constant region (CL) and a heavy chain constant region (CH) wherein the antibody is of the human IgG1 isotype.

In one aspect the invention relates to an antibody as described above which has a modified Fc region wherein the amino acid residue at the position corresponding to position E345 or E430 in a human IgG1 heavy chain according to Eu numbering is selected from the group comprising: A, C, D, F, G, H, I, K, L, M, N, Q, R, S, T, V, W and Y.

In one aspect the invention relates to any of the antibodies as described above and which further has a modified Fc region wherein the amino acid residue at the position corresponding to position P329 in a human IgG1 heavy chain according to Eu numbering is R.

In one aspect the invention relates to an antibody comprising a heavy chain variable (VH) region CDR1, CDR2, and CDR3 comprising the sequences as set forth in SEQ ID NOs: 5, 6, and 7, respectively, and a light chain variable (VL) region CDR1, CDR2, and CDR3 comprising the sequences as set forth in SEQ ID NO: 9, 10 and 11, respectively and further comprising a modified Fc region wherein the amino acid residue at the positions corresponding to position E345 and P329 in a human IgG1 heavy chain according to Eu numbering are both R.

In one aspect the invention relates to a human or a humanized antibody.

In one aspect the invention relates to an antibody comprising:

a. The VH region comprising the amino acid sequence set forth in SEQ ID No: 4;
b. The VL region comprising the amino acid sequence set forth in SEQ ID No: 8;
c. The CH region comprising the amino acid sequence set forth in SEQ ID No: 15; and
d. The CL region comprising the amino acid sequence set forth in SEQ ID No: 16.

In one aspect the invention relates to an antibody comprising:

a. The VH region comprising the amino acid sequence set forth in SEQ ID No: 4;

b. The VL region comprising the amino acid sequence set forth in SEQ ID No: 8;

c. The CH region comprising the amino acid sequence set forth in SEQ ID No: 15; and d. The CL region comprising the amino acid sequence set forth in SEQ ID No: 17.

In one aspect the invention relates to an antibody comprising a heavy chain comprising the amino acid sequence set forth in SEQ ID NO: 35 and a light chain comprising the amino acid sequence set forth in SEQ ID NO: 25.

In one aspect, the invention relates to an isolated nucleic acid encoding the antibody according to any aspect or embodiment herein.

In one aspect, the invention relates to an expression vector comprising such a nucleic acid.

In one aspect, the invention relates to a recombinant host cell which produces an antibody according to any aspect or embodiment herein.

In one aspect, the invention relates to a method of producing an antibody according to any aspect or embodiment herein, comprising cultivating such a recombinant host cell in a culture medium and under conditions suitable for producing the antibody.

In one aspect, the invention relates to a pharmaceutical composition comprising an antibody as defined in any aspect or embodiment herein, and a pharmaceutically acceptable carrier.

In one aspect, the invention relates to an antibody according to any aspect or embodiment herein for use as a medicament.

In one aspect, the invention relates to an antibody according to any aspect or embodiment herein for use in treating or preventing cancer.

In one aspect the invention relates to a method of treating a disease, the method comprising administering an antibody according to any aspect or embodiment herein, a composition according to any aspect or embodiment herein, or a pharmaceutical composition according to any aspect or embodiment herein, to a subject in need thereof.

In one aspect the invention relates to a kit-of-parts, such as a kit for use as a companion diagnostic/for identifying within a population of patients those patients which have a propensity to respond to treatment with an antibody according to any aspect or embodiment herein.

In one aspect the invention relates to an anti-idiotypic antibody, which binds to the antigen-binding region capable of binding to CD27 as defined in any one aspect or embodiment herein.

LEGENDS TO THE FIGURES

FIG. 1 shows CD27 agonist activity of anti-CD27 antibodies and hexamerization-enhanced Fc variants thereof as determined in a CD27 Jurkat Reporter BioAssay. Thaw-and-Use GloResponse NFκB-luc2/CD27 Jurkat reporter cells were incubated for 6 h with antibody concentration series (from left to right: 0.04 μg/mL, 0.30 μg/mL, 2.50 μg/mL, and 20 μg/mL) of the indicated antibodies. Luciferase activity, as a read-out for CD27 intracellular signaling, was quantified by determining the luminescence (RLU: relative luminescence units). The following antibodies were included as WT IgG1 and/or variants with an E430G or E345R mutation, as indicated: non-binding anti-HIV-gp120 control antibody comprising the E345R mutation (IgG1-b12-E345R, ctrl), anti-CD27 antibodies IgG1-CD27-A, IgG1-CD27-B, IgG1-CD27-C, IgG1-CD27-D, IgG1-CD27-E, and IgG1-CD27-F, and prior art anti-CD27 benchmark antibodies IgG1-CD27-131A and IgG1-CD27-15.

Figure 2:
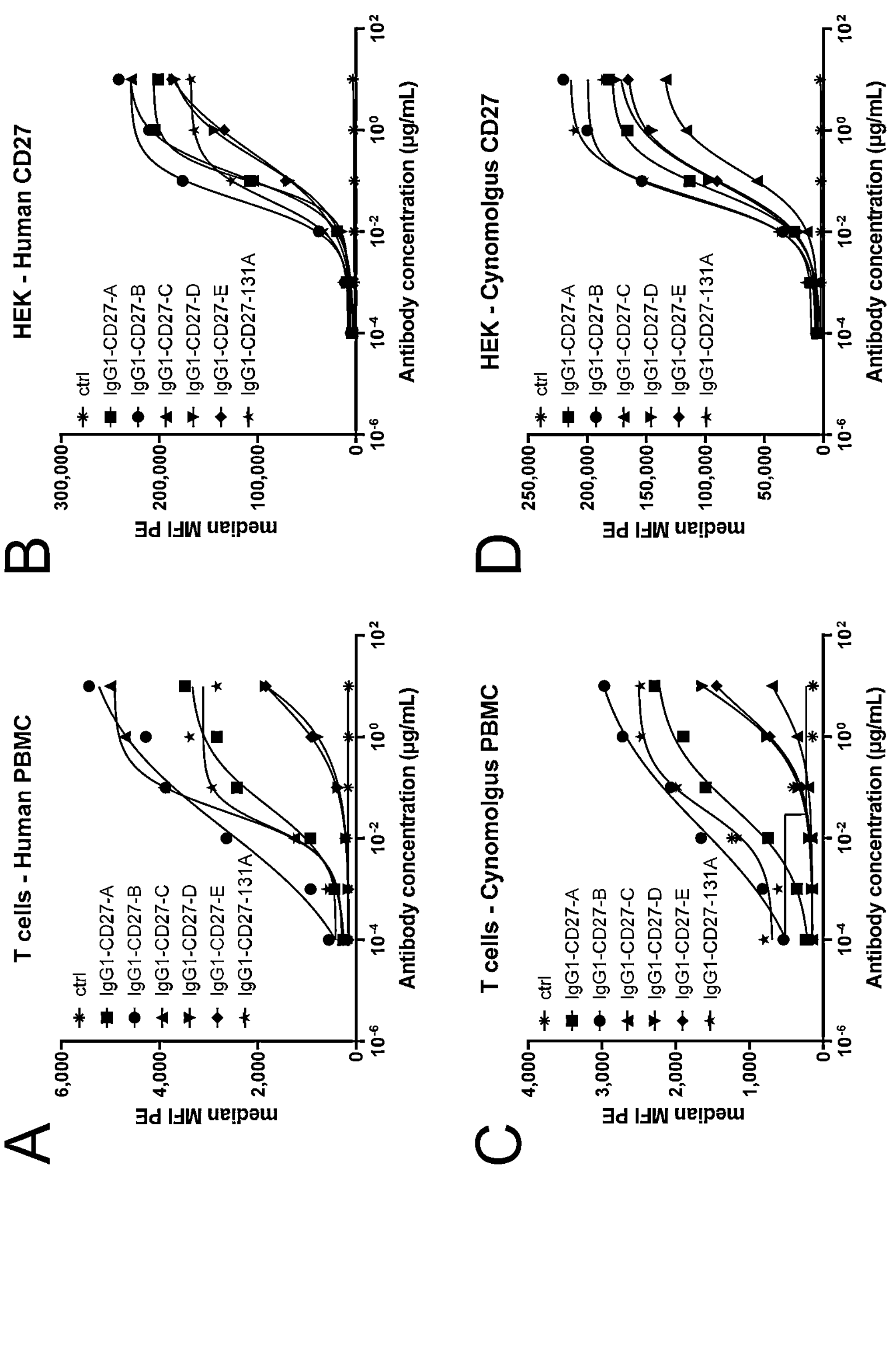

FIG. 2 shows binding of anti-CD27 antibodies to (A,B) human and (C,D) cynomolgus monkey CD27 expressed on (A,C) T cells in PBMC or (B,D) CD27-transfected HEK293F cells, as determined by flow cytometry. Antibody binding is presented as the median fluorescence intensity (MFI). The anti-HIV-gp120 antibody IgG1-b12-FEAR (ctrl) was included as non-binding negative control antibody.

Figure 3:
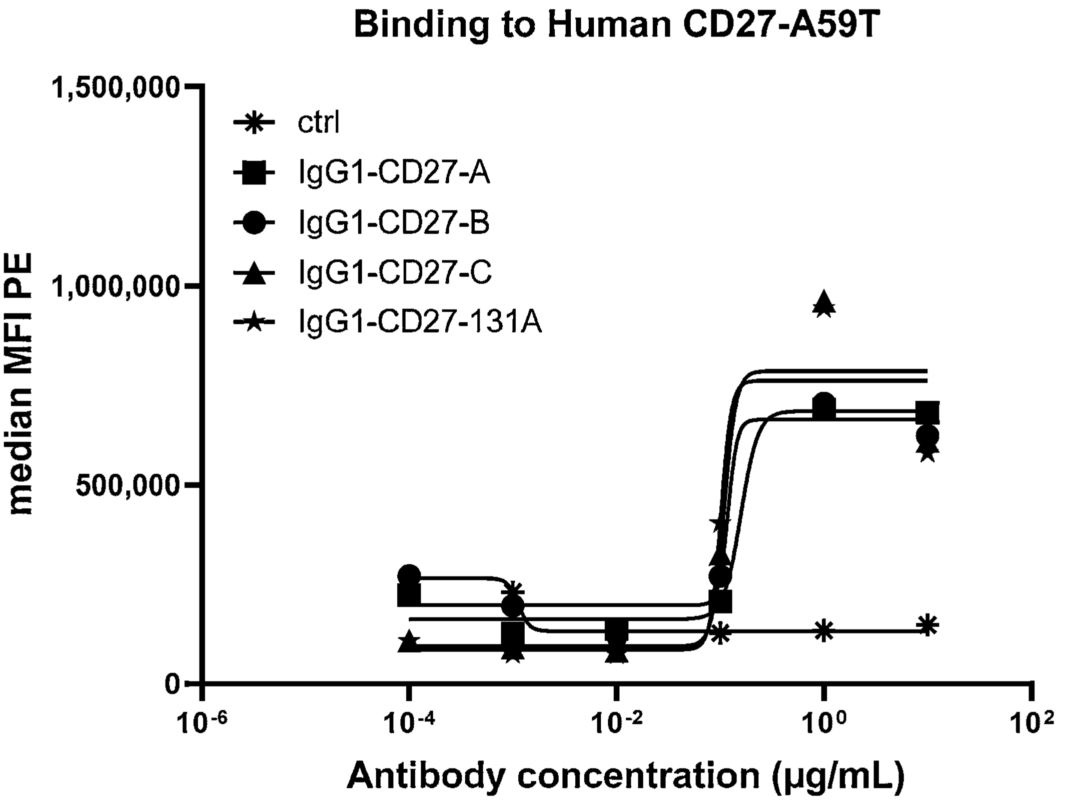

FIG. 3 shows binding of anti-CD27 antibodies IgG1-CD27-A, IgG1-CD27-B, and IgG1-CD27-C to human CD27-A59T variant expressed on HEK293F cells, as determined by flow cytometry. Antibody binding is presented as the median MFI. The anti-HIV-gp120 antibody IgG1-b12-FEAL (ctrl) was included as non-binding negative control antibody.

Figure 4A:
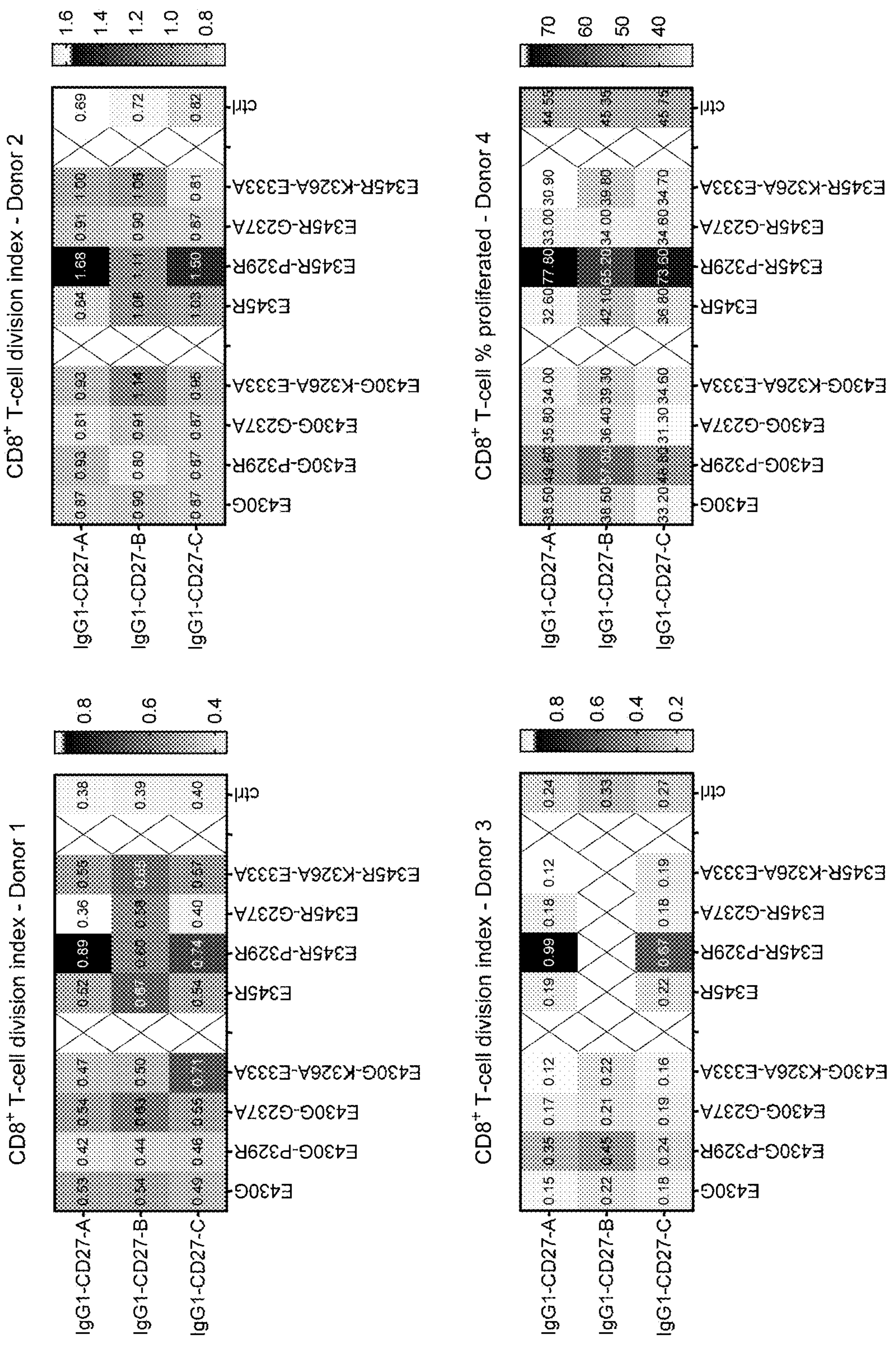
Figure 4B:
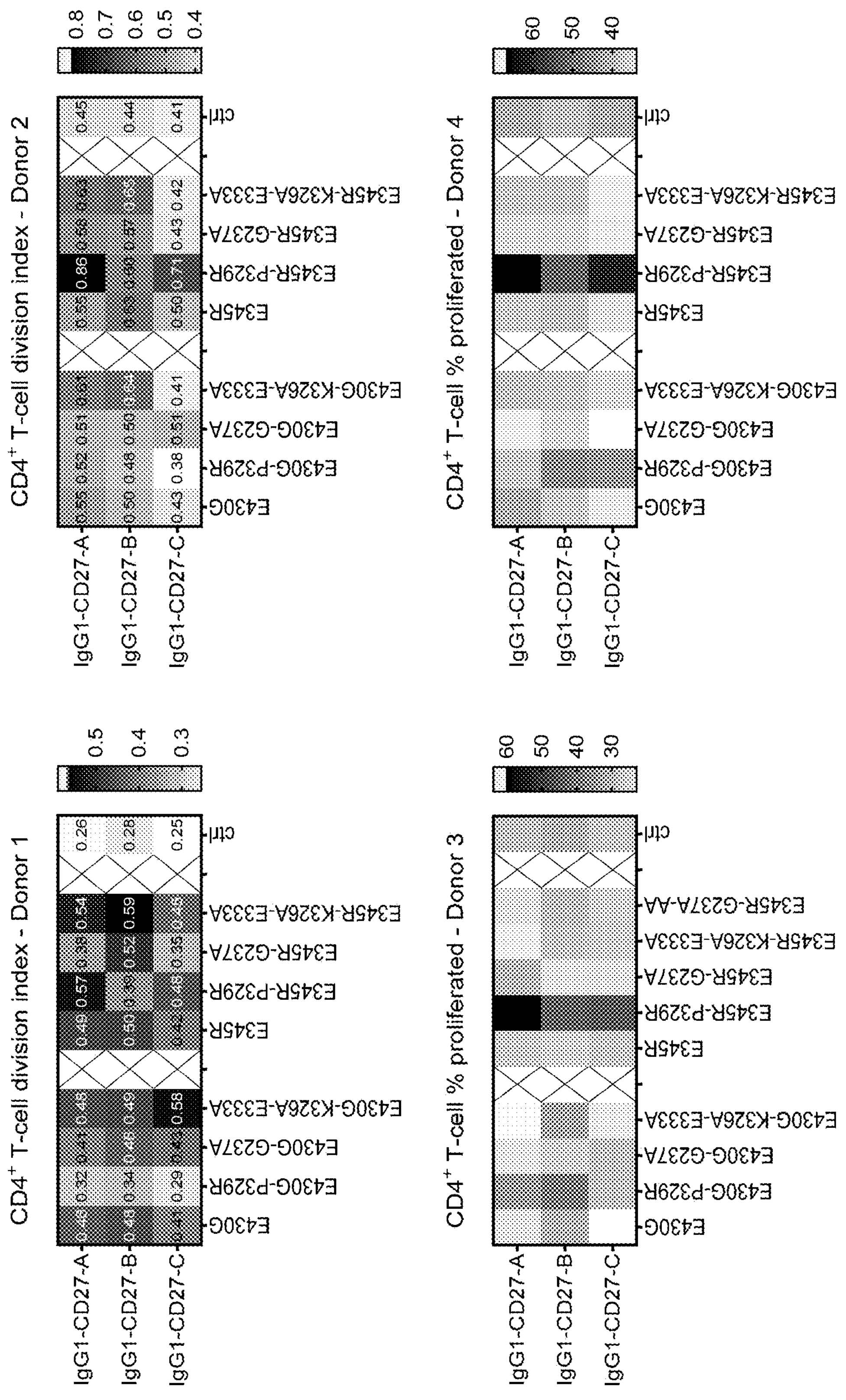

FIG. 4 shows heatmaps of the proliferation of TCR stimulated (A) $CD8^+$ and (B) $CD4^+$ T cells in the presence of 1 μg/mL CD27-specific antibody variants IgG1-CD27-A, -B, or -C harboring the Fc mutations E430R or E345R in combination with the Fc mutations P329R, G237A, or K326A-E33A, as determined by flow cytometry in a CSFE dilution assay. PMBC from four human healthy donors were used as a source of T cells. T-cell proliferation was expressed as the T-cell division index or the percentage of proliferated T cells, that was calculated by gating for the cells that have gone through CFSE dilution ($CFSE^{low\ peaks}$) by using the FlowJo software.

Figure 5:
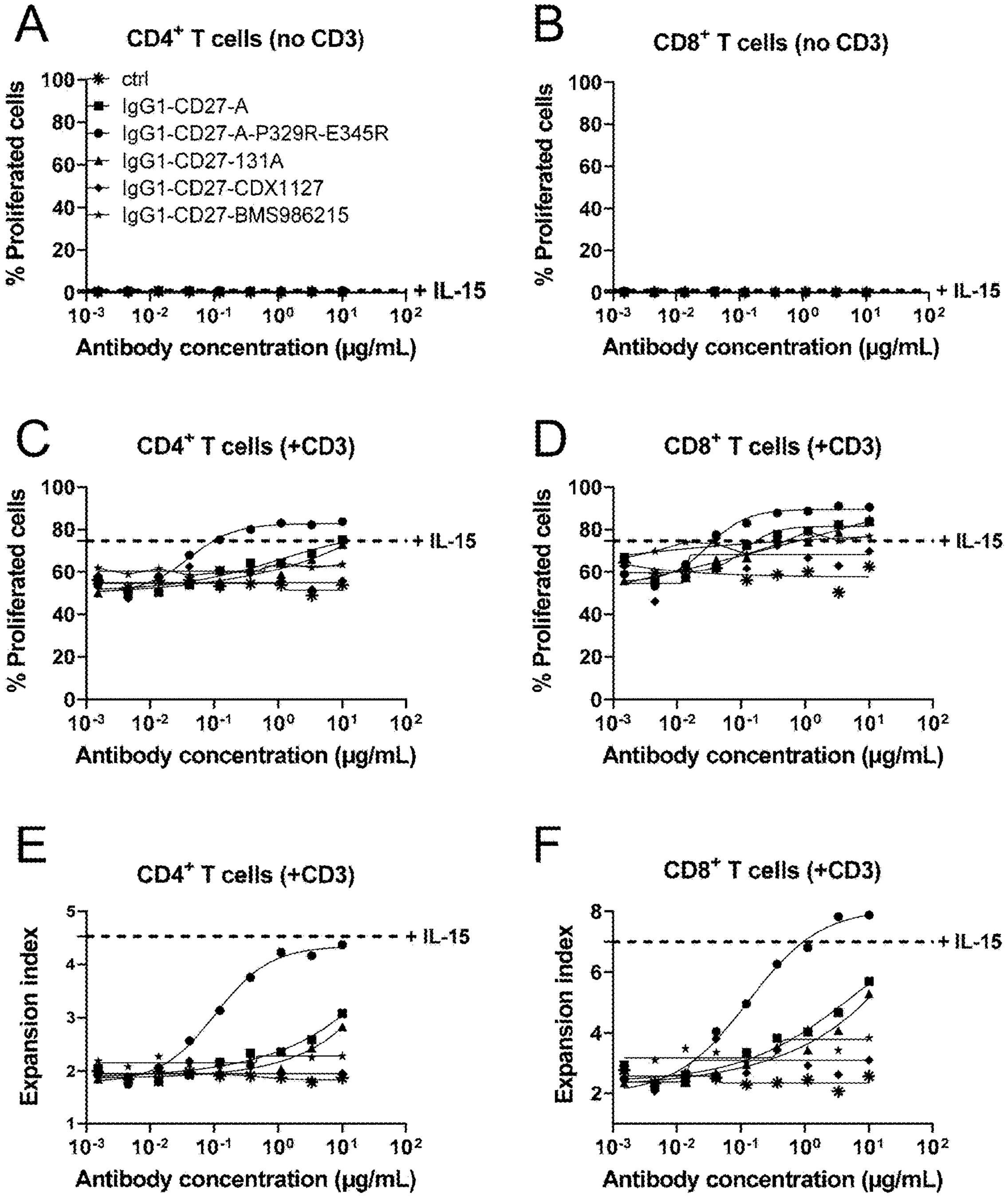

FIG. 5 shows the (A-D) percentage of proliferated T cells, (E, F) the expansion index of (A, B) unstimulated or (C-F) TCR stimulated (A, C, E) $CD4^+$ or (B, D, F) $CD8^+$ T cells after incubation of human healthy donor PBMC with IgG1-CD27-A, IgG1-CD27-A-P329R-E345R or prior art anti-CD27 clones IgG1-CD27-131A, IgG1-CD27-CDX1127, and IgG1-CD27-BMS986215, as determined by flow cytometry. The anti-HIV-gp120 antibody variant IgG1-b12-E345R-P329R (ctrl) was included as non-binding negative control antibody. % Proliferated cells were calculated by gating for the cells that have gone through CFSE dilution ($CFSE^{low\ peaks}$). Expansion index identifies the fold increase of cells in the wells and was calculated using the Proliferation Modeling tool in FlowJo version 10. Manual adjustments to the peaks were made where necessary to define the number of the peaks present more consistently.

Figure 6:
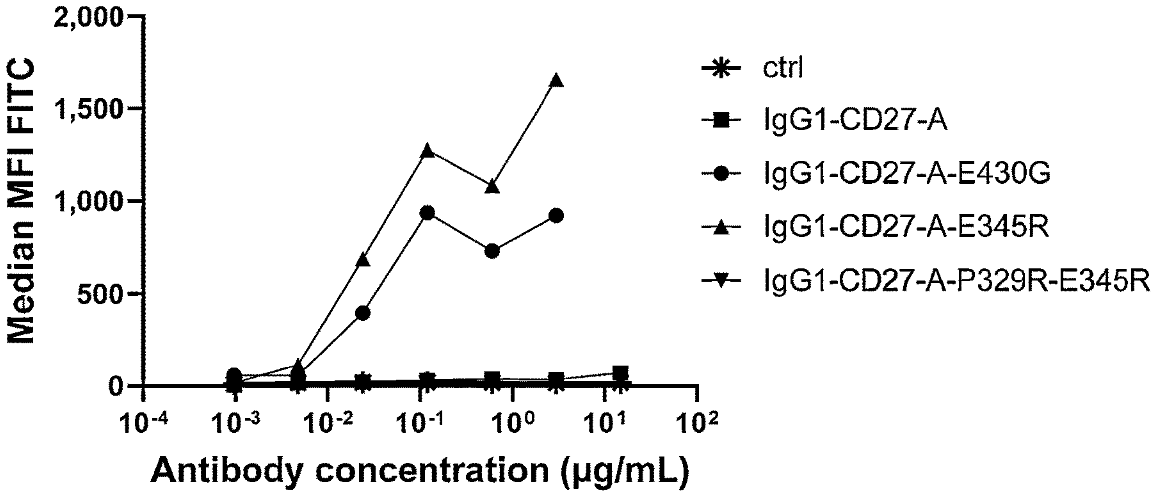

FIG. 6 shows binding of C1q to membrane-bound CD27 antibodies of the invention, as determined by FACS. IgG1-CD27-A variants containing a E430G or E345R hexamerization-enhancing mutation (IgG1-CD27-A-E430G and IgG1-CD27-A-E345R) and the P329R mutation (IgG1-CD27-A-P329R-E345R) were tested for their capacity to bind to C1q. The anti-HIV-gp120 antibody IgG1-b12-F405L (ctrl) was included as non-binding negative control antibody.

Figure 7:
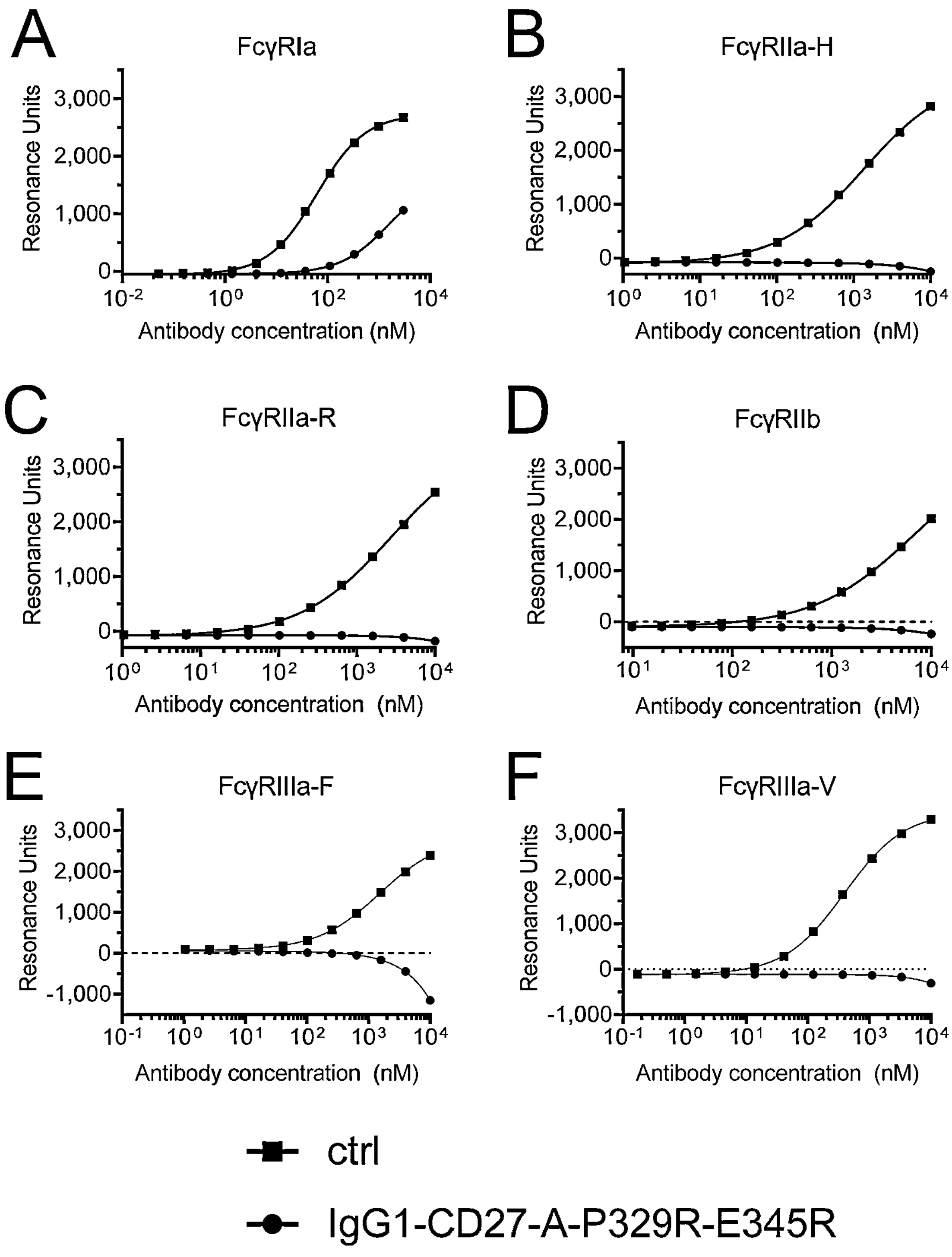

FIG. 7 shows binding of IgG1-CD27-A-P329R-E345R to human Fc receptors as determined by surface plasmon resonance (SPR). Biacore surface chips were covalently linked with anti-His antibody and coated with recombinant His-tagged Fc receptors (A) FcγRIa, (B) FcγRIIa-H, (C) FcγRIIa-R, (D) FcγRIIb, (E) FcγRIIIa-F, or (F) FcγRIIIa-V. The anti-HIV-gp120 antibody IgG1-b12 (ctrl) was included as a reference. Shown are absolute resonance units as determined by Biacore SPR after background subtraction (no Fc receptor flow-cell).

Figure 8:
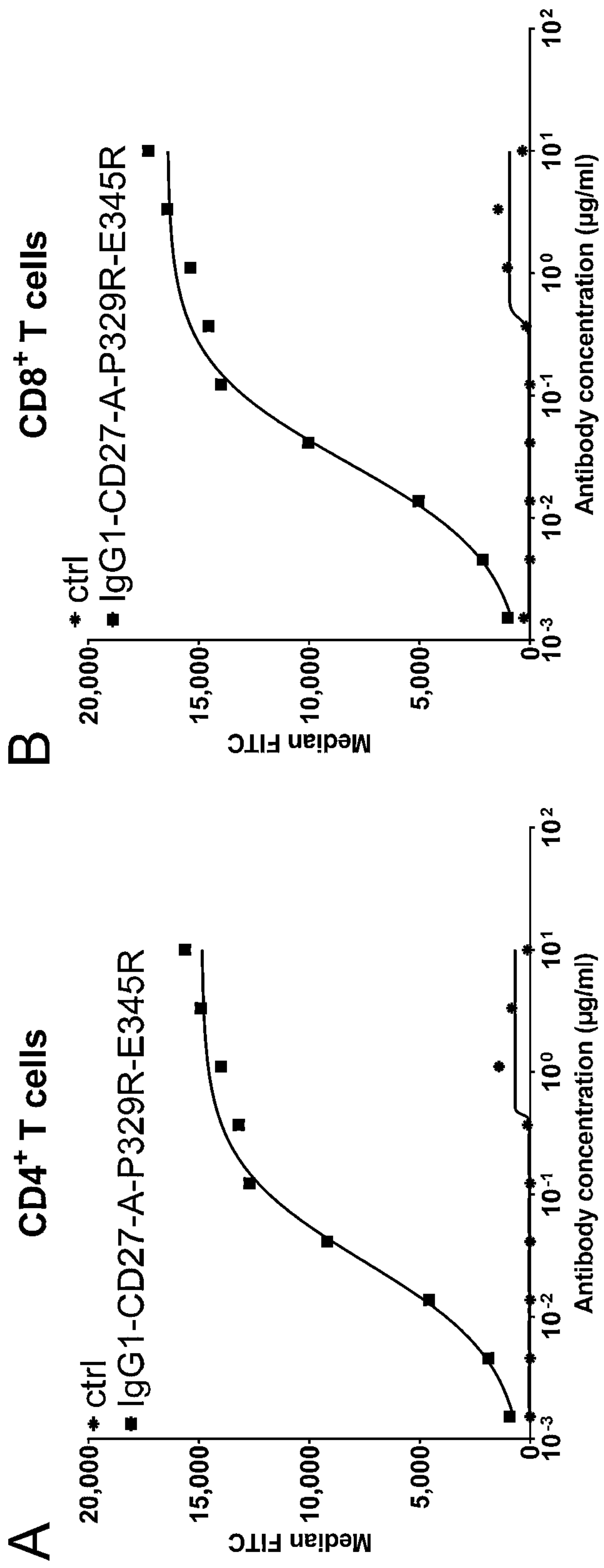

FIG. 8 shows binding of IgG1-CD27-A-P329R-E345R to human (A) $CD4^+$ and (B) $CD8^+$ T-cell subsets in human healthy donor PBMC samples, as determined by flow cytometry. Negative control antibody IgG1-b12-P329R-E345R (ctrl) is an anti-HIV gp120 non-binding isotype control antibody comprising the P329R and E345R mutations. Data presented is the mean MFI+/−SD of duplicate samples.

FIG. 9 shows CD27 agonist activity of anti-CD27 antibodies in presence and absence of FcγR-mediated crosslinking, as determined in a reporter assay. A fixed number of NFκB-luc2/CD27 Jurkat reporter cells was cultured with (A-E) IgG1-CD27-A-P329R-E345R or IgG1-CD27-A, (F-J) IgG1-CD27-131A, IgG1-CD27-CDX1127 or IgG1-CD27-BMS986215, in (A,F) absence or (B-J) presence of FcγRIIb-CHO-K1 cells, at a NFκB-luc2/CD27 Jurkat: FcγRIIb CHO-K1 ratio of (B,G) 1:1, (C,H) 1:1/3, (D,I) 1:1/9, or (E,J) 1:1/27. IgG1-b12-P329R-E345R and IgG1-b12 are anti-HIV gp120 non-binding control antibodies (ctrl). Luminescence was measured as a readout for CD27 activation and presented as relative luminescence units (RLU).

Figure 10:
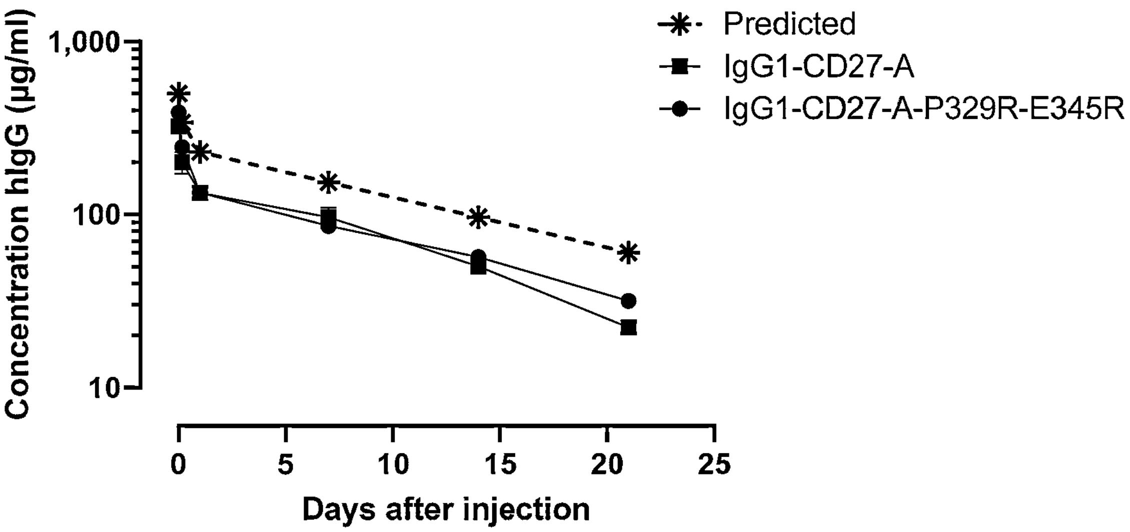

FIG. 10 shows the human IgG levels in plasma ofSCID mice, after intravenous injection of 25 mg/kg IgG-CD27-A or IgG-CD27-A-P329R-E345R antibodies. Total human IgG plasma concentrations were determined by sandwich ELISA and plotted against time after injection. Data shown are mean plasma concentrations+/−SEM of blood samples per group (n=3 mice).

Figure 11:
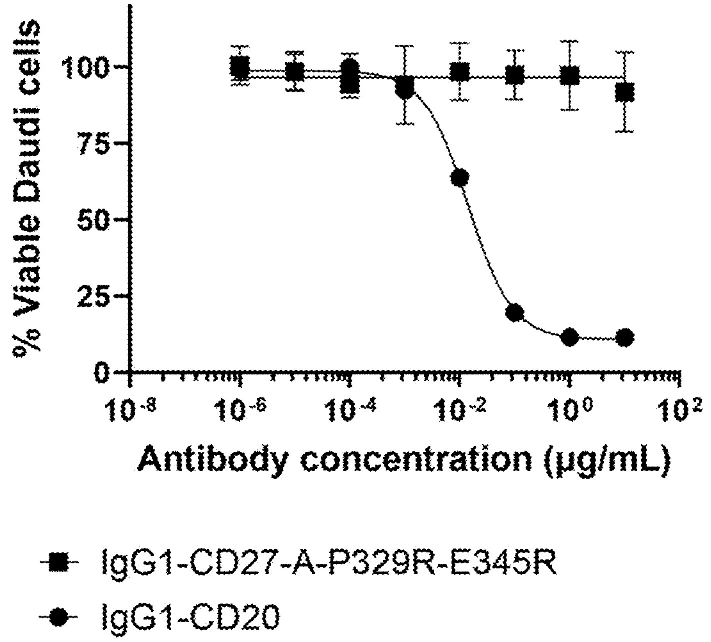

FIG. 11 shows the percentage of viable $CD27^+$ Daudi cells after co-culturing for 4 h with hMDM (E:T=2:1) in the presence of IgG1-CD27-A-P329R-E345R or wild-type CD20 antibody IgG1-CD20. Daudi cells were labeled with CellTrace™ Violet and cell viability was measured by flow cytometry. Data shown are the mean of duplicates±SD percentage of viable Daudi cells (TO-PRO-$3^-$CTV$^+$ CD11b$^-$) normalized to the no antibody controls for one donor out of four tested in two experiments.

Figure 12:
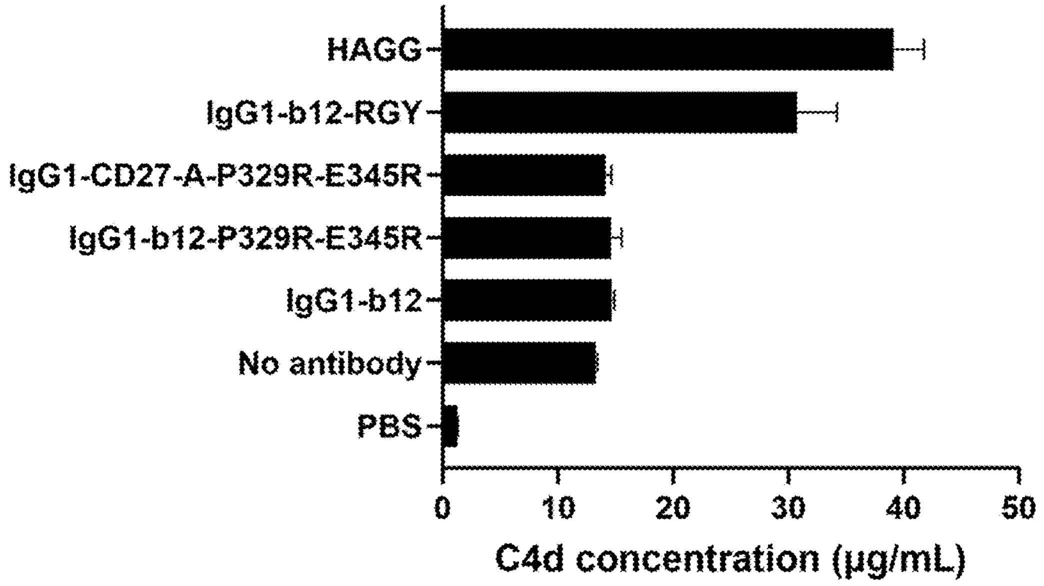

FIG. 12 shows C4d deposition upon incubation of IgG1-CD27-A-P329R-E345R in NHS as determined by ELISA. IgG1-b12-P329R-E345R is an isotype control antibody and IgG1-b12 is a control antibody with a WT Fc domain; IgG1-b12-RGY is a positive control antibody for C4d deposition (hexameric antibody in solution). Shown is mean±SD of triplicates of one representative experiment out of three performed.

Figure 13:
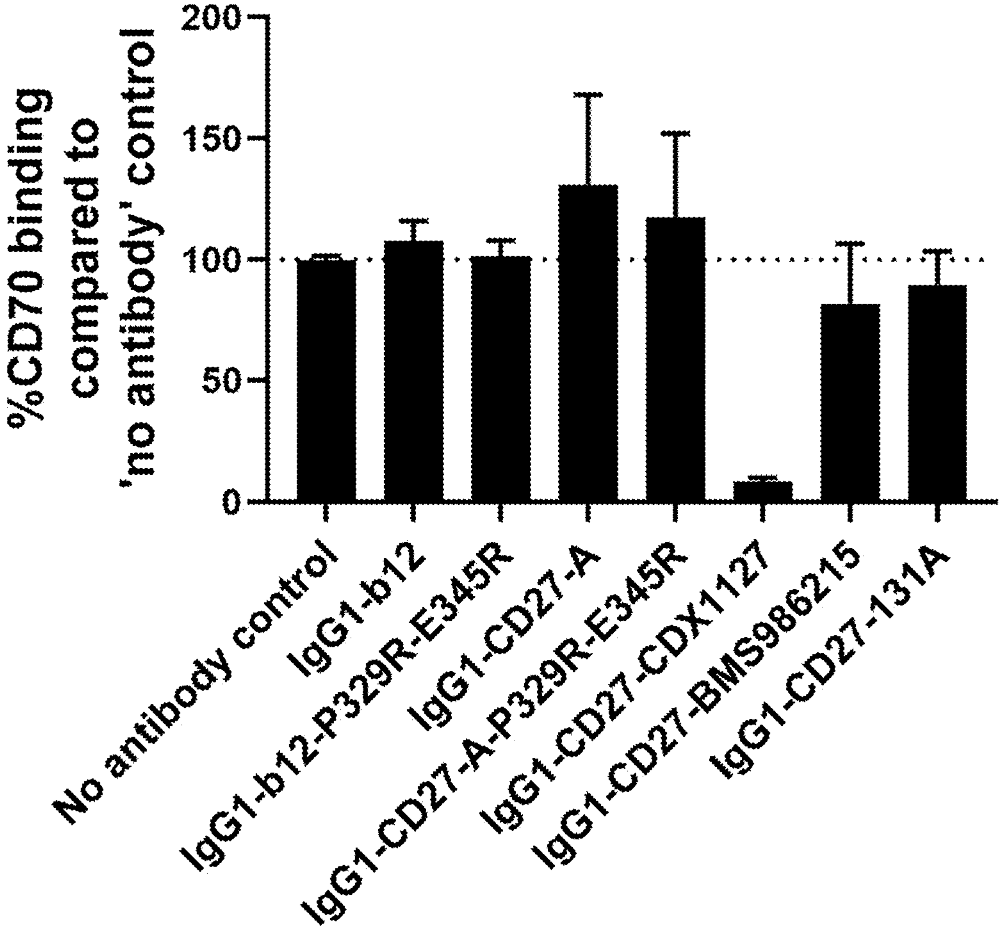

FIG. 13 shows the inhibition of CD70 binding on Daudi cells by anti-CD27 antibodies. $CD27^+$ Daudi cells were incubated with 6 μg/mL biotinylated recombinant human CD70 ECD in the presence or absence of 50 μg/mL of the non-binding control antibodies (IgG1-b12-P329E-E345R or IgG1-b12) or CD27 antibodies (IgG1-CD27-A, IgG1-CD27-A-P329R-E345R, IgG1-CD27-CDX1127, IgG1-CD27-BMS986215, or IgG1-CD27-131A). Binding of the biotinylated CD70 fragment to the Daudi cells was detected by flow cytometry using BV421-labeled streptavidin. Data shown are the gMFI±SD from duplicate wells of one representative experiment out of three performed.

FIG. 14 shows expression levels of T-cell activation markers in polyclonally activated $CD4^+$ and $CD8^+$ T cells upon treatment with anti-CD27 antibodies. Human healthy donor PBMC were incubated with 0.1 μg/mL CD3 antibody and 30 μg/mL of IgG1-CD27-A-P329R-E345R, CD27 antibody benchmarks or non-binding control antibody IgG1-b12-P329R-E345R for two or five days. The expression levels of T-cell activation markers HLA-DR, CD69, GITR, CD25, CD107a, and 4-1BB on the surface of (A) $CD4^+$ and (B) $CD8^+$ T cells in antibody-treated samples were quantified by flow cytometry and presented as mean fold change in MFI (±SD) relative to the nonbinding control sample of the same donor. Dotted lines indicate the fold change for cells treated with IgG1-b12-P329R-E345R, which was used as a nonbinding control and set to 1. Data shown are from three donors tested in duplicate in one experiment.

Figure 15:
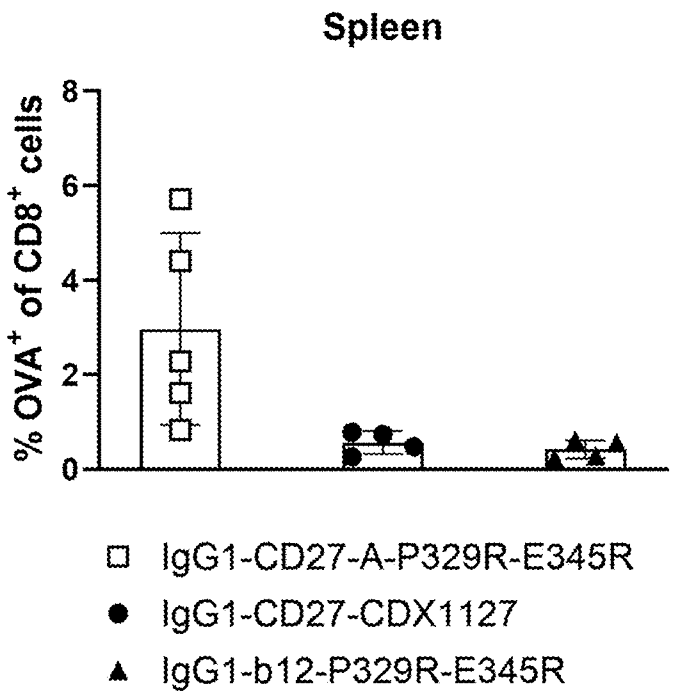

FIG. 15 shows percentages of OVA-specific $CD8^+$ T cells in spleen of hCD27-KI mice after immunization with OVA and treatment with anti-CD27 antibodies. hCD27-KI mice were injected s.c. with 5 mg OVA on days 0, 12 and 21, and simultaneously treated i.v. with 30 mg/kg IgG1-CD27-A-P329R-E345R, IgG1-CD27-CDX1127 or non-binding control antibody IgG1-b12-P329R-E345R. On day 28, mice were euthanized, spleens were resected, and processed as single cell suspensions. Expansion of OVA specific $CD8^+$ T cells was evaluated by flow cytometry. Data shown are the mean of % OVA$^+$ of $CD8^+$ cells±SD per treatment group (5 mice per group) from one experiment performed.

Figure 16:
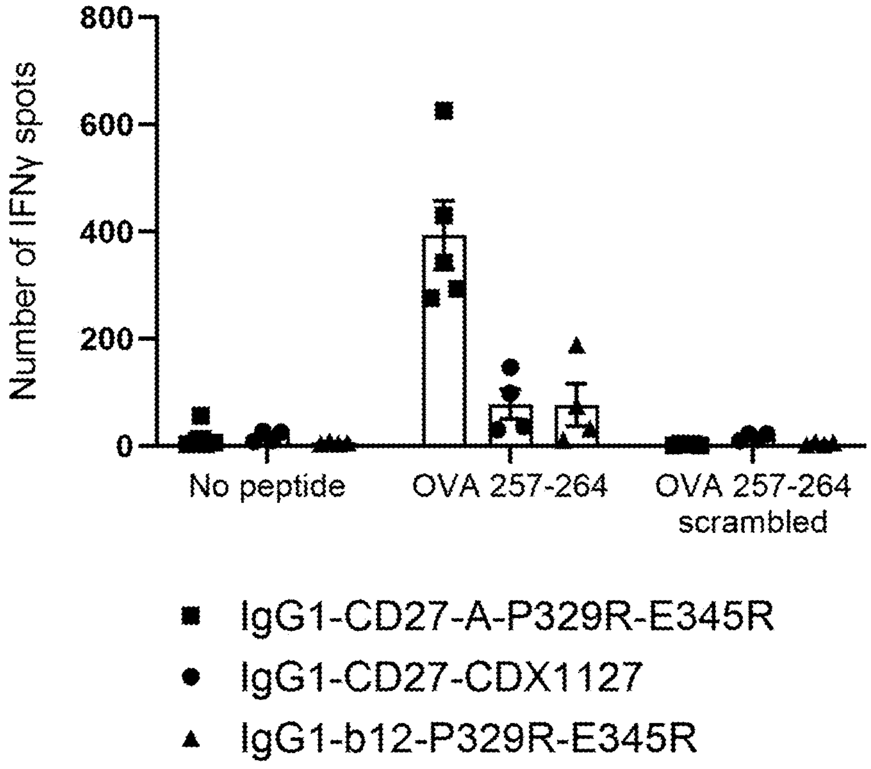

FIG. 16 shows the number of IFNγ-producing splenocytes on day 28 after immunization with OVA and treatment with anti-CD27 antibodies as measured by IFNγ-ELISpot. hCD27-KI mice were injected s.c. with 5 mg OVA on days 0, 12 and 21, and simultaneously treated i.v. with 30 mg/kg IgG1-CD27-A-P329R-E345R, IgG1-CD27-CDX1127, or non-binding control antibody IgG1-b12-P329R-E345R. On day 28, spleens were resected, processed as single cell suspensions and IFNγ-producing splenocytes were detected using IFNγ-ELISpot. Data shown are the mean number of spots per well±SEM of each treatment group from one experiment performed (5 mice per group).

Figure 17:
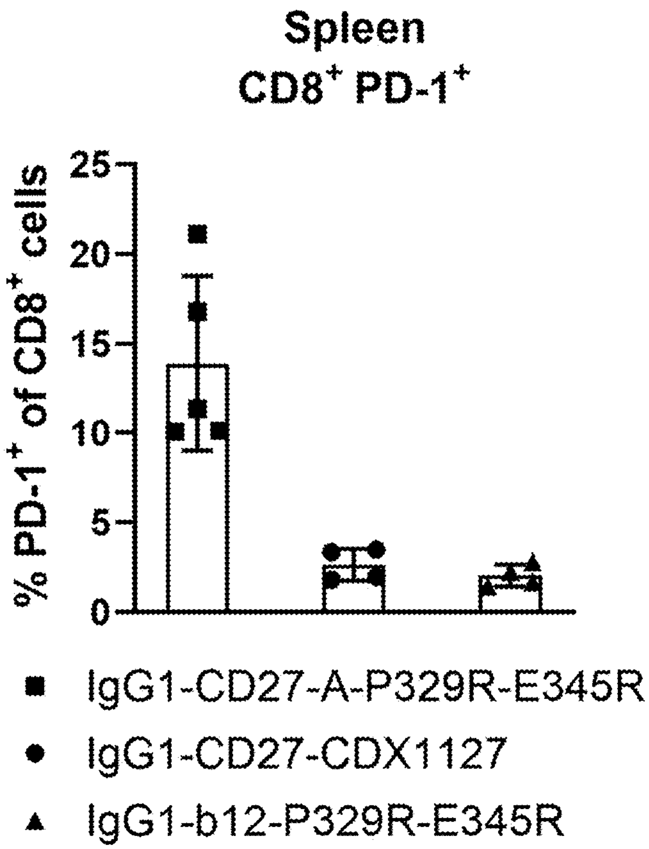

FIG. 17 shows the percentage of activated $CD8^+$ T cells in the spleen of hCD27-KI mice after immunization with OVA and treatment with anti-CD27 antibodies. hCD27-KI mice were injected s.c. with 5 mg OVA on days 0, 12 and 21, and simultaneously treated i.v. with 30 mg/kg IgG1-CD27-A-P329R-E345R, IgG1-CD27-CDX1127, or non-binding control antibody IgG1-b12-P329R-E345R. On day 28, mice were euthanized, spleens were resected, and processed as single cell suspensions. Activation of $CD8^+$ T cells was evaluated in spleen samples by measuring the percentage PD-$1^+$ of $CD8^+$ cells in spleen by flow cytometry. Data shown are the mean±SD per treatment group (5 mice per group) from one experiment performed.

Figure 18:
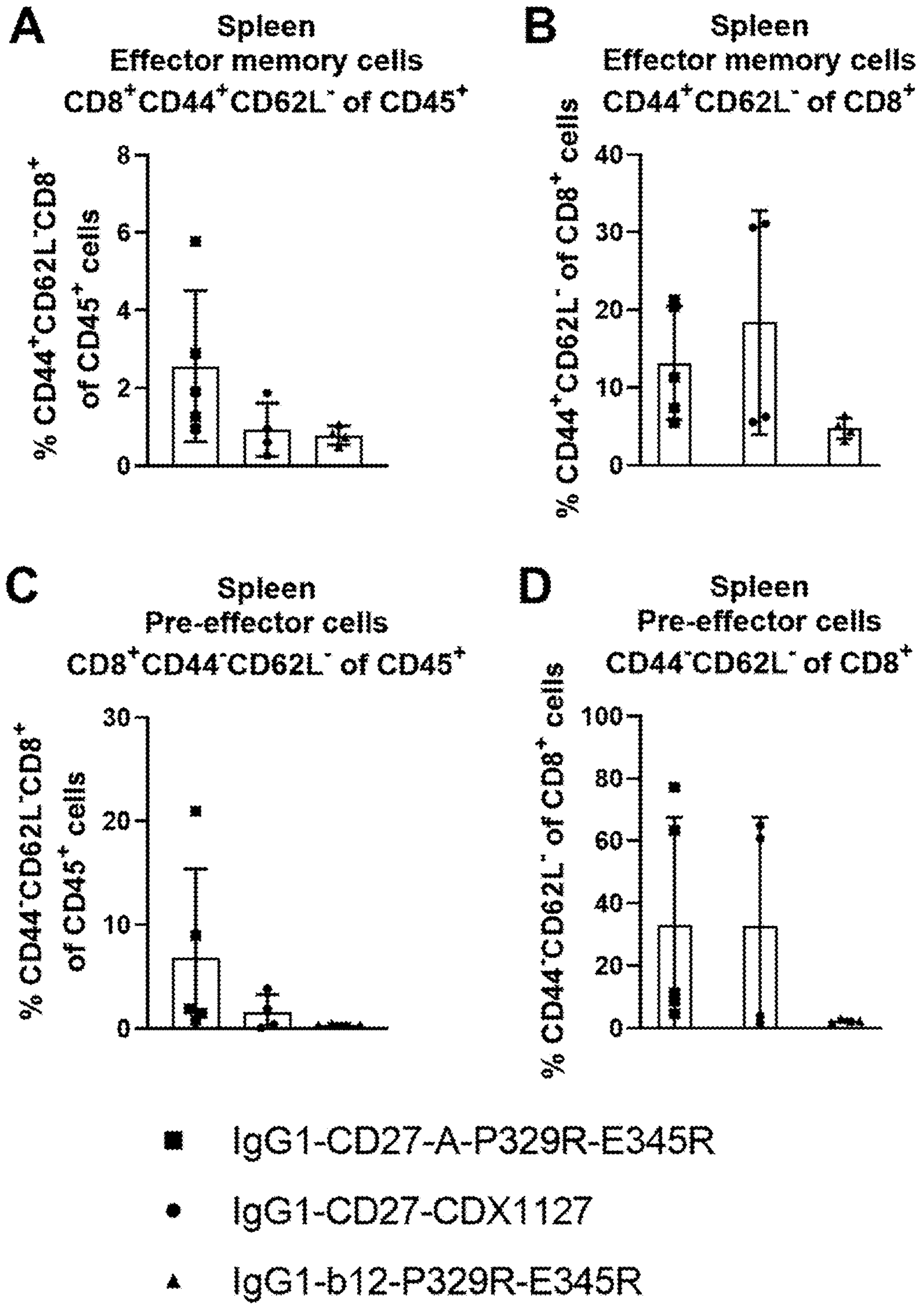

FIG. 18 shows percentages of effector $CD8^+$ T cells in the spleen of hCD27-KI mice after immunization with OVA and treatment with anti-CD27 antibodies. hCD27-KI mice were injected s.c. with 5 mg OVA on days 0, 12 and 21, and simultaneously treated i.v. with 30 mg/kg IgG1-CD27-A-P329R-E345R, IgG1-CD27-CDX1127, or non-binding control antibody IgG1-b12-P329R-E345R. On day 28 mice, were euthanized, spleens were resected, and processed as single cell suspensions. Expansion of memory T cells was evaluated by expression of CD44 and CD62L by flow cytometry. Data shown are the mean±SD per treatment group (5 mice per group) from one experiment performed. (A) Percentage $CD8^+CD44^+CD62L^-$ effector memory of $CD45^+$ cells. (B) Percentage $CD44^+CD62L^-$ effector memory of $CD8^+$ T cells. (C) Percentage $CD8^+CD44^-$ $CD62L^-$ pre-effector of $CD45^+$ cells. (D) Percentage $CD44^-$ $CD62L^-$ pre-effector of $CD8^+$ T cells.

Figure 19:
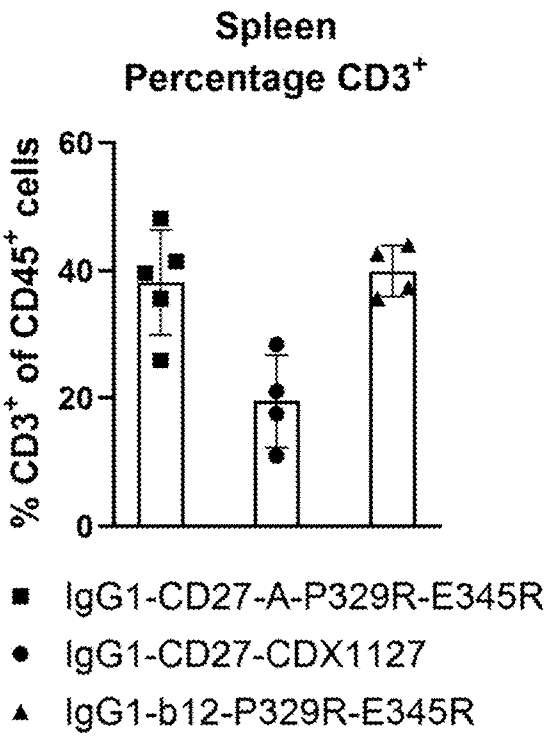

FIG. 19 shows percentage of T cells in the spleen of hCD27-KI mice after immunization with OVA and treatment with anti-CD27 antibodies. hCD27-KI mice were injected s.c. with 5 mg OVA on days 0, 12 and 21, and simultaneously treated i.v. with 30 mg/kg IgG1-CD27-A-P329R-E345R, IgG1-CD27-CDX1127, or non-binding control antibody IgG1-b12-P329R-E345R. On day 28, mice were euthanized, spleens were resected, and processed as single cell suspensions. $CD3^+$ cells in the blood and spleens were evaluated by flow cytometry. Data shown are the mean±SD per treatment group (5 mice per group) from one experiment performed.

Figure 20:
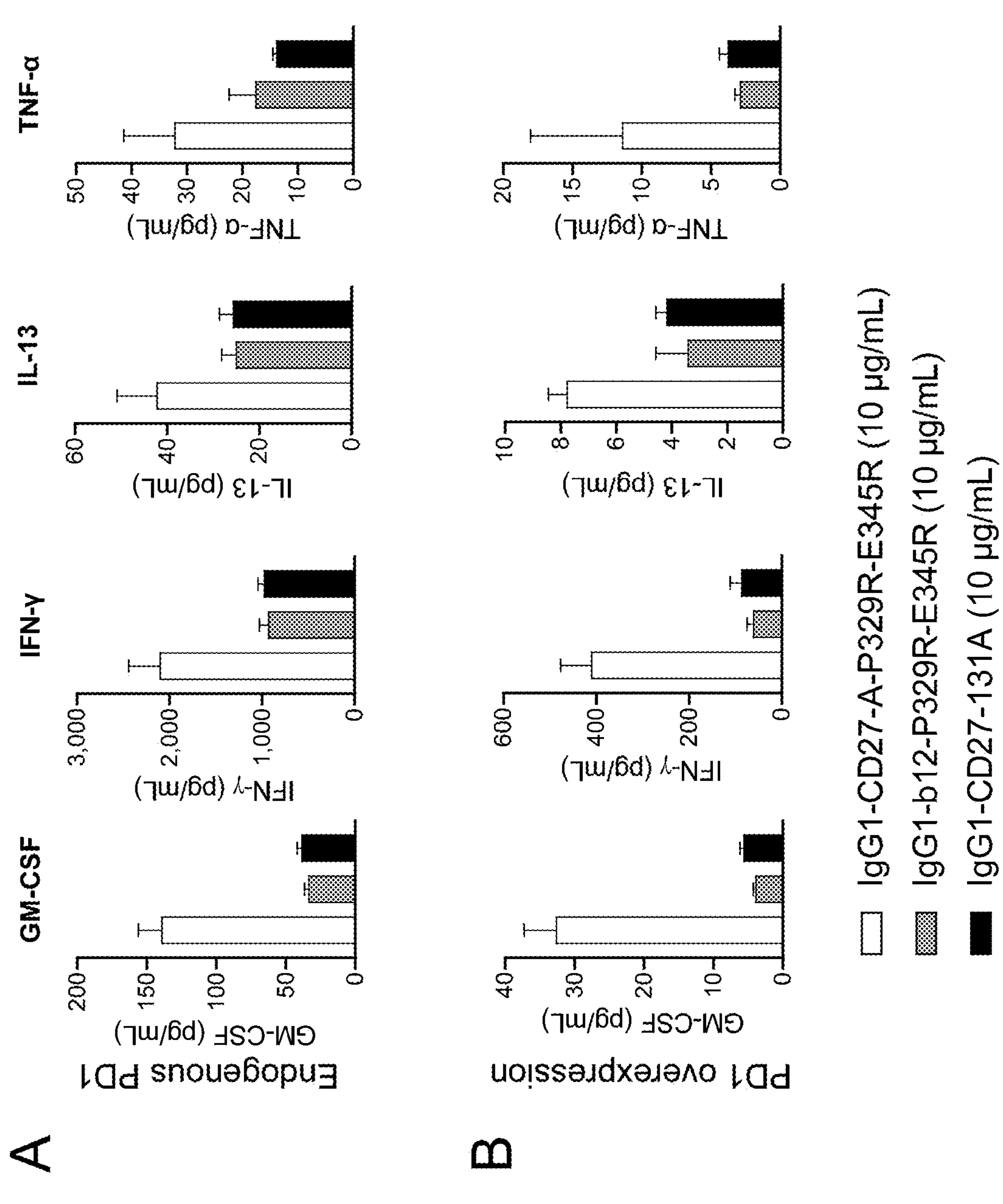

FIG. 20 shows the effect of IgG1-CD27-A-P329R-E345R on T-cell cytokine production in antigen-specific studies. Cocultures of CLDN6-TCR-expressing CD8+ T cells that (A) express endogenous PD-1 or (B) overexpress PD-1 and autologous CLDN6-expressing iDC were incubated with 10 μg/mL IgG1-CD27-A-P329R-E345R, CD27 benchmark antibody IgG1-CD27-131A, or nonbinding control antibody IgG1-b12-P329R-E345R for two days. Cytokine levels in coculture supernatants were analyzed by multiplex ECLIA. Data shown are mean concentrations±SD of triplicate wells from one representative donor out of seven tested in two experiments performed. Abbreviations: CLDN6=claudin 6; ECLIA=electrochemiluminescence assay; iDC=immature dendritic cell; PD-1=programmed cell death protein 1; SD=standard deviation; TCR=T cell receptor.

Figure 21:
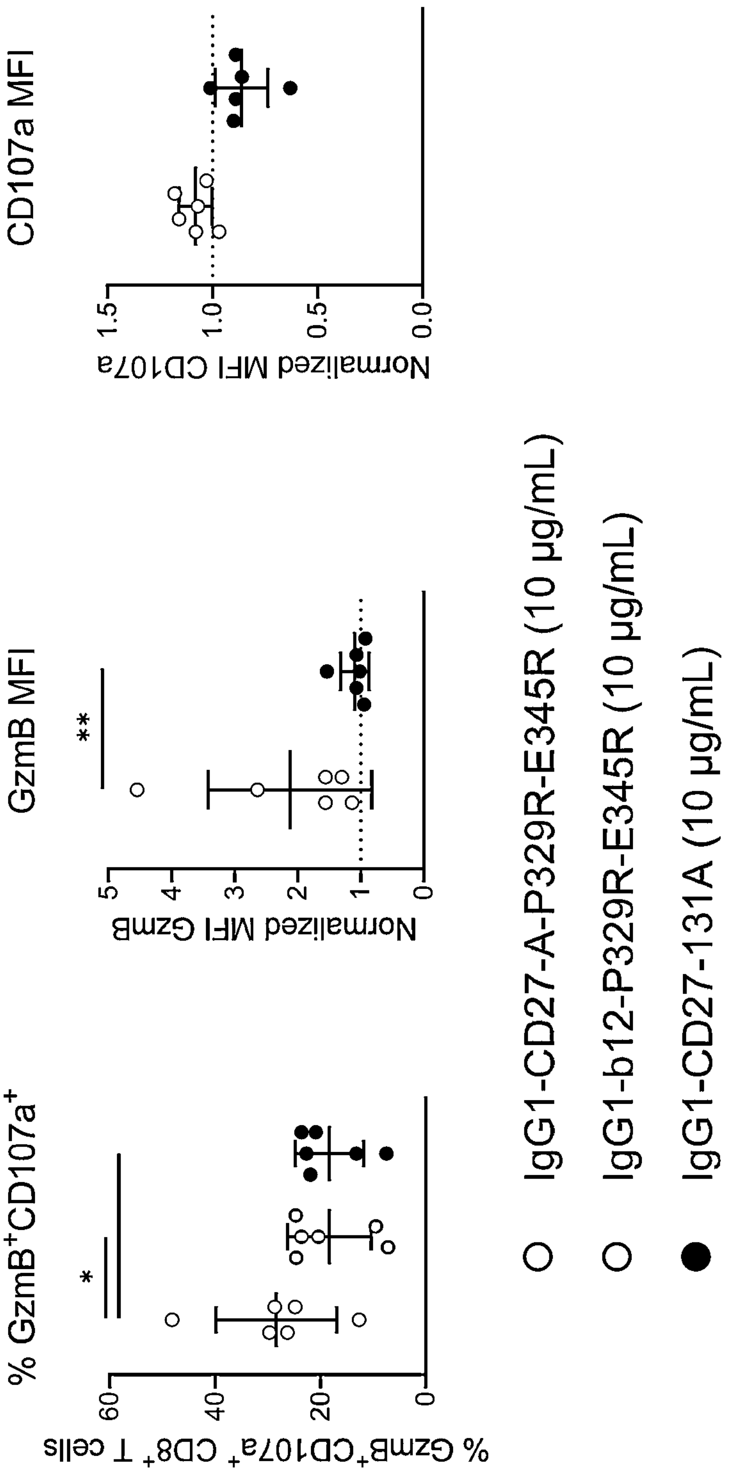

FIG. 21 shows expression of cytotoxicity-associated molecules in antigen-specific CD8+ T cells incubated with IgG1-CD27-A-P329R-E345R. CLDN6-TCR-electroporated CD8+ T cells were cocultured with hCLDN6-MDA-MB-231 cells in the presence of IgG1-CD27-A-P329R-E345R, CD27 benchmark IgG1-CD27-131A, or nonbinding control antibody IgG1-b12-P329R-E345R for two days. Intracellular expression of GzmB and CD107a was determined by flow cytometry. The percentage of CD8+ T cells expressing both GzmB and CD107a, as well as expression levels of GzmB and CD107a (MFI normalized to IgG1-b12-P329R-E345R) in CD8+ T cells is shown. Data shown are mean±SD of six donors tested in single replicate in experiments two experiments. **, P<0.01; *, P<0.05; Friedman-test with Dunn's multiple comparisons test. Abbreviations: CLDN6=claudin 6; GzmB=granzyme B; MFI=mean fluorescence intensity; SD=standard deviation; TCR=T-cell receptor.

Figure 22:
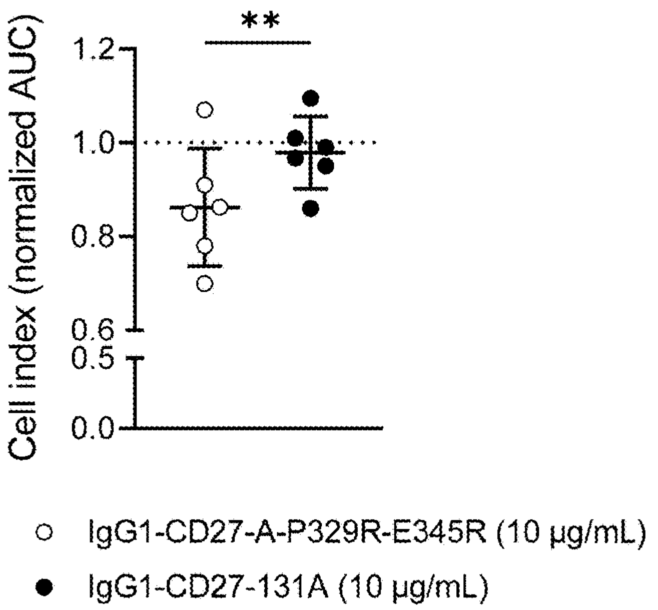

FIG. 22 shows antigen-specific CD8+ T-cell mediated tumor cell kill in the presence of IgG1-CD27-A-P329R-E345R. CD8+ T-cell mediated kill of hCLDN6-MDA-MB-231 cells was evaluated by real-time cell analysis. CLDN6 TCR electroporated CD8+ T cells were cocultured with hCLDN6-MDA-MB-231 cells in the presence of IgG1-CD27-A-P329R-E345R, CD27 benchmark IgG1-CD27-131A, or nonbinding control antibody IgG1-b12-P329R-E345R for five days. Cell index values were derived from impedance measurements conducted at two-hour intervals. AUC were obtained from cell index data over five days of coculture. The AUC of each treatment condition was normalized to IgG1-b12-P329R-E345R-treated cultures from the same donor. Data shown are mean±SD from six donors tested in duplicate in experiments in two experiments. **, P<0.01; Friedman-test with Dunn's multiple comparisons test. Abbreviations: AUC=area under the curve; CLDN6=claudin 6; SD=standard deviation; TCR=T-cell receptor.

Figure 23:
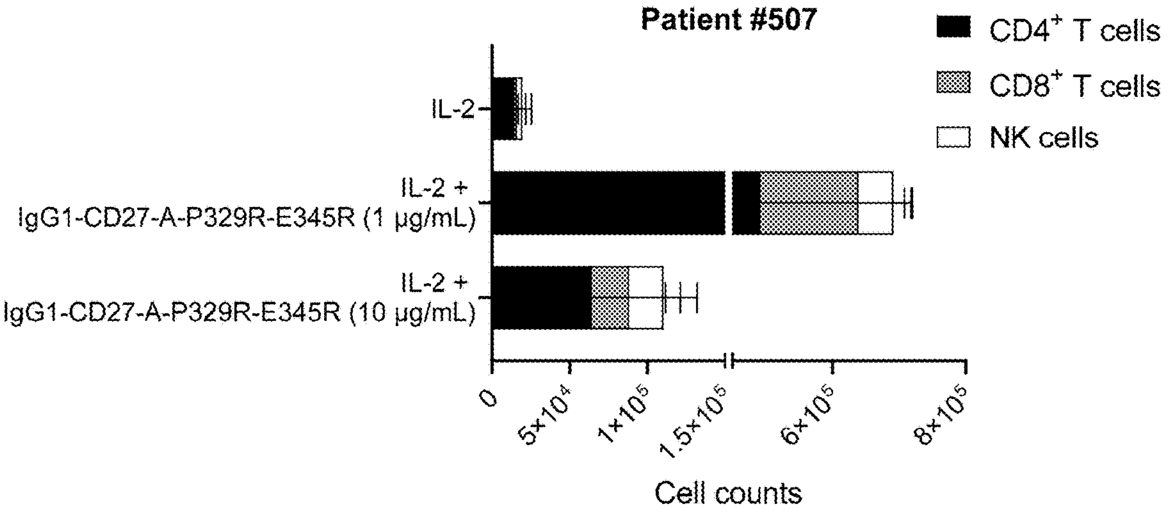

FIG. 23 shows absolute cell numbers of CD4+ and CD8+ T cells and NK cells in primary tumor cultures after treatment with IgG1-CD27-A-P329R-E345R. Human NSCLC tumor tissues were cultured with low-dose IL-2 (45 to 50 U/mL) in the presence or absence of 10 μg/mL IgG1-CD27-A-P329R-E345R. Absolute cell counts of the TIL subsets were determined by flow cytometry after 14 days of treatment. Data shown are average±SD of four replicate wells from one out of five tumor tissues tested in one experiment out of four performed. Abbreviations: IL=interleukin; NK=natural killer; NSCLC=non-small cell lung cancer; SD=standard deviation; U/mL=units per mL.

Figure 24:
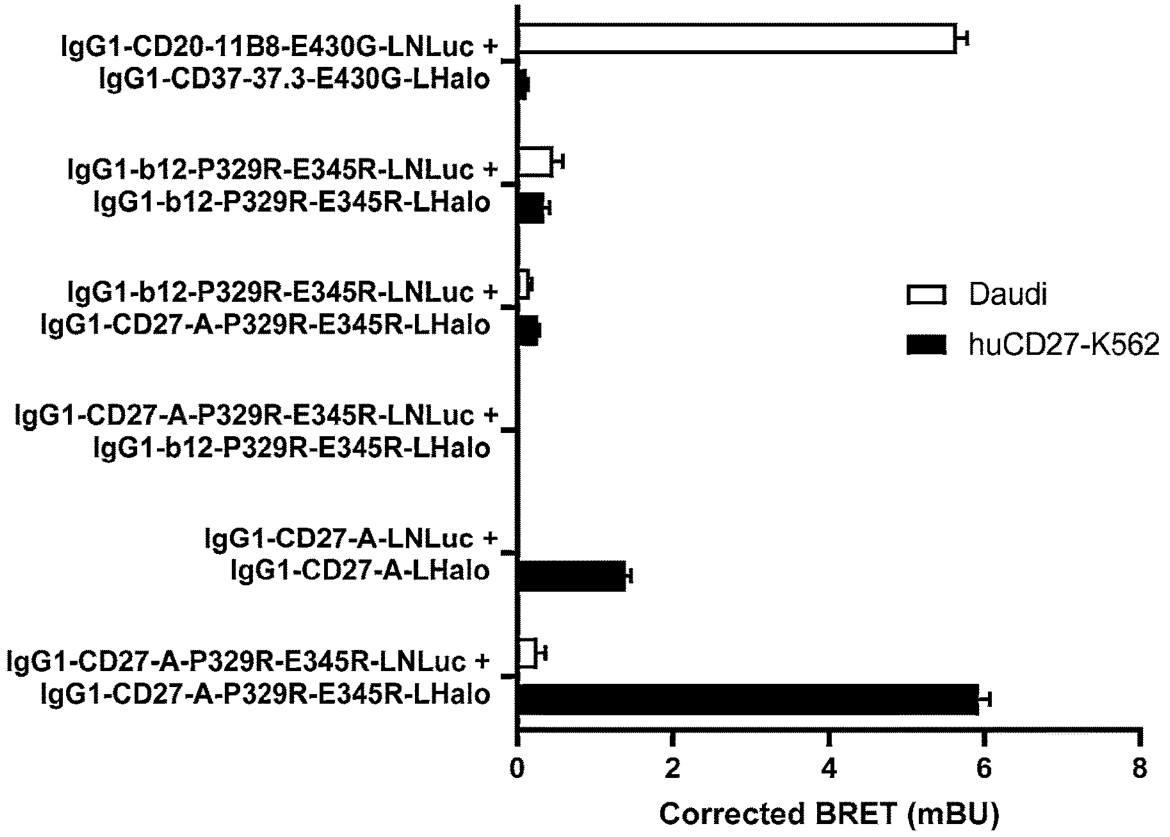

FIG. 24 shows molecular proximity determined by bioluminescence resonance energy transfer (BRET) analysis between IgG1-CD27-A-P329R-E345R antibodies on the cell surface of Daudi and huCD27-K562 cells. Cells were incubated with mixtures of NanoLuc- (donor) and HaloTag- (acceptor) tagged antibodies (5 μg/mL each): IgG1-CD27-A-P329R-E345R, WT IgG1-CD27-A or nonbinding control IgG1-b12-P329R-E345R as indicated. The antibody pair IgG1-CD20-11B8-E430G-LNLuc and IgG1-CD37-37.3-E430G-LHalo was used as positive control. BRET was calculated in milliBRET units (mBU)=(618 $nm_{em}$/460 $nm_{em}$)×1000, and corrected for donor bleed-through by subtracting no-ligand control values. Data shown are the corrected BRET from duplicate wells of one representative experiment out of three performed.

Figure 25:
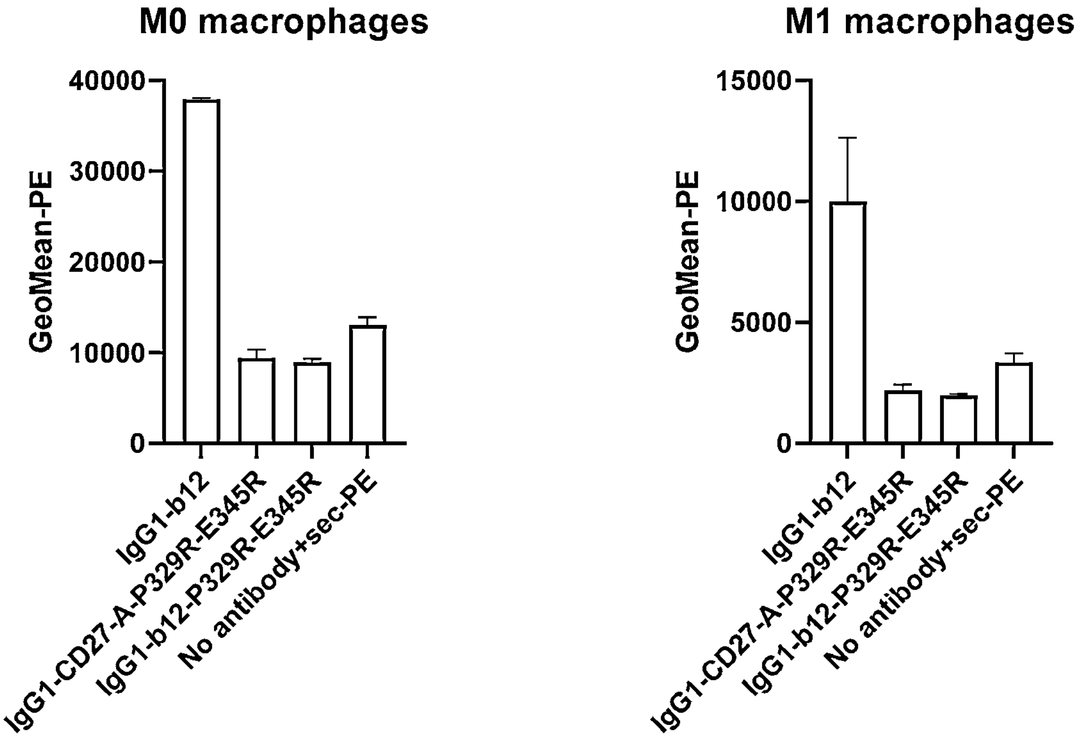

FIG. 25 shows binding of IgG1-CD27-A-P329R-E345R to M0 and M1 macrophages compared to a WT IgG1 antibody (IgG1-b12) with an irrelevant antigen-binding region as a positive control for FcγRIa binding, and a variant of the same antibody carrying the P329R and E345R mutations (IgG1-b12-P329R-E345R). Binding of the antibodies to the macrophages was detected by flow cytometry using PE-labeled goat anti-human secondary antibody. Data shown are mean+SD of two donors tested.

DETAILED DESCRIPTION OF THE INVENTION

Definitions

The term "antibody" (Ab) in the context of the present invention refers to an immunoglobulin molecule, a fragment of an immunoglobulin molecule, or a derivative of either thereof, which has the ability to specifically bind to an antigen. The antibody of the present invention comprises an Fc-domain of an immunoglobulin and an antigen-binding region. An antibody generally contains two CH2-CH3 regions and a connecting region, e.g., a hinge region, e.g. at least an Fc-domain. Thus, the antibody of the present invention may comprise an Fc region and an antigen-binding region. The variable regions of the heavy and light chains of the immunoglobulin molecule contain a binding domain that interacts with an antigen. The constant or "Fc" regions of the antibodies may mediate the binding of the immunoglobulin to host tissues or factors, including various cells of the immune system (such as effector cells) and components of the complement system such as C1q, the first component in the classical pathway of complement activation. As used herein, unless contradicted by context, the Fc region of an immunoglobulin typically contains at least a CH2 domain and a CH3 domain of an immunoglobulin CH, and may comprise a connecting region, e.g., a hinge region. An Fc-region is typically in dimerized form via, e.g., disulfide bridges connecting the two hinge regions and/or non-covalent interactions between the two CH3 regions. The dimer may be a homodimer (where the two Fc region monomer amino acid sequences are identical) or a heterodimer (where the two Fc region monomer amino acid sequences differ in one or more amino acids). An Fc region-fragment of a full-length antibody can, for example, be generated by digestion of the full-length antibody with papain, as is well-known in the art. An antibody as defined herein may, in addition to an Fc region and an antigen-binding region, further comprise one or both of an immunoglobulin CH1 region and a CL region. An antibody may also be a multispecific antibody, such as a bispecific antibody or similar molecule. The term "bispecific antibody" refers to an antibody having specificities for at least two different, typically non-overlapping, epitopes. Such epitopes may be on the same or different targets. If the epitopes are on different targets, such targets may be on the same cell or different cells or cell types. As indicated above, unless otherwise stated or clearly contradicted by the context, the term antibody herein includes fragments of an antibody which comprise at least a portion of an Fc-region and which retain the ability to specifically bind to the antigen. Such fragments may be provided by any known technique, such as enzymatic cleavage, peptide synthesis and recombinant expression techniques. It has been shown that the antigen-binding function of an antibody may be performed by fragments of a full-length antibody. Examples of binding fragments encompassed within the term "Ab" or "antibody" include, without limitation, monovalent antibodies (described in WO2007059782 by Genmab); heavy-chain antibodies, consisting only of two heavy chains and naturally occurring in e.g. camelids (e.g., Hamers-Casterman (1993) Nature 363: 446); ThioMabs, Roche, WO2011069104); strand-exchange engineered domain (SEED or Seed-body) which are asymmetric and bispecific antibody-like molecules (Merck, WO2007110205); Triomab (Pharma/Fresenius Biotech, Lindhofer et al. 1995 J Immunol 155:219; WO2002020039); FcAAdp (Regeneron, WO2010151792); Azymetric Scaffold (Zymeworks/Merck, WO2012/058768); mAb-Fv (Xencor, WO2011/028952); Xmab (Xencor); Dual variable domain immunoglobulin (Abbott, DVD-Ig, U.S. Pat. No. 7,612, 181); Dual domain double head antibodies (Unilever; Sanofi Aventis, WO20100226923); Di-diabody (ImClone/Eli Lilly); Knobs-into-holes antibody formats (Genentech, WO9850431); DuoBody (Genmab, WO 2011/131746); Bispecific IgG1 and IgG2 (Pfizer/Rinat, WO11143545); DuetMab (Medimmune, US2014/0348839); Electrostatic steering antibody formats (Amgen, EP1870459 and WO 2009089004; Chugai, US201000155133; Oncomed, WO2010129304A2); bispecific IgG1 and IgG2 (Rinat neurosciences Corporation, WO11143545); CrossMAbs (Roche, WO2011117329); LUZ-Y (Genentech); Biclonic (Merus, WO2013157953); Dual Targeting domain antibodies (GSK/Domantis); Two-in-one Antibodies or Dual action Fabs recognizing two targets (Genentech, Novimmune, Adimab); Cross-linked Mabs (Karmanos Cancer Center); covalently fused mAbs (AIMM); CovX-body (CovX/Pfizer); FynomAbs (Covagen/Janssen ilag); DutaMab (Dutalys/Roche); iMab (Medimmune); IgG-like Bispecific (ImClone/Eli Lilly, Shen, J., et al. J Immunol Methods, 2007. 318(1-2): p. 65-74); TIG-body, DIG-body and PIG-body (Pharmabcine); Dual-affinity retargeting molecules (Fc-DART or Ig-DART, Macrogenics, WO/2008/157379, WO/2010/080538); BEAT (Glenmark); Zybodies (Zyngenia); approaches with common light chain (Crucell/Merus, U.S. Pat. No. 7,262,028) or common heavy chains (KABodies by NovImmune, WO2012023053), as well as fusion proteins comprising a polypeptide sequence fused to an antibody fragment containing an Fc-region like scFv-fusions, like BsAb by ZymoGenetics/BMS, HERCULES by Biogen Idec (U.S. Pat. No. 7,951,918); SCORPIONS (Emergent BioSolutions/Trubion and Zymogenetics/BMS); Ts2Ab (MedImmune/AZ (Dimasi, N., et al. J Mol Biol, 2009. 393(3): p. 672-92); scFv fusion (Genentech/Roche); scFv fusion (Novartis); scFv fusion (Immunomedics); scFv fusion (Changzhou Adam Biotech Inc, CN 102250246); TvAb (Roche, WO 2012025525, WO 2012025530); mAb2 (f-Star, WO2008/003116); and dual scFv-fusion. It should be understood that the term antibody, unless otherwise specified, includes monoclonal antibodies (such as human monoclonal antibodies), polyclonal antibodies, chimeric antibodies, humanized antibodies, monospecific antibodies (such as bivalent monospecific antibodies), bispecific antibodies, antibodies of any isotype and/or allotype; antibody mixtures (recombinant polyclonals) for instance generated by technologies exploited by Symphogen and Merus (Oligoclonics), multimeric Fc proteins as described in WO2015/158867, and fusion proteins as described in WO2014/031646. While these different antibody fragments and formats are generally included within the meaning of antibody, they collectively and each independently are unique features of the present invention, exhibiting different biological properties and utility.

An "agonistic antibody" for a natural receptor is a compound which binds the receptor to form a receptor-antibody complex and which activates said receptor, thereby initiating a pathway signaling and further biological process.

The term "agonism" and "agonistic" are used interchangeably herein and refer to or describe an antibody which is capable of, directly or indirectly, substantially inducing, promoting, or enhancing CD27 biological activity or activation. Optionally, an "agonistic CD27 antibody" is an antibody which is capable of activating CD27 receptor by a similar mechanism as the ligand for CD27, known as CD70 (Tumor Necrosis Factor Superfamily member 7, TNFSF7; CD27 ligand, CD27L), which results in an activation of one or more intracellular signaling pathway which may include activation of NF-KB and MAPK8/JNK pathways. "Agonism" as defined herein may be determined according to Example 2 herein.

A "CD27 antibody" or "anti-CD27 antibody" as described herein is an antibody which binds specifically to the protein CD27, in particular to human CD27.

A "variant" as used herein refers to a protein or polypeptide sequence which differs in one or more amino acid residues from a parent or reference sequence. A variant may, for example, have a sequence identity of at least 80%, such as 90%, or 95%, or 97%, or 98%, or 99%, to a parent or reference sequence. Also, or alternatively, a variant may differ from the parent or reference sequence by 12 or less, such as 11, 10, 9, 8, 7, 6, 5, 4, 3, 2 or 1 mutation(s) such as substitutions, insertions, or deletions of amino acid residues. Accordingly, a "variant antibody" or an "antibody variant", used interchangeably herein, refers to an antibody that differs in one or more amino acid residues as compared to a parent or reference antibody, e.g., in the antigen-binding region, Fc-region or both. Likewise, a "variant Fc region" or "Fc region variant" refers to an Fc region that differs in one or more amino acid residues as compared to a parent or reference Fc region, optionally differing from the parent or reference Fc region amino acid sequence by 12 or less, such as 11, 10, 9, 8, 7, 6, 5, 4, 3, 2 or 1 mutation(s) such as substitutions, insertions, or deletions of amino acid residues. The parent or reference Fc region is typically the Fc region of a human wild-type antibody which, depending on the context, may be a particular isotype. A variant Fc region may, in dimerized form, be a homodimer or heterodimer, e.g., where one of the amino acid sequences of the dimerized Fc region comprises a mutation while the other is identical to a parent or reference wild-type amino acid sequence. Examples of wild-type (typically a parent or reference sequence) IgG CH and variant IgG constant region amino acid sequences, which comprise Fc region amino acid sequences, are set out in Table 3.

The term "immunoglobulin heavy chain" or "heavy chain of an immunoglobulin" as used herein is intended to refer to one of the heavy chains of an immunoglobulin. A heavy chain is typically comprised of a heavy chain variable region (abbreviated herein as VH) and a heavy chain constant region (abbreviated herein as CH) which defines the isotype of the immunoglobulin. The heavy chain constant region typically is comprised of three domains, CH1, CH2, and CH3. The term "immunoglobulin" as used herein is intended to refer to a class of structurally related glycoproteins consisting of two pairs of polypeptide chains, one pair of light (L) low molecular weight chains and one pair of heavy (H) chains, all four potentially inter-connected by disulfide bonds. The structure of immunoglobulins has been well characterized (see for instance Fundamental Immunology Ch. 7 Paul, W., 2nd ed. Raven Press, N.Y. 1989). Within the structure of the immunoglobulin, the two heavy chains are inter-connected via disulfide bonds in the so-called "hinge region". Equally to the heavy chains, each light chain is typically comprised of several regions; a light chain variable region (abbreviated herein as VL) and a light chain constant region. The light chain constant region typically is comprised of one domain, CL. Furthermore, the VH and VL regions may be further subdivided into regions of hypervariability (or hypervariable regions which may be hypervariable in sequence and/or form of structurally defined loops), also termed complementarity determining regions (CDRs), interspersed with regions that are more conserved, termed framework regions (FRs). Each VH and VL is typically composed of three CDRs and four FRs, arranged from amino-terminus to carboxy-terminus in the following order: FR1, CDR1, FR2, CDR2, FR3, CDR3, FR4. CDR sequences herein are defined according to IMGT (see Lefranc M P. et al., Nucleic Acids Research, 27, 209-212, 1999] and Brochet X. Nucl. Acids Res. 36, W503-508 (2008)).

When used herein, the terms "half molecule", "Fab-arm" and "arm" refer to one heavy chain-light chain pair. When a bispecific antibody is described to comprise a half-molecule antibody "derived from" a first antibody, and a half-molecule antibody "derived from" a second antibody, the term "derived from" indicates that the bispecific antibody was generated by recombining, by any known method, said half-molecules from each of said first and second antibodies into the resulting bispecific antibody. In this context, "recombining" is not intended to be limited by any particular method of recombining and thus includes all of the methods for producing bispecific antibodies described herein below, including for example recombining by "half-molecule exchange" also described in the art as "Fab-arm exchange" and the DuoBody® method, as well as recombining at nucleic acid level and/or through co-expression of two half-molecules in the same cells.

The term "antigen-binding region" or "binding region" or antigen-binding domain as used herein, refers to the region of an antibody which is capable of binding to the antigen. This binding region is typically defined by the VH and VL domains of the antibody which may be further subdivided into regions of hypervariability (or hypervariable regions which may be hypervariable in sequence and/or form of structurally defined loops), also termed complementarity determining regions (CDRs), interspersed with regions that are more conserved, termed framework regions (FRs). The antigen can be any molecule, such as a polypeptide, e.g., present on a cell, bacterium, or virion. The terms "antigen-binding region" and "antigen-binding site" and "antigen-binding domain" may, unless contradicted by the context, be used interchangeably in the context of the present invention.

The terms "antigen" and "target" may, unless contradicted by the context, be used interchangeably in the context of the present invention.

The term "binding" as used herein refers to the binding of an antibody to a predetermined antigen or target, typically with a binding affinity corresponding to a $K_D$ of $1E^6$ M or less, e.g. $5E^7$ M or less, $1E^7$ M or less, such as $5E^8$ M or less, such as $1E^0$ M or less, such as $5E^9$ M or less, or such as $1E^9$ M or less, when determined by biolayer interferometry using the antibody as the ligand and the antigen as the analyte and binds to the predetermined antigen with an affinity corresponding to a $K_D$ that is at least ten-fold lower, such as at least 100-fold lower, for instance at least 1,000-fold lower, such as at least 10,000-fold lower, for instance at least 100,000-fold lower than its affinity for binding to a non-specific antigen (e.g., BSA, casein) other than the predetermined antigen or a closely-related antigen.

The term "$K_D$" (M), as used herein, refers to the dissociation equilibrium constant of a particular antibody-antigen interaction, and is obtained by dividing $k_d$ by $k_a$.

The term "$k_d$" ($sec^{-1}$), as used herein, refers to the dissociation rate constant of a particular antibody-antigen interaction. Said value is also referred to as the $k_{off}$ value or off-rate.

The term "$k_a$" ($M^{-1} \times sec^{-1}$), as used herein, refers to the association rate constant of a particular antibody-antigen interaction. Said value is also referred to as the $k_{on}$ value or on-rate.

The term "CD27" as used herein, refers to the human protein entitled CD27, also known as tumor necrosis factor receptor superfamily member 7 (TNFRSF7). In the amino acid sequence shown in SEQ ID NO: 1 (Uniprot ID P26842), amino acid residues 1-19 are a signal peptide, and amino acid residues 20-240 are the mature polypeptide. Unless contradicted by context, CD27 may also refer to variants of CD27, isoforms and orthologs thereof. A naturally occurring variant of human CD27 comprising a A59T mutation is shown in SEQ ID NO: 2.

In cynomolgus monkey (*Macaca fascicularis*), the CD27 protein has the amino acid sequence shown in SEQ ID NO: 3 (Genbank XP_005569963). In the 240 amino acid sequence shown in SEQ ID NO: 3, the signal peptide is not defined.

The term "antibody binding region" refers to a region of the antigen, which comprises the epitope to which the antibody binds. An antibody binding region may be determined by epitope binding using biolayer interferometry, by alanine scan, or by shuffle assays (using antigen constructs in which regions of the antigen are exchanged with that of another species and determining whether the antibody still binds to the antigen or not). The amino acids within the antibody binding region that are involved in the interaction with the antibody may be determined by hydrogen/deuterium exchange mass spectrometry and by crystallography of the antibody bound to its antigen.

The term "epitope" means an antigenic determinant which is specifically bound by an antibody. Epitopes usually consist of surface groupings of molecules such as amino acids, sugar side chains or a combination thereof and usually have specific three-dimensional structural characteristics, as well as specific charge characteristics. Conformational and non-conformational epitopes are distinguished in that the binding to the former but not the latter is lost in the presence of denaturing solvents. The epitope may comprise amino acid residues which are directly involved in the binding, and other amino acid residues, which are not directly involved in the binding, such as amino acid residues which are effectively blocked or covered by the antibody when it is bound to the antigen (in other words, the amino acid residue is within or closely adjacent to the footprint of the specific antibody).

The terms “monoclonal antibody”, “monoclonal Ab”, “monoclonal antibody composition”, “mAb”, or the like, as used herein refer to a preparation of antibody molecules of single molecular composition. A monoclonal antibody composition displays a single binding specificity and affinity for a particular epitope. Accordingly, the term “human monoclonal antibody” refers to antibodies displaying a single binding specificity which have variable and constant regions derived from human germline immunoglobulin sequences. The human monoclonal antibodies may be produced by a hybridoma which includes a B cell obtained from a transgenic or trans-chromosomal non-human animal, such as a transgenic mouse or rat, having a genome comprising a human heavy chain transgene and a light chain transgene, fused to an immortalized cell. Monoclonal antibodies may also be produced from recombinantly modified host cells, or systems that use cellular extracts supporting in vitro transcription and/or translation of nucleic acid sequences encoding the antibody.

The term “isotype” as used herein refers to the immunoglobulin class (for instance IgG, IgG1, IgG2, IgG3, IgG4, IgD, IgA, IgE, or IgM) or any allotypes thereof, such as IgG1m(za) and IgG1m(f)) that is encoded by heavy chain constant region genes. Further, each heavy chain isotype can be combined with either a kappa (κ) or lambda (λ) light chain.

The term “full-length antibody” when used herein, indicates that the antibody is not a fragment, but contains all of the domains of the particular isotype normally found for that isotype in nature, e.g., the VH, CH1, CH2, CH3, hinge, VL and CL domains for an IgG1 antibody. In a full-length variant antibody, the heavy and light chain constant and variable domains may in particular contain amino acid substitutions that improve the functional properties of the antibody when compared to the full-length parent or wild type antibody. A full-length antibody according to the present invention may be produced by a method comprising the steps of (i) cloning the CDR sequences into a suitable vector comprising complete heavy chain sequences and complete light chain sequence, and (ii) expressing the complete heavy and light chain sequences in suitable expression systems. It is within the knowledge of the skilled person to produce a full-length antibody when starting out from either CDR sequences or full variable region sequences. Thus, the skilled person would know how to generate a full-length antibody according to the present invention.

The term “human antibody”, as used herein, is intended to include antibodies comprising variable and framework regions derived from human germline immunoglobulin sequences and a human immunoglobulin constant domain. The human antibodies of the invention may include amino acid residues not encoded by human germline immunoglobulin sequences (e.g., mutations, insertions or deletions introduced by random or site-specific mutagenesis in vitro or by somatic mutation in vivo). However, the term “human antibody”, as used herein, is not intended to include antibodies in which CDR sequences derived from the germline of another non-human species, such as a mouse, have been grafted onto human framework sequences.

The term “humanized antibody” as used herein, refers to a genetically engineered non-human antibody, which contains human antibody constant domains and non-human variable domains modified to contain a high level of sequence homology to human variable domains. This can be achieved by grafting of the six non-human antibody complementarity-determining regions (CDRs), which together form the antigen binding site, onto a homologous human acceptor framework region (FR) (see WO92/22653 and EP0629240). In order to fully reconstitute the binding affinity and specificity of the parental antibody, the substitution of framework residues from the parental antibody (i.e., the non-human antibody) into the human framework regions (back-mutations) may be required. Structural homology modeling may help to identify the amino acid residues in the framework regions that are important for the binding properties of the antibody. Thus, a humanized antibody may comprise non-human CDR sequences, primarily human framework regions optionally comprising one or more amino acid back-mutations to the non-human amino acid sequence, and fully human constant regions. Optionally, additional amino acid modifications, which are not necessarily back-mutations, may be applied to obtain a humanized antibody with preferred characteristics, such as affinity and biochemical properties.

The term “Fc region” or “Fc domain” as used herein may be used interchangeably and refers to a region of the heavy chain constant region comprising, in the direction from the N- to C-terminal end of the antibody, at least a hinge region, a CH2 region and a CH3 region. An Fc region of the antibody may mediate the binding of the immunoglobulin to host tissues or factors, including various cells of the immune system (such as effector cells) and components of the complement system.

The term “parent polypeptide” or “parent antibody”, is to be understood as a polypeptide or antibody, which is identical to a polypeptide or antibody according to the invention, but where the parent polypeptide or parent antibody is without mutations, unless otherwise stated or clearly contradicted by the context. For example, the antibody IgG1-CD27-A of the invention is the parent antibody of IgG1-CD27-A-P329R-E345R.

The term “hinge region” as used herein refers to the hinge region of an immunoglobulin heavy chain. Thus, for example the hinge region of a human IgG1 antibody corresponds to amino acids 216-230 according to the Eu numbering (Eu-index) as set forth in Kabat, E. A. et al., Sequences of proteins of immunological interest. 5th Edition—US Department of Health and Human Services, NIH publication No. 91-3242, pp 662,680,689 (1991). However, the hinge region may also be any of the other subtypes as described herein.

The term “CH1 region” or “CH1 domain” as used herein refers to the CH1 region of an immunoglobulin heavy chain. Thus, for example the CH1 region of a human IgG1 antibody corresponds to amino acids 118-215 according to the Eu numbering as set forth in Kabat (ibid). However, the CH1 region may also be any of the other subtypes as described herein.

The term “CH2 region” or “CH2 domain” as used herein refers to the CH2 region of an immunoglobulin heavy chain. Thus, for example the CH2 region of a human IgG1 antibody corresponds to amino acids 231-340 according to the Eu numbering as set forth in Kabat (ibid). However, the CH2 region may also be any of the other subtypes as described herein.

The term “CH3 region” or “CH3 domain” as used herein refers to the CH3 region of an immunoglobulin heavy chain. Thus, for example the CH3 region of a human IgG1 antibody corresponds to amino acids 341-447 according to the Eu numbering as set forth in Kabat (ibid). However, the CH3 region may also be any of the other subtypes as described herein.

The term "Fc-mediated effector functions" or "Fc effector functions" as used herein are used interchangeably and is intended to refer to functions that are a consequence of binding a polypeptide or antibody to its target or antigen on a cell membrane wherein the Fc-mediated effector function is attributable to the Fc region of the polypeptide or antibody. Examples of Fc-mediated effector functions include (i) C1q binding, (ii) complement activation, (iii) complement-dependent cytotoxicity (CDC), (iv) antibody-dependent cell-mediated cytotoxity (ADCC), (v) Fc-gamma receptor (FcTR)-binding, (vi) antibody-dependent, FcγR-mediated antigen crosslinking, (vii) antibody-dependent cellular phagocytosis (ADCP), (viii) complement-dependent cellular cytotoxicity (CDCC), (ix) complement-enhanced cytotoxicity, (x) binding to complement receptor of an opsonized antibody mediated by the antibody, (xi) opsonisation, and (xii) a combination of any of (i) to (xi).

The term "decreased Fc effector function(s)" or "Decreased Fc-mediated effector functions", as used herein are used interchangeably and is intended to refer to an Fc effector function that is decreased for an antibody when directly compared to the Fc effector function of the parent polypeptide or antibody in the same assay.

The term "inertness", "inert" or "non-activating" as used herein, refers to an Fc region which is at least not able to bind any FcγR, induce Fc-mediated cross-linking of FcγRs, or induce FcγR-mediated cross-linking of target antigens via two Fc regions of individual antibodies, or is not able to bind C1q. Thus, in certain embodiments of the invention the Fc region is inert. Therefore, in certain embodiments some or all of the Fc-mediated effector functions are attenuated or completely absent.

The term "oligomerization", as used herein, is intended to refer to a process that converts monomers to a finite degree of polymerization. Antibodies according to the invention can form oligomers, such as hexamers, via non-covalent association of Fc-regions after target binding, e.g., at a cell surface. Oligomerization of anti-CD27 antibodies upon cell surface binding through Fc:Fc interactions may increase CD27 clustering resulting in activation of CD27 intracellular signaling. The capacity of antibodies comprising the E345R or E430G mutation to form oligomers, such as hexamers, upon cell surface binding can be evaluated as described in: de Jong R N et al, PLoS Biol. 2016 Jan. 6; 14(1):e1002344. Fc-Fc-mediated oligomerization of antibodies occurs after target binding on a (cell) surface through the intermolecular association of Fc-regions between neighboring antibodies and is increased by introduction of a E345R or a E430G mutation (numbering according to Eu-index).

The term "clustering", as used herein, refers to oligomerization of antibodies through non-covalent interactions.

The term "Fc-Fc enhancing", as used herein, is intended to refer to increasing the binding strength between, or stabilizing the interaction between, the Fc regions of two Fc-region containing antibodies so that the antibodies form oligomers such as hexamers on the cell surface. This enhancement can be obtained by certain amino acid mutations in the Fc regions of the antibodies, such as E345R or E430G. The term "monovalent antibody", in the context of the present invention, refers to an antibody molecule that can interact with a specific epitope on an antigen, with only one antigen binding domain (e.g. one Fab arm). In the context of a bispecific antibody, "monovalent antibody binding" refers to the binding of the bispecific antibody to one specific epitope on an antigen with only one antigen binding domain (e.g. one Fab arm).

The term "monospecific antibody" in the context of the present invention, refers to an antibody that has binding specificity to one epitope only. The antibody may be a monospecific, monovalent antibody (i.e. carrying only one antigen binding region) or a monospecific, bivalent antibody (i.e. an antibody with two identical antigen binding regions).

The term "bispecific antibody" refers to an antibody comprising two non-identical antigen binding domains, e.g. two non-identical Fab-arms or two Fab-arms with non-identical CDR regions. In the context of this invention, bispecific antibodies have specificity for at least two different epitopes. Such epitopes may be on the same or different antigens or targets. If the epitopes are on different antigens, such antigens may be on the same cell or different cells, cell types or structures, such as extracellular matrix or vesicles and soluble protein. A bispecific antibody may thus be capable of crosslinking multiple antigens, e.g. two different cells. A particular bispecific antibody of the present invention is capable of binding to CD27 and a second target.

The term "bivalent antibody" refers to an antibody that has two antigen binding regions, which bind to epitopes on one or two targets or antigens or binds to one or two epitopes on the same antigen. Hence, a bivalent antibody may be a monospecific, bivalent antibody or a bispecific, bivalent antibody.

The term "amino acid" and "amino acid residue" may herein be used interchangeably and are not to be understood limiting. Amino acids are organic compounds containing amine (—$NH_2$) and carboxyl (—COOH) functional groups, along with a side chain (R group) specific to each amino acid. In the context of the present invention, amino acids may be classified based on structure and chemical characteristics. Thus, classes of amino acids may be reflected in one or both of the following tables:

TABLE 1

Main classification based on structure and general chemical characterization of R group

| Class | Amino acid |
|---|---|
| Acidic Residues | D and E |
| Basic Residues | K, R, and H |
| Hydrophilic Uncharged Residues | S, T, N, and Q |
| Aliphatic Uncharged Residues | G, A, V, L, and I |
| Non-polar Uncharged Residues | C, M, and P |
| Aromatic Residues | F, Y, and W |

TABLE 2

Alternative Physical and Functional Classifications of Amino Acid Residues

| Class | Amino acid |
|---|---|
| Hydroxyl group containing residues | S and T |
| Aliphatic residues | I, L, V, and M |
| Cycloalkenyl-associated residues | F, H, W, and Y |
| Hydrophobic residues | A, C, F, G, H, I, L, M, R, T, V, W, and Y |
| Negatively charged residues | D and E |
| Polar residues | C, D, E, H, K, N, Q, R, S, and T |
| Positively charged residues | H, K, and R |
| Small residues | A, C, D, G, N, P, S, T, and V |

TABLE 2-continued

| Alternative Physical and Functional Classifications of Amino Acid Residues | |
|---|---|
| Class | Amino acid |
| Very small residues | A, G, and S |
| Residues involved in turn formation | A, C, D, E, G, H, K, N, Q, R, S, P, and T |
| Flexible residues | Q, T, K, S, G, P, D, E, and R |

Substitution of one amino acid for another may be classified as a conservative or non-conservative substitution. In the context of the invention, a "conservative substitution" is a substitution of one amino acid with another amino acid having similar structural and/or chemical characteristics, such substitution of one amino acid residue for another amino acid residue of the same class as defined in any of the two tables above: for example, leucine may be substituted with isoleucine as they are both aliphatic, branched hydrophobes. Similarly, aspartic acid may be substituted with glutamic acid since they are both small, negatively charged residues.

In the context of the present invention, a substitution in an antibody is indicated as:

Original amino acid—position—substituted amino acid;

Referring to the well-recognized nomenclature for amino acids, the three-letter code, or one letter code, is used, including the codes "Xaa" or "X" to indicate any amino acid residue. Thus, Xaa or X may typically represent any of the 20 naturally occurring amino acids. The term "naturally occurring" as used herein refers to any one of the following amino acid residues; glycine, alanine, valine, leucine, isoleucine, serine, threonine, lysine, arginine, histidine, aspartic acid, asparagine, glutamic acid, glutamine, proline, tryptophan, phenylalanine, tyrosine, methionine, and cysteine. Accordingly, the notation "K409R" or "Lys409Arg" means, that the antibody comprises a substitution of Lysine with Arginine in amino acid position 409.

Substitution of an amino acid at a given position to any other amino acid is referred to as:

Original amino acid—position; or e.g. "K409"

For a modification where the original amino acid(s) and/or substituted amino acid(s) may comprise more than one, but not all amino acid(s), the more than one amino acid may be separated by "," or "/". E.g. the substitution of Lysine with Arginine, Alanine, or Phenylalanine in position 409 is:

"Lys409Arg,Ala,Phe" or "Lys409Arg/Ala/Phe" or "K409R,A,F" or "K409R/A/F" or "K409 to R, A, or F".

Such designation may be used interchangeably in the context of the invention but have the same meaning and purpose.

Furthermore, the term "a substitution" embraces a substitution into any one or the other nineteen natural amino acids, or into other amino acids, such as non-natural amino acids. For example, a substitution of amino acid K in position 409 includes each of the following substitutions: 409A, 409C, 409D, 409E, 409F, 409G, 409H, 409I, 409L, 409M, 409N, 409Q, 409R, 409S, 409T, 409V, 409W, 409P, and 409Y. This is, by the way, equivalent to the designation 409X, wherein the X designates any amino acid other than the original amino acid. These substitutions may also be designated K409A, K409C, etc. or K409A,C, etc. or K409A/C/etc. The same applies by analogy to each and every position mentioned herein, to specifically include herein any one of such substitutions.

The antibody according to the invention may also comprise a deletion of an amino acid residue. Such deletion may be denoted "del", and includes, e.g., writing as K409del. Thus, in such embodiments, the Lysine in position 409 has been deleted from the amino acid sequence.

The term "host cell", as used herein, is intended to refer to a cell into which an expression vector has been introduced. It should be understood that such terms are intended to refer not only to the particular subject cell, but also to the progeny of such a cell. Because certain modifications may occur in succeeding generations due to either mutation or environmental influences, such progeny may not, in fact, be identical to the parent cell, but are still included within the scope of the term "host cell" as used herein. Recombinant host cells include, for example, transfectomas, such as CHO cells, HEK-293 cells, Expi293F cells, PER.C6 cells, NS0 cells, and lymphocytic cells, and prokaryotic cells such as *E. coli* and other eukaryotic hosts such as plant cells and fungi.

The term "transfectoma", as used herein, includes recombinant eukaryotic host cells expressing the antibody or a target antigen, such as CHO cells, PER.C6 cells, NS0 cells, HEK-293 cells, Expi293F cells, plant cells, or fungi, including yeast cells.

For purposes of the present invention, the sequence identity between two amino acid sequences is determined using the Needleman-Wunsch algorithm (Needleman and Wunsch, 1970, J. Mol. Biol. 48: 443-453) as implemented in the Needle program of the EMBOSS package (EMBOSS: The European Molecular Biology Open Software Suite, Rice et al., 2000, Trends Genet. 16: 276-277), preferably version 5.0.0 or later. The parameters used are gap open penalty of 10, gap extension penalty of 0.5, and the EBLOSUM62 (EMBOSS version of BLOSUM62) substitution matrix. The output of Needle labeled "longest identity" (obtained using the –nobrief option) is used as the percent identity and is calculated as follows:

$$(\text{Identical Residues}\times 100)/(\text{Length of Alignment}-\text{Total Number of Gaps in Alignment}).$$

The retention of similar residues may also or alternatively be measured by a similarity score, as determined by use of a BLAST program (e.g., BLAST 2.2.8 available through the NCBI using standard settings BLOSUM62, Open Gap=11 and Extended Gap=1). Suitable variants typically exhibit at least about 45%, such as at least about 55%, at least about 65%, at least about 75%, at least about 85%, at least about 90%, at least about 95%, or more (e.g., about 99%) similarity to the parent sequence.

The term "internalized" or "internalization" as used herein, refers to a biological process in which molecules such as the antibody according to the present invention, are engulfed by the cell membrane and drawn into the interior of the cell. Internalization may also be referred to as "endocytosis".

As used herein, the term "effector cell" refers to an immune cell which is involved in the effector phase of an immune response. Exemplary immune cells include a cell of a myeloid or lymphoid origin, for instance lymphocytes (such as B cells and T cells including cytolytic T cells (CTLs)), killer cells, natural killer cells, macrophages, monocytes, eosinophils, polymorphonuclear cells, such as neutrophils, granulocytes, mast cells, and basophils. Some effector cells express Fc receptors (FcgRs) or complement receptors and carry out specific immune functions. In some embodiments, an effector cell such as, e.g., a natural killer cell, is capable of inducing ADCC. For example, monocytes, macrophages, neutrophils, dendritic cells and Kupffer cells which express FcgRs, are involved in specific killing of target cells and/or presenting antigens to other components of the immune system, or binding to cells that present antigens. In some embodiments the ADCC can be further enhanced by antibody driven classical complement activation resulting in the deposition of activated C3 fragments on the target cell. C3 cleavage products are ligands for complement receptors (CRs), such as CR3, expressed on myeloid cells. The recognition of complement fragments by CRs on effector cells may promote enhanced Fc receptor-mediated ADCC. In some embodiments antibody driven classical complement activation leads to C3 fragments on the target cell. These C3 cleavage products may promote direct complement-dependent cellular cytotoxicity (CDCC). In some embodiments, an effector cell may phagocytose a target antigen, target particle or target cell which may depend on antibody binding and mediated by FcγRs expressed by the effector cells. The expression of a particular FcR or complement receptor on an effector cell may be regulated by humoral factors such as cytokines. For example, expression of FcγRI has been found to be up-regulated by interferon γ (IFN γ) and/or G-CSF. This enhanced expression increases the cytotoxic activity of FcγRI-bearing cells against targets. An effector cell can phagocytose a target antigen or phagocytose or lyse a target cell. In some embodiments antibody driven classical complement activation leads to C3 fragments on the target cell. These C3 cleavage products may promote direct phagocytosis by effector cells or indirectly by enhancing antibody mediated phagocytosis. In certain embodiments herein where the antibody has an inert Fc region the antibody does not induce an Fc-mediated effector function.

"Effector T cells" or "Teffs" or "Teff" as used herein refers to T lymphocytes that carry out a function of an immune response, such as killing tumor cells and/or activating an antitumor immune-response which can result in clearance of the tumor cells from the body. Examples of Teff phenotypes include $CD3^+CD4^+$ and $CD3^+CD8^+$. Teffs may secrete, contain, or express markers such as IFNγ, granzyme B and ICOS. It is appreciated that Teffs may not be fully restricted to these phenotypes.

"Memory T cells" as used herein refers to T lymphocytes that remain in the body for a long period of time after an infection is removed. Examples of memory T cells include central memory T cells (CD45RA-CCR7+) and effector memory T cells (CD45RA-CCR7−). It is appreciated that memory T cells may not be fully restricted to these phenotypes.

"Regulatory T cells" or "Tregs" or "Treg" as used herein refers to T lymphocytes that regulate the activity of other T cell(s) and/or other immune cells, usually by suppressing their activity. An example of a Treg phenotype is $CD3^+CD4^+CD25^+$CD127dim. Tregs may further express Foxp3. It is appreciated that Tregs may not be fully restricted to this phenotype.

As used herein, the term "complement activation" refers to the activation of the classical complement pathway, which is initiated by a large macromolecular complex called C1 binding to antibody-antigen complexes on a surface. C1 is a complex, which consists of 6 recognition proteins C1q and a hetero-tetramer of serine proteases, C1r2C1s2. C1 is the first protein complex in the early events of the classical complement cascade that involves a series of cleavage reactions that starts with the cleavage of C4 into C4a and C4b and C2 into C2a and C2b. C4b is deposited and forms together with C2a an enzymatic active convertase called C3 convertase, which cleaves complement component C3 into C3b and C3a, which forms a C5 convertase This C5 convertase splits C5 in C5a and C5b and the last component is deposited on the membrane and that in turn triggers the late events of complement activation in which terminal complement components C5b, C6, C7, C8 and C9 assemble into the membrane attack complex (MAC). The complement cascade results in the creation of pores in the cell membrane which causes lysis of the cell, also known as complement-dependent cytotoxicity (CDC). In certain embodiments herein where the antibody has an inert Fc region the antibody does not induce complement activation.

Complement activation can be evaluated by using C1q binding efficacy, CDC kinetics CDC assays (as described in WO2013/004842, WO2014/108198) or by the method Cellular deposition of C3b and C4b described in Beurskens et al., J Immunol Apr. 1, 2012 vol. 188 no. 7, 3532-3541.

The term "C1q binding" as used herein, is intended to refer to the binding of C1q in the context of the binding of C1q to an antibody bound to its antigen. The antibody bound to its antigen is to be understood as happening both in vivo and in vitro in the context described herein. C1q binding can be evaluated for example by using antibody immobilized on artificial surfaces or by using antibody bound to a predetermined antigen on a cellular or virion surface, as described in Example 8 herein. The binding of C1q to an antibody oligomer is to be understood herein as a multivalent interaction resulting in high avidity binding. A decrease in C1q binding, for example resulting from the introduction of a mutation in the antibody of the invention, may be measured by comparing the C1q binding of the mutated antibody to the C1q binding of its parent antibody (the antibody of the invention without the mutation within the same assay).

The term "treatment" refers to the administration of an effective amount of a therapeutically active antibody of the present invention with the purpose of easing, ameliorating, arresting, or eradicating (curing) symptoms or disease states.

The term "effective amount" or "therapeutically effective amount" refers to an amount effective, at dosages and for periods of time necessary, to achieve a desired therapeutic result. A therapeutically effective amount of an antibody may vary according to factors such as the disease state, age, sex, and weight of the individual, and the ability of the antibody to elicit a desired response in the individual. A therapeutically effective amount is also one in which any toxic or detrimental effects of the antibody variant are outweighed by the therapeutically beneficial effects.

The term "pharmacokinetic profile" as used herein can be determined as the plasma IgG levels over time as described in Example 12 herein.

Specific Embodiments of the Invention

In a first aspect the invention provides an antibody comprising at least one antigen-binding region capable of binding to human CD27 wherein said antibody comprises a heavy chain variable (VH) region CDR1, CDR2, and CDR3 comprising the sequences as set forth in SEQ ID NOs: 5, 6, and 7, respectively, and a light chain variable (VL) region CDR1, CDR2, and CDR3 comprising the sequences as set forth in SEQ ID NO: 9, 10 and 11, respectively. In a further aspect the invention provides an antibody comprising two of said antigen-binding regions comprising the VH region CDR1, CDR2, and CDR3 comprising the sequences as set forth in SEQ ID NOs: 5, 6, and 7, respectively, and the VL region CDR1, CDR2, and CDR3 comprising the sequences as set forth in SEQ ID NO: 9, 10 and 11 respectively. Hereby anti-CD27 antibodies are provided which are able to bind to human CD27 and further to bind to a variant of human CD27 comprising a mutation of A59T. In an embodiment of the invention the antibody binds CD27 e.g. on T cells and is agonistic upon binding to its target. Hereby an antibody is provided which stimulates the activation and proliferation of T-cells. The antibody may further stimulate memory formation and survival of T-cells. Such an antibody is useful e.g. in the treatment of cancer. The antibody is further capable of binding to cynomolgus CD27 which is useful for toxicological studies of the antibody.

It is well known in the art that mutations in the VH and VL of an antibody can be made to, for example, increase the affinity of an antibody to its target antigen, reduce its potential immunogenicity and/or to increase the yield of antibodies expressed by a host cell. Accordingly, in some embodiments, antibodies comprising variants of the CDR, VH and/or VL sequences of an antibody according to the invention are also contemplated, particularly functional variants of the VH and/or VL region as set forth in SEQ ID NO: 4 and SEQ ID NO: 8, respectively. Functional variants may differ in one or more amino acids as compared to the parent VH and/or VL sequence, e.g., in one or more CDRs, but still allows the antigen-binding region to retain at least a substantial proportion (at least about 50 percent, 60 percent, 70 percent, 80 percent, 90 percent, 95 percent or more) or even retain all of the affinity and/or specificity of the parent antibody. Typically, such functional variants retain significant sequence identity to the parent sequence. Exemplary variants include those which differ from the respective parent VH or VL region by 12 or less, such as 11, 10, 9, 8, 7, 6, 5, 4, 3, 2 or 1 mutation(s) such as substitutions, insertions or deletions of amino acid residues. Exemplary variants include those which differ from the VH and/or VL and/or CDR regions of the parent sequences mainly by conservative amino acid substitutions; for instance, 12, such as 11, 10, 9, 8, 7, 6, 5, 4, 3, 2 or 1 of the amino acid substitutions in the variant can be conservative. In a further aspect of the invention the antibody may comprise at most 1, 2 or 3 mutations in the VH CDR region and/or in the VL CDR region, respectively. Such mutations may be substitutions. It is preferred that such substitutions do not significantly change the binding affinity and/or binding specificity of the anti-CD27 antibody of the invention. Accordingly, the present invention encompasses variants of the anti-CD27 antibody of the invention which variants have the same functional features as the antibody comprising the VH region CDR sequences as set forth in SEQ ID NOs: 5, 6, and 7, and the VL region CDR sequences as set forth in SEQ ID NO: 9, 10 and 11.

In another aspect of the invention the antibody comprises a VH region comprising a sequence which is at least 80% identical to the VH region as set forth in SEQ ID NO: 4. In another aspect of the invention the antibody comprises a VH region comprising a sequence which is at least 85% identical to the VH region as set forth in SEQ ID NO: 4. In another aspect of the invention the antibody comprises a VH region comprising a sequence which is at least 90% identical to the VH region as set forth in SEQ ID NO: 4. In another aspect of the invention the antibody comprises a VH region comprising a sequence which is at least 95% identical to the VH region as set forth in SEQ ID NO: 4. In another aspect of the invention the antibody comprises a VH region comprising a sequence which is at least 96% identical to the VH region as set forth in SEQ ID NO: 4. In another aspect of the invention the antibody comprises a VH region comprising a sequence which is at least 97% identical to the VH region as set forth in SEQ ID NO: 4. In another aspect of the invention the antibody comprises a VH region comprising a sequence which is at least 98% identical to the VH region as set forth in SEQ ID NO: 4. In another aspect of the invention the antibody comprises a VH region comprising a sequence which is at least 99% identical to the VH region as set forth in SEQ ID NO: 4. In another aspect of the invention the antibody comprises a VH region comprising a sequence as set forth in SEQ ID NO: 4.

In another aspect of the invention the antibody comprises a VH region comprising a sequence which is at least 80% identical to the VH region as set forth in SEQ ID NO: 8. In another aspect of the invention the antibody comprises a VH region comprising a sequence which is at least 85% identical to the VH region as set forth in SEQ ID NO: 8. In another aspect of the invention the antibody comprises a VH region comprising a sequence which is at least 90% identical to the VH region as set forth in SEQ ID NO: 8. In another aspect of the invention the antibody comprises a VH region comprising a sequence which is at least 95% identical to the VH region as set forth in SEQ ID NO: 8. In another aspect of the invention the antibody comprises a VH region comprising a sequence which is at least 96% identical to the VH region as set forth in SEQ ID NO: 8. In another aspect of the invention the antibody comprises a VH region comprising a sequence which is at least 97% identical to the VH region as set forth in SEQ ID NO: 8. In another aspect of the invention the antibody comprises a VH region comprising a sequence which is at least 98% identical to the VH region as set forth in SEQ ID NO: 8. In another aspect of the invention the antibody comprises a VH region comprising a sequence which is at least 99% identical to the VH region as set forth in SEQ ID NO: 8. In another aspect of the invention the antibody comprises a VH region comprising a sequence as set forth in SEQ ID NO: 8.

In another aspect of the invention the antibody comprises the VH and VL regions comprising the sequences as set forth in SEQ ID NO: 4 and SEQ ID NO: 8, respectively.

In one aspect the antibody of the invention is an isolated antibody.

In one embodiment the antibody is a human antibody. In another embodiment the antibody is a humanized antibody. In another aspect the antibody is a chimeric antibody.

The antibody of the invention is in a preferred embodiment a full-length antibody. Accordingly, the antibody of the invention may further comprise a light chain constant region (CL) and a heavy chain constant region (CH). The CH preferably comprises a CH1 region, a hinge region, a CH2 region and a CH3 region.

The antibody according to the invention may comprise a light chain constant region which is a human kappa light chain. In another aspect it may comprise a human lambda light chain constant region.

The antibody according to the invention may preferably further comprise a heavy chain constant region, which is of a human IgG isotype. It may optionally comprise a modified human IgG constant region. Such human IgG comprise the Fc region which comprise the CH2 and CH3 region. By modifying the IgG constant region in the Fc region, it is for example possible to regulate the Fc effector functions of the antibody or to increase the Fc-Fc interactions and thereby the antibodies tendency to form clusters such as hexamers. In one aspect of the invention the human IgG or modified human IgG is selected from IgG1, IgG2, IgG3 or IgG4. In one embodiment it is IgG1. In another aspect it is IgG2. In yet another aspect it is IgG3. In a further aspect it is IgG4.

In one particular aspect the IgG is a modified human IgG comprising one or more amino acid substitutions in the Fc region. In one embodiment it may be a human IgG1 comprising one or more amino acid substitutions in the Fc region. In a further aspect of the invention the IgG1 comprises two or more amino acid substitutions in the Fc region. In one embodiment the IgG1 Fc region has two amino acid substitutions.

In a further aspect of the invention, the modified human IgG heavy chain constant region comprises in the Fc region at most 10 amino acid substitutions. In another aspect it comprises at most 9 amino acid substitutions. In another aspect it comprises at most 8 amino acid substitutions. In another aspect it comprises at most 7 amino acid substitutions. In another aspect it comprises at most 6 amino acid substitutions. In another aspect it comprises at most 5 amino acid substitutions. In another aspect it comprises at most 4 amino acid substitutions. In another aspect it comprises at most 3 amino acid substitutions. In another aspect it comprises at most 2 amino acid substitutions in the Fc region.

Mutations in amino acid residues at positions corresponding to E430, E345 and S440 in a human IgG1 heavy chain, wherein the amino acid residues are numbered according to the EU index, can improve the ability of an antibody to induce CDC. Without being bound by theory, it is believed that by substituting one or more amino acid(s) in these positions, oligomerization of the antibody can be stimulated, thereby modulating Fc-mediated effector functions so as to, e.g., increase C1q binding, complement activation, CDC, ADCP, internalization or other relevant function(s) that may provide in vivo efficacy.

The present invention in one aspect relates to a variant antibody comprising an antigen-binding region and a variant Fc region.

In certain embodiments, an antibody variant binding to human CD27 comprises:

(a) a heavy chain comprising a VH region comprising a VH CDR1 comprising the sequence as set forth in SEQ ID NO:5, a VH CDR2 comprising the sequence as set forth in SEQ ID NO:6, a VH CDR3 comprising the sequence as set forth in SEQ ID NO:7 and a human IgG1 CH region comprising a mutation in one or more of E430, E345 and S440, the amino acid residues being numbered according to the EU index;

(b) a light chain comprising a VL region comprising a VL CDR1 comprising the sequence as set forth in SEQ ID NO:9, a VL CDR2 comprising the sequence as set forth in SEQ ID NO:10, and a VL CDR3 comprising the sequence as set forth in SEQ ID NO:11.

In other certain embodiments, an antibody variant binding to human CD27 comprises:

(a) a heavy chain comprising a VH region comprising SEQ ID NO:4 and a human IgG1 CH region comprising a mutation in one or more of E430, E345 and S440, the amino acid residues being numbered according to the EU index, and (b) a light chain comprising a VL region comprising SEQ ID NO:8.

A variant antibody of the present invention comprises a variant Fc region or a variant human IgG1 CH region comprising a mutation in one or more of P329, E430 and E345. In the following, reference to the mutations in the Fc region may similarly apply to the mutation(s) in the human IgG1 CH region and vice versa.

As described herein, the position of an amino acid to be mutated in the Fc region can be given in relation to (i.e., "corresponding to") its position in a naturally occurring (wildtype) human IgG1 heavy chain, when numbered according to the Eu index. So, if the parent Fc region already contains one or more mutations and/or if the parent Fc region is, for example, an IgG2, IgG3 or IgG4 Fc region, the position of the amino acid corresponding to an amino acid residue such as, e.g., E430 in a human IgG1 heavy chain numbered according to the Eu index can be determined by alignment. Specifically, the parent Fc region is aligned with a wild-type human IgG1 heavy chain sequence so as to identify the residue in the position corresponding to E430 in the human IgG1 heavy chain sequence. Any wildtype human IgG1 constant region amino acid sequence can be useful for this purpose, including any one of the different human IgG1 allotypes set forth in Table 3.

In one aspect of the invention the modification in the IgG Fc region induces increased CD27 agonism compared to the identical antibody but comprising a wild type IgG Fc region of the same isotype, such as IgG1. This may for example be obtained by introducing an amino acid other than E at the amino acid position corresponding to position E345 and/or E430 in a human IgG1 heavy chain according to Eu numbering. In one embodiment of the invention the amino acid residue at the position corresponding to position E345 in a human IgG1 heavy chain according to Eu numbering is selected from the group comprising: A, C, D, F, G, H, I, K, L, M, N, Q, P, R, S, T, V, W and Y. In another aspect of the invention the amino acid residue at the position corresponding to position E430 in a human IgG1 heavy chain according to Eu numbering is selected from the group comprising: A, C, D, F, G, H, I, K, L, M, N, Q P, R, S, T, V, W.

In a preferred embodiment the amino acid residue at the position corresponding to position E345 in a human IgG1 heavy chain according to Eu numbering is R. Accordingly, the antibody of the invention may comprise an E345R substitution in the Fc region. In another aspect of the invention the amino acid residue at the position corresponding to position E430 in a human IgG1 heavy chain according to Eu numbering is G. Accordingly, the antibody of the invention may comprise a E430G substitution in the Fc region. In another embodiment, the antibody comprises an amino acid substitution selected from the group comprising E430G, E345K, E430S, E430F, E430T, E345Q, E345R, E345Y.

Hereby, antibodies are provided which have enhanced Fc-Fc interaction which may lead to antibody-dependent clustering of CD27 on the cell surface upon antibody binding, thereby increasing the agonism of the antibody of the invention.

In another embodiment of the antibody of the invention the amino acid residue at the position corresponding to position P329 in a human IgG1 heavy chain according to Eu numbering is substituted with an amino acid selected from the group comprising: A, C, D, E, F, G, H, I, K, L, M, N, Q, R, S, T, V, W and Y. Accordingly, the antibody of the invention may further comprise a mutation in position 329.

In a further aspect of the invention the antibody has the amino acid residue R at the position corresponding to position P329 in a human IgG1 heavy chain according to Eu numbering. Accordingly, the antibody of the invention may have a P329R substitution in the Fc region. Without being bound by theory, it is believed that the antibody of the invention comprising an E345R mutation in the Fc region (as e.g. set out in SEQ ID NO: 13) has increased serum clearance. The inventors found that further introducing a mutation at position 329, such as P329R (as e.g. set out in SEQ ID NO: 15) restored the clearance of the antibody of the invention to the level of the antibody comprising a wt IgG1 as e.g. set out in SEQ ID NO: 12.

In another preferred embodiment the amino acid residues at the positions corresponding to positions P329 and E345 in a human IgG1 heavy chain according to Eu numbering are both R. Hereby an antibody is provided which has increased CD27 receptor agonism and comparable pharmacokinetic properties, such as e.g. serum clearance, when compared to an antibody comprising the same VH and VL region and comprising an identical IgG1 heavy chain constant region with the exception of comprising the wildtype amino acid P at position 329 and the wildtype amino acid E at position 345.

Thus, in an embodiment the invention provides a CD27 binding antibody which has increased receptor agonism upon binding to CD27 and which further has pharmacokinetic properties which are comparable, such as similar or even identical pharmacokinetic properties, when compared to the pharmacokinetic properties of an antibody comprising the same VH and VL region but comprising a wild type IgG1 heavy chain constant region such as e.g. set out in SEQ ID NO: 12. In other words the invention provides a CD27 binding antibody which has pharmacokinetic properties which are not significantly different than the pharmacokinetic properties of an identical CD27 binding antibody except for comprising a wild type IgG1 heavy chain constant region.

In other embodiments of the invention the antibody comprises a variant Fc region according to any one of the preceding sections, which variant Fc region is a variant of a human IgG Fc region selected from the group consisting of a human IgG1, IgG2, IgG3 and IgG4 Fc region. That is, the mutation in one or more of the amino acid residues corresponding to E430 and E345 and P329 is/are made in a parent Fc region which is a human IgG Fc region selected from the group consisting of an IgG1, IgG2, IgG3 and IgG4 Fc region. Preferably, the parent Fc region is a naturally occurring (wildtype) human IgG Fc region, such as a human wildtype IgG1, IgG2, IgG3 or IgG4 Fc region, or a mixed isotype thereof. Thus, the variant Fc region may, except for the recited mutation (in one or more of the amino acid residues selected from E430 and E345 and P329), be a human IgG1, IgG2, IgG3 or IgG4 isotype, or a mixed isotype thereof.

In one embodiment, the parent Fc region and/or human IgG1 CH region is a wild-type human IgG1 isotype.

Thus, the variant Fc region may except for the recited mutation (in E430 or E345 or P329), be a human IgG1 Fc region.

In a specific embodiment, the parent Fc region and/or human IgG1 CH region is a human wild-type IgG1m(f) isotype.

In a specific embodiment, the parent Fc region and/or human IgG1 CH region is a human wild-type IgG1m(z) isotype.

In a specific embodiment, the parent Fc region and/or human IgG1 CH region is a human wild-type IgG1m(a) isotype.

In a specific embodiment, the parent Fc region and/or human IgG1 CH region is a human wild-type IgG1m(x) isotype.

In a specific embodiment, the parent Fc region and/or human IgG1 CH region is a human wild-type IgG1 of a mixed allotype, such as IgG1m(za), IgG1m(zax), IgG1m (fa), or the like.

Thus, the variant Fc region and/or human IgG1 CH region may, except for the recited mutation (in E430 or E345 or P329), be a human IgG1m(f), IgG1m(a), IgG1m(x), IgG1m (z) allotype or a mixed allotype of any two or more thereof.

In a specific embodiment, the parent Fc region and/or human IgG1 CH region is a human wild-type IgG1m(za) isotype.

In a specific embodiment, the parent Fc region is a human wild-type IgG2 isotype.

In a specific embodiment, the parent Fc region is a human wild-type IgG3 isotype.

In a specific embodiment, the parent Fc region is a human wild-type IgG4 isotype.

CH region amino acid sequences of specific examples of wild-type human IgG isotypes and IgG1 allotypes are set forth in Table 3.

In another aspect the invention provides an antibody which comprises a heavy chain constant region comprising an amino acid sequence selected from the group comprising: SEQ ID Nos 12, 13, 14, 15, 18, 19, 20, 21, 22, 23, 27, 28, 29, 30, 31, 32, 33, 34 and 36. In one aspect the heavy chain constant region has the amino acid sequence of SEQ ID NO: 12. In one aspect the heavy chain constant region has the amino acid sequence of SEQ ID NO: 13. In one aspect the heavy chain constant region has the amino acid sequence of SEQ ID NO: 14. In one aspect the heavy chain constant region has the amino acid sequence of SEQ ID NO: 15. In one aspect the heavy chain constant region has the amino acid sequence of SEQ ID NO: 18. In one aspect the heavy chain constant region has the amino acid sequence of SEQ ID NO: 19. In one aspect the heavy chain constant region has the amino acid sequence of SEQ ID NO: 20. In one aspect the heavy chain constant region has the amino acid sequence of SEQ ID NO: 21. In one aspect the heavy chain constant region has the amino acid sequence of SEQ ID NO: 22. In one aspect the heavy chain constant region has the amino acid sequence of SEQ ID NO: 23. In one aspect the heavy chain constant region has the amino acid sequence of SEQ ID NO: 27. In one aspect the heavy chain constant region has the amino acid sequence of SEQ ID NO: 28. In one aspect the heavy chain constant region has the amino acid sequence of SEQ ID NO: 29. In one aspect the heavy chain constant region has the amino acid sequence of SEQ ID NO: 30. In one aspect the heavy chain constant region has the amino acid sequence of SEQ ID NO: 31. In one aspect the heavy chain constant region has the amino acid sequence of SEQ ID NO: 32. In one aspect the heavy chain constant region has the amino acid sequence of SEQ ID NO: 33. In one aspect the heavy chain constant region has the amino acid sequence of SEQ ID NO: 34. In one aspect the heavy chain constant region has the amino acid sequence of SEQ ID NO: 36.

In an embodiment the antibody according to the invention comprises:

a. The VH region comprising the amino acid sequence set forth in SEQ ID No: 4
b. The VL region comprising the amino acid sequence set forth in SEQ ID No: 8
c. The CH region comprising the amino acid sequence set forth in SEQ ID No: 15 and
d. The CL region comprising the amino acid sequence set forth in SEQ ID No: 16.

In another embodiment the antibody according to the invention comprises:

a. The VH region comprising the amino acid sequence set forth in SEQ ID No: 4
b. The VL region comprising the amino acid sequence set forth in SEQ ID No: 8
c. The CH region comprising the amino acid sequence set forth in SEQ ID No: 12 and d. The CL region comprising the amino acid sequence set forth in SEQ ID No: 16.

In another embodiment the antibody according to the invention comprises:

a. The VH region comprising the amino acid sequence set forth in SEQ ID No: 4 b. The VL region comprising the amino acid sequence set forth in SEQ ID No: 8 c. The CH region comprising the amino acid sequence set forth in SEQ ID No: 13 and d. The CL region comprising the amino acid sequence set forth in SEQ ID No: 16.

In another embodiment the antibody according to the invention comprises:

a. The VH region comprising the amino acid sequence set forth in SEQ ID No: 4 b. The VL region comprising the amino acid sequence set forth in SEQ ID No: 8 c. The CH region comprising the amino acid sequence set forth in SEQ ID No: 14 and d. The CL region comprising the amino acid sequence set forth in SEQ ID No: 16.

In another embodiment the antibody according to the invention comprises:

a. The VH region comprising the amino acid sequence set forth in SEQ ID No: 4 b. The VL region comprising the amino acid sequence set forth in SEQ ID No: 8 c. The CH region comprising the amino acid sequence set forth in SEQ ID No: 18 and d. The CL region comprising the amino acid sequence set forth in SEQ ID No: 16.

In another embodiment the antibody according to the invention comprises:

a. The VH region comprising the amino acid sequence set forth in SEQ ID No: 4 b. The VL region comprising the amino acid sequence set forth in SEQ ID No: 8 c. The CH region comprising the amino acid sequence set forth in SEQ ID No: 19 and d. The CL region comprising the amino acid sequence set forth in SEQ ID No: 16.

In another embodiment the antibody according to the invention comprises:

a. The VH region comprising the amino acid sequence set forth in SEQ ID No: 4 b. The VL region comprising the amino acid sequence set forth in SEQ ID No: 8 c. The CH region comprising the amino acid sequence set forth in SEQ ID No: 20 and d. The CL region comprising the amino acid sequence set forth in SEQ ID No: 16.

In another embodiment the antibody according to the invention comprises:

a. The VH region comprising the amino acid sequence set forth in SEQ ID No: 4 b. The VL region comprising the amino acid sequence set forth in SEQ ID No: 8 c. The CH region comprising the amino acid sequence set forth in SEQ ID No: 21 and d. The CL region comprising the amino acid sequence set forth in SEQ ID No: 16.

In another embodiment the antibody according to the invention comprises:

a. The VH region comprising the amino acid sequence set forth in SEQ ID No: 4 b. The VL region comprising the amino acid sequence set forth in SEQ ID No: 8 c. The CH region comprising the amino acid sequence set forth in SEQ ID No: 22 and d. The CL region comprising the amino acid sequence set forth in SEQ ID No: 16.

In another embodiment the antibody according to the invention comprises:

a. The VH region comprising the amino acid sequence set forth in SEQ ID No: 4 b. The VL region comprising the amino acid sequence set forth in SEQ ID No: 8 c. The CH region comprising the amino acid sequence set forth in SEQ ID No: 23 and d. The CL region comprising the amino acid sequence set forth in SEQ ID No: 16.

In another embodiment the antibody according to the invention comprises:

a. The VH region comprising the amino acid sequence set forth in SEQ ID No: 4 b. The VL region comprising the amino acid sequence set forth in SEQ ID No: 8 c. The CH region comprising the amino acid sequence set forth in SEQ ID No: 27 and d. The CL region comprising the amino acid sequence set forth in SEQ ID No: 16.

In another embodiment the antibody according to the invention comprises:

a. The VH region comprising the amino acid sequence set forth in SEQ ID No: 4 b. The VL region comprising the amino acid sequence set forth in SEQ ID No: 8 c. The CH region comprising the amino acid sequence set forth in SEQ ID No: 28 and d. The CL region comprising the amino acid sequence set forth in SEQ ID No: 16.

In another embodiment the antibody according to the invention comprises:

a. The VH region comprising the amino acid sequence set forth in SEQ ID No: 4 b. The VL region comprising the amino acid sequence set forth in SEQ ID No: 8 c. The CH region comprising the amino acid sequence set forth in SEQ ID No: 29 and d. The CL region comprising the amino acid sequence set forth in SEQ ID No: 16.

In another embodiment the antibody according to the invention comprises:

a. The VH region comprising the amino acid sequence set forth in SEQ ID No: 4 b. The VL region comprising the amino acid sequence set forth in SEQ ID No: 8 c. The CH region comprising the amino acid sequence set forth in SEQ ID No: 30 and d. The CL region comprising the amino acid sequence set forth in SEQ ID No: 16.

In another embodiment the antibody according to the invention comprises:

a. The VH region comprising the amino acid sequence set forth in SEQ ID No: 4 b. The VL region comprising the amino acid sequence set forth in SEQ ID No: 8 c. The CH region comprising the amino acid sequence set forth in SEQ ID No: 31 and d. The CL region comprising the amino acid sequence set forth in SEQ ID No: 16.

In another embodiment the antibody according to the invention comprises:

a. The VH region comprising the amino acid sequence set forth in SEQ ID No: 4
b. The VL region comprising the amino acid sequence set forth in SEQ ID No: 8
c. The CH region comprising the amino acid sequence set forth in SEQ ID No: 32 and
d. The CL region comprising the amino acid sequence set forth in SEQ ID No: 16.

In another embodiment the antibody according to the invention comprises:

a. The VH region comprising the amino acid sequence set forth in SEQ ID No: 4
b. The VL region comprising the amino acid sequence set forth in SEQ ID No: 8
c. The CH region comprising the amino acid sequence set forth in SEQ ID No: 33 and
d. The CL region comprising the amino acid sequence set forth in SEQ ID No: 16.

In another embodiment the antibody according to the invention comprises:

a. The VH region comprising the amino acid sequence set forth in SEQ ID No: 4
b. The VL region comprising the amino acid sequence set forth in SEQ ID No: 8
c. The CH region comprising the amino acid sequence set forth in SEQ ID No: 34 and
d. The CL region comprising the amino acid sequence set forth in SEQ ID No: 16.

In another embodiment the antibody according to the invention comprises:

a. The VH region comprising the amino acid sequence set forth in SEQ ID No: 4
b. The VL region comprising the amino acid sequence set forth in SEQ ID No: 8
c. The CH region comprising the amino acid sequence set forth in SEQ ID No: 36 and
d. The CL region comprising the amino acid sequence set forth in SEQ ID No: 16.

In alternative embodiments of the above antibodies the CL region may be the amino acid sequence set forth in SEQ ID No: 17.

In an embodiment the antibody according to the invention comprises:

e. The VH region comprising the amino acid sequence set forth in SEQ ID No: 4
f. The VL region comprising the amino acid sequence set forth in SEQ ID No: 8
g. The CH region comprising the amino acid sequence set forth in SEQ ID No: 15 and
h. The CL region comprising the amino acid sequence set forth in SEQ ID No: 17.

In another embodiment the antibody according to the invention comprises:

e. The VH region comprising the amino acid sequence set forth in SEQ ID No: 4
f. The VL region comprising the amino acid sequence set forth in SEQ ID No: 8
g. The CH region comprising the amino acid sequence set forth in SEQ ID No: 12 and
h. The CL region comprising the amino acid sequence set forth in SEQ ID No: 17.

In another embodiment the antibody according to the invention comprises:

e. The VH region comprising the amino acid sequence set forth in SEQ ID No: 4
f. The VL region comprising the amino acid sequence set forth in SEQ ID No: 8
g. The CH region comprising the amino acid sequence set forth in SEQ ID No: 13 and
h. The CL region comprising the amino acid sequence set forth in SEQ ID No: 17.

In another embodiment the antibody according to the invention comprises:

e. The VH region comprising the amino acid sequence set forth in SEQ ID No: 4
f. The VL region comprising the amino acid sequence set forth in SEQ ID No: 8
g. The CH region comprising the amino acid sequence set forth in SEQ ID No: 14 and
h. The CL region comprising the amino acid sequence set forth in SEQ ID No: 17.

In another embodiment the antibody according to the invention comprises:

e. The VH region comprising the amino acid sequence set forth in SEQ ID No: 4
f. The VL region comprising the amino acid sequence set forth in SEQ ID No: 8
g. The CH region comprising the amino acid sequence set forth in SEQ ID No: 18 and
h. The CL region comprising the amino acid sequence set forth in SEQ ID No: 17.

In another embodiment the antibody according to the invention comprises:

e. The VH region comprising the amino acid sequence set forth in SEQ ID No: 4
f. The VL region comprising the amino acid sequence set forth in SEQ ID No: 8
g. The CH region comprising the amino acid sequence set forth in SEQ ID No: 19 and
h. The CL region comprising the amino acid sequence set forth in SEQ ID No: 17.

In another embodiment the antibody according to the invention comprises:

e. The VH region comprising the amino acid sequence set forth in SEQ ID No: 4
f. The VL region comprising the amino acid sequence set forth in SEQ ID No: 8
g. The CH region comprising the amino acid sequence set forth in SEQ ID No: 20 and
h. The CL region comprising the amino acid sequence set forth in SEQ ID No: 17.

In another embodiment the antibody according to the invention comprises:

e. The VH region comprising the amino acid sequence set forth in SEQ ID No: 4
f. The VL region comprising the amino acid sequence set forth in SEQ ID No: 8
g. The CH region comprising the amino acid sequence set forth in SEQ ID No: 21 and
h. The CL region comprising the amino acid sequence set forth in SEQ ID No: 17.

In another embodiment the antibody according to the invention comprises:

e. The VH region comprising the amino acid sequence set forth in SEQ ID No: 4
f. The VL region comprising the amino acid sequence set forth in SEQ ID No: 8
g. The CH region comprising the amino acid sequence set forth in SEQ ID No: 22 and
h. The CL region comprising the amino acid sequence set forth in SEQ ID No: 17.

In another embodiment the antibody according to the invention comprises:

e. The VH region comprising the amino acid sequence set forth in SEQ ID No: 4
f. The VL region comprising the amino acid sequence set forth in SEQ ID No: 8
g. The CH region comprising the amino acid sequence set forth in SEQ ID No: 23 and
h. The CL region comprising the amino acid sequence set forth in SEQ ID No: 17.

In another embodiment the antibody according to the invention comprises:

e. The VH region comprising the amino acid sequence set forth in SEQ ID No: 4
f. The VL region comprising the amino acid sequence set forth in SEQ ID No: 8
g. The CH region comprising the amino acid sequence set forth in SEQ ID No: 27 and
h. The CL region comprising the amino acid sequence set forth in SEQ ID No: 17.

In another embodiment the antibody according to the invention comprises:

e. The VH region comprising the amino acid sequence set forth in SEQ ID No: 4
f. The VL region comprising the amino acid sequence set forth in SEQ ID No: 8
g. The CH region comprising the amino acid sequence set forth in SEQ ID No: 28 and
h. The CL region comprising the amino acid sequence set forth in SEQ ID No: 17.

In another embodiment the antibody according to the invention comprises:

e. The VH region comprising the amino acid sequence set forth in SEQ ID No: 4
f. The VL region comprising the amino acid sequence set forth in SEQ ID No: 8
g. The CH region comprising the amino acid sequence set forth in SEQ ID No: 29 and
h. The CL region comprising the amino acid sequence set forth in SEQ ID No: 17.

In another embodiment the antibody according to the invention comprises:

e. The VH region comprising the amino acid sequence set forth in SEQ ID No: 4
f. The VL region comprising the amino acid sequence set forth in SEQ ID No: 8
g. The CH region comprising the amino acid sequence set forth in SEQ ID No: 30 and
h. The CL region comprising the amino acid sequence set forth in SEQ ID No: 17.

In another embodiment the antibody according to the invention comprises:

e. The VH region comprising the amino acid sequence set forth in SEQ ID No: 4
f. The VL region comprising the amino acid sequence set forth in SEQ ID No: 8
g. The CH region comprising the amino acid sequence set forth in SEQ ID No: 31 and
h. The CL region comprising the amino acid sequence set forth in SEQ ID No: 17.

In another embodiment the antibody according to the invention comprises:

e. The VH region comprising the amino acid sequence set forth in SEQ ID No: 4
f. The VL region comprising the amino acid sequence set forth in SEQ ID No: 8
g. The CH region comprising the amino acid sequence set forth in SEQ ID No: 32 and
h. The CL region comprising the amino acid sequence set forth in SEQ ID No: 17.

In another embodiment the antibody according to the invention comprises:

e. The VH region comprising the amino acid sequence set forth in SEQ ID No: 4
f. The VL region comprising the amino acid sequence set forth in SEQ ID No: 8
g. The CH region comprising the amino acid sequence set forth in SEQ ID No: 33 and
h. The CL region comprising the amino acid sequence set forth in SEQ ID No: 17.

In another embodiment the antibody according to the invention comprises:

e. The VH region comprising the amino acid sequence set forth in SEQ ID No: 4
f. The VL region comprising the amino acid sequence set forth in SEQ ID No: 8
g. The CH region comprising the amino acid sequence set forth in SEQ ID No: 34 and
h. The CL region comprising the amino acid sequence set forth in SEQ ID No: 17.

In another embodiment the antibody according to the invention comprises:

e. The VH region comprising the amino acid sequence set forth in SEQ ID No: 4
f. The VL region comprising the amino acid sequence set forth in SEQ ID No: 8
g. The CH region comprising the amino acid sequence set forth in SEQ ID No: 36 and
h. The CL region comprising the amino acid sequence set forth in SEQ ID No: 17.

In another embodiment the antibody according to the invention comprises a heavy chain comprising the amino acid sequence set forth in SEQ ID NO: 24 and a light chain comprising the amino acid sequence set forth in SEQ ID NO: 25.

In another embodiment the antibody according to the invention comprises a heavy chain comprising the amino acid sequence set forth in SEQ ID NO: 35 and a light chain comprising the amino acid sequence set forth in SEQ ID NO: 25.

In yet another aspect the invention provides an antibody which comprises a heavy chain constant region that is modified so that the antibody induces an Fc-mediated effector function to a lesser extent relative to an identical antibody except for the modification. An example hereof is the CD27 binding antibody of the invention comprising a P329R and an E345R substitution. Such antibody induces one or more Fc-mediated effector function(s) to a lesser extent compared to the antibody comprising the same sequence except not comprising the P329R substitution and also compared to the same antibody comprising the same sequence except not comprising the P329R and E345R substitutions, such as a wildtype IgG1 heavy chain. In one embodiment the Fc-mediated effector function is decreased by at least 20%. In another aspect the Fc-mediated effector function is decreased by at least 30%. In another aspect the Fc-mediated effector function is decreased by at least 40%. In another aspect the Fc-mediated effector function is decreased by at least 50%. In another aspect the Fc-mediated effector function is decreased by at least 60%. In another aspect the Fc-mediated effector function is decreased by at least 70%. In another aspect the Fc-mediated effector function is decreased by at least 80%. In another aspect the Fc-mediated effector function is decreased by at least 90%. In another aspect the antibody does not induce one or more Fc-mediated effector functions. The one or more Fc-effector functions that are decreased or not at all induced may be selected from the following group: complement-dependent cytotoxicity (CDC), complement-dependent cell-mediated cytotoxicity (CDCC), complement activation, antibody-dependent cell-mediated cytotoxicity (ADCC), antibody-dependent cell-mediated phagocytosis (ADCP), C1q binding and FcγR binding. Accordingly, in one embodiment the antibody of the invention induces CDC to a degree which is decreased by at least 20%, such as at least 30%, or at least 40%, or at least 50%, or at least 60%, or at least 70%, or at least 80%, or decreased by at least 90% relative to the identical antibody but a wildtype IgG1 HC constant region. In another embodiment the antibody of the invention does not induce CDC.

In another aspect, the antibody of the invention induces CDCC to a degree which is decreased by at least 20%, such as at least 30%, or at least 40%, or at least 50%, or at least 60%, or at least 70%, or at least 80%, or decreased by at least 90% relative to the identical antibody but having a wildtype IgG1 HC constant region. In another embodiment the antibody of the invention does not induce CDCC.

In another aspect, the antibody of the invention induces ADCC to a degree which is decreased by at least 20%, such as at least 30%, or at least 40%, or at least 50%, or at least 60%, or at least 70%, or at least 80%, or decreased by at least 90% relative to the identical antibody but having a wildtype IgG1 HC constant region. In another embodiment the antibody of the invention does not induce ADCC.

In another aspect, the antibody of the invention induces ADCP to a degree which is decreased by at least 20%, such as at least 30%, or at least 40%, or at least 50%, or at least 60%, or at least 70%, or at least 80%, or decreased by at least 90% relative to the identical antibody but having a wildtype IgG1 HC constant region. In another embodiment the antibody of the invention does not induce ADCP.

In another aspect, the antibody of the invention induces C1q binding to a degree which is decreased by at least 20%, such as at least 30%, or at least 40%, or at least 50%, or at least 60%, or at least 70%, or at least 80%, or decreased by at least 90% relative to the identical antibody but having a wildtype IgG1 HC constant region. In another embodiment the antibody of the invention does not induce C1q binding.

Preferably the C1q binding is determined as in example 8.

In another aspect, the antibody of the invention induces FcγR binding to a degree which is decreased by at least 20%, such as at least 30%, or at least 40%, or at least 50%, or at least 60%, or at least 70%, or at least 80%, or decreased by at least 90% relative to the identical antibody but having a wildtype IgG1 HC constant region. In another embodiment the antibody of the invention does not induce FcγR binding. Preferably the FcγR binding is determined as in example 9.

In one embodiment the antibody of the invention has reduced C1q binding and reduced FcγR binding compared to the antibody comprising the same amino acid sequences except not comprising the P329R substitution.

In one embodiment, the antibody according to any aspect or embodiment herein is, except for the recited mutations, a human antibody.

In an embodiment of the invention the antibody is a monovalent antibody.

In another embodiment the antibody is a bivalent antibody.

Further, the antibody of the invention may be a monospecific antibody.

In one embodiment, the antibody according to any aspect or embodiment herein is a monoclonal antibody, such as a human monoclonal antibody, such as a human bivalent monoclonal antibody, such as a human bivalent full-length monoclonal antibody.

In a preferred embodiment, the antibody according to any aspect or embodiment herein is, except for the optional recited mutations in the Fc region, an IgG1 antibody, such as a full length IgG1 antibody, such as a human full-length IgG1 antibody, optionally a human monoclonal full-length bivalent IgG1,κ antibody, e.g. a human monoclonal full-length bivalent IgG1m(f),κ antibody.

An antibody according to the present invention is advantageously in a bivalent monospecific format, comprising two antigen-binding regions binding to the same epitope. However, bispecific formats where one of the antigen-binding regions binds to a different epitope are also contemplated. So, the antibody according to any aspect or embodiment herein can, unless contradicted by context, be either a monospecific antibody or a bispecific antibody.

Accordingly, in another embodiment, the antibody of the invention is a bispecific antibody comprising a first antigen binding region capable of binding human CD27 as described herein and comprising a second antigen binding region capable of binding to a different epitope on human CD27. In another embodiment, the antibody of the invention is a bispecific antibody comprising a first antigen binding region capable of binding human CD27 as described herein and comprising a second antigen binding region capable of binding a different target. Such target may be on a different cell or on the same cell as CD27.

In an aspect of the invention the antibody is capable of binding to human CD27 having the sequence as set forth in SEQ ID NO: 1. However, human CD27 may in some individuals be expressed as a variant hereof. Thus, in another aspect the antibody of the invention is further capable of binding to a human CD27 variant, such as for example the human CD27 variant as set forth in SEQ ID NO: 2. In another embodiment, the antibody of the invention if further capable of binding to cynomolgus CD27, such as set forth in SEQ ID NO: 3.

In a further embodiment of the invention the antibody is capable of binding CD27-expressing human T cells.

In another embodiment of the invention the antibody is capable of binding CD27-expressing cynomolgus T cells.

In one embodiment of the invention the full length IgG1 antibody has had the C-terminal Lysine of the HC cleaved off. Such an antibody is also considered a "full length antibody".

In another embodiment of the invention the antibody is capable of inducing proliferation of human T cells such as $CD4^+$ and $CD8^+$ T-cells, such as T helper cells and cytotoxic T cells. Such activity may be assayed as described in Example 6 or 7 herein.

In another embodiment of the invention the antibody is capable of inducing activation of human CD27-expressing Jurkat reporter T cells such as described in Example 2 herein.

In another embodiment of the invention the antibody is capable of inducing activation of human CD27-expressing Jurkat reporter T cells in the absence of Fcγ receptor IIb cross-linking such as described in Example 11 herein.

In another embodiment of the invention the antibody is capable of inducing proliferation of CD4+ and $CD8^+$ T cells with a central memory T cell phenotype.

In another embodiment of the invention the antibody is capable of inducing IFN gamma production.

Antibodies are well known as therapeutics which may be used in treatment of various diseases. Another method for administration of an antibody to a subject in need thereof includes administration of a nucleic acid or a combination of nucleic acids encoding said antibody for in vivo expression of said antibody.

Hence, in one aspect, the present invention also relates to a nucleic acid encoding the heavy chain of an antibody according to the present invention, wherein said heavy chain comprises a VH region comprising a VH CDR1 comprising the sequence as set forth in SEQ ID NO:5, a VH CDR2 comprising the sequence as set forth in SEQ ID NO:6, a VH CDR3 comprising the sequence as set forth in SEQ ID NO:7 and a human IgG1 CH region.

In another aspect, the present invention also relates to a nucleic acid encoding the heavy chain of an antibody according to the present invention, wherein said heavy chain comprises a VH region comprising a VH CDR1 comprising the sequence as set forth in SEQ ID NO:5, a VH CDR2 comprising the sequence as set forth in SEQ ID NO:6, a VH CDR3 comprising the sequence as set forth in SEQ ID NO:7 and a human IgG1 CH region with a mutation in one or both of E430 and E345, the amino acid residues being numbered according to the Eu index.

In another aspect, the present invention also relates to a nucleic acid encoding the heavy chain of an antibody according to the present invention, wherein said heavy chain comprises a VH region comprising a VH CDR1 comprising the sequence as set forth in SEQ ID NO:5, a VH CDR2 comprising the sequence as set forth in SEQ ID NO:6, a VH CDR3 comprising the sequence as set forth in SEQ ID NO:7 and a human IgG1 CH region with a mutation in one or both of P329 and E345, the amino acid residues being numbered according to the Eu index.

In one aspect the present invention also relates to a nucleic acid or a combination of nucleic acids, encoding an antibody according to the present invention.

In some embodiments the present invention relates to a nucleic acid or a combination of nucleic acids encoding an antibody comprising:

a) an antigen-binding region comprising a VH CDR1 comprising the sequence as set forth in SEQ ID NO:5, a VH CDR2 comprising the sequence as set forth in SEQ ID NO:6, a VH CDR3 comprising the sequence as set forth in SEQ ID NO:7, a VL CDR1 comprising the sequence as set forth in SEQ ID NO:9, a VL CDR2 comprising the sequence as set forth in SEQ ID NO:10, and a VL CDR3 comprising the sequence as set forth in SEQ ID NO:11, and
b) a variant Fc region comprising a mutation in one or both amino acids corresponding to P329 and E345 and in a human IgG1 heavy chain, wherein the amino acid residues are numbered according to the Eu index.

In one embodiment, the antibody of the present invention is encoded by one nucleic acid. Thus, the nucleotide sequences encoding the antibody of the present invention are present in one nucleic acid sequence or the same nucleic acid molecule.

In another embodiment the antibody of the present invention is encoded by a combination of nucleic acid sequences, typically by two nucleic acid sequences. In one embodiment said combination of nucleic acid sequences comprise a nucleic acid sequence encoding the heavy chain of said antibody and a nucleic acid sequence encoding the light chain of said antibody.

In some embodiments the present invention relates to a nucleic acid sequence or a combination of nucleic acid sequences encoding an antibody comprising:

a) a heavy chain comprising a VH region comprising a VH CDR1 comprising the sequence as set forth in SEQ ID NO:5, a VH CDR2 comprising the sequence as set forth in SEQ ID NO:6, a VH CDR3 comprising the sequence as set forth in SEQ ID NO:7 and a human IgG1 CH region comprising a mutation in one or both of P329 and E345, the amino acid residues being numbered according to the Eu index;
b) a light chain comprising a VL region comprising a VL CDR1 comprising the sequence as set forth in SEQ ID NO:9, a VL CDR2 comprising the sequence as set forth in SEQ ID NO:10, and a VL CDR3 comprising the sequence as set forth in SEQ ID NO:11.

In one embodiment, the antibody of the present invention is encoded by one nucleic acid. Thus, the nucleotide sequences encoding the antibody of the present invention are present in one nucleic acid or the same nucleic acid molecule.

In another embodiment the antibody of the present invention is encoded by a combination of nucleic acid sequences, typically by two nucleic acid sequences. In one embodiment said combination of nucleic acid sequences comprise a nucleic acid sequence encoding the heavy chain of said antibody and a nucleic acid sequence encoding the light chain of said antibody.

As described above the nucleic acid sequences may be used as a mean for supplying therapeutic proteins, such as antibodies, to a subject in need thereof.

In some embodiments, said nucleic acid may be deoxyribonucleic acid (DNA). DNAs and methods of preparing DNA suitable for in vivo expression of therapeutic proteins, such as antibodies are well known to a person skilled in the art and include but is not limited to that described by Patel A et al., 2018, Cell Reports 25, 1982-1993.

In some embodiments, said nucleic acid may be ribonucleic acid (RNA), such as messenger RNA (mRNA). In some embodiments, the mRNA may comprise only naturally occurring nucleotides. In some embodiments the mRNA may comprise modified nucleotides, wherein modified refers to said nucleotides being chemically different from the naturally occurring nucleotides. In some embodiments the mRNA may comprise both naturally occurring and modified nucleotides.

Different nucleic acid sequences suitable for in vivo expression of therapeutic proteins, such as antibodies, in a subject are well known to a person skilled in the art. For example, a mRNA suitable for expression of a therapeutic antibody in a subject, often comprise an Open Reading Frame (ORF), flanked by Untranslated Regions (UTRs) comprising specific sequences, and 5' and 3'-ends being formed by a cap structure and a poly(A)tail (see e.g. Schlake et al., 2019, Molecular Therapy Vol. 27 No 4 April).

Examples of methods for optimization of RNA and RNA molecules suitable, e.g. mRNA, for in vivo expression include, but are not limited to those described in U.S. Pat. Nos. 9,254,311; 9,221,891; US20160185840 and EP3118224.

Naked nucleic acid sequence(s) which are administered to a subject for in vivo expression are prone to degradation and/or of causing an immunogenic response in the subject. Furthermore, for in vivo expression of the antibody encoded by the nucleic acid sequences said nucleic acid sequences typically is administered in a form suitable for the nucleic acid sequences to enter the cells of the subject. Different methods for delivering a nucleic acid sequence for in vivo expression exist and include both methods involving mechanical and chemical means. For example, such methods may involve electroporation or tattooing the nucleic acid onto the skin (Patel et al., 2018, Cell Reports 25, 1982-1993). Other methods suitable for administration of the nucleic acid sequences to a subject involve administration of the nucleic acid in a suitable formulation. Thus, the present invention also relates to a delivery vehicle comprising a nucleic acid of the present invention.

In some embodiments, said delivery vehicle may comprise a nucleic acid sequence encoding a heavy chain of an antibody according to the present invention. Thus in one embodiment said nucleic acid sequence may encode a heavy chain comprising a VH region comprising a VH CDR1 comprising the sequence as set forth in SEQ ID NO:5, a VH CDR2 comprising the sequence as set forth in SEQ ID NO:6, a VH CDR3 comprising the sequence as set forth in SEQ ID NO:7 and a human IgG1 CH region with a mutation in one or both of P329 and E345, the amino acid residues being numbered according to the Eu index.

In some embodiments, the present invention also relates to a delivery vehicle comprising a nucleic acid sequence encoding a light chain of an antibody according to the present invention. Thus, in one embodiment said nucleic acid sequence may encode a light chain comprising a VL region comprising a VL CDR1 comprising the sequence as set forth in SEQ ID NO:9, a VL CDR2 comprising the sequence as set forth in SEQ ID NO:10, and a VL CDR3 comprising the sequence as set forth in SEQ ID NO:11.

The present invention also relates to a mixture of delivery vehicles comprising a delivery vehicle comprising a nucleic acid sequence encoding a heavy chain of an antibody according to the present invention and delivery vehicle comprising a nucleic acid sequence encoding a light chain of an antibody according to the present invention. Thus in one embodiment said mixture of delivery vehicles comprise a delivery vehicle comprising a nucleic acid sequence encoding a heavy chain comprising a VH region comprising a VH CDR1 comprising the sequence as set forth in SEQ ID NO:5, a VH CDR2 comprising the sequence as set forth in SEQ ID NO:6, a VH CDR3 comprising the sequence as set forth in SEQ ID NO:7 and a human IgG1 CH region with a mutation in one or both of E430 and E345, the amino acid residues being numbered according to the Eu index; and a delivery vehicle comprising a nucleic acid sequence encoding a light chain comprising a VL region comprising a VL CDR1 comprising the sequence as set forth in SEQ ID NO:9, a VL CDR2 comprising the sequence as set forth in SEQ ID NO:10, and a VL CDR3 comprising the sequence as set forth in SEQ ID NO:11.

In some embodiments, said delivery vehicle comprises a nucleic acid sequence or a combination of nucleic acid sequences encoding the heavy and a nucleic light chain of an antibody according to the present invention.

Thus in one embodiment said delivery vehicle may comprise a nucleic acid sequence encoding a heavy chain comprising a VH region comprising a VH CDR1 comprising the sequence as set forth in SEQ ID NO:5, a VH CDR2 comprising the sequence as set forth in SEQ ID NO:6, a VH CDR3 comprising the sequence as set forth in SEQ ID NO:7 and a human IgG1 CH region with a mutation in one or both of E430 and E345 the amino acid residues being numbered according to the Eu index; and a light chain comprising a VL region comprising a VL CDR1 comprising the sequence as set forth in SEQ ID NO:9, a VL CDR2 comprising the sequence as set forth in SEQ ID NO:10, and a VL CDR3 comprising the sequence as set forth in SEQ ID NO:11.

In yet an embodiment said delivery vehicle may comprise a nucleic acid sequence encoding a heavy chain comprising a VH region comprising a VH CDR1 comprising the sequence as set forth in SEQ ID NO:5, a VH CDR2 comprising the sequence as set forth in SEQ ID NO:6, a VH CDR3 comprising the sequence as set forth in SEQ ID NO:7 and a human IgG1 CH region with the mutations P329R and E345R the amino acid residues being numbered according to the Eu index; and a light chain comprising a VL region comprising a VL CDR1 comprising the sequence as set forth in SEQ ID NO:9, a VL CDR2 comprising the sequence as set forth in SEQ ID NO:10, and a VL CDR3 comprising the sequence as set forth in SEQ ID NO:11.

In another embodiment said delivery vehicle may comprise a nucleic acid sequence encoding a heavy chain comprising a VH region comprising a VH CDR1 comprising the sequence as set forth in SEQ ID NO:5, a VH CDR2 comprising the sequence as set forth in SEQ ID NO:6, a VH CDR3 comprising the sequence as set forth in SEQ ID NO:7 and a WT human IgG1 CH region; and a light chain comprising a VL region comprising a VL CDR1 comprising the sequence as set forth in SEQ ID NO:9, a VL CDR2 comprising the sequence as set forth in SEQ ID NO:10, and a VL CDR3 comprising the sequence as set forth in SEQ ID NO:11.

Thus, the nucleic acid sequences encoding the heavy and light chain of the antibody according to the present invention are present in one (the same) nucleic acid molecule.

In another embodiment said delivery vehicle may comprise a nucleic acid sequence encoding a heavy chain comprising a VH region comprising a VH CDR1 comprising the sequence as set forth in SEQ ID NO:5, a VH CDR2 comprising the sequence as set forth in SEQ ID NO:6, a VH CDR3 comprising the sequence as set forth in SEQ ID NO:7 and a WT human IgG1 CH region; and a nucleic acid encoding a light chain comprising a VL region comprising a VL CDR1 comprising the sequence as set forth in SEQ ID NO:9, a VL CDR2 comprising the sequence as set forth in SEQ ID NO:10, and a VL CDR3 comprising the sequence as set forth in SEQ ID NO:11.

In another embodiment said delivery vehicle may comprise a nucleic acid sequence encoding a heavy chain comprising a VH region comprising a VH CDR1 comprising the sequence as set forth in SEQ ID NO:5, a VH CDR2 comprising the sequence as set forth in SEQ ID NO:6, a VH CDR3 comprising the sequence as set forth in SEQ ID NO:7 and a human IgG1 CH region with a mutation in one or both of E430 and E345 the amino acid residues being numbered according to the Eu index; and a nucleic acid sequence encoding a light chain comprising a VL region comprising a VL CDR1 comprising the sequence as set forth in SEQ ID NO:9, a VL CDR2 comprising the sequence as set forth in SEQ ID NO:10, and a VL CDR3 comprising the sequence as set forth in SEQ ID NO:11.

In another embodiment said delivery vehicle may comprise a nucleic acid sequence encoding a heavy chain comprising a VH region comprising a VH CDR1 comprising the sequence as set forth in SEQ ID NO:5, a VH CDR2 comprising the sequence as set forth in SEQ ID NO:6, a VH CDR3 comprising the sequence as set forth in SEQ ID NO:7 and a human IgG1 CH region with the mutations of P329R and E345R the amino acid residues being numbered according to the Eu index; and a nucleic acid sequence encoding a light chain comprising a VL region comprising a VL CDR1 comprising the sequence as set forth in SEQ ID NO:9, a VL CDR2 comprising the sequence as set forth in SEQ ID NO:10, and a VL CDR3 comprising the sequence as set forth in SEQ ID NO:11.

Thus, the nucleic acid sequences encoding the heavy and light chain of the antibody variant according to the present invention are present on separate or different nucleic acid molecules.

In some embodiments said delivery vehicle may be a lipid formulation. The lipids of the formulation may particle(s), such as a lipid nanoparticle(s) (LNPs). The nucleic acid sequence or combination of nucleic acid sequences of the present may be encapsulated within said particle, e.g. within said LNP.

Different lipid formulations suitable for administration of a nucleic acid to a subject for in vivo expression are well known to a person skilled in the art. For example, said lipid formulation may typically comprise lipids, ionizable amino lipids, PEG-lipids, cholesterol or any combination thereof.

Various forms and methods for preparation of lipid formulations suitable for administration of a nucleic acid sequence to a subject for expression of a therapeutic antibody are well known in the art. Examples of such lipid formulations include but are not limited to those described in US20180170866 (Arcturus), EP 2391343 (Arbutus), WO 2018/006052 (Protiva), WO2014152774 (Shire Human Genetics), EP 2 972 360 (Translate Bio), U.S. Ser. No. 10/195,156 (Moderna), and US20190022247 (Acuitas).

The invention also provides isolated nucleic acid sequences and vectors encoding an antibody variant according to any one of the aspects and embodiments described herein, as well as vectors and expression systems encoding the variants. Suitable nucleic acid constructs, vectors and expression systems for antibodies and variants thereof are known in the art, and include, but are not limited to, those described in the Examples. In embodiments where the variant antibody comprises HC and LC that are separate polypeptides rather than contained in a single polypeptide (e.g., as in a scFv-Fc fusion protein), the nucleotide sequences encoding the heavy and light chains may be present in the same or different nucleic acids or vectors.

Accordingly, in one aspect the invention provides an isolated nucleic acid sequence or a combination of nucleic acid sequences encoding the antibody according to any aspect or embodiment herein. The invention also provides a nucleic acid sequence encoding a VH region comprising a VH CDR1 comprising the sequence as set forth in SEQ ID NO:5, a VH CDR2 comprising the sequence as set forth in SEQ ID NO:6, a VH CDR3 comprising the sequence as set forth in SEQ ID NO:7.

Further, the invention provides a nucleic acid sequence encoding a VL region comprising a VL CDR1 comprising the sequence as set forth in SEQ ID NO:9, a VL CDR2 comprising the sequence as set forth in SEQ ID NO:10, a VL CDR3 comprising the sequence as set forth in SEQ ID NO:11.

Further, the invention provides a nucleic acid sequence encoding a VH region comprising the amino acid sequence as set forth in SEQ ID NO: 4. The invention also relates to a nucleic acid sequence encoding a VL region comprising the amino acid sequence as set forth in SEQ ID NO: 8.

In a further aspect the invention provides a nucleic acid sequence encoding the heavy chain of the antibody according to any aspect or embodiment descried herein. In a further aspect the invention provides a nucleic acid sequence encoding the light chain of the antibody according to any aspect or embodiment descried herein. In another aspect the invention relates to a nucleic acid sequence encoding a heavy chain comprising a VH region comprising the sequence as set forth in SEQ ID NO:4 and a human IgG1 CH region comprising a mutation of P329 and/or of E345, with the amino acid residues being numbered according to the Eu index. In yet another aspect the invention provides a nucleic acid sequence encoding a light chain comprising a VL region comprising the sequence as set forth in SEQ ID NO:8 and a human kappa constant region comprising the sequence as set forth in SEQ ID NO:16. In yet another aspect the invention provides a nucleic acid sequence encoding a light chain comprising a VL region comprising the sequence as set forth in SEQ ID NO:8 and a human lambda constant region comprising the sequence as set forth in SEQ ID NO:17.

In an embodiment of the invention the nucleic acid sequence or combination of nucleic acid sequences are RNA or DNA. In an embodiment of the invention the nucleic acid sequence or combination of nucleic acid sequences is/are mRNA.

The invention further provides an expression vector comprising the nucleic acid sequence or combination thereof according to any aspect or embodiment described herein.

In another aspect the invention relates to a nucleic acid sequence or a combination of nucleic acid sequences as described herein for use in expression in mammalian cells.

In a further embodiment the invention relates to a recombinant host cell, which produces an antibody as defined herein, optionally wherein the host cell comprises the expression vector described above. In certain embodiments the recombinant host cell is a eukaryotic or prokaryotic cell.

In another aspect the invention relates to a method of producing an antibody according to any aspect or embodiment herein, comprising cultivating the recombinant host cell as described above in a culture medium and under conditions suitable for producing the antibody and, optionally, purifying or isolating the antibody from the culture medium.

In one aspect, the invention relates to a nucleic acid or an expression vector comprising (i) a nucleotide sequence encoding a heavy chain sequence of an antibody according to any one of the embodiments disclosed herein;
(ii) a nucleotide sequence encoding a light chain sequence of an antibody according to any one of the embodiments disclosed herein; or
(iii) both (i) and (ii).

In one aspect, the invention relates to a nucleic acid or an expression vector comprising a nucleotide sequence encoding a heavy chain sequence of an antibody variant according to any one of the embodiments disclosed herein.

In one aspect, the invention relates to a nucleic acid sequence or an expression vector comprising a nucleotide sequence encoding a heavy chain sequence and a light chain sequence of an antibody according to any one of the embodiments disclosed herein.

In one aspect, the invention relates to a combination of a first and a second nucleic acid or a combination of a first and second expression vector, optionally in the same host cell, where the first comprises a nucleotide sequence according to (i), and the second comprises a nucleotide sequence according to (ii).

An expression vector in the context of the present invention may be any suitable vector, including chromosomal, non-chromosomal, and synthetic nucleic acid vectors (a nucleic acid sequence comprising a suitable set of expression control elements). Examples of such vectors include derivatives of SV40, bacterial plasmids, phage DNA, baculovirus, yeast plasmids, vectors derived from combinations of plasmids and phage DNA, and viral nucleic acid (RNA or DNA) vectors. In one embodiment, a nucleic acid is comprised in a naked DNA or RNA vector, including, for example, a linear expression element (as described in for instance Sykes and Johnston, Nat Biotech 17, 355 59 (1997)), a compacted nucleic acid vector (as described in for instance U.S. Pat. No. 6,077,835 and/or WO 00/70087), a plasmid vector such as pBR322, pUC 19/18, or pUC 118/119, a "midge" minimally-sized nucleic acid vector (as described in for instance Schakowski et al., Mol Ther 3, 793 800 (2001)), or as a precipitated nucleic acid vector construct, such as a CaP04-precipitated construct (as described in for instance WO200046147, Benvenisty and Reshef, PNAS USA 83, 9551 55 (1986), Wigler et al., Cell 14, 725 (1978), and Coraro and Pearson, Somatic Cell Genetics 7, 603 (1981)). Such nucleic acid vectors and the usage thereof are well known in the art (see for instance U.S. Pat. Nos. 5,589,466 and 5,973,972).

In one embodiment, the vector is suitable for expression of the antibody in a bacterial cell. Examples of such vectors include expression vectors such as BlueScript (Stratagene), pIN vectors (Van Heeke & Schuster, J Biol Chem 264, 5503 5509 (1989), pET vectors (Novagen, Madison WI) and the like).

An expression vector may also or alternatively be a vector suitable for expression in a yeast system. Any vector suitable for expression in a yeast system may be employed. Suitable vectors include, for example, vectors comprising constitutive or inducible promoters such as alpha factor, alcohol oxidase and PGH (reviewed in: F. Ausubel et al., ed. Current Protocols in Molecular Biology, Greene Publishing and Wiley InterScience New York (1987), and Grant et al., Methods in Enzymol 153, 516 544 (1987)).

An expression vector may also or alternatively be a vector suitable for expression in mammalian cells, e.g. a vector comprising glutamine synthetase as a selectable marker, such as the vectors described in Bebbington (1992) Biotechnology (NY) 10:169-175.

A nucleic acid and/or vector may also comprise a nucleic acid sequence encoding a secretion/localization sequence, which can target a polypeptide, such as a nascent polypeptide chain, to the periplasmic space or into cell culture media. Such sequences are known in the art and include secretion leader or signal peptides.

The expression vector may comprise or be associated with any suitable promoter, enhancer, and other expression-facilitating elements. Examples of such elements include strong expression promoters (e.g., human CMV IE promoter/enhancer as well as RSV, SV40, SL3 3, MMTV, and HIV LTR promoters), effective poly (A) termination sequences, an origin of replication for plasmid product in *E. coli*, an antibiotic resistance gene as selectable marker, and/or a convenient cloning site (e.g., a polylinker). Nucleic acids may also comprise an inducible promoter as opposed to a constitutive promoter such as CMV IE.

In one embodiment, the antibody-encoding expression vector may be positioned in and/or delivered to the host cell or host animal via a viral vector.

The invention also provides a recombinant host cell which produces an antibody as disclosed herein, optionally wherein the host cell comprises the isolated nucleic acid(s) or vector(s) according to the present invention. Typically, the host cell has been transformed or transfected with the nucleic acid(s) or vector(s). The recombinant host cell of claim can be, for example, a eukaryotic cell, a prokaryotic cell, or a microbial cell, e.g., a transfectoma. In a particular embodiment the host cell is a eukaryotic cell. In a particular embodiment the host cell is a prokaryotic cell. In some embodiments, the antibody is a heavy-chain antibody. In most embodiments, however, the antibody will contain both a heavy and a light chain and thus said host cell expresses both heavy- and light-chain-encoding construct, either on the same or a different vector.

Examples of host cells include yeast, bacterial, plant and mammalian cells, such as CHO, CHO—S, HEK, HEK293, HEK-293F, Expi293F, PER.C6, NS0 cells, Sp2/0 cells or lymphocytic cells. In one embodiment the host cell is a CHO (Chinese Hamster Ovary) cell. For example, in one embodiment, the host cell may comprise a first and second nucleic acid construct stably integrated into the cellular genome, wherein the first encodes the heavy chain and the second encodes the light chain of an antibody variant as disclosed herein. In another embodiment, the present invention provides a cell comprising a non-integrated nucleic acid, such as a plasmid, cosmid, phagemid, or linear expression element, which comprises a first and second nucleic acid construct as specified above.

In one embodiment, said host cell is a cell which is capable of Asn-linked glycosylation of proteins, e.g. a eukaryotic cell, such as a mammalian cell, e.g. a human cell.

In one embodiment, said host cell is a host cell which is not capable of efficiently removing C-terminal lysine K447 residues from antibody heavy chains. For example, Table 2 in Liu et al. (2008) J Pharm Sci 97: 2426 (incorporated herein by reference) lists a number of such antibody production systems, e.g. Sp2/0, NS/0 or transgenic mammary gland (goat), wherein only partial removal of C-terminal lysines is obtained. In one embodiment, the host cell is a host cell with altered glycosylation machinery. Such cells have been described in the art and can be used as host cells in which to express variants of the invention to thereby produce an antibody with altered glycosylation. See, for example, Shields, R. L. et al. (2002) J. Biol. Chem. 277: 26733-26740; Umana et al. (1999) Nat. Biotech. 17:176-1, as well as EP1176195; WO03/035835; and WO99/54342. Additional methods for generating engineered glycoforms are known in the art, and include but are not limited to those described in Davies et al., 2001, Biotechnol Bioeng 74:288-294; Shields et al, 2002, J Biol Chem 277:26733-26740; Shinkawa et al., 2003, J Biol Chem 278:3466-3473), U.S. Pat. No. 6,602,684, WO00/61739A1; WO01/292246A1; WO02/311140A1; WO 02/30954A1; Potelligent™ technology (Biowa, Inc. Princeton, N.J.); GlycoMAb™ glycosylation engineering technology (GLYCART biotechnology AG, Zurich, Switzerland); US 20030115614; Okazaki et al., 2004, JMB, 336: 1239-49, as well as those described in WO2018/114877 WO2018/114878 and WO2018/114879.

In an even further aspect, the invention relates to a transgenic non-human animal or plant comprising nucleic acids encoding one or two sets of a human heavy chain and a human light chain, wherein the animal or plant produces an antibody as disclosed herein.

In one embodiment, there is provided an antibody obtained or obtainable by the method described above.

In another aspect, the present invention also relates to a method of increasing or decreasing at least one effector function of an antibody of the invention comprising introducing a mutation into the antibody in one or more amino acid residue(s) corresponding to E430, E345, and P329 in the Fc region of a human IgG1 heavy chain, numbered according to the Eu-index.

So, in certain embodiments, there is provided a method of increasing an effector function of a parent antibody, such as an Fc-mediated effector function or such as increasing the biological activity of the antibody, such as CD27 agonism, said parent antibody comprising an Fc region and an antigen-binding region binding to CD27, which method comprises introducing into the Fc region a mutation in one or both amino acid residues corresponding to E430 and E345 in the Fc region of a human IgG1 heavy chain, wherein the amino acid residues are numbered according to the Eu index; and wherein the antigen-binding region comprises a VH CDR1 comprising the sequence as set forth in SEQ ID NO:5, a VH CDR2 comprising the sequence as set forth in SEQ ID NO:6, a VH CDR3 comprising the sequence as set forth in SEQ ID NO:7, a VL CDR1 comprising the sequence as set forth in SEQ ID NO:9, a VL CDR2 comprising the sequence as set forth in SEQ ID NO:10, and a VL CDR3 comprising the sequence as set forth in SEQ ID NO:11.

In other certain embodiments, there is provided a method of decreasing an effector function, such as C1q binding or FcgR binding, of a parent antibody comprising a VH CDR1 comprising the sequence as set forth in SEQ ID NO:5, a VH CDR2 comprising the sequence as set forth in SEQ ID NO:6, a VH CDR3 comprising the sequence as set forth in SEQ ID NO:7, a VL CDR1 comprising the sequence as set forth in SEQ ID NO:9, a VL CDR2 comprising the sequence as set forth in SEQ ID NO:10, and a VL CDR3 comprising the sequence as set forth in SEQ ID NO:11 and further comprising an amino acid substitution of E345R in the Fc region of a human IgG1 heavy chain, wherein the amino acid residues are numbered according to the Eu index, the method comprising introducing a further amino acid substitution in the Fc region at the amino acid position corresponding to P329 of a human IgG1 heavy chain, numbered according to the Eu-index. In a preferred embodiment of the invention the method comprises the substitution of P329R. Hereby an effector function of the parent antibody, such as C1q binding or FcgR binding may be decreased or may be completely eliminated.

In one embodiment of any one of the aforementioned methods, the effector function which is increased comprises CD27 agonism.

In one embodiment of any one of the aforementioned methods, the effector function is C1q binding.

In one embodiment of any one of the aforementioned methods, the effector function is FcgR binding.

In one embodiment of any one of the aforementioned methods, the effector functions that are decreased comprises both C1q- and FcgR binding.

In one embodiment of any of the aforementioned methods, the mutation in the one or more amino acid residues is selected from the group comprising: E430G, E430S, E430F, E430T, E345K, E345Q, E345R, E345Y and P329K. For example, the mutation in the one or more amino acid residue(s) may comprise or consist of E430G or E345R.

In one embodiment of any of the aforementioned methods, the Fc region of the antibody is, apart from the recited mutation(s), a human IgG1, IgG2, IgG3 or IgG4 Fc region, or an isotype mixture thereof. Optionally comprising an Fc region of one of the sequences set forth as SEQ ID NO:12, SEQ ID NO:13, SEQ ID NO:14, SEQ ID NO:15, SEQ ID NO:18, SEQ ID NO:19, SEQ ID NO:20, SEQ ID NO:21, SEQ ID NO:22, SEQ ID NO:23, SEQ ID NO:27, SEQ ID NO:28, SEQ ID NO:29, SEQ ID NO:30, SEQ ID NO:31, SEQ ID NO:32, SEQ ID NO:33, SEQ ID NO:34, and SEQ ID NO:36. In a particular embodiment, the Fc region of the antibody is a human IgG1 Fc region. For example, the antibody can be a human full-length IgG1 antibody, optionally a human monoclonal full-length bivalent IgG1,K antibody. Additionally, the antibody can be a monospecific or bispecific antibody, such as a monospecific antibody.

While the Fc region of the antibody may be a naturally occurring (wild-type) sequence, in some embodiments, the Fc region of the antibody comprises one or more further mutations, as described elsewhere herein.

The present invention also relates to an antibody obtained or obtainable according to any of the above described methods.

The present invention also relates to a composition comprising an antibody according to the present invention, a nucleic acid according to the present invention, an expression vector according to the present invention or a host cell according to the present invention.

In a further embodiment the composition according to the present invention is a pharmaceutical composition, typically comprising a pharmaceutically acceptable carrier. In one embodiment the pharmaceutical composition contains an antibody as defined in any aspect or embodiment disclosed herein, or an expression vector as defined in any aspect or embodiment disclosed herein.

In yet a further embodiment, the invention relates to a pharmaceutical composition comprising:

an antibody as defined in any of the aspects and embodiments disclosed herein, and a pharmaceutically acceptable carrier.

In one embodiment the pharmaceutical composition is administered by intravenous or subcutaneous injection or infusion.

The invention also relates to kit-of-parts, such as a kit for use as a companion diagnostic for identifying within a population of patients those patients which have a propensity to respond to treatment with an antibody as defined herein, comprising an antibody as defined in any aspect or embodiment disclosed herein; and instructions for use of said kit.

The invention also relates to kit-of-parts for use in therapy comprising an antibody according to the invention, or a composition comprising an antibody according to the invention, optionally wherein the kit-of-parts contains more than one dosage of the antibody.

In one embodiment, the kit-of-parts comprises such an antibody or composition in one or more containers such as vials.

In one embodiment, the kit-of-parts comprises such an antibody or composition for simultaneous, separate or sequential use in therapy.

The antibodies of the present invention have numerous therapeutic utilities involving the treatment of diseases and disorders that may be treated by activating immune cells expressing CD27. For example, the antibodies may be administered to cells in culture, e.g., in vitro or ex vivo, or to human subjects, e.g., in vivo, to treat or prevent a variety of disorders and diseases. As used herein, the term "subject" is intended to include human and non-human animals which may benefit or respond to the antibody. Subjects may for instance include human patients having diseases or disorders that may be corrected or ameliorated by modulating CD27 function so that e.g. $CD4^+$ and/or $CD8^+$ T-cell populations are expanded. Accordingly, the antibodies may be used to elicit in vivo or in vitro proliferation of T-cell populations such as T-helper cells and cytotoxic T-cells.

Thus, in one aspect, the present invention relates to the antibodies according to the present invention, the nucleic acid or combination of nucleic acids according to the present invention, the delivery vehicle according to the present invention, the expression vector according to the present invention, the host cell according to the present invention, the composition according to the present invention, or the pharmaceutical composition according to the present invention for use as a medicament.

In one aspect, the present invention relates to the use of the antibodies according to the present invention, the nucleic acid or combination of nucleic acids according to the present invention, the delivery vehicle according to the present invention, the expression vector according to the present invention, the host cell according to the present invention, the composition according to the present invention, or the pharmaceutical composition according to the present invention in the preparation of a medicament for treating or preventing a disease or disorder.

In one aspect, the present invention relates to a method of treatment of a disease or disorder comprising administering the antibody according to the present invention, the nucleic acid or combination of nucleic acids according to the present invention, the delivery vehicle according to the present invention, the expression vector according to the present invention, the host cell according to claim the present invention, the composition according to the present invention, or the pharmaceutical composition according to the present invention to a subject in need thereof.

In one aspect, the invention relates to the antibody according to any aspect or embodiment for use as a medicament.

In one aspect, the invention relates to the use of the antibody according to any aspect or embodiment in the preparation of a medicament for treating or preventing a disease or disorder.

In one aspect, the invention relates to the antibody according to any aspect or embodiment for use in the treatment or prevention of a disease or disorder.

In one aspect, the invention relates to the antibody according to any aspect or embodiment for use in diagnostic or for use in a diagnostic method.

In one aspect, the invention relates to a method of treating a disease or disorder, comprising administering the antibody according to any aspect or embodiment to a subject in need thereof, typically in a therapeutically effective amount and/or for a time sufficient to treat the disease or disorder.

In one aspect, the invention relates to a pharmaceutical composition comprising the antibody according to any aspect or embodiment, for use as a medicament.

In one aspect, the invention relates to a pharmaceutical composition comprising the antibody according to any aspect or embodiment for use in the treatment or prevention of a disease or disorder.

In one aspect, the invention relates to a method of treatment of a disease or disorder comprising administering a pharmaceutical composition comprising the antibody according to any aspect or embodiment to a subject in need thereof, typically in a therapeutically effective amount and/or for a time sufficient to treat the disease or disorder.

In one aspect, the present invention relates to a method of treating a disease or disorder, comprising the steps of:

- selecting a subject suffering from the disease or disorder, and
- administering to the subject the antibody according to any aspect or embodiment, or a pharmaceutical composition comprising the antibody, typically in a therapeutically effective amount and/or for a time sufficient to treat the disease or disorder.

In one embodiment, the disease or disorder is cancer, i.e. a tumorigenic disorder, such as for example, a hematological cancer or a solid tumor malignancy. In another embodiment the disease or disorder is an inflammatory and/or autoimmune disease or disorder.

In a further aspect, the invention relates to an anti-idiotypic antibody which binds to an antibody comprising at least one antigen-binding region capable of binding to CD27, i.e. an antibody according to the invention as described herein. In particular embodiments, the anti-idiotypic antibody binds to the antigen-binding region capable of binding to CD27 as described herein.

An anti-idiotypic (Id) antibody is an antibody which recognizes unique determinants generally associated with the antigen-binding site of an antibody. An anti-Id antibody may be prepared by immunizing an animal of the same species and genetic type as the source of an anti-CD27 monoclonal antibody with the monoclonal antibody against which an anti-Id is being prepared. The immunized animal typically can recognize and respond to the idiotypic determinants of the immunizing antibody by producing an antibody to these idiotypic determinants (the anti-Id antibody). A method for producing such antibodies is described in for instance U.S. Pat. No. 4,699,880. Such antibodies are further features of the present invention.

An anti-Id antibody may also be used as an "immunogen" to induce an immune response in yet another animal, producing a so-called anti-anti-Id antibody. An anti-anti-Id antibody may be epitopically identical to the original monoclonal antibody, which induced the anti-Id antibody. Thus, by using antibodies to the idiotypic determinants of a monoclonal antibody, it is possible to identify other clones expressing antibodies of identical specificity. Anti-Id antibodies may be varied (thereby producing anti-Id antibody variants) and/or derivatized by any suitable technique, such as those described elsewhere herein with respect to CD27-specific antibodies of the present invention. For example, a monoclonal anti-Id antibody may be coupled to a carrier such as keyhole limpet hemocyanin (KLH) and used to immunize BALB/c mice. Sera from these mice typically will contain anti-anti-Id antibodies that have the binding properties similar, if not identical, to an original/parental anti-CD27 antibody.

Fc regions may have at their C-terminus a lysine. The origin of this lysine is a naturally occurring sequence found in humans from which these Fc regions are derived. During cell culture production of recombinant antibodies, this terminal lysine can be cleaved off by proteolysis by endogenous carboxypeptidase(s), resulting in a constant region having the same sequence but lacking the C-terminal lysine. For manufacturing purposes of antibodies, the DNA encoding this terminal lysine can be omitted from the sequence such that antibodies are produced without the lysine. Antibodies produced from nucleic acid sequences that either do, or do not encode a terminal lysine are substantially identical in sequence and in function since the degree of processing of the terminal lysine is typically high when e.g. using antibodies produced in CHO-based production systems (Dick, L. W. et al. Biotechnol. Bioeng. 2008; 100: 1132-1143).

Hence, it is understood that proteins in accordance with the invention, such as antibodies, can be generated with or without encoding or having a terminal lysine. It is also understood in accordance with the invention that, sequences with a terminal lysine, such as a constant region sequence having a terminal lysine, can be understood as the corresponding sequences without a terminal lysine, and that sequences without a terminal lysine can also be understood as the corresponding sequences with a terminal lysine.

EXAMPLES

Example 1: Generation of Anti-Human CD27 Antibodies and Fc Variants Thereof

Generation of anti-human CD27 antibodies through immunization and hybridoma generation was performed at Aldevron GmbH (Freiburg, Germany). cDNA's encoding human CD27 (full length and ECD) were cloned into Aldevron proprietary expression plasmids. Anti-CD27 antibodies were generated by immunization of OmniRat animals (transgenic rats expressing a diversified repertoire of antibodies with fully human idiotypes; Ligand Pharmaceuticals Inc.) using intradermal application of human CD27 cDNA-coated gold-particles using a hand-held device for particle-bombardment ("gene gun"). Serum samples were collected after a series of immunizations and tested by flow cytometry on HEK cells transiently transfected with the aforementioned expression plasmid for full length human CD27 expression. Antibody-producing cells were isolated from rat spleen and fused with mouse myeloma cells (Ag8) according to standard procedures. RNA from hybridomas producing CD27-specific antibody was extracted for sequencing.

Out of a panel of 71 CD27 antibodies six antibodies were selected for further characterization based on binding to primary T cells and diversity in CD27 binding competition assays in vitro. These six antibodies are named IgG1-CD27-A, IgG1-CD27-B, IgG1-CD27-C, IgG1-CD27-D, IgG1-CD27-E and IgG1-CD27-F herein.

The variable regions, in some cases with single point mutations to remove amino acid residues that were considered a liability for manufacturing (e.g., free cysteines or glycosylation sites), of heavy and light chains of interest were gene synthesized and cloned into expression vectors containing the backbone sequences for human antibody light chains and a human IgG1 heavy chain.

Fc variants of the six different antibodies were generated by introduction of one or more of the following amino acid mutations, according to Eu numbering: E345R, E430G, P329R, G237A, K326A, E333A, see Tables 3 and 5 below. After functional characterization in vitro as described below, CD27-specific IgG1-CD27-A was considered to have the most optimal biological properties. Sequences of the prior art CD27-targeting antibodies used herein as benchmarks have been obtained as follows: IgG1-CD27-15 (WO2012004367; SEQ ID Nos 3 and 4), IgG1-CD27-131A (WO2018/058022; SEQ ID Nos 10 and 15), IgG1-CD27-CDX1127 (WO2016145085; SEQ ID Nos: 1 and 2), and IgG1-CD27-BMS986215 (WO2019195452A1; SEQ ID Nos 8 and 9). The VH and VL sequences of a type I anti-human CD20 antibody have been described previously in WO2019/145455A1 (SEQ ID Nos 35 and 39).

TABLE 3 list of amino acid sequences

| SEQ ID NO: | Identifier | Domain | Amino acid sequence | Organism |
|---|---|---|---|---|
| 1 | Human CD27 | ORF | MARPHPWWLCVLGTLVGLSATPAPKSCPERHYWAQ GKLCCQMCEPGTFLVKDCDQHRKAAQCDPCIPGVSFS PDHHTRPHCESCRHCNSGLLVRNCTITANAECACRNG WQCRDKECTECDPLPNPSLTARSSQALSPHPQPTHLP YVSEMLEARTAGHMQTLADFRQLPARTLSTHWPPQRSL CSSDFIRILVIFSGMFLVFTLAGALFLHQRRKYRSNKG ESPVEPAEPCHYSCPREEEGSTIPIQEDYRKPEPACSP | *Homo sapiens* |
| 2 | CD27-A59T variant | ORF | MARPHPWWLCVLGTLVGLSATPAPKSCPERHYWAQ GKLCCQMCEPGTFLVKDCDQHRKTAQCDPCIPGVSFS PDHHTRPHCESCRHCNSGLLVRNCTITANAECACRNG WQCRDKECTECDPLPNPSLTARSSQALSPHPQPTHLP YVSEMLEARTAGHMQTLADFRQLPARTLSTHWPPQRSL CSSDFIRILVIFSGMFLVFTLAGALFLHQRRKYRSNKG ESPVEPAEPCHYSCPREEEGSTIPIQEDYRKPEPACSP | *Homo sapiens* |
| 3 | Cyno CD27 | ORF | MARPHPWWLCFLGTLVGLSATPAPKSCPERHYWAQ GKLCCQMCEPGTFLVKDCDQHRKAAQCHPCIPGVSF SPDHHTRPHCESCRHCNSGLLIRNCTITANAVCACRN GWQCRDKECTECDPPPNPSLTTWPSQALGPHPQPTH LPYVNEMLEARTAGHMQTLADFRHLPARTLSTHWPPQ RSLCSSDFIRILVIFSGMFLVFTLAGTLFLHQQRKYRS NKGESPMEPAEPCPYSCPREEEGSTIPIQEDYRKPEPA SSP | *Macaca fascicularis* |
| 4 | CD27-A VH | VH | QVQLMQSGSELKKPGASVKVSCRASGYTFTTYAMNW VRQAPGQGPEWMGWINTNTGNPTYAQGFTGRFVFSL DTTVTTTYLQISSLKAEDTAVYFCAREAGSFDYWGQ GTLVTVSS | synthetic construct |
| 5 | CD27-A VH CDR1 | VH_CDR1 | GYTFTTYA | synthetic construct |
| 6 | CD27-A VH CDR2 | VH_CDR2 | INTNTGNP | synthetic construct |
| 7 | CD27-A VH CDR3 | VH_CDR3 | AREAGSFDY | synthetic construct |

TABLE 3-continued list of amino acid sequences

| SEQ ID NO: | Identifier | Domain | Amino acid sequence | Organism |
|---|---|---|---|---|
| 8 | CD27-A VL | VL | QSALTQPASVSGSPGQSITISCTGTSSDVYYYNYVSWY<br>QQHPGRAPKLVIYDVSNRPSGVSNRFSGSKSGNTASL<br>TISGLRAEDEADYYCSSYTVNRVWVFGGGTKLTVL | synthetic construct |
| 9 | CD27-A VLCDR1 | VL_CDR1 | SSDVYYYNY | synthetic construct |
| 10 | CD27-A VLCDR2 | VL_CDR2 | DVS | synthetic construct |
| 11 | CD27-A VLCDR3 | VL_CDR3 | SSYTVNRVWV | synthetic construct |
| 12 | Constant region human IgG1m(f) | Constant | ASTKGPSVFPLAPSSKSTSGGTAALGCLVKDYFPEPVTV<br>SWNSGALTSGVHTFPAVLQSSGLYSLSSVVTVPSSSLG<br>TQTYICNVNHKPSNTKVDKRVEPKSCDKTHTCPPCPA<br>PELLGGPSVFLFPPKPKDTLMISRTPEVTCVVVDVSHE<br>DPEVKFNWYVDGVEVHNAKTKPREEQYNSTYRVVSV<br>LTVLHQDWLNGKEYKCKVSNKALPAPIEKTISKAKGQP<br>REPQVYTLPPSREEMTKNQVSLTCLVKGFYPSDIAVE<br>WESNGQPENNYKTTPPVLDSDGSFFLYSKLTVDKSRW<br>QQGNVFSCSVMHEALHNHYTQKSLSLSPGK | synthetic construct |
| 13 | Constant region human IgG1-E345R | Constant | ASTKGPSVFPLAPSSKSTSGGTAALGCLVKDYFPEPVTV<br>SWNSGALTSGVHTFPAVLQSSGLYSLSSVVTVPSSSLG<br>TQTYICNVNHKPSNTKVDKRVEPKSCDKTHTCPPCPA<br>PELLGGPSVFLFPPKPKDTLMISRTPEVTCVVVDVSHE<br>DPEVKFNWYVDGVEVHNAKTKPREEQYNSTYRVVSV<br>LTVLHQDWLNGKEYKCKVSNKALPAPIEKTISKAKGQP<br>R**R**PQVYTLPPSREEMTKNQVSLTCLVKGFYPSDIAVE<br>WESNGQPENNYKTTPPVLDSDGSFFLYSKLTVDKSRW<br>QQGNVFSCSVMHEALHNHYTQKSLSLSPGK | synthetic construct |
| 14 | Constant region human IgG1-P329R | Constant | ASTKGPSVFPLAPSSKSTSGGTAALGCLVKDYFPEPVTV<br>SWNSGALTSGVHTFPAVLQSSGLYSLSSVVTVPSSSLG<br>TQTYICNVNHKPSNTKVDKRVEPKSCDKTHTCPPCPA<br>PELLGGPSVFLFPPKPKDTLMISRTPEVTCVVVDVSHE<br>DPEVKFNWYVDGVEVHNAKTKPREEQYNSTYRVVSV<br>LTVLHQDWLNGKEYKCKVSNKAL**R**APIEKTISKAKGQP<br>REPQVYTLPPSREEMTKNQVSLTCLVKGFYPSDIAVE<br>WESNGQPENNYKTTPPVLDSDGSFFLYSKLTVDKSRW<br>QQGNVFSCSVMHEALHNHYTQKSLSLSPGK | synthetic construct |
| 15 | Constant region human IgG1-delK E345R+P 329R | Constant | ASTKGPSVFPLAPSSKSTSGGTAALGCLVKDYFPEPVTV<br>SWNSGALTSGVHTFPAVLQSSGLYSLSSVVTVPSSSLG<br>TQTYICNVNHKPSNTKVDKRVEPKSCDKTHTCPPCPA<br>PELLGGPSVFLFPPKPKDTLMISRTPEVTCVVVDVSHE<br>DPEVKFNWYVDGVEVHNAKTKPREEQYNSTYRVVSV<br>LTVLHQDWLNGKEYKCKVSNKAL**R**APIEKTISKAKGQP<br>R**R**PQVYTLPPSREEMTKNQVSLTCLVKGFYPSDIAVE<br>WESNGQPENNYKTTPPVLDSDGSFFLYSKLTVDKSRW<br>QQGNVFSCSVMHEALHNHYTQKSLSLSPG | synthetic construct |
| 16 | Human kappa LC | Constant | RTVAAPSVFIFPPSDEQLKSGTASVVCLLNNFYPREAKV<br>QWKVDNALQSGNSQESVTEQDSKDSTYSLSSTLTLSK<br>ADYEKHKVYACEVTHQGLSSPVTKSFNRGEC | synthetic construct |
| 17 | Human lambda LC | Constant | GQPKAAPSVTLFPPSSEELQANKATLVCLISDFYPGAVT<br>VAWKADSSPVKAGVETTTPSKQSNNKYAASSYLSLTPE<br>QWKSHRSYSCQVTHEGSTVEKTVAPTECS | synthetic construct |
| 18 | Constant region human IgG1m(f) -delK | Constant | ASTKGPSVFPLAPSSKSTSGGTAALGCLVKDYFPEPVTV<br>SWNSGALTSGVHTFPAVLQSSGLYSLSSVVTVPSSSLG<br>TQTYICNVNHKPSNTKVDKRVEPKSCDKTHTCPPCPA<br>PELLGGPSVFLFPPKPKDTLMISRTPEVTCVVVDVSHE<br>DPEVKFNWYVDGVEVHNAKTKPREEQYNSTYRVVSV<br>LTVLHQDWLNGKEYKCKVSNKALPAPIEKTISKAKGQP<br>REPQVYTLPPSREEMTKNQVSLTCLVKGFYPSDIAVE<br>WESNGQPENNYKTTPPVLDSDGSFFLYSKLTVDKSRW<br>QQGNVFSCSVMHEALHNHYTQKSLSLSPG | synthetic construct |
| 19 | Constant region human | Constant | ASTKGPSVFPLAPSSKSTSGGTAALGCLVKDYFPEPVTV<br>SWNSGALTSGVHTFPAVLQSSGLYSLSSVVTVPSSSLG<br>TQTYICNVNHKPSNTKVDKPVEPKSCDKTHTCPPCPA | synthetic construct |

TABLE 3-continued list of amino acid sequences

| SEQ ID NO: | Identifier | Domain | Amino acid sequence | Organism |
|---|---|---|---|---|
| | IgG1m (a) | | PELLGGPSVFLFPPKPKDTLMISRTPEVTCVVVDVSHE<br>DPEVKFNWYVDGVEVHNAKTKPREEQYNSTYRVVSV<br>LTVLHQDWLNGKEYKCKVSNKALPAPIEKTISKAKGQP<br>REPQVYTLPPSRDELTKNQVSLTCLVKGFYPSDIAVEW<br>ESNGQPENNYKTTPPVLDSDGSFFLYSKLTVDKSRWQ<br>QGNVFSCSVMHEALHNHYTQKSLSLSPGK | |
| 20 | Constant region human IgG1m (x) | Constant | ASTKGPSVFPLAPSSKSTSGGTAALGCLVKDYFPEPVTV<br>SWNSGALTSGVHTFPAVLQSSGLYSLSSVVTVPSSSLG<br>TQTYICNVNHKPSNTKVDKPVEPKSCDKTHTCPPCPA<br>PELLGGPSVFLFPPKPKDTLMISRTPEVTCVVVDVSHE<br>DPEVKFNWYVDGVEVHNAKTKPREEQYNSTYRVVSV<br>LTVLHQDWLNGKEYKCKVSNKALPAPIEKTISKAKGQP<br>REPQVYTLPPSREEMTKNQVSLTCLVKGFYPSDIAVE<br>WESNGQPENNYKTTPPVLDSDGSFFLYSKLTVDKSRW<br>QQGNVFSCSVMHEGLHNHYTQKSLSLSPGK | synthetic construct |
| 21 | Constant region human IgG2 | Constant | ASTKGPSVFPLAPCSRSTSESTAALGCLVKDYFPEPVTV<br>SWNSGALTSGVHTFPAVLQSSGLYSLSSVVTVPSSNFG<br>TQTYTCNVDHKPSNTKVDKTVERKCCVECPPCPAPPV<br>AGPSVFLFPPKPKDTLMISRTPEVTCVVVDVSHEDPEV<br>QFNWYVDGVEVHNAKTKPREEQFNSTFRVVSVLTVV<br>HQDWLNGKEYKCKVSNKGLPAPIEKTISKTKGQPREP<br>QVYTLPPSREEMTKNQVSLTCLVKGFYPSDIAVEWES<br>NGQPENNYKTTPPMLDSDGSFFLYSKLTVDKSRWQQ<br>GNVFSCSVMHEALHNHYTQKSLSLSPGK | synthetic construct |
| 22 | Constant region human IgG3 | Constant | ASTKGPSVFPLAPCSRSTSGGTAALGCLVKDYFPEPVT<br>VSWNSGALTSGVHTFPAVLQSSGLYSLSSVVTVPSSSL<br>GTQTYTCNVNHKPSNTKVDKRVELKTPLGDTTHTCPR<br>CPEPKSCDTPPPCPRCPEPKSCDTPPPCPRCPEPKSCD<br>TPPPCPRCPAPELLGGPSVFLFPPKPKDTLMISRTPEVT<br>CVVVDVSHEDPEVQFKWYVDGVEVHNAKTKPREEQY<br>NSTFRVVSVLTVLHQDWLNGKEYKCKVSNKALPAPIEK<br>TISKTKGQPREPQVYTLPPSREEMTKNQVSLTCLVKGF<br>YPSDIAVEWESSGQPENNYNTTPPMLDSDGSFFLYSKL<br>TVDKSRWQQGNIFSCSVMHEALHNRFTQKSLSLSPGK | synthetic construct |
| 23 | Constant region human IgG4 | Constant | ASTKGPSVFPLAPCSRSTSESTAALGCLVKDYFPEPVTV<br>SWNSGALTSGVHTFPAVLQSSGLYSLSSVVTVPSSSLG<br>TKTYTCNVDHKPSNTKVDKRVESKYGPPCPSCPAPEFL<br>GGPSVFLFPPKPKDTLMISRTPEVTCVVVDVSQEDPEV<br>QFNWYVDGVEVHNAKTKPREEQFNSTYRVVSVLTVL<br>HQDWLNGKEYKCKVSNKGLPSSIEKTISKAKGQPREP<br>QVYTLPPSQEEMTKNQVSLTCLVKGFYPSDIAVEWES<br>NGQPENNYKTTPPVLDSDGSFFLYSRLTVDKSRWQEG<br>NVFSCSVMHEALHNHYTQKSLSLSLGK | synthetic construct |
| 24 | CD27-A IgG1 HC with E345R + P 329R | Heavy chain constant + VH | QVQLMQSGSELKKPGASVKVSCRASGYTFTTYAMNW<br>VRQAPGQGPEWMGWINTNTGNPTYAQGFTGRFVF<br>SLDTTVTTTYLQISSLKAEDTAVYFCAREAGSFDYWGQ<br>GTLVTVSSASTKGPSVFPLAPSSKSTSGGTAALGCLVKD<br>YFPEPVTVSWNSGALTSGVHTFPAVLQSSGLYSLSSVV<br>TVPSSSLGTQTYICNVNHKPSNTKVDKRVEPKSCDKTH<br>TCPPCPAPELLGGPSVFLFPPKPKDTLMISRTPEVTCVV<br>VDVSHEDPEVKFNWYVDGVEVHNAKTKPREEQYNST<br>YRVVSVLTVLHQDWLNGKEYKCKVSNKALRAPIEKTIS<br>KAKGQPRRPQVYTLPPSREEMTKNQVSLTCLVKGFYP<br>SDIAVEWESNGQPENNYKTTPPVLDSDGSFFLYSKLTV<br>DKSRWQQGNVFSCSVMHEALHNHYTQKSLSLSPGK | synthetic construct |
| 25 | CD27-A LC | Light chain constant + VL | QSALTQPASVSGSPGQSITISCTGTSSDVYYYNYVSWY<br>QQHPGRAPKLVIYDVSNRPSGVSNRFSGSKSGNTASL<br>TISGLRAEDEADYYCSSYTVNRVWVFGGGTKLTVLGQ<br>PKAAPSVTLFPPSSEELQANKATLVCLISDFYPGAVTVA<br>WKADSSPVKAGVETTTPSKQSNNKYAASSYLSLTPEQ<br>WKSHRSYSCQVTHEGSTVEKTVAPTECS | synthetic construct |

TABLE 3-continued list of amino acid sequences

| SEQ ID NO: | Identifier | Domain | Amino acid sequence | Organism |
|---|---|---|---|---|
| 26 | Mouse CD27 | ORF | MAWPPPYWLCMLGTLVGLSATLAPNSCPDKHYWTG GGLCCRMCEPGTFFVKDCEQDRTAAQCDPCIPGTSFS PDYHTRPHCESCRHCNSGFLIRNCTVTANAECSCSKN WQCRDQECTECDPPLNPALTRQPSETPSPQPPPTHLP HGTEKPSWPLHRQLPNSTVYSQRSSHRPLCSSDCIRIF VTFSSMFLIFVLGAILFFHQRRNHGPNEDRQAVPEEPC PYSCPREEEGSAIPIQEDYRKPEPAFYP | *Mus musculus* |
| 27 | Human IgG1-Fc-E345R+P 329R | Constant | ASTKGPSVFPLAPSSKSTSGGTAALGCLVKDYFPEPVTV SWNSGALTSGVHTFPAVLQSSGLYSLSSVVTVPSSSLG TQTYICNVNHKPSNTKVDKRVEPKSCDKTHTCPPCPA PELLGGPSVFLFPPKPKDTLMISRTPEVTCVVVDVSHE DPEVKFNWYVDGVEVHNAKTKPREEQYNSTYRVVSV LTVLHQDWLNGKEYKCKVSNKAL**R**APIEKTISKAKGQP R**R**PQVYTLPPSREEMTKNQVSLTCLVKGFYPSDIAVE WESNGQPENNYKTTPPVLDSDGSFFLYSKLTVDKSRW QQGNVFSCSVMHEALHNHYTQKSLSLSPGK | synthetic construct |
| 28 | Constant region human IgG1m(f) (without c-terminal lysine) | Constant | ASTKGPSVFPLAPSSKSTSGGTAALGCLVKDYFPEPVTV SWNSGALTSGVHTFPAVLQSSGLYSLSSVVTVPSSSLG TQTYICNVNHKPSNTKVDKRVEPKSCDKTHTCPPCPA PELLGGPSVFLFPPKPKDTLMISRTPEVTCVVVDVSHE DPEVKFNWYVDGVEVHNAKTKPREEQYNSTYRVVSV LTVLHQDWLNGKEYKCKVSNKALPAPIEKTISKAKGQP REPQVYTLPPSREEMTKNQVSLTCLVKGFYPSDIAVE WESNGQPENNYKTTPPVLDSDGSFFLYSKLTVDKSRW QQGNVFSCSVMHEALHNHYTQKSLSLSPG | synthetic construct |
| 29 | Constant region human IgG1-E345R (without c-terminal lysine) | Constant | ASTKGPSVFPLAPSSKSTSGGTAALGCLVKDYFPEPVTV SWNSGALTSGVHTFPAVLQSSGLYSLSSVVTVPSSSLG TQTYICNVNHKPSNTKVDKRVEPKSCDKTHTCPPCPA PELLGGPSVFLFPPKPKDTLMISRTPEVTCVVVDVSHE DPEVKFNWYVDGVEVHNAKTKPREEQYNSTYRVVSV LTVLHQDWLNGKEYKCKVSNKALPAPIEKTISKAKGQP R**R**PQVYTLPPSREEMTKNQVSLTCLVKGFYPSDIAVE WESNGQPENNYKTTPPVLDSDGSFFLYSKLTVDKSRW QQGNVFSCSVMHEALHNHYTQKSLSLSPG | synthetic construct |
| 30 | Constant region human IgG1-P329R (without c-terminal lysine) | Constant | ASTKGPSVFPLAPSSKSTSGGTAALGCLVKDYFPEPVTV SWNSGALTSGVHTFPAVLQSSGLYSLSSVVTVPSSSLG TQTYICNVNHKPSNTKVDKRVEPKSCDKTHTCPPCPA PELLGGPSVFLFPPKPKDTLMISRTPEVTCVVVDVSHE DPEVKFNWYVDGVEVHNAKTKPREEQYNSTYRVVSV LTVLHQDWLNGKEYKCKVSNKAL**R**APIEKTISKAKGQP REPQVYTLPPSREEMTKNQVSLTCLVKGFYPSDIAVE WESNGQPENNYKTTPPVLDSDGSFFLYSKLTVDKSRW QQGNVFSCSVMHEALHNHYTQKSLSLSPG | synthetic construct |
| 31 | Constant region human IgG1m(a) (without c-terminal lysine) | Constant | ASTKGPSVFPLAPSSKSTSGGTAALGCLVKDYFPEPVTV SWNSGALTSGVHTFPAVLQSSGLYSLSSVVTVPSSSLG TQTYICNVNHKPSNTKVDKPVEPKSCDKTHTCPPCPA PELLGGPSVFLFPPKPKDTLMISRTPEVTCVVVDVSHE DPEVKFNWYVDGVEVHNAKTKPREEQYNSTYRVVSV LTVLHQDWLNGKEYKCKVSNKALPAPIEKTISKAKGQP REPQVYTLPPSRDELTKNQVSLTCLVKGFYPSDIAVEW ESNGQPENNYKTTPPVLDSDGSFFLYSKLTVDKSRWQ QGNVFSCSVMHEALHNHYTQKSLSLSPG | synthetic construct |
| 32 | Constant region human IgG1m(x) (without c-terminal lysine) | Constant | ASTKGPSVFPLAPSSKSTSGGTAALGCLVKDYFPEPVTV SWNSGALTSGVHTFPAVLQSSGLYSLSSVVTVPSSSLG TQTYICNVNHKPSNTKVDKPVEPKSCDKTHTCPPCPA PELLGGPSVFLFPPKPKDTLMISRTPEVTCVVVDVSHE DPEVKFNWYVDGVEVHNAKTKPREEQYNSTYRVVSV LTVLHQDWLNGKEYKCKVSNKALPAPIEKTISKAKGQP REPQVYTLPPSREEMTKNQVSLTCLVKGFYPSDIAVE WESNGQPENNYKTTPPVLDSDGSFFLYSKLTVDKSRW QQGNVFSCSVMHEGLHNHYTQKSLSLSPG | synthetic construct |

TABLE 3-continued list of amino acid sequences

| SEQ ID NO: | Identifier | Domain | Amino acid sequence | Organism |
|---|---|---|---|---|
| 33 | Constant region human IgG2 (without c-terminal lysine) | Constant | ASTKGPSVFPLAPCSRSTSESTAALGCLVKDYFPEPVTV SWNSGALTSGVHTFPAVLQSSGLYSLSSVVTVPSSNFG TQTYTCNVDHKPSNTKVDKTVERKCCVECPPCPAPPV AGPSVFLFPPKPKDTLMISRTPEVTCVVVDVSHEDPEV QFNWYVDGVEVHNAKTKPREEQFNSTFRVVSVLTVV HQDWLNGKEYKCKVSNKGLPAPIEKTISKTKGQPREP QVYTLPPSREEMTKNQVSLTCLVKGFYPSDIAVEWES NGQPENNYKTTPPMLDSDGSFFLYSKLTVDKSRWQQ GNVFSCSVMHEALHNHYTQKSLSLSPG | synthetic construct |
| 34 | Constant region human IgG3 (without c-terminal lysine) | Constant | ASTKGPSVFPLAPCSRSTSGGTAALGCLVKDYFPEPVT VSWNSGALTSGVHTFPAVLQSSGLYSLSSVVTVPSSSL GTQTYTCNVNHKPSNTKVDKRVELKTPLGDTTHTCPR CPEPKSCDTPPPCPRCPEPKSCDTPPPCPRCPEPKSCD TPPPCPRCPAPELLGGPSVFLFPPKPKDTLMISRTPEVT CVVVDVSHEDPEVQFKWYVDGVEVHNAKTKPREEQY NSTFRVVSVLTVLHQDWLNGKEYKCKVSNKALPAPIEK TISKTKGQPREPQVYTLPPSREEMTKNQVSLTCLVKGF YPSDIAVEWESSGQPENNYNTTPPMLDSDGSFFLYSKL TVDKSRWQQGNIFSCSVMHEALHNRFTQKSLSLSPG | synthetic construct |
| 35 | CD27-A IgG1 HC with E345R + P 329R (without c-terminal lysine) | Heavy chain constant + VH | QVQLMQSGSELKKPGASVKVSCRASGYTFTTYAMNW VRQAPGQGPEWMGWINTNTGNPTYAQGFTGRFVF SLDTTVTTTYLQISSLKAEDTAVYFCAREAGSFDYWGQ GTLVTVSSASTKGPSVFPLAPSSKSTSGGTAALGCLVKD YFPEPVTVSWNSGALTSGVHTFPAVLQSSGLYSLSSVV TVPSSSLGTQTYICNVNHKPSNTKVDKRVEPKSCDKTH TCPPCPAPELLGGPSVFLFPPKPKDTLMISRTPEVTCVV VDVSHEDPEVKFNWYVDGVEVHNAKTKPREEQYNST YRVVSVLTVLHQDWLNGKEYKCKVSNKAL**R**APIEKTIS KAKGQPR**R**PQVYTLPPSREEMTKNQVSLTCLVKGFYP SDIAVEWESNGQPENNYKTTPPVLDSDGSFFLYSKLTV DKSRWQQGNVFSCSVMHEALHNHYTQKSLSLSPG | synthetic construct |
| 36 | Human IgG1-Fc-E345R + P 329R (without c-terminal lysine) | Constant | ASTKGPSVFPLAPSSKSTSGGTAALGCLVKDYFPEPVTV SWNSGALTSGVHTFPAVLQSSGLYSLSSVVTVPSSSLG TQTYICNVNHKPSNTKVDKRVEPKSCDKTHTCPPCPA PELLGGPSVFLFPPKPKDTLMISRTPEVTCVVVDVSHE DPEVKFNWYVDGVEVHNAKTKPREEQYNSTYRVVSV LTVLHQDWLNGKEYKCKVSNKAL**R**APIEKTISKAKGQP R**R**PQVYTLPPSREEMTKNQVSLTCLVKGFYPSDIAVE WESNGQPENNYKTTPPVLDSDGSFFLYSKLTVDKSRW QQGNVFSCSVMHEALHNHYTQKSLSLSPG | synthetic construct |
| 37 | IgG1-CD27-A-P329R-E345R-LNIuc LC | LC | QSALTQPASVSGSPGQSITISCTGTSSDVYYYNYVSWY QQHPGRAPKLVIYDVSNRPSGVSNRFSGSKSGNTASL TISGLRAEDEADYYCSSYTVNRVWVFGGGTKLTVLGQ PKAAPSVTLFPPSSEELQANKATLVCLISDFYPGAVTVA WKADSSPVKAGVETTTPSKQSNNKYAASSYLSLTPEQ WKSHRSYSCQVTHEGSTVEKTVAPTECS**SLGSSGVFTL EDFVGDWRQTAGYNLDQVLEQGGVSSLFQNLGVSV TPIQRIVLSGENGLKIDIHVIIPYEGLSGDQMGQIEKIF KVVYPVDDHHFKVILHYGTLVIDGVTPNMIDYFGRP YEGIAVFDGKKITVTGTLWNGNKIIDERLINPDGSLLF RVTINGVTGWRLCERILA** | synthetic construct |
| 38 | IgG1-CD27-A-P329R-E345R-LHalo LC | LC | QSALTQPASVSGSPGQSITISCTGTSSDVYYYNYVSWY QQHPGRAPKLVIYDVSNRPSGVSNRFSGSKSGNTASL TISGLRAEDEADYYCSSYTVNRVWVFGGGTKLTVLGQ PKAAPSVTLFPPSSEELQANKATLVCLISDFYPGAVTVA WKADSSPVKAGVETTTPSKQSNNKYAASSYLSLTPEQ WKSHRSYSCQVTHEGSTVEKTVAPTECS**SLEPTTEDLY FQSDNDGSEIGTGFPFDPHYVEVLGERMHYVDVGPR DGTPVLFLHGNPTSSYVWRNIIPHVAPTHRCIAPDLI GMGKSDKPDLGYFFDDHVRFMDAFIEALGLEEVVLV IHDWGSALGFHWAKRNPERVKGIAFMEFIRPIPTWD EWPEFARETFQAFRTTDVGRKLIIDQNVFIEGTLPMG VVRPLTEVEMDHYREPFLNPVDREPLWRFPNELPIA GEPANIVALVEEYMDWLHQSPVPKLLFWGTPGVLIP PAEAARLAKSLPNCKAVDIGPGLNLLQEDNPDLIGSEI ARWLSTLEISG** | synthetic construct |

TABLE 3-continued list of amino acid sequences

| SEQ ID NO: | Identifier | Domain | Amino acid sequence | Organism |
|---|---|---|---|---|
| 39 | IgG1-b12-P329R-E345R-LNLuc LC | LC | EIVLTQSPGTLSLSPGERATFSCRSSHSIRSRRVAWYQH<br>KPGQAPRLVIHGVSNRASGISDRFSGSGSGTDFTLTITR<br>VEPEDFALYYCQVYGASSYTFGQGTKLERKRTVAAPSV<br>FIFPPSDEQLKSGTASVVCLLNNFYPREAKVQWKVDN<br>ALQSGNSQESVTEQDSKDSTYSLSSTLTLSKADYEKHK<br>VYACEVTHQGLSSPVTKSFNRGEC**SLGSSGVFTLEDFV**<br>**GDWRQTAGYNLDQVLEQGGVSSLFQNLGVSVTPIQ**<br>**RIVLSGENGLKIDIHVIIPYEGLSGDQMGQIEKIFKVVY**<br>**PVDDHHFKVILHYGTLVIDGVTPNMIDYFGRPYEGIA**<br>**VFDGKKITVTGTLWNGNKIIDERLINPDGSLLFRVTIN**<br>**GVTGWRLCERILA** | synthetic construct |
| 40 | IgG1-b12-P329R-E345R-LHalo LC | LC | EIVLTQSPGTLSLSPGERATFSCRSSHSIRSRRVAWYQH<br>KPGQAPRLVIHGVSNRASGISDRFSGSGSGTDFTLTITR<br>VEPEDFALYYCQVYGASSYTFGQGTKLERKRTVAAPSV<br>FIFPPSDEQLKSGTASVVCLLNNFYPREAKVQWKVDN<br>ALQSGNSQESVTEQDSKDSTYSLSSTLTLSKADYEKHK<br>VYACEVTHQGLSSPVTKSFNRGEC**SLEPTTEDLYFQSD**<br>**NDGSEIGTGFPFDPHYVEVLGERMHYVDVGPRDGT**<br>**PVLFLHGNPTSSYVWRNIIPHVAPTHRCIAPDLIGMG**<br>**KSDKPDLGYFFDDHVRFMDAFIEALGLEEVVLVIHD**<br>**WGSALGFHWAKRNPERVKGIAFMEFIRPIPTWDEW**<br>**PEFARETFQAFRTTDVGRKLIIDQNVFIEGTLPMGVV**<br>**RPLTEVEMDHYREPFLNPVDREPLWRFPNELPIAGEP**<br>**ANIVALVEEYMDWLHQSPVPKLLFWGTPGVLIPPAE**<br>**AARLAKSLPNCKAVDIGPGLNLLQEDNPDLIGSEIAR**<br>**WLSTLEISG** | synthetic construct |
| 41 | IgG1-CD27-A-LNLuc LC | LC | QSALTQPASVSGSPGQSITISCTGTSSDVYYYNYVSWY<br>QQHPGRAPKLVIYDVSNRPSGVSNRFSGSKSGNTASL<br>TISGLRAEDEADYYCSSYTVNRVWVFGGGTKLTVLGQ<br>PKAAPSVTLFPPSSEELQANKATLVCLISDFYPGAVTVA<br>WKADSSPVKAGVETTTPSKQSNNKYAASSYLSLTPEQ<br>WKSHRSYSCQVTHEGSTVEKTVAPTECS**SLGSSGVFTL**<br>**EDFVGDWRQTAGYNLDQVLEQGGVSSLFQNLGVSV**<br>**TPIQRIVLSGENGLKIDIHVIIPYEGLSGDQMGQIEKIF**<br>**KVVYPVDDHHFKVILHYGTLVIDGVTPNMIDYFGRP**<br>**YEGIAVFDGKKITVTGTLWNGNKIIDERLINPDGSLLF**<br>**RVTINGVTGWRLCERILA** | synthetic construct |
| 42 | IgG1-CD27-A-LHalo LC | LC | QSALTQPASVSGSPGQSITISCTGTSSDVYYYNYVSWY<br>QQHPGRAPKLVIYDVSNRPSGVSNRFSGSKSGNTASL<br>TISGLRAEDEADYYCSSYTVNRVWVFGGGTKLTVLGQ<br>PKAAPSVTLFPPSSEELQANKATLVCLISDFYPGAVTVA<br>WKADSSPVKAGVETTTPSKQSNNKYAASSYLSLTPEQ<br>WKSHRSYSCQVTHEGSTVEKTVAPTECS**SLEPTTEDLY**<br>**FQSDNDGSEIGTGFPFDPHYVEVLGERMHYVDVGPR**<br>**DGTPVLFLHGNPTSSYVWRNIIPHVAPTHRCIAPDLI**<br>**GMGKSDKPDLGYFFDDHVRFMDAFIEALGLEEVVLV**<br>**IHDWGSALGFHWAKRNPERVKGIAFMEFIRPIPTWD**<br>**EWPEFARETFQAFRTTDVGRKLIIDQNVFIEGTLPMG**<br>**VVRPLTEVEMDHYREPFLNPVDREPLWRFPNELPIA**<br>**GEPANIVALVEEYMDWLHQSPVPKLLFWGTPGVLIP**<br>**PAEAARLAKSLPNCKAVDIGPGLNLLQEDNPDLIGSEI**<br>**ARWLSTLEISG** | synthetic construct |
| 43 | IgG1-CD20-11B8-E430G-LNLuc LC | LC | EIVLTQSPATLSLSPGERATLSCRASQSVSSYLAWYQQK<br>PGQAPRLLIYDASNRATGIPARFSGSGSGTDFTLTISSLE<br>PEDFAVYYCQQRSDWPLTFGGGTKVEIKRTVAAPSVFI<br>FPPSDEQLKSGTASVVCLLNNFYPREAKVQWKVDNAL<br>QSGNSQESVTEQDSKDSTYSLSSTLTLSKADYEKHKVY<br>ACEVTHQGLSSPVTKSFNRGEC**SLGSSGVFTLEDFVG**<br>**DWRQTAGYNLDQVLEQGGVSSLFQNLGVSVTPIQRI**<br>**VLSGENGLKIDIHVIIPYEGLSGDQMGQIEKIFKVVYP**<br>**VDDHHFKVILHYGTLVIDGVTPNMIDYFGRPYEGIAV**<br>**FDGKKITVTGTLWNGNKIIDERLINPDGSLLFRVTING**<br>**VTGWRLCERILA** | synthetic construct |
| 44 | IgG1-CD37-37.3-E430G-LHalo LC | LC | DIQMTQSPASLSVSVGETVTITCRASENIRSNLAWYQ<br>QKQGKSPQLLVNVATNLADGVPSRFSGSGSGTQYSLK<br>INSLQSEDFGTYYCQHYWGTTWTFGGGTKLEIKRTVA<br>APSVFIFPPSDEQLKSGTASVVCLLNNFYPREAKVQWK<br>VDNALQSGNSQESVTEQDSKDSTYSLSSTLTLSKADYE<br>KHKVYACEVTHQGLSSPVTKSFNRGEC**SLEPTTEDLYF** | synthetic construct |

TABLE 3-continued

| list of amino acid sequences | | | | |
|---|---|---|---|---|
| SEQ ID NO: | Identifier | Domain | Amino acid sequence | Organism |
| | | | QSDNDGSEIGTGFPFDPHYVEVLGERMHYVDVGPR<br>DGTPVLFLHGNPTSSYVWRNIIPHVAPTHRCIAPDLI<br>GMGKSDKPDLGYFFDDHVRFMDAFIEALGLEEVVLV<br>IHDWGSALGFHWAKRNPERVKGIAFMEFIRPIPTWD<br>EWPEFARETFQAFRTTDVGRKLIIDQNVFIEGTLPMG<br>VVRPLTEVEMDHYREPFLNPVDREPLWRFPNELPIA<br>GEPANIVALVEEYMDWLHQSPVPKLLFWGTPGVLIP<br>PAEAARLAKSLPNCKAVDIGPGLNLLQEDNPDLIGSEI<br>ARWLSTLEISG | |

Example 2: Agonist Activity of Anti-CD27 Antibodies in a CD27 Activation Reporter Cell Assay CD27 agonist activity of the different anti-CD27 antibodies with and without an E345R or an E430G hexamerization-enhancing Fc mutation was measured using the CD27 Thaw and Use Bioassay kit (Promega, Custom Assay Services, CAS #CS1979A25). The kit contains NF-κB Reporter-Jurkat recombinant cells expressing the firefly luciferase gene under the control of NF-κB response elements with constitutive expression of human CD27 and was used essentially according to the manufacturer's instructions. Briefly, Thaw-and-Use GloResponse NFκB-luc2/CD27 Jurkat cells were thawed and incubated in 96-well flat bottom culture plates (PerkinElmer, Cat #6005680) with antibody dilution series (final concentration range 0.04-20 μg/mL) in Bio-Glo Luciferase Assay Buffer for 6 h at 37 °C, 5% $CO_2$. The anti-CD27 antibodies were wild-type (WT*) IgG1-CD27-A, IgG1-CD27-B, IgG1-CD27-C, IgG1-CD27-D, IgG1-CD27-E, IgG1-CD27-F, and variants of each one harboring the E430G or E345R mutation. Anti-CD27 benchmark antibodies were IgG1-CD27-131A (WT and E430G variant) and a non-hexamerizing IgG1-CD27-15 (IgG1-CD27-15-P329R-E345R-K439E, that carries a combination of Fc mutations that prevents hexamerization and thus the mutations are functionally irrelevant in the context of this experiment and is therefore referred to as WT in the figure) and a hexamerizing variant of IgG1-CD27-15 comprising a E345R mutation. An anti-HIV gp120 human antibody, IgG1-b12-E345R, was used as a non-binding negative control antibody (ctrl). After the antibody incubation, Bio-Glo Luciferase Assay Reagent (equilibrated to RT) was added to each well and incubated at RT for 5-10 min. Luminescence was measured using an EnVision Multilabel Reader (PerkinElmer) and presented as relative luminescence units (RLU) in bar diagrams generated using GraphPad Prism software.

Introduction of a hexamerization-enhancing Fc mutation (E345R or E430G) resulted in enhanced CD27 agonism compared to the corresponding WT antibody for antibody clones IgG1-CD27-A to -E and for the benchmark antibodies IgG1-CD27-131A (tested with E430G) and IgG1-CD27-15 (tested with E345R) (FIG. 1).

Whereas IgG-CD27-A, B and C demonstrated enhanced CD27 agonist activity after introduction of E430G or E345R at all concentrations tested, IgG1-CD27-D and E variant containing hexamerization-enhancing mutations did not show increased agonism at the lowest antibody concentrations. IgG1-CD27-F variants with the E430G or E345R mutations only showed enhanced CD27 agonism at the highest antibody concentration tested. For variants IgG1-CD27-A to -E, introduction of the E345R mutation resulted in stronger CD27 activation than the E430G mutation. Antibodies IgG1-CD27-A to -E having the E345R mutation showed higher or similar CD27 activation levels compared to IgG1-CD27-131A having the E430G mutation or CD27-15 having the E345R mutation, respectively.

*The WT antibodies for IgG1-CD27-B and IgG1-CD27-F carried a F405L mutation in the IgG Fc domain, which is functionally irrelevant in the context of this experiment.

Example 3 Binding Affinities of Anti-Human CD27 Antibodies for Recombinant Human, Mouse and Cynomolgus Monkey CD27

The binding affinities of five anti-human CD27 IgG1 antibodies (IgG1-CD27-A, -B, -C, -D and -E) for recombinant human, cynomolgus monkey and mouse CD27 protein were determined using label-free biolayer interferometry on an Octet HTX instrument (ForteBio, Portsmouth, UK). Experiments were performed using bispecific antibodies comprising one CD27-specific Fab-arm and a non-binding Fab-arm, so that the antibody is monovalent for CD27. These bispecific antibodies were generated by controlled Fab-arm exchange between the CD27 antibodies and non-binding antibodies (as described in Labrijn A F et al., Nat Protoc. 2014 October; 9(10):2450-63).

To determine the affinity of the CD27 antibodies for human and mouse CD27, 100 nM recombinant His-tagged mouse or human CD27 protein (Sino Biological, Cat #10039-H08B1 [human], Cat #50110-M08H [mouse]) was loaded to pre-conditioned anti-Penta-HIS (HIS1K) biosensors (ForteBio, Cat #18-5120) for 600 sec.

To assess the affinity of the CD27 antibodies for cynomolgus monkey CD27, 5 μg/mL of recombinant cynomolgus monkey CD27-Fc fusion protein (R&D systems, Cat #9904-CD-100) was loaded to activated Amine Reactive 2nd Generation (AR2G) biosensors (ForteBio, Cat #18-5092).

After baseline measurements in Sample Diluent (ForteBio, Cat #18-1104) for 300 sec, the association (200 sec) and dissociation (1,000 sec) of CD27 antibodies was determined for antibody concentration series of 0.78-800 nM with two-fold dilution steps in Sample Diluent. An antibody molecular mass of 150 kDa was used for calculations. Reference sensors were incubated with Sample Diluent.

Data were acquired using Data Acquisition Software v11.1.1.19 (ForteBio) and analyzed with Data Analysis Software v9.0.0.14 (ForteBio). Data traces were corrected per antibody by subtraction of the reference sensor. The Y-axis was aligned to the last 10 sec of the baseline and Interstep Correction alignment to dissociation and Savitzky-Golay filtering were applied. Data traces were excluded from analysis when the response was <0.05 nm and calculated equilibrium was near to saturation (Req/Rmax>95% using a dissociation time of 50 sec). The data was fitted with the 1:1 model using a window of interest for the association set at 200 sec and dissociation time set at 50 sec. The dissociation time was chosen based on the coefficient of determination ($R^2$), which is an estimate of the goodness of the curve fit (preferentially >0.98), visual inspection of the curve, and at least 5% signal decay during the association step.

Affinities for human CD27 could be accurately determined for three CD27 antibodies (IgG1-CD27-A,B,C) with $K_D$ values in the nanomolar range (Table 4). For IgG1-CD27-D, and -E, BioLayer Interferometry experiments confirmed binding to human CD27 with affinities in a similar range, although suboptimal curve fitting did not allow calculation of accurate $K_D$ values (as indicated in Table 4).

IgG1-CD27-A and -B also showed binding to recombinant cynomolgus monkey CD27, with $K_D$ values in the same range as for human CD27. Results obtained with IgG1-CD27-C, -D and -E also confirmed binding to cynomolgus monkey CD27 with affinities in a similar range, although suboptimal curve fitting did not allow calculation of accurate $K_D$ values (as indicated in Table 4).

Binding to recombinant mouse CD27 was only observed for antibody IgG1-CD27-C.

human or cynomolgus monkey CD27 using 293fectin Transfection Reagent (ThermoFisher, Cat #12347019) according to the manufacturer's instructions.

Human and cynomolgus monkey PBMC were purified from buffy coats obtained from human healthy donors (Sanquin Blood Bank, the Netherlands) or from a cynomolgus monkey (BPRC, the Netherlands, Cat #S-1135) by low density gradient centrifugation using Lymphocyte Separation Medium (LSM; Corning, Cat #25-072CV) according to the manufacturer's instructions.

Cells were seeded in 96-Wells plates (100,000 cells per well; Greiner Bio-one, Cat #650180) for sequential incubations, with washing steps in between with FACS buffer, consisting of PBS (Lonza, Cat #BE17-517Q)+1% BSA (Roche, Cat #10735086001)+0.02% Sodium Azide (Bio-World, Cat #41920044-3). The following incubations were applied: antibody concentration series (0.0001-10 μg/mL final concentration) for 30 min at 4 °C; live/dead marker FVS510 (BD, Cat #564406, diluted 1:1,000 in PBS) for 20 min at RT; PE-labeled polyclonal goat anti-human IgG (Jackson Immuno Research, Cat #109-116-098, diluted 1:500) for 30 min at 4 °C; and anti-CD3 antibody for T-cell identification (anti-human CD3: BD, Cat #555335, diluted 1:10; anti-cyno CD3: Miltenyi, Cat #130-091-998, diluted 1:10) for 30 min at 4 °C. All samples were analyzed on a FACSCelesta flow cytometer (BD) and FlowJo software. Data were processed and visualized using GraphPad Prism.

All tested antibodies showed dose-dependent binding to human CD27, both on human T cells and transfected HEK293F cells (FIG. 2 A,B). Highest maximal binding was observed for IgG1-CD27-B and IgG1-CD27-C compared to intermediate binding for IgG1-CD27-A and IgG1-CD27-131A, and low binding for IgG1-CD27-D and IgG1-CD27-E, with the differences being most pronounced using human T-cells. For binding to cynomolgus money CD27 T cells, highest binding was observed for IgG1-CD27-B, followed by Ig1-CD27-131A and IgG1-CD27-A. Lower binding was observed for IgG1-CD27-D and -E, whereas IgG1-CD27-C showed minimal binding to cynomolgus monkey T cells. All CD27 antibodies showed dose-dependent binding to HEK cells transfected with cynomolgus monkey CD27. Highest maximal binding was observed for IgG1-CD27-B and IgG1-CD27-131-A, somewhat lower binding was observed for

TABLE 4

Binding affinities of IgG1-CD27-A to -E antibodies to CD27 from the indicated species.

| Sample | Loading sample | $K_D$ (M) | $k_{on}$ (1/Ms) | $k_{dis}$ (1/s) |
|---|---|---|---|---|
| IgG1-CD27-A | Human CD27-His | 1.3E−07 | 1.3E+05 | 1.8E−02 |
| | Mouse CD27-His | n.b. | | |
| | Cyno CD27-Fc | 1.2E−07 | 1.7E+05 | 2.0E−02 |
| IgG1-CD27-B | Human CD27-His | 5.4E−08 | 3.3E+05 | 1.8E−02 |
| | Mouse CD27-His | n.b. | | |
| | Cyno CD27-Fc | 3.5E−08 | 6.5E+05 | 2.3E−02 |
| IgG1-CD27-C | Human CD27-His | 7.0E−08 | 1.4E+05 | 9.8E−03 |
| | Mouse CD27-His | 4.3E−07 | 5.0E+04 | 2.2E−02 |
| | Cyno CD27-Fc | 5.1E−08* | 1.2E+05* | 6.4E−03* |
| IgG1-CD27-D | Human CD27-His | 4.5E−08* | 1.4 + 05* | 6.4E−03* |
| | Mouse CD27-His | n.b. | n.b. | n.b. |
| | Cyno CD27-Fc | 2.1E−08* | 2.4E+05* | 5.0E−03* |
| IgG1-CD27-E | Human CD27-His | 4.9E−08* | 1.3 + 05* | 6.4E−03* |
| | Mouse CD27-His | n.b. | n.b. | n.b. |
| | Cyno CD27-Fc | 3.5E−08* | 1.6E+05* | 5.5E−03* |

*binding was observed but $K_D$, $k_{on}$ and $k_{dis}$ are less reliable values due to suboptimal curve fitting, resulting in unreliable interpretation using the 1:1 model.
n.b.: no binding observed.

Example 4: Binding of Anti-CD27 Antibodies to Cell Surface-Expressed Human and Cynomolgus Monkey CD27

Binding of anti-CD27 antibodies IgG1-CD27-A to -E* and prior art IgG1-CD27-131A* to cell surface-expressed human and cynomolgus monkey CD27 was analyzed by flow cytometry using transiently transfected HEK293F cells and primary T cells, which endogenously express CD27. Non-binding control antibody IgG1-b12-FEAR was used as negative control antibody.

FreeStyle 293-F suspension cells (HEK293F; ThermoFisher, Cat #R79007) were transiently transfected with mammalian expression vector pSB encoding full length IgG1-CD27-A, -D and -E. IgG1-CD27-C showed the lowest binding to HEK cells transfected with cynomolgus monkey CD27 (FIG. 2 C,D).

In conclusion, IgG1-CD27-A and IgG1-CD27-B showed dose-dependent binding to human and cynomolgus monkey CD27 expressed endogenously on human or cynomolgus monkey T cells, and transiently expressed in transfected HEK cells. IgG1-CD27-A and IgG-CD27-131A showed comparable binding to human T cells, whereas IgG1-CD27-B showed higher maximal binding.

*N.B. IgG1-CD27-A, -B, -C, -D and -E carried mutations F405L-L234F-L235E-D265A in the IgG Fc domain, which are functionally irrelevant in the context of this experiment. IgG1-CD27-131A carried a functionally irrelevant F405L mutation in the IgG1 Fc domain.

Example 5: Binding of Anti-CD27 Antibodies to a Natural Human CD27-A59T Variant Approximately 19% of the human population expresses a natural CD27 variant harboring an A59T mutation in the extracellular domain (SEQ ID NO. 2). Binding to human CD27-A59T was tested by flow cytometry for anti-CD27 antibodies IgG1-CD27-A, IgG1-CD27-B, IgG1-CD27-C* and benchmark IgG1-CD27-131A. Non-binding antibody IgG1-b12-FEAL was used as a negative control antibody. Transiently transfected HEK293F cells expressing human CD27-A59T (15,000 cells per well) were incubated with concentration series (0.0001-10 μg/mL using 10-fold dilution steps) of primary test antibodies IgG1-CD27-A to -C, non-binding control antibody IgG1-b12 (ctrl), and the prior art benchmark IgG-CD27-131A, which has been described previously to bind to CD27-A59T (WO2018/058022). After incubation, antibodies were PE-labeled with polyclonal goat anti-human IgG. Binding was analyzed on a FACSCelesta flow cytometer (BD) and FlowJo software. Data were processed and visualized using GraphPad Prism v.8.

The tested anti-CD27 antibodies IgG1-CD27-A, IgG1-CD27-B, IgG1-CD27-C, and IgG1-CD27-131A showed dose-dependent binding to CD27-A59T-transfected HEK293F cells with similar binding curves among the different antibodies (Figure EXAMPLE 5).

*N.B. IgG1-CD27-A, -B and -C carried mutations F405L-L234F-L235E-D265A in the IgG Fc domain, which are functionally irrelevant in the context of this experiment. IgG1-CD27-131A carried a functionally irrelevant F405L mutation in the IgG1 Fc domain.

Example 6: Induction of Human T Cell Proliferation by Anti-CD27 Antibodies

As enhanced IgG hexamerization through Fc-Fc interactions upon introduction of the E345R or E430G mutation enhanced CD27 agonist activity of anti CD27 antibodies (example 2), the capacity of IgG1-CD27-A, IgG1-CD27-B, and IgG1-CD27-C antibody variants carrying the E430G or E345R mutations to increase proliferation of TCR activated T cells was tested in vitro.

Additionally, Fc mutations that were reported to reduce binding to C1q and FcgR (G237A or P329R) or that enhance binding to C1q (K326A/E333A double mutation) were introduced to test their potential effect on CD27 agonist activity of CD27 antibodies carrying the E345R or E430G mutations. The K326A/E333A double mutation was previously shown to enhance C1q binding and to contribute to enhanced agonistic activity of DR5-specific humanized IgG1 antibodies comprising an Fc-Fc interaction enhancing mutation (WO2018/146317A1). The mutations G237A, P329R, or K326A/E333A were introduced, in addition to E430G or E345R, to IgG1-CD27-A, IgG1-CD27-B and IgG1-C (Table 5) and their effect on T-cell proliferation was determined using human PBMC obtained from healthy donors (Sanquin Blood Bank, the Netherlands).

TABLE 5

Mutations in the Fc domain of antibodies IgG1-CD27-A, IgG1-CD27-B, or IgG1-CD27-C and their biological effect

| | Fc mutation | | | | |
|---|---|---|---|---|---|
| | E430G | E345R | P329R | G237A | K326/E333A |
| | Described effect | | | | |
| Antibody* | Enhanced hexamerization | Enhanced hexamerization | Reduced C1q/ FcgR binding | Reduced C1q/ FcgR binding | Enhanced C1q binding |
| IgG1-CD27-X-E430G | + | | | | |
| IgG1-CD27-X-P329R-E430G | + | | + | | |
| IgG1-CD27-X-G237A-E430G | + | | | + | |
| IgG1-CD27-X-K326A-E333A-E430G | + | | | | + |
| IgG1-CD27-X-E345R | | + | | | |
| IgG1-CD27-X-P329R-E345R | | + | + | | |
| IgG1-CD27-X-G237A-E345R | | + | | + | |
| IgG1-CD27-X-K326A-E333A-E345R | | + | | | + |

*X in IgG1-CD27-X, refers to IgG1-CD27 clones IgG1-CD27-A, IgG1-CD27-B, or IgG1-CD27-C.

PBMCs were resuspended in PBS at a density of $5\times10^6$ cells/mL and labeled with CFSE using CellTrace CFSE Cell Proliferation Kit (Invitrogen, Cat #C34564; 1:10,000), according to the manufacturer's instructions. CFSE-labeled PBMCs (100,000 cells/well) were incubated in 96-well round-bottom plates (Greiner Bio-one, Cat #650180) with 0.1 μg/mL anti-CD3 antibody clone UCHT1 (Stemcell Technologies, Cat #60011) to activate T cells, and CD27 antibodies (1 μg/mL final concentration) in T-cell Activation Medium (ATCC, Cat #80528190) supplemented with 5%

Normal Human Serum (NHS; Sanquin, Product #B0625) for 96 h at 37 °C/5% $CO_2$. For identification of viable cells in $CD4^+$ and $CD8^+$ T-cell subsets by flow cytometry, cells were sequentially incubated with live/dead marker FVS510 (1:1,000) for 20 min at RT and a staining mix for lymphocyte markers, containing APC-eFluor780-labeled anti-human CD4 antibody (Invitrogen, Cat #47-0048-42, 1:50), AlexaFluor700-labeled anti-human CD8a antibody (BioLegend, Cat #301028; 1:100), PE-Cy7-labeled mouse anti-human CD14 antibody (BD Biosciences, Cat #557742; 1:50) and BV785-labeled anti-human CD19 antibody (BioLegend, Cat #363028; 1:50) for 30 min at 4 °C in the dark. Samples were measured on a FACSCelesta (BD Biosciences) flow cytometer and CFSE dilution peaks in the viable $CD4^+$ and $CD8^+$ T-cell subsets (FVS510-CD14-CD19-$CD4^+$ and FVS510-CD14-CD19-$CD8^+$) were analyzed using FlowJo 10 software as a readout for T-cell proliferation. T-cell proliferation was expressed as the percentage of proliferated cells or the division index both calculated by using the FlowJo software (version 10). Percentage of proliferated (divided) cells was determined by gating for the cells that have gone through CFSE dilution ($CFSE^{low\ peaks}$). The division index is the average number of divisions that the cells underwent. Heatmaps were generated using GraphPad Prism version 8. Proliferation assays were performed using PBMC from four different healthy donors.

Variants of IgG1-CD27-A, -B and -C carrying an E430G or E345R mutation induced a small increase in proliferation of $CD8^+$ T cells compared to control antibody in two out of the four donors tested. The introduction of additional mutations (P329R, G237A or K326A/E333A) into IgG1-CD27-A, -B or -C variants carrying an E430G mutation showed variable effects on $CD8^+$ T cell proliferation across the four PBMC donors. In contrast, introduction of the P329R mutation into IgG1-CD27-A and IgG1-CD27-C variants carrying an E345R mutation consistently increased their capacity to enhance proliferation of activated $CD8^+$ T cells. This particularly applied to IgG1-CD27-A: whereas the measured $CD8^+$ T cell proliferation was comparable for IgG-CD27-A-E345R, IgG1-CD27-B-E345R and IgG1-CD27-C-E345R in each of the donors, introduction of an additional P329R mutation consistently led to a higher increase in $CD8^+$ T cell proliferation for clone IgG1-CD27-A-E345R compared to IgG1-CD27-B-E345R or IgG1-CD27-C-E345R. Thus, the effect of the E345R mutation in combination with the P329R mutation on proliferation of TCR activated $CD8^+$ T cells was consistently larger for clone IgG1-CD27-A than for IgG1-CD27-B and IgG1-CD27-C. Across all antibody variants tested, IgG1-CD27-A-E345R-P329R induced the largest increase in $CD8^+$ T cell proliferation in all donors (FIG. 4A).

The addition of the mutations G237A or K326A-E333A into CD27 antibody variants carrying the E345R mutation did not or only minimally increase the proliferation of $CD8^+$ T cells in any of the clones tested, as compared to antibodies comprising the single mutations E345R (FIG. 4A).

Also in $CD4^+$ T cells, the highest and most consistent increase in T cell proliferation was observed in presence of IgG1-CD27-A-E345R-P329R. Whereas $CD4^+$ T cell proliferation was generally comparable between IgG1-CD27-A, -B and -C variants carrying only the E430G or E345R mutations, introduction of an additional P329R mutation led to a larger increase in $CD4^+$ T cell proliferation for the IgG1-CD27-A variant carrying the E345R variant compared to IgG1-CD27-A-E430G or IgG1-CD27-B or -C variants carrying either the E430G or the E345R mutation. This effect was observed in three out of four donors tested. In donor 1, the effect of additional mutations in addition to E430G or E345R on $CD4^+$ T cell proliferation was generally small, and effects observed in this donor were not reproduced in the other three donors.

The combination of the E345R with the P329R mutations also consistently increased $CD4^+$ T cell proliferation for IgG1-CD27-C, although the difference between the E345R mutation alone and the combination of E345R and P329R was smaller for clone IgG1-CD27-C than for clone-A. For clone IgG1-CD27-B, a modest increase in $CD4^+$ T cell proliferation was observed for IgG1-CD27-B-E345R-P329R compared to IgG1-CD27-B-E345R in two out of the four donors.

Introduction of the P329R, G327A or K326A/E333A mutations into IgG1-CD27-A, -B, or -C variants carrying the E430G mutation did not, or not consistently, induce effects on $CD4^+$ T cell proliferation. Similarly, no or inconsistent effects were observed after introduction of the G327A or K326A/E333A in IgG1-CD27-A, -B or -C variants carrying the E345R mutation.

In summary, IgG1-CD27-A-E345R-P329R consistently induced the highest increase in proliferation of activated $CD8^+$ and $CD4^+$ T cells, demonstrating that IgG1-CD27-A-E345R-P329R induces most efficient CD27 agonism. DR5-specific, hexamerization-enhanced antibodies with the P329R mutation previously showed reduced capacity to induce DR5 agonism compared to DR5-specific hexamerization-enhanced antibodies without the P329R mutation (Overdijk et al, Mol Canc Ther 2020). It was thus considered surprising that introduction of the P329R mutation in addition to the E345R mutation in IgG1-CD27-A enhanced CD27 agonist activity. Moreover, it is not known why the combined effect of the E345R+P329R mutations was consistently larger for IgG1-CD27-A than for IgG1-CD27-B or IgG1-CD27-C.

Example 7: Induction of Human T-Cell Proliferation by Anti-CD27 Antibody IgG1-CD27-A-P329R-E345R The capacity of IgG1-CD27-A-P329R-E345R to increase proliferation of TCR stimulated human $CD4^+$ and $CD8^+$ T-cells was analyzed in CSFE dilution assays using human healthy donor PBMC, and compared to prior art anti-CD27 clones IgG1-CD27-131A*, IgG1-CD27-CDX1127, and IgG1-CD27-BMS986215*. The T-cell proliferation assays were performed as described in Example 6, with minor deviations (75,000 cells/well; concentration range 0.002-10 μg/mL). Samples using T-cells without anti-CD3 stimulation were included to test potential CD27 agonist activity of the antibodies in absence of T-cell receptor activation (FIGS. 5A and 5B). Such activity is unwanted as it would pose a safety risk if the antibody was able to induce proliferation of resting T cells.

Percentage of proliferated T cells (FIG. 5A, B, C, D) was calculated as the percentage of cells with reduced CFSE fluorescence, indicating cell divisions using FlowJo software. Expansion index (FIGS. 5E and 5F) identifies the fold increase of cells in the wells and was calculated using the Proliferation Modeling tool in FlowJo version 10. Manual adjustments to the peaks were made where necessary to define the number of the peaks present more consistently.

None of the CD27 antibodies of the invention and the prior art antibodies tested here induced proliferation of unstimulated T cells (i.e., in absence of CD3 crosslinking (FIGS. 5A and B).

Most of the CD27 antibodies induced some proliferation of activated $CD4^+$ and $CD8^+$ T-cells at the highest antibody concentrations tested (FIGS. 5C and D). Based on this, an expansion index was calculated (FIGS. 5E and F). Antibody IgG1-CD27-A-P329R-E345R of the invention more profoundly enhanced proliferation of CD4+ and CD8$^+$ T cells in vitro compared to the prior art anti-CD27 clones IgG1-CD27-131A, IgG1-CD27-CDX1127 and IgG1-CD27-BMS986215.

*For IgG1-CD27-131A and IgG1-CD27-BMS986215, variants carrying a F405L mutation, that is functionally irrelevant in the context of this experiments, were used.

Example 8: C1q Binding to Membrane-Bound CD27 Antibodies

The P329R mutation was previously described to reduce interaction of IgG1 antibodies with C1q and FcgR (Overdijk et al, Molecular Cancer Therapeutics 2020). The effect of the P329R mutation on C1q binding of IgG1-CD27-A comprising the E345R mutation was tested in cellular C1q binding assays in vitro using human healthy donor T cells. Anti-HIV gp120 antibody IgG1-b12-F405L was used as non-binding isotype control antibody (ctrl). T cells were enriched from human healthy donor PBMCs using RosetteSep Human T cell Enrichment cocktail (Stemcell, Cat #15061) and resuspended in culture medium (RPMI 1640 [Gibco, Cat #A10491-01] supplemented with 0.1% BSA and 1% Pen/Strep [Lonza, Cat #DE17-603E]). T cells (2×10$^6$ cells/well) were pre-incubated in polystyrene 96-well round-bottom plates with antibody dilution series (8× five-fold dilution starting at 15 μg/mL final assay concentration) for 15 min at 37 °C to allow the antibodies to bind to the T cells. Then, cells were cooled on ice, supplemented with NHS as a source of human C1q (20% NHS final assay concentration) and incubated on ice for 45 min. Cells were subsequently incubated on ice with FITC-labeled Rabbit anti-human C1q antibody (DAKO, Cat #F0254; 20 μg/mL) for 30 min and resuspended in FACS buffer with TO-PRO-3 (ThermoFisher, Cat #T3605; 1:5,000 dilution). C1q binding was determined by flow cytometry measuring the FITC signal on live cells.

Membrane bound WT IgG1-CD27-A antibody did not show C1q binding (FIG. 6). Introduction of the hexamerization-enhancing mutation E430G or E345R (IgG1-CD27-A-E430G and IgG1-CD27-A-E345R) resulted in binding of C1q to CD27 antibodies on the T-cell surface, in line with the increased binding avidity of the hexameric C1q protein to hexameric antibody ring structures on the cell surface (FIG. 6). Introduction of the P329R mutation in IgG1-CD27-A-E345R (IgG1-CD27-A-P329R-E345R) resulted in loss of C1q binding (FIG. 6), demonstrating that IgG1-CD27-A-P329R-E345R was unable to bind C1q.

These data show that IgG1-CD27-A-P329R-E345R is unable to bind C1q upon binding to CD27 on the cell surface of T cells. This indicates that C1q binding does not contribute to antibody-induced CD27 agonist activity of IgG1-CD27-A-P329R-E345R. This is in contrast to what was previously described for other hexamerization-enhanced agonistic antibodies. Moreover, lack of C1q binding indicates that IgG1-CD27-A-P329R-E345R is unable to activate the classical pathway of complement activation. Thus, IgG1-CD27-A-P329R-E345R is not expected to induce complement activation and CDC on T cells which activity would be unwanted.

Example 9: Binding of Anti-CD27 Antibodies to Human Fc Receptors

Binding of IgG1-CD27-A-P329R-E345R to human FcγR variants was analyzed using a Biacore surface plasmon resonance (SPR) system and compared to an anti-HIV gp120 antibody IgG1-b12 (ctrl). Biacore Series S Sensor Chips CM5 (Cytiva, Cat #29104988) were covalently coated with anti-His antibody using amine-coupling and His capture kits (Cytiva, Cat #BR100050 and Cat #29234602) according to the manufacturer's instructions. Next, 125 nM Fcγ-receptor FcγRIa, FcγRIIa (167-His [H] and 167-Arg [R]), FcγRIIb or FcγRIIIa (176-Phe [F] and 176-Val [V]) (Sino Biological, Cat #10256-H08S-B, Cat #10374-H27H, Cat #10374-H27H1-B, Cat #10259-H27H-B, Cat #10389-H27H-B and Cat #10389-H27H1-B) in HBS-P+(Cytiva, Cat #BR100827) were captured onto the surface. After three cycles of buffer, antibody samples were injected for 36 cycles to generate binding curves using antibody ranges of 0-3,000 nM for FcγRI and 0-10,000 nM for the other FcγRs. Each sample that was analyzed on an FcR-coated surface (Active Surface) was also analyzed on a parallel flow-cell without FcR (Reference Surface), which was used for background correction. Dissociation from the anti-His-coated surface was performed by regeneration of the surface using 10 mM Glycine-HCl pH 1.5 (Cytiva, Cat #BR100354). Sensograms were generated using Biacore Insight Evaluation software (Cytiva) and a four-parameter logistic (4PL) fit was applied to calculate relative binding of IgG1-CD27-A-P329R-E345R against the reference sample (ctrl).

Binding of IgG1-CD27-A-P329R-E345R to high affinity receptor FcγRIa was strongly reduced compared to the ctrl antibody, although some binding was observed at higher antibody concentrations (FIG. 7A). IgG1-CD27-A-P329R-E345R did not bind to the human low affinity receptors FcγRIIa (FIGS. 7B and C), FcγRIIb (FIG. 7D) and FcγRIIIa (FIGS. 7E and F).

In conclusion, IgG1-CD27A-P329R-E345R shows minimal (FcγRIa) or no (FcγRIIa, FcγRIIb, and FcγRIIIa) binding to human IgG Fc receptors.

Example 10: Binding of Anti-CD27 Antibody IgG1-CD27-A-E345R-P329R to Human T Cells Binding of IgG1-CD27-A-P329R-E345R to CD27 on human healthy donor T cells was characterized in more detail using flow cytometry. Anti-HIV gp120 antibody variant IgG1-b12-P329R-E345R was used as non-binding control antibody (ctrl). Human PBMCs were isolated from buffy coats obtained from human healthy donors. PBMC (1×10$^5$ cells/well) in FACS buffer were added to polystyrene 96-well round-bottom plates (Greiner bio-one, Cat #650101) and pelleted by centrifugation at 300×g for 3 min at 4 °C. The cells were resuspended in 50 μL/well serial antibody dilutions in FACS buffer (range 0.0015 to 10 μg/mL in 3-fold dilution steps) and incubated for 30 min at 4 °C. Cells were pelleted, washed twice with FACS buffer and incubated in 50 μL/well with FITC-conjugated secondary antibody (FITC AffiniPure F(ab')$_2$ fragment goat anti-human IgG, F(ab')$_2$ fragment specific, Jackson ImmunoResearch, Cat #109-096-097, diluted 1:100) for 30 min at 4 °C in the dark. Cells were pelleted again, washed twice with FACS buffer and incubated for 30 min at 4 °C in the dark in 50 μL/well of a staining mix for lymphocyte markers, containing BV711-labeled anti-human CD19 antibody (BioLegend, Cat #302246, 1:50), AlexaFluor700-labeled anti-human CD8a antibody (BioLegend, Cat #301028, 1:100), APC-eFluor780-labeled anti-human CD4 antibody (Invitrogen, Cat #47-0048-42, 1:50), PE-CF594-labeled mouse anti-human CD56 antibody (BD Biosciences, Cat #564849, 1:100), PE-Cy7-labeled mouse anti-human CD14 antibody (BD Biosciences, Cat #557742, 1:50) and eFluor450-labeled anti-human CD3 antibody (Invitrogen, Cat #48-0037-42, 1:200). Cells were pelleted again, washed twice using FACS buffer, and resuspended in 80 μL FACS buffer containing death cell marker 7-Amino-Actinomycin D (7-AAD; BD Biosciences, Cat #51-68981E, 1:240 diluted). The samples were measured by flow cytometry on an LSRFortessa (BD) flow cytometer and analyzed using FlowJo software. Binding curves were analyzed using non-linear regression (sigmoidal dose-response with variable slope) using GraphPad Prism 8 software.

Anti-CD27 antibody IgG1-CD27-A-P329R-E345R showed dose-dependent binding to healthy donor T cells, with similar binding characteristics for $CD4^+$ and $CD8^+$ T cells (FIG. 8).

Example 11: FcγR-Independent Induction of CD27 Cell Signaling by Anti-CD27 Antibody IgG1-CD27-A-P329R-E345R A CD27-specific monoclonal antibody that can induce CD27 signaling independent of secondary FcγR-mediated cross-linking may be immunostimulatory in the absence of FcγR-positive cells, which would be an advantage in tumors where the frequency of FcγR-bearing cells is low.

CD27 agonist activity of IgG1-CD27-A-P329R-E345R was tested in the presence or absence of FcγR-bearing cells and compared to the corresponding WT antibody IgG1-CD27-A and prior art antibodies IgG1-CD27-131A*, IgG1-CD27-CDX1127, and IgG1-CD27-BMS986215*. Non-binding antibody IgG1-b12-P329R-E345R was used as a negative control (ctrl). CD27 reporter assays were performed, essentially as described in Example 2, with the exception that in the current example, Thaw-and-Use Glo-Response NFκB-luc2/CD27 Jurkat cells were cultured in the presence of human FcyRIIb-expressing cells that can facilitate FcgR-mediated crosslinking of membrane-bound antibodies.

Thaw-and-Use effector FcγRIIb CHO-K1 cells (Promega, Cat #JA2251) were plated in 96-well flat bottom culture plates (PerkinElmer, Cat #0815), undiluted or at three increasing dilutions (1/3, 1/9. 1/27) and incubated overnight at 37 °C/5% $CO_2$. Supernatants of the adherent FcyRIIb-expressing cells was replaced by a Thaw-and-Use NFκB-luc2/CD27 Jurkat cell suspension of a fixed cell concentration in Bio-Glo Luciferase Assay Buffer (starting at a NFκB-luc2/CD27 Jurkat: FcγRIIb CHO-K1 ratio of 1:1 for undiluted FcγRIIb CHO-K1 cells), containing serial dilutions of antibody (final concentration range 0.0002-10 μg/mL). After 6 h incubation at 37 °C/5% $CO_2$, plates were equilibrated to RT and bioluminescence was measured and presented as RLU as described in Example 2.

IgG1-CD27-A-P329R-E345R induced dose-dependent CD27 activation, which was independent of FcγRIIb-expressing cells (FIG. 9A). In contrast, the corresponding WT antibody IgG1-CD27-A, without the E345R hexamerization-enhancing mutation and the P329R mutation, only showed CD27 agonism in the presence of FcγRIIb-expressing cells (FIG. 9A-E). Similarly, CD27 activation by the prior art antibodies IgG1-CD27-131A, IgG1-CD27-CDX1127 and IgG1-CD27-BMS986215 was also dependent on the presence of FcγRIIb-expressing cells and decreased gradually with decreasing NFκB-luc2/CD27 Jurkat: FcγRIIb CHO-K1 ratios (FIG. 9 F-J).

In conclusion, these data indicate that IgG1-CD27-A-P329R-E345R can induce CD27 agonism independent of secondary FcγR-mediated cross-linking. This is in contrast to prior art anti-CD27 antibodies that were dependent on the presence of FcγR-bearing cells to induce CD27 agonism.

*For IgG1-CD27-131A and IgG1-CD27-BMS986215, variants carrying a F405L mutation, that is functionally irrelevant in the context of this experiment, were used.

Example 12: Pharmacokinetic (PK) Analysis of Anti-CD27 Antibody IgG1-CD27-A-P329R-E345R in Absence of Target Binding, Studied in Mice The pharmacokinetic characteristics of anti-CD27 antibody IgG1-CD27-A-P329R-E345R*, in absence of target binding, was analyzed in mice and compared to the corresponding WT antibody IgG1-CD27-A*. IgG1-CD27-A does not bind to mouse CD27 (Example 3, Table 4), and thus the experiment was designed to test pharmacokinetic behaviour of IgG1-CD27-A and IgG1-CD27-A-P329R-E345R in vivo, in absence of target binding. The study was carried out by Crown Bioscience (China) by qualified personnel, in accordance with the approved IACUC protocol and Crown Bioscience, Inc. Standard Operating Procedures. 11-12 weeks old female SCID mice (C.B-17, Vital River Laboratory Animal Technology Co., Ltd. (VR, Beijing, China; 3 mice per group) were injected intravenously with 500 μg antibody (25 mg/kg) in a 200 μL injection volume. 40 μL blood samples were collected at 10 minutes, 4 hours, 1 day, 2 days, 7 days, 14 days and 21 days after antibody administration, plasma was collected from blood samples and stored at −80 °C until determination of total human IgG concentrations by ELISA. 96-well ELISA plates (Greiner, Cat #655092) were coated overnight at 4 °C with 2 μg/mL anti-human IgG (Sanquin, The Netherlands, Article #M9105, Lot #8000260395) and subsequently blocked for 1 h with PBSA (PBS supplemented with 0.2% bovine serum albumin [BSA, Roche, Cat #10735086001]). Next, with washing steps in between, the anti-human IgG-coated plates were sequentially incubated on a plate shaker for 1 h at RT with the plasma samples that were serially diluted in ELISA Buffer (PBSA supplemented with 0.05% Tween 20 [Sigma-Aldrich, Cat #P1379]), for 1 h at RT with polyclonal peroxidase-conjugated goat anti-human IgG secondary antibody (Jackson, Cat #109-035-098), and finally with 2,2'-azino-bis(3-ethylbenzthiazoline-6-sulfonic acid) (ABTS; Roche, Cat #11112422001). The reaction was stopped by adding 2% Oxalic Acid (Riedel de Haen, Cat #33506). Dilution series of the respective materials used for injection were used to generate reference curves. Absorbance was measured in an EL808 Microtiter plate reader (BioSPX) at 405 nm and total human IgG concentrations (in μg/mL) were plotted.

There was no substantial difference between the PK profile of IgG1-CD27-A-P329R-E345R and the counterpart WT antibody IgG1-CD27-A (FIG. 10), as determined by measuring plasma IgG levels at different timepoints after intravenous injection in mice.

Although a steeper decline in the initial (distribution) phase was observed for IgG1-CD27-A-P329R-E345R and its WT counterpart (IgG1-CD27-A) compared to predictions for human IgG1 in mice, the terminal elimination of both antibodies was in line with predictions rates for human wild-type IgG1 based on a 2-compartment model (Bleeker W K, Teeling J L, Hack C E. Blood. 2001 Nov. 15; 98(10):3136-42).

Together, this demonstrates that introduction of the P329R and E345R mutations did not affect the pharmacokinetics properties of IgG1-CD27-A in absence of target binding.

N.B. the experiment described in this example used variants of IgG1-CD27-A and IgG1-CD27-A-P329R-E345R carrying a F405L mutation, which is functionally irrelevant in the context of this experiment.

Example 13: Induction of Antibody-Dependent Cellular Phagocytosis by Anti-CD27 Antibody IgG1-CD27-A-P329R-E345R Antibody-dependent cellular cytotoxicity (ADCC) is mediated primarily through FcγRIIIa expressed on NK cells, whereas antibody-dependent cellular phagocytosis (ADCP) can be mediated by monocytes, macrophages, neutrophils, and dendritic cells via FcγRI, FcγRIIIa, and FcγRIII (Hayes, J. M et al 2016). To understand the effect of residual binding of anti-CD27 antibody IgG1-CD27-A-P329R-E345R to FcγRIa (Example 9) on effector functions of FcγRIa-expressing immune cells, the capacity of IgG1-CD27-A-P329R-E345R to induce ADCP was analyzed in vitro using CTV-labeled $CD27^+$ Burkitt's lymphoma Daudi cells as target cells, and human monocyte-derived macrophages (hMDM) as effector cells (E:T=2:1).

hMDMs were isolated from PBMCs by positive selection using CD14 MicroBeads (Miltenyi Biotec, cat. no. 130-050-201), according to the manufacturer's instruction. PBMCs were centrifuged (1,200 RPM, 5 min, RT) and resuspended in ice-cold monocyte isolation buffer (PBS, 0.5% BSA, 2 mM EDTA) at a density of $1.25\times10^7$ PBMCs/mL. 20 μL CD14 MicroBeads were added per 80 μL of PBMC suspension and incubated with agitation at 4 °C for 15 min on a rollerbank. 30 mL of ice-cold monocyte isolation buffer was added, PBMC/CD14 MicroBeads mixtures centrifuged (300×g, 10 min, 4 °C) and resuspended in 6 mL ice-cold monocyte isolation buffer. LS columns (Miltenyi Biotec, cat. no. 130-042-401) were rinsed with 3 mL ice-cold monocyte isolation buffer and each column loaded with 3 mL PBMC/CD14 MicroBeads mixtures. After flow through of the $CD14^-$ cells and three washes of the column in ice-cold monocyte isolation buffer, $CD14^+$ monocytes were recovered in 3 mL of ice-cold monocyte isolation buffer by using a plunger. The $CD14^+$ cells were counted on a Cellometer Auto 2000 Cell Viability Counter (Nexcelom Bioscience) using ViaStain™ Viability Dye acridine orange/propidium iodide (AOPI; Nexcelom Bioscience, cat. no. CS2-0106), and resuspended at a density of $0.8\times10^6$ cells/mL in Cellgene© GMP DC medium (CellGenix, cat. no. 20801-0500) supplemented with macrophage colony-stimulating factor (M-CSF; Gibco, cat. no. PH9501; 50 ng/mL final concentration) and 3 mL of monocyte suspension (i.e., $2.4\times10^6$ monocytes) in 100 $mm^2$ Nunc™ dishes with UpCell™ Surface, which allows cell harvesting by leaving plates at RT (Thermo Fisher Scientific, cat. no. 174902). After three days of incubation, 2 mL of fresh medium containing 5×M-CSF was added to the plates. After incubation for seven days (37 °C, 5% $CO_2$), macrophages were detached from the surface by leaving plates at RT for 1 to 1.5 h. Detached macrophages were pelleted by centrifugation, counted using AOPI, and resuspended at a density of $1\times10^6$ cells/mL in culture medium (RPMI 1640 with 10% DBSI).

Human Burkitt's lymphoma Daudi cells (ATCC© CCL-213™) were labeled using the CellTrace™ Violet Cell Proliferation Kit (Thermo Fisher Scientific, cat. no. C34557), according to the manufacturer's instructions. Briefly, Cell Trace Violet (CTV) was added to a final concentration of 0.2 μM to $1\times10^6$ Daudi cells/mL in PBS and incubated in the dark at 37 °C for 20 min (15 mL incubation volume). 10 mL DBSI was added to inactivate unbound dye. Cells were pelleted by centrifugation (300×g, 5 min), washed in PBS, and counted with AOPI. CTV-labeled Daudi cells were resuspended at a density of $0.5\times10^6$ cells/mL in culture medium.

For the ADCP assay, hMDM (50,000 cells/well) and CTV-labeled Daudi cells (25,000 cells/well) were seeded together (E:T=2:1) on ice in 96-well plates in a final volume of 150 μL culture medium and incubated with anti-CD27 antibody IgG1-CD27-A-P329R-E345R or anti-CD20 antibody IgG1-CD20 (0.000001 to 10 μg/mL concentration range in 10-fold dilutions), for 4 h (37 °C, 5% $CO_2$). After incubation, 100 μL Human BD Fc Block™ (BD Biosciences, cat. no. 564220; 1:100 in FACS buffer) was added and incubated at 4 °C for 10 min. Cells were pelleted by centrifugation (300×g, 5 min), resuspended in FACS buffer containing PE-Cy7 conjugated antihuman CD11b antibody (BioLegend, cat. no. 301322; 1:80) and TO-PRO-3 (Thermo Fisher Scientific, cat. no. T3605; 1:25,000) and incubated at 4 °C for 30 min. Cells were washed, resuspended in FACS buffer and collected and analyzed on a FACSymphony™ A3 Cell Analyzer (BD Biosciences). Data were analyzed using FlowJo software to measure viable target cell numbers and phagocytic hMDM and processed and visualized using GraphPad Prism software.

The percentage of viable Daudi cells for each condition was calculated according to the following formula:

$$\%\text{ viable Daudi cells} = \left(\frac{\%\ TO\text{-}PRO\text{-}3^{-}CD11b^{-}CTV^{+}\text{cells incubated with test antibody}}{\%\ TO\text{-}PRO\text{-}3^{-}CD11b^{-}\ CTV^{+}\text{cells incubated without test antibody}}\right)\times 100$$

The quantity of phagocytic hMDM for each condition was determined as

% TO-P RO-3-$CD11b^+CTV^+$ cells.

IgG1-CD27-A-P329R-E345R did not increase the percentage of phagocytic hMDM or reduce the percentage of viable Daudi cells in the phagocytosis assay, using hMDM from four different human healthy donors. This demonstrates that residual FcγRIa binding did not result in FcγRIa-mediated effector functions for IgG1-CD27-A-P329R-E345R (data from representative human healthy donor shown in FIG. 11). The positive control antibody IgG1-CD20 efficiently induced phagocytosis of Daudi cells, that express high levels of CD20, as demonstrated by an increase in the percentage of phagocytic hMDM and a decrease in the percentage of viable Daudi cells.

In conclusion, residual binding to FcγRIa was not sufficient to induce IgG1-CD27-A-P329R-E345R-dependent ADCP of $CD27^+$ cells.

Example 14: Fluid-Phase, Target-Independent, Complement Activation by Anti-CD27 Antibody IgG1-CD27-A-P329R-E345R as Determined by Measurement of C4d Deposition Fc-Fc interaction-enhanced antibodies generally exist as monomeric IgG1 molecules in solution, and hexamerize on the cell surface upon target binding to form a C1q docking place in case of an active Fc region (Diebolder, C. A et al 2014; de Jong, R. N et al, 2016). The IgG Fc domain of anti-CD27 antibody IgG1-CD27-A-P329R-E345R is silenced by introduction of the P329R mutation, which results in lack of C1q binding to membrane-bound IgG1-CD27-A-P329R-E345R (FIG. 6). To confirm that IgG1-CD27-A-P329R-E345R is unable to activate complement in solution in the absence of target binding, fluid phase, target-independent, complement activation was investigated by determination of C4d deposition, which is considered a measure for activation of the classical complement pathway. Fluid phase C4d fragment deposition by IgG1-CD27-A-P329R-E345R was analyzed by an enzyme-linked immunosorbent assay (ELISA) using the MicroVue™ C4d Enzyme Immunoassay (EIA; Quidel, cat. no. A008) and was performed according to the manufacturer's protocol. Heat Aggregated Gamma Globulin (HAGG; Complement Activator; Quidel, cat. no. A114) was used as a positive control for the assay. IgG1-b12 and IgG1-b12-RGY (WO2014006217A1)) were included as control antibodies. Introduction of E345R/E430G/S440Y (RGY) Fc mutations in an IgG1 antibody has been described to induce the formation of hexamers in solution, resulting in fluid phase complement activation (Diebolder, C. A et al, 2014; Wang, G., R. N et al, 2016; de Jong, R. N et al, 2016). IgG1-b12-P329R-E345R was included as isotype control antibody.

Antibody dilutions were prepared in phosphate-buffered saline (PBS) to a concentration of 1 mg/mL, except for HAGG, which was diluted to a concentration of 10 mg/mL. Then, the test samples were further diluted to a concentration of 100 μg/mL (for monoclonal IgG) or 1,000 μg/mL (for HAGG) in 90% (final concentration) normal human serum (NHS) (CompTech, Lot. no. 42a) and incubated at 37 °C for 1 h. In parallel, 'No antibody' samples (no antibody, 90% NHS) and 'PBS only' samples (no antibody, no NHS) were included as negative controls. Next, the samples were diluted 1:250 in cold kit-provided Complement Specimen Diluent. In the meantime, the strips coated with mouse anti-human C4d antibody were placed in a 96-wells plate and the assay wells were washed three times with 250 to 300 μL Wash Buffer with a 1-min waiting step after the first wash. The test samples were added to the wells (100 μL/well) and as a negative control, Complement Specimen Diluent only (blank) was used in the ELISA. In parallel, 100 μL of the standards (Standard A-E) and internal controls provided by the kit were added to separate wells. The plates were incubated for 30 min at RT. Then, the plates were washed five times with Wash Buffer as described above. 50 μL of C4d Conjugate (peroxidase-conjugated goat anti-human C4d) was added to the wells and the plates were incubated for 30 min at RT. After five washing steps with Wash Buffer as described above, 100 μL of C4d Substrate [0.7% 2-2'-Azino-di-(3-ethylbenzthiazoline sulfonic acid diammonium salt] was added and again the plates were incubated for 30 min at RT. Finally, 50 μL kit-provided Stop Solution was added and within 1 h, the optical density was measured at 405 nm using an ELISA Plate Reader (EL808 BioSPX, BioTek).

IgG1-CD27-A-P329R-E345R and the control antibody IgG1-b12-P329R-E345R (having the same Fc backbone as IgG1-CD27-A-P329R-E345R) did not induce fluid phase C4d deposition at the tested concentration of 100 μg/mL; the measured C4d levels were similar to background levels of the control antibody with a wild-type Fc domain (IgG1-b12) and the no antibody control (FIG. 12). In contrast, the positive control antibody IgG1-b12-RGY, that is known to form hexamers in solution, induced C4d deposition to the same level as HAGG.

These data show that IgG1-CD27-A-P329R-E345R did not induce target-independent, fluid phase complement activation in vitro.

Example 15: Capacity of Anti-CD27 Antibody IgG1-CD27-A-P329R-E345R to Compete for Ligand-Binding with CD70

To determine if anti-CD27 antibody IgG1-CD27-A-P329R-E345R interferes with the interaction of CD27 with its natural ligand CD70, binding of a saturating concentration of biotinylated recombinant human CD70 extracellular domain (ECD) to CD27, endogenously expressed on human Burkitt's lymphoma cell line Daudi, was studied in the presence and absence of excess IgG1-CD27-A-P329R-E345R.

Daudi cells (ATCC© CCL-213™) cultured in RPMI 1640 medium (Gibco, cat. no. A10491-01) supplemented with 10% donor bovine serum with iron (DBSI; Gibco, cat. no. 20731-030) were seeded at 50,000 cells/well in round bottom 96-well plates (Greiner Bio One, cat. no. 650261). Cells were pelleted by centrifugation (300×g, 3 min at 4 °C) and resuspended in FACS buffer (PBS, 1% BSA [Roche, cat. no. 1073508600]) containing anti-CD27 or control antibodies (50 μg/mL final concentration). Biotinylated recombinant human CD70 ECD (Abcam, cat. no. ab271443) was added at a saturating concentration (6 μg/mL) and cells were incubated at 4 °C for 30 min.

Cells were washed twice and resuspended in FACS buffer containing Brilliant Violet (BV) 421™ labeled streptavidin (BioLegend, cat. no. 405225; 0.0025 μg/mL final concentration) and R phycoerythrin (PE) labeled polyclonal AffiniPure F(ab')$_2$ fragment goat-anti-human IgG Fc (Jackson ImmunoResearch, cat. no. 109 116098; 0.0025 μg/mL final concentration) at 4 °C for 30 min. Cells were washed twice, resuspended in FACS buffer containing TO-PRO-3 iodide (Thermo Fisher Scientific, cat. no. T3605; 1:25,000) and analyzed. Data were collected on a BD FACSymphony™ A3 flow cytometer (BD Biosciences) and analyzed using FlowJo software. For compensation, one drop of UltraComp eBeads™ Compensation Beads (Life Technologies, cat. no. 01-2222-42) was added to each well. 2 μL of each antibody was added and mix was incubated for 20 min. Plates were spun down and beads were resuspended in FACS buffer and measured. For viability compensation, cells were treated at 65 °C for 10 min and mixed 1:1 with viable cells. Cells were spun down and resuspended in TO-PRO-3 diluted in FACS buffer. Data were processed and visualized using GraphPad Prism.

IgG1-CD27-A-P329R-E345R or IgG1-CD27-A did not block binding of the CD70 ECD to CD27$^+$ Daudi cells, as CD70 binding levels were comparable to those for Daudi cells incubated with the nonbinding isotype control antibodies IgG1-b12-P329R-E345R or IgG1-b12, or cells without antibody (FIG. 13). Also, prior art anti-CD27 antibodies IgG1-CD27-BMS986215 and IgG1-CD27-131A showed a weak blocking effect on CD27 binding to CD70 ECD. In contrast, CD70 was unable to bind to surface CD27 on Daudi cells in presence of prior art anti-CD27 antibody IgG1-CD27-CDX1127 (FIG. 13) that was previously reported to block ligand-binding (Vitale et al, 2012).

In conclusion, IgG1-CD27-A-P329R-E345R binding does not block CD27 binding by its natural ligand CD70 on Daudi cells.

Example 16: T-Cell Activation Marker Expression Upon Incubation of Polyclonally Stimulated Human PBMC with Anti-CD27 Antibodies The effect of IgG1-CD27-A-P329R-E345R on expression of T-cell activation markers in polyclonally activated T cells was studied using PBMC obtained from three different healthy human donors. Expression of HLA-DR, CD25, CD107a, and 4-1BB were analyzed after incubating PBMCs with IgG1-CD27-A-P329R-E345R or prior art anti-CD27 antibodies for two and five days.

Freshly isolated 75,000 PBMC/well were seeded in 96-well U bottom plates (Greiner Bio-One) in cell culture medium. Duplicate wells were incubated simultaneously with anti-CD3 antibody (UCHT1 clone; Stemcell; 0.1 μg/mL); and IgG1-CD27-A-P329R-E345R (0.0005 to 30 μg/mL in threefold dilutions); or prior art anti-CD27 antibodies IgG1-CD27-CDX1127, IgG1-CD27-131A, and IgG1-CD27-BMS986215 (30 μg/mL); or nonbinding control antibody IgG1-b12-P329R-E345R (10 μg/mL). To determine expression of each activation marker in absence of treatment, duplicate control wells with untreated (no anti-CD3 or anti-CD27 antibodies) cells were supplemented with culture medium alone. To set the gates for identifying activation marker positive cells, fluorescence minus one (FMO) controls were used. For the FMO controls, all the antibodies used in the experiment except for one corresponding to an activation marker in duplicate wells was added to 75,000 PBMC/well from one donor activated with anti-CD3 antibody. Untreated cells from each donor in single wells with no staining antibody were included as negative controls. To detect viable cells, untreated cells from each donor were stained with 4',6-diamidino-2-phenylindole (DAPI) alone in single wells.

After incubation for two or five days (37 °C, 5% $CO_2$), plates were washed once with FACS buffer and resuspended in an antibody mixture in FACS buffer containing antibodies for T-cell activation markers 4-1BB, CD25, CD107a, human leukocyte antigen (HLA)-DR; and antibodies for gating $CD4^+$ and $CD8^+$ T-cell subsets in flow cytometry. After incubation at 4 °C for 30 min, all plates were washed twice with FACS buffer and cells were resuspended in FACS buffer. The samples were analyzed on a BD LSRFortessa Cell Analyzer using FlowJo software to determine the median fluorescence intensity (MFI) and percentage of positive cells for each T-cell activation marker on $CD4^+$ and $CD8^+$ T cells. Anti-CD27 antibody induced changes in the expression levels of the T-cell activation markers were presented as the fold change in MFI of the anti-CD27 antibody sample relative to the nonbinding control antibody IgG1-b12-P329R-E345R. The samples were analyzed on a BD LSRFortessa™ Cell Analyzer (BD Biosciences) using FlowJo software.

IgG1-CD27-A-P329R-E345R increased expression of CD25, CD107a and 4-1BB on activated $CD4^+$ T cells (FIG. 14A). These effects were more pronounced after 2 days of incubation than after 5 days of incubation. On $CD8^+$ T cells, incubation with IgG1-CD27-A-P329R-E345R resulted in an increased expression of HLA-DR, CD107a and 4-1BB both after 2 and 5 days of incubation (FIG. 14B).

The expression of T-cell activation markers was also assessed upon incubation for 2 and 5 days with three prior art antibodies. IgG1-CD27-131A and IgG1-CD27-BMS986215 induced a comparable increase in expression of HLA-DR, 4-1BB, CD25, and CD107a on $CD4^+$ and $CD8^+$ T cells, while the effect of incubation for 2 or 5 days with IgG1-CD27-CDX1127 on T-cell activation marker expression was less pronounced.

In conclusion, incubation of polyclonally activated PBMC with IgG1-CD27-A-P329R-E345R resulted in an increased expression of activation markers HLA-DR, CD25, CD107a and 4-1BB on $CD4^+$ and $CD8^+$ T cells.

Example 17: Percentages of OVA-Specific $CD8^+$ T Cells in OVA Protein-Immunized Mice after Injection of Anti-CD27 Antibodies in a Human CD27-KI Mouse Model The effect of IgG1-CD27-A-P329R-E345R treatment on expansion of antigen-specific T cells in the hCD27 KI OVA model in splenocytes was analyzed by flow cytometry.

Homozygous human CD27 (hCD27)-KI mice on a C57BL/6 background (hCD27 KI mice) were obtained from Beijing Biocytogen Co., Ltd. (strain name C57BL/6-Cd27tm1(CD27)/Bcgen, Stock no. 110006). This strain was developed in collaboration with the HuGEMM™ platform of Crown Bioscience, featuring a humanized drug target (CD27 in this case) within mice with a functional immune system. In hCD27 KI mice, exons 1-5 of the mouse CD27 gene encoding the extracellular domain were replaced by human CD27 exons 1-5. OVA-specific T cells were induced in vivo by subcutaneous (s.c.) injection of the immunogen ovalbumin (OVA) in hCD27-KI mice and the agonist effect of IgG1-CD27-A-P329R-E345R was tested by simultaneously treating the mice intravenously (i.v.) with the antibody.

On day 0, the mice were injected s.c. with 5 mg OVA (InvivoGen, cat. no. vac-pova-100, lot. no. EFP-42-04) and treated by i.v. injection into the tail vain with IgG1-CD27-A-P329R-E345R (30 mg/kg), IgG1-CD27-CDX1127 (30 mg/kg) or IgG1-b12-P329R-E345R (30 mg/kg). On day 12 and day 21, mice were boosted with OVA and treated with antibody as on day 0. On day 10, day 19 and day 24, blood was collected via cheek pouch or saphena in BD Microtainer© blood collection tubes containing di-potassium ethylenediaminetetraacetic acid (K2-EDTA; BD, cat. no. 365974) and immediately used in further analysis. On day 28, mice were euthanized and spleens were resected under sterile conditions.

Resected spleen tissue in RPMI1640 medium (Thermo Fisher Scientific, cat. no. C22400500BT) was transferred to gentleMACs™ C Tubes (Miltenyi Biotec, cat. no. 130-093-237) and mechanically dissociated to a single cell suspension using the gentleMACS™ Dissociator (Miltenyi, cat. no. 130-093-235), according to the manufacturer's instructions. After dissociation, the cell suspension was filtered through a 70 μm cell strainer (Falcon, cat. no. 352350). Next, samples were washed twice by resuspension in 3 mL wash buffer (sterile PBS [Hyclone, SH0256.01B] supplemented with 4% FBS [Gibco, cat. no. 10099 141]). Cells were counted on a Cellometer Auto T4 (Nexcelom Bioscience) and the number of cells was adjusted to $2\times10^6$ splenocytes per tube.

$2\times10^6$ splenocytes were transferred to FACS tubes (Falcon, cat. no. 352052) and resuspended in wash buffer (sterile PBS [Hyclone, SHO256.01B] supplemented with 4% FBS [Gibco, cat. no. 10099 141]) supplemented with 1 μg/mL purified rat anti-mouse CD16/CD32 (Mouse BD Fc Block™, BD Biosciences, cat. no. 553141). After a preincubation at 2-8 °C for 10 min in the dark, 10 μL PE-labeled OVA-tetramer (MBL Life science, cat. no. TS 5001 1C) was added, and the samples were gently vortexed before further incubating at 2-8 °C for 30-60 min in the dark. Without washing, labeled antibodies and compounds used for flow cytometry gating of T-cell subsets were added. The samples were gently vortexed and incubated at 2-8 °C for an additional 30 min in the dark. Next, samples were washed twice by resuspension in 2 mL wash buffer and centrifuged at 300×g for 5 min. Finally, the cells were resuspended in 250 μL wash buffer and analyzed on a BD LSRFortessa™ X-20 Cell Analyzer (BD Biosciences). Data were processed using Kaluza Analysis Software (Beckman Coulter).

IgG1-CD27-A-P329R-E345R increased the percentages of OVA-specific $CD8^+$ T cells in the blood and spleen of mice simultaneously injected with OVA protein vaccination. The percentages of OVA-specific $CD8^+$ T cells in mice treated with 30 mg/kg IgG1-CD27-CDX1127 were lower than the IgG1-CD27-A-P329R-E345R-treated group and comparable to the IgG1-b12-P329R-E345R-treated group (FIG. 15).

Example 18: IFNγ Secretion by OVA-Specific $CD8^+$ T Cells from Spleens of OVA-Immunized Mice Injected with Anti-CD27 Antibodies Resected spleen tissue in RPMI1640 medium (see Example 17) was gently mashed over a 70 μm cell strainer (Falcon, cat. no. 352350), pelleted by centrifugation (1,500 rpm, 5 min), and resuspended in 10 mL Ammonium-Chloride-Potassium (ACK) Lysing Buffer (Invitrogen, cat. no. A1049201). After 3-5 min incubation at RT, samples were washed twice with 10-20 mL PBS and resuspended in 5 mL Cellular Technology Limited (CTL) Test™ Medium (ImmunoSpot, cat. no. CTLT-005) supplemented with 50 U/mL penicillin and 50 μg/mL streptomycin (pen/strep, Gibco, cat. no. 15070-063). The collected splenocytes were filtered again through a 70 μm cell strainer and counted on a Vi-CELL™ XR Cell Viability Analyzer (Beckman Coulter) to adjust the concentration to $3.125\times10^6$ cells/mL with CTL-Test Medium containing pen/strep.

IFNγ production by splenocytes was analyzed using the Mouse IFN-γ ELISpotPLUS kit (Mabtech, cat. no. 3321-4HPW-2), essentially as described by the manufacturer. Pre-coated MultiScreenHTS IP Filter (MSIP) white plates (mAb AN18) were washed four times with 200 μL sterile PBS per well and conditioned with 200 μL CTL-Test Medium containing pen/strep (RT, 30 min). Medium was removed and $5\times10^5$ splenocytes/well were incubated in duplicate with 2 μg/mL $OVA_{257-264}$ peptide SIINFEKL (Invivogen, cat. no. vac-sin), or scrambled control peptide FILKSINE (SB-PEPTIDE, cat. no. SB073-1MG) in a total volume of 180 μL/well for 20 h in a humidified incubator (37 °C, 5% $CO_2$). As a positive control for IFNγ production, splenocytes were incubated in parallel with a cell stimulation cocktail consisting of 500 ng/mL phorbol myristate acetate (PMA) and 10 μg/mL ionomycin (PMA+Ionomycin, Dakewe Biotech, cat. no. DKW ST PI). Cultures of splenocytes without peptide were included as a negative control. After incubation, the cells were removed and the plates were washed five times with PBS. Next, plates were sequentially incubated, with five wash steps with PBS in between, with Biotinylated detection mAb (R4-6A2; RT, 2 h), Streptavidin-horseradish peroxidase (HRP; RT, 1 h), and finally 3,3',5,5'-tetramethylbenzidine (TMB) substrate solution (all provided by the kit). When distinct spots emerged, the reaction was stopped by washing extensively in deionized water. Spots were counted on an AID iSpot ELISpot Reader (Autoimmun Diagnostika [AID] GMBH, ELR08IFL) using spotAID V8 software (AID). ELISpot data were analyzed and presented in bar diagrams using GraphPad Prism software and presented as the mean number of spots per well±SEM from all mice per treatment group (n=5).

Splenocytes from all IgG1-CD27-A-P329R-E345R-treated animal groups showed increased IFNγ production in response to treatment with OVA peptide, as demonstrated by ELISpot analysis (FIG. 16). Stimulation of the splenocytes with a scrambled control peptide induced no or minimal IFNγ production, suggesting that IFNγ was produced by OVA-specific T cells. In contrast, no IFNγ production was observed in splenocytes from mice treated with 30 mg/kg IgG1-CD27-CDX1127.

Example 19: Effect of IgG1-CD27-A-P329R-E345R Treatment on T-Cell Activation in OVA-Immunized Mice In Vivo The effect of IgG1-CD27-A-P329R-E345R treatment on $CD8^+$ T-cell activation was studied in vivo by analyzing the expression of PD-1 on $CD8^+$ T cells derived from OVA-treated hCD27-KI mice. Mice were treated as described in Example 17. Also, methods to obtain and analyze splenocytes by FACS are described in Example 17.

IgG1-CD27-A-P329R-E345R induced an increase in the percentage of $CD8^+$ T cells expressing activation marker PD-1 on day 28. $CD8^+PD\text{-}1^+$ T-cell percentages were low in animals treated with IgG1-CD27-CDX1127 or control antibody IgG1-b12-P329R-E345R (FIG. 17).

Example 20: Effect of IgG1-CD27-A-P329R-E345R Treatment on In Vivo Induction of T-Cell Subsets in OVA-Immunized Mice The effect of IgG1-CD27-A-P329R-E345R on the expansion of T-cell subsets was studied by analyzing the expression of CD44 and CD62L in splenocyte samples from OVA-treated hCD27-KI mice. Memory $CD8^+$ T cells derived from spleens of IgG1-CD27-A-P329R-E345R-treated, OVA-immunized, hCD27-KI mice were quantified by flow cytometry. Memory T cells were classified as effector memory ($CD44^+CD62L^-$) and pre-effector T cells ($CD44\text{-}CD62L^-$; Nakajima, Y., K et al 2018). Mice were treated as described in Example 17. Also, methods to obtain and analyze splenocytes by FACS are described in Example 17.

IgG1-CD27-A-P329R-E345R (30 mg/kg) induced increased percentages of pre-effector T cells and effector memory $CD8^+$ T cells in the spleen on day 28 when compared to splenocytes of mice treated with IgG1-b12-P329R-E345R (FIG. 18). Within the $CD45^+$ population, IgG1-CD27-A-P329R-E345R induced higher percentages of pre-effector T cells and effector memory T cells than IgG1-CD27-CDX1127 (30 mg/kg), while comparable mean percentages of these T-cell populations were induced by both anti-CD27 antibodies in the $CD8^+$ fraction of splenocytes.

Example 21: Effect of IgG1-CD27-A-P329R-E345R Treatment on In Vivo Expansion of T Cells in OVA-Immunized Mice The effect of IgG1-CD27-A-P329R-E345R on expansion of T cells was studied by analyzing the expression of CD3 in splenocyte and blood samples from OVA-treated hCD27-KI mice. Mice were treated as described in Example 17. Also, methods to obtain and analyze splenocytes and blood samples by flow cytometry are described in Example 17.

Treatment of OVA-immunized hCD27-KI mice with 30 mg/kg IgG1-CD27-A-P329R-E345R did not increase the percentage of $CD3^+$ T cells in the spleen, compared to treatment with the non-binding control antibody IgG1-b12-P329R-E345R (FIG. 19). In contrast, treatment with benchmark antibody IgG1-CD27-CDX1127 (30 mg/kg) resulted in a decrease of $CD3^+$ T cells in the spleen. Similar observations were made in peripheral blood samples.

Example 22: Effect of IgG1-CD27-A-P329R-E345R on T-Cell Cytokine Production in Antigen-Specific Studies The capacity of IgG1-CD27-A-P329R-E345R to increase cytokine production was studied using T cells that had been stimulated by their cognate antigen. PBMC were isolated from buffy coats obtained from healthy human donors by Ficoll-Paque density gradient separation (GE Healthcare, cat. no. 17 1440 03) according to the manufacturer's instructions.

Human magnetic CD14 and CD8 MicroBeads (Miltenyi Biotec, cat. no. 130 050 201 and 130 045 201, respectively) were used for positive selection of $CD14^+$ monocytes and negative selection of $CD14^-$ PBL from human PBMC, and positive selection of $CD8^+$ T cells from frozen PBL. Cell suspensions were centrifuged and resuspended in magnetic-activated cell sorting (MACS) buffer (Dulbecco's phosphate-buffered saline [DPBS] with 5 μM EDTA and 0.2% human albumin) at $1\times10^7$ live cells per 80 μL MACS buffer. Per $1\times10^7$ cells, 12 μL CD14 or CD8 MicroBeads were added. Subsequent MACS separation was performed using an automated magnetic cell separation instrument or by manual separation. Automated MACS separation was performed using an autoMACS® Pro Separator (Miltenyi Biotec), according to the manufacturer's instructions. Eluted $CD14^+$ monocytes and $CD8^+$ T cells were centrifuged (8 min, 300×g at RT) resuspended in X-VIVO 15 medium (Lonza), and counted with erythrosine B solution for further use; i.e., monocyte differentiation into iDC or electroporation of $CD8^+$ T cells with PD-1 and/or CLDN6-specific T-cell receptor (TCR) mRNA.

For the generation of monocyte-derived iDC, up to $40\times10^6$ PBMC-derived $CD14^+$ monocytes were cultured (37 °C, 5% $CO_2$) for five days in T175 flasks in DC medium (RPMI 1640, 5% pooled human serum [PHS; One Lambda, cat. no. A25761], 1× minimum essential medium non-essential amino acid solution [MEM NEAA, Life Technologies, cat. no. 11140 035], 1 mM sodium pyruvate [Life Technologies, cat. no. 11360 039]) supplemented with 100 ng/mL human granulocyte/macrophage colony-stimulating factor (GM-CSF; Miltenyi Biotec, cat. no. 130-093-868) and 50 ng/mL human IL-4 (Miltenyi Biotec, cat. no. 130093 924). After three days in culture, half of the medium per flask was replaced. Nonadherent monocytes in the medium taken from the flask were pelleted (8 min, 300×g at RT), resuspended in fresh DC medium supplemented with 200 ng/mL GM-CSF and 100 ng/mL IL-4, and then returned into the originator flask. After the five days of incubation, the iDC which adhered to the culture flask were detached using 10 mL DPBS containing 2 mM EDTA (37 °C, 10 min). The isolated iDC were washed, pelleted (8 min, 300×g at RT) and used for electroporation with CLDN6 mRNA.

Human $CD8^+$ T cells were electroporated with RNA encoding the alpha and beta chains of a mouse TCR specific for human CLDN6, either alone or together with RNA encoding PD-1, and human monocyte-derived iDC were electroporated with RNA encoding human CLDN6. Up to $5\times10^6$ iDC or $15\times10^6$ $CD8^+$ T cells were electroporated in 250 μL X-VIVO 15 medium at RT using an ECM 830 Square Wave Electroporation System (BTX©). Cells were mixed with RNA, pulsed (500 V, 3 ms for T cells or 300 V, 12 ms for iDC), and immediately diluted with 750 μL pre-warmed assay medium (IMDM GlutaMAX [Life technologies, cat. no. 31980030] with 5% PHS). Electroporated iDC were transferred to 6- or 12-well plates and cultured O/N (37 °C, 5% $CO_2$). After O/N incubation, electroporated $CD8^+$ T cells and iDC were evaluated by flow cytometry to evaluate cell purity, expression of transfected RNA (PD-1 and CLDN6-TCR on $CD8^+$ T cells and CLDN6 on iDC), and baseline expression of CD27 and PD-1 on $CD8^+$ T cells and PD-L1 on iDC. Approximately 78% to 93%, 78% to 92%, and 36% to 98% of electroporated $CD8^+$ T cells expressed CLDN6-TCR, PD-1, and endogenous CD27, respectively. Approximately 47% to 91% and 94% to 99% of electroporated iDC expressed CLDN6 and endogenous PD-L1, respectively (not shown).

$CD8^+$ T cells and iDC were seeded at a 10:1 ratio ($7.5\times10^4$ T cells and $7.5\times10^3$ iDC per well) in a 96-well round-bottom plate. IgG1-CD27-A-P329R-E345R was diluted in assay medium and 25 μL of diluted IgG1-CD27-A-P329R-E345R was added to the wells, to reach a final concentration of 10 μg/mL. Similarly, the control antibodies IgG1-CD27-131A and IgG1-b12-P329R-E345R were added to reach final concentrations of 10 μg/mL. Antigen-specific T-cell activity upon antibody treatment was analyzed in vitro by measuring cytokines in the supernatant of T cells transduced to express CLDN6-TCR, which were co-cultured with iDC transduced to express and present CLDN6. Supernatants were collected after two days, and concentrations of multiple proinflammatory cytokines and chemokines were determined by multiplex electrochemiluminescence assays (ECLIA) using the 10-spot U-PLEX ImmunoOncology Group 1 (human) kit (MSD; cat. no. K151AEL 2) following the manufacturer's instructions.

For the 10-spot U-PLEX Immuno-Oncology Group 1 kit, biotinylated capture antibodies were pre-incubated at RT with the assigned linkers, which have a biotin-binding domain, for 30 min, followed by 30 min incubation with Stop Solution. Plates were coated with a mix of the linker coupled capture antibodies by incubating at RT with shaking for 1 hr. Plates were washed three times with 1×MSD Wash Buffer. Supernatant samples or kit standards were diluted 1:2 in Assay Diluent, added to the wells and incubated at RTfor 2 h with constant shaking. The plates were washed three times with Wash Buffer, and incubated with SULFO-TAG-conjugated detection antibodies from the kit at RT for 1 h with constant shaking. The plates were washed three times with Wash Buffer before adding Read Buffer B to catalyze the electrochemiluminescent reaction. The plates were immediately analyzed by measuring light intensity on a MESO QuickPlex SQ 120 imager (MSD).

IgG1-CD27-A-P329R-E345R-induced changes in cytokine production were assessed by multiplex ECLIA in supernatants from the $CD8^+$ T cell/iDC co-cultures after two days of incubation (n=4 different donors). IgG1-CD27-A-P329R-E345R induced a significant increase in the production of GM-CSF and IFN-γ in $CD8^+$ T cell/iDC co-cultures with $CD8^+$ T cells expressing endogenous levels of PD-1 (FIG. 20A), while also an increase in IL-13 and TNFα production was observed. A considerable increase for the same cytokines was observed in cultures containing PD-1-overexpressing T cells (FIG. 20B). While cytokine levels were generally decreased when T cells overexpressed PD-1, the relative increase (fold increase) in cytokine production in presence of IgG1-CD27-A-P329R-E345R was highest in this setting (FIGS. 20A and B). In contrast, prior art anti-CD27 antibody IgG1-CD27-131A showed minimal effect on cytokine production compared to the nonbinding control antibody IgG1-b12-P329R-E345R (FIGS. 20A and B).

Example 23: Expression of Cytotoxicity-Associated Molecules by Antigen-Specific CD8$^+$ T Cells Incubated with IgG1-CD27-A-P329R-E345R The induction of T-cell mediated cytotoxicity upon antibody treatment was studied by analyzing the expression of cytotoxicity-associated molecules on the antigen-specific T cells by flow cytometry in co-cultures of human healthy donor T cells transduced to express a CLDN6-TCR and MDA-MB-231_hCLDN6 target cells.

MDA-MB-231_hCLDN6 cells were generated by lentiviral transduction. To this end, $2\times10^5$ MDA-MB-231 cells in 250 μL Dulbecco's modified eagle medium (DMEM, Thermo Fisher Scientific, cat. no. 31966-047) supplemented with 10% FBS (non-heat-inactivated) were seeded per well in a 12-well tissue culture plate. The cells were incubated for 1-2 h at 37 °C. (7.5% $CO_2$). Supernatants containing lentiviral vectors encoding human CLDN6 (pL64b42E(EF1a-hClaudin6)Hygro-T2A-GFP) were thawed on ice and diluted in a total volume of 750 μL DMEM/10% FBS to obtain titers of $2\times10^5$, $8\times10^4$, and $3.2\times10^4$ TU/mL. These titers corresponded to MOI of 1, 0.4, and 0.16, respectively. The supernatants were then added to the MDA-MB-231 cells, and the cells were incubated for 72 h at 37 °C. (5% $CO_2$) without disturbance. For the experiments described in the current Example, MDA-MB-231-hCLDN6 cells were cultured in DMEM/10% FBS. Cells were passaged or harvested for experiments at 70% to 90% confluence. Cells were detached by treatment with Accutase (Thermo Fisher Scientific, cat. no. A11105010) for 5 min (37 °C, 7.5% $CO_2$), and resuspended by addition of culture medium. Cells were centrifuged (300×g, 4 min at RT) and counted. MDA-MB-231_hCLDN6 cells were not cultured for more than 20 passages.

MDA-MB-231_hCLDN6 cells were seeded at 1.2 to $1.5\times10^4$ cells/well, in 96-well flat-bottom plates (for flow cytometry analysis) and xCELLigence E-plates (Agilent, cat. no. 05232368001; for impedance measurement) and allowed to settle at RT for 30 min. Next, plates were incubated for one day in the incubator and the xCELLigence real-time cell analysis (RTCA) instrument (ACEA Biosciences), respectively (37 °C, 5% $CO_2$).

Isolated CD8$^+$ T cells (see Example 22) were electroporated with CLDN6-specific TCR mRNA and incubated O/N. After CD8$^+$ T-cell isolation and electroporation, T-cell cultures contained 49% to 99% CD8$^+$ T cells. Of these electroporated CD8$^+$ T cells, approximately 78% to 93% expressed CLDN6-TCR and 59% to 98% of CLDN6-TCR$^+$ CD8$^+$ cells were CD27$^+$. Cells were centrifuged (8 min, 300×g at RT), resuspended in DMEM/10% FBS and counted. The cells were centrifuged again, resuspended at $3\times10^6$ cells/mL in DMEM/10% FBS, and added to the wells containing the previously seeded MDA-MB-231_hCLDN6 cells ($1.5\times10^5$ CD8$^+$ T cells/well; T cell:tumor cell, effector: target, ratio of 10:1). IgG1-CD27-A-P329R-E345R, IgG1-CD27-131A, and the nonbinding control antibody IgG1-b12-P329R-E345R were added to the co-cultures at 10 μg/mL. CD107a and GzmB expression were determined by flow cytometry.

After two days of incubation in the presence of 10 μg/mL IgG1-CD27-A-P329R-E345R, the percentage of GzmB$^+$ CD107a$^+$CD8$^+$ T cells was significantly enhanced compared to treatment with the nonbinding control antibody or prior art anti-CD27 antibody IgG1-CD27-131A (FIG. 21).

In conclusion, these data show that IgG1-CD27-A-P329R-E345R was able to induce cytotoxicity-associated molecules on activated antigen-specific T cells.

Example 24: Capacity of IgG1-CD27-A-P329R-E345R to Induce T-Cell Mediated Tumor Cytotoxicity To evaluate T-cell mediated cytotoxicity, CLDN6-TCR-electroporated CD8$^+$ T cells were co-cultured with MDA-MB-231_hCLDN6 cells in the presence of IgG1-CD27-A-P329R-E345R, prior art anti-CD27 antibody IgG1-CD27-131A, or nonbinding control antibody IgG1-b12-P329R-E345R for five days in an xCELLigence real-time cell analysis instrument (Acea Biosciences), with impedance measurements at two-hour intervals, as described in Example 23. Cell index values were derived from impedance measurements conducted at two-hour intervals. Area-under-the-curve (AUC) were obtained from cell index data over five days of co-culture. AUC were normalized to co-cultures treated with IgG1-b12-P329R-E345R. The magnitude of impedance is dependent on cell number, cell morphology, and cell size and on the strength of cell attachment to the plate, which altogether is used in this particular case as an indirect readout of tumor cell mass. Decrease in impedance in this experimental setting is considered a surrogate of tumor-cell killing by CD8$^+$ T cells. It should be noted that impedance may underestimate tumor cell killing due to proliferation of T cells.

IgG1-CD27-A-P329R-E345R induced a decrease in cell index, indicative of tumor-cell killing. IgG1-CD27-131A did not have a visible effect on cell index, indicating minimal capacity to increase tumor-cell killing (FIG. 22).

Example 25: Capacity of IgG1-CD27-A-P329R-E345R to Induce Expansion of Tumor-Infiltrating Lymphocytes The capacity of IgG1-CD27-A-P329R-E345R to induce expansion of tumor-infiltrating lymphocyte (TIL) subsets (CD4$^+$ and CD8$^+$ T cells, NK cells, and regulatory T cells [Treg]) was evaluated ex vivo using cryopreserved tumors that had been surgically resected from NSCLC patients.

Surgically resected human NSCLC tissues were received in transport medium (HypoThermosol® FRS Preservation Solution [BioLife Solutions, cat. no. 101104], 7.5 μg/mL Amphotericin B [Thermo Fisher Scientific, cat. no. 15290026], and 300 units/mL (U/mL) pen/strep [Thermo Fisher Scientific, cat. no. 15140-122]). Samples were washed three times in wash medium (5 mL X-VIVO 15 [Lonza], 2.5 μg/mL Amphotericin B, [Thermo Fisher Scientific] and 100 U/mL pen/strep [Thermo Fisher Scientific]) and transferred to a cell culture dish. Fatty tissue and necrotic areas were removed with a scalpel, and the tissue was cut into fragments of approximately 5 mm$^3$. Each fragment was placed in an individual cryovial, and 1 mL freezing medium (FBS, 10% DMSO) was added to each vial. The vials were transferred into a controlled freeze-chamber (Mr. Frosty freezing container), which was placed in a −80 °C freezer. After at least 16 h at −80 °C, the vials were transferred to liquid nitrogen for long-term storage.

4 to 6 cryopreserved vials containing tumor fragments of approximately 5 mm$^3$ from one tumor specimen were thawed per experiment in a 37 °C water bath for approximately 2 min and washed five times with wash medium and transferred to a cell culture dish. The tumor fragments were further dissected with a scalpel into fragments of approximately 1 mm$^3$. Most of the fragments were used for TIL expansion upon culturing with IL-2 and treatment antibody and remaining fragments were used to determine expression of specific cell surface markers at baseline, without any treatment.

Two tumor fragments per well (on average) were seeded in 24-well plates (2 mL/well total volume capacity used in assay) in 0.1 mL prewarmed TIL cultivation medium (X-VIVO 15 [Lonza] with 2% human serum albumin [HSA; CSL Behring, cat. no. PZN-00504775], 100 U/mL pen/strep [Thermo Fisher Scientific], and 2.5 µg/mL Amphotericin B [Thermo Fisher Scientific]) containing 45 to 50 U/mL IL-2 (Proleukin S; Novartis Pharma, cat. no. PZN-02238131). IgG1-CD27-A-P329R-E345R was diluted in TIL cultivation medium containing 45 to 50 U/mL IL-2 and 900 µL of this dilution was added to the wells as appropriate. Final IgG1-CD27-A-P329R-E345R concentrations in the wells were 1 or 10 µg/mL. As a control, medium containing 45 to 50 U/mL IL-2 without antibodies was added to tumor fragments in separate wells. A total of 8 to 16 wells were incubated for each experimental condition per donor (37 °C, 5% $CO_2$).

After three days of culture, fresh TIL cultivation medium containing 45 to 50 U/mL IL-2 and IgG1-CD27-A-P329R-E345R was added to the wells (1 mL/well, same antibody concentrations as above). Between day 5 and 14/17 after assay initiation, the cultures were regularly monitored with a microscope for proliferation of TIL that migrated from the tissue fragments and the formation of TIL microclusters. If >25 TIL microclusters were observed in one well after seven or eight culture days, cells and tissue fragments from two identically treated original wells were resuspended and pooled into one well of a 6-well plate (5 to 6 mL/well total volume capacity used in assay) with the culture medium and fresh IL 2 containing TIL cultivation medium was added (estimated 33 U/mL IL-2 final concentration).

Every two to three days, cultures were supplemented with fresh IL-2-containing TIL cultivation medium. IL-2 concentrations in the medium added to cultures were reduced to 10 U/mL, or first reduced to 25 U/mL and then to 10 U/mL thereafter after supplementing the wells with medium throughout the assay. On day 14 or 17, the cells were harvested for flow cytometry analysis.

IgG1-CD27-A-P329R-E345R enhanced expansion of TIL subtypes compared to control cultures treated with IL-2 alone, with the largest relative increase in cell count observed for $CD8^+$ T cells and Tregs, followed by $CD4^+$ T cells, and NK cells. For all TIL subsets, expansion was more pronounced with IgG1-CD27-A-P329R-E345R at 1 µg/mL than 10 µg/mL (Table 6 and FIG. 23).

TABLE 6

Fold-expansion of IgG1-CD27-A-P329R-E345R-treated TIL

Tumor tissues derived from human NSCLC specimens were cultured with low-dose IL-2 in the presence or absence of IgG1-CD27-A-P329R-E345R. Absolute cell counts of the indicated cell subsets were determined by flow cytometry after 14 to 17 days of treatment. Fold differences in cell numbers for IgG1-CD27-A-P329R-E345R-treated cultures relative to cultures treated with IL-2 are shown. Data shown are from five tumor tissues from individual patients tested in five independent experiments. P = 0.0236, 1 µg/mL vs. 10 µg/mL IgG1-CD27-A-P329R-E345R (two-way ANOVA).

| Cell population IgG1-CD27-A-P329R-E345R concentration | All TIL | | $CD4^+$ T cells | | $CD8^+$ T cells | | Treg | | NK cells | |
|---|---|---|---|---|---|---|---|---|---|---|
| (µg/mL) | 1 | 10 | 1 | 10 | 1 | 10 | 1 | 10 | 1 | 10 |
| Patient #578 | 14.9 | 2.1 | 19.3 | 2.3 | 19.6 | 2.9 | 86.9 | 2.1 | 11.3 | 1.1 |
| Patient #507 | 27.9 | 5.1 | 33.7 | 4.4 | 107.1 | 17.4 | 32.2 | 11.9 | 14.4 | 6.0 |
| Patient #594 | 0.6 | 1.5 | 0.4 | 1.0 | 1.8 | 2.2 | 0.4 | 2.3 | 0.8 | 2.6 |
| Patient #592 | 0.9 | 0.8 | 0.4 | 0.2 | 2.9 | 1.7 | 4.8 | 2.6 | 2.3 | 1.2 |
| Patient #561 | 0.8 | 1.6 | 0.2 | 2.9 | 0.8 | 1.0 | n.d. | n.d. | 1.1 | 1.2 |
| Average ± SD [a] | 11.1 ± 11.3 | 2.4 ± 1.6 | 13.5 ± 14.0 | 2.0 ± 1.6 | 32.9 ± 43.4 | 6.1 ± 6.6 | 31.1 ± 34.5 | 4.9 ± 4.1 | 7.2 ± 5.8 | 2.7 ± 2.0 |

[a] Average and SD calculations exclude patient #561 for better comparability between cell populations.

Abbreviations:

ANOVA = analysis of variance;

n.d. = not determined;

NK = natural killer;

NSCLC = non-small cell lung cancer;

SD = standard deviation;

TIL = tumor-infiltrating lymphocyte;

Treg = regulatory T cell.

Example 26: BRET Analysis to Assess Intermolecular Interactions of IgG1-CD27-A-P329R-E345R Molecules on the Cell Surface The capacity of CD27 antibodies harboring the hexamerization-enhancing mutation (E345R) to increase intermolecular Fc-Fc interactions after binding to CD27 on the cell surface was determined using bioluminescence resonance energy transfer (BRET) analysis. This molecular proximity-based assay detects protein interactions by measuring energy transfer from a bioluminescent protein donor to a fluorescent protein acceptor. Energy transfer occurs only when the donor and acceptor are in close proximity (<10 nm [Wu and Brand, 1994; Dacres et al, 2012]).

First, cell surface expression of CD27, as well as CD20 and CD37 (as positive control molecules), was determined on huCD27-K562, a human chronic myelogenous leukemia cell line genetically modified to stably express human CD27, and on Daudi cells, using an indirect immunofluorescence assay (QIFIKIT, Agilent Technologies, cat no. K0078). Cells were seeded at 100,000 cells/well and incubated with 10 µg/mL primary antibody (CD27: IgG1-7730-143-C102S-FEAL; CD20: IgG1-11B8-FEAR; CD37: IgG1-3009-010-FEAR). This was followed by incubation with a FITC-labeled polyclonal goat anti-human IgG (Jackson Immuno Research, cat. no. 109-096-097), in parallel with QIFIKIT beads coated with a defined number of antibody molecules. The number of antibody molecules per cell was determined by interpolating the measured mean fluorescence intensity (MFI) of a test sample on the calibration curve generated by plotting the MFI of the individual bead populations against the known number of antibody molecules per bead. Samples were measured on an LSRFortessa Cell Analyzer flow cytometer (BD Biosciences) and analyzed using FlowJo software.

QiFi analysis showed moderate CD27 expression and high CD20 and CD37 expression on Daudi cells, whereas huCD27-K562 cells expressed high levels of CD27, but no CD20 and CD37 (Table 7).

TABLE 7

| Cell surface expression in antibody molecules per cell | | |
|---|---|---|
| | huCD27-K562 | Daudi |
| CD27 | 390,373 | 15,484 |
| CD20 | — | 180,217 |
| CD37 | — | 219,663 |

BRET assay (NanoBRET™ System, Promega, cat no. N1661) was performed essentially according to the manufacturer's instructions. To generate NanoLuc (donor) and HaloTag (acceptor) tagged antibodies, variable light chain sequences with either NanoLuc or HaloTag (Table 3, sequences 37-44) were prepared by gene synthesis, cloned into appropriate expression vectors and full-length antibodies produced as described in Example 1. For analysis, $0.5\times10^5$ huCD27-K562 or Daudi cells were seeded in 96-well round-bottom plates (Greiner Bio-One, cat. no. 650101) in a total volume of 100 µL. Cells were pelleted by centrifugation (3 min at 300×g) and resuspended in 50 µL assay medium (Opti-MEM I [Gibco, cat. no. 11058-021]+4% FBS [ATCC, cat. no. 30-2020]) containing mixtures of NanoLuc- or HaloTag-tagged antibody pairs each at a concentration of 5 µg/mL. Next, 50 µL HaloTag NanoBret 618 ligand (Promega, cat. no. G980A, 1:1000 dilution in assay medium) was added. For each antibody mixture, a no-ligand control sample was prepared in parallel, by adding 50 µL medium without HaloTag NanoBret 618 ligand. Cells were incubated for 30 min at 37 °C in the dark, washed twice with medium and resuspended in 100 µL assay medium without FBS. 25 µL NanoBRET NanoGLO substrate (Promega, cat. no. N1571, 1:200 dilution in assay medium without FBS) was added to each well. Plates were shaken for 30 s and 120 µL of each sample was transferred to an OptiPlate (Perkin Elmer, cat. no. 6005299). An EnVision Multilabel Reader (Perkin Elmer) was used to measure donor emission at 460 nm and acceptor emission at 618 nm.

BRET was calculated in milliBRET units (mBU)= $(618\ nm_{em}/460\ nm_{em})\times1000$.

Results are reported as Corrected BRET, which is corrected for donor-contributed background or bleedthrough, and calculated as: mBU ligand—mBU no-ligand control.

The proximity of NanoLuc- and HaloTag-labeled IgG1-CD27-A-P329R-E345R antibodies after binding CD27 on the cell surface was compared to WT IgG1-CD27-A antibodies carrying the same tags. IgG1-CD20-11B8-E430G-LNLuc and IgG1-CD37-37.3-E430G-LHalo antibodies, containing an E430G mutation that induces hexamerization (WO2019243636A1), were used as a positive control for proximity-induced BRET. IgG1-CD20-11B8-E430G and IgG1-CD37-37.3-E430G were previously shown to form heterohexamers upon binding to cells expressing CD20 and CD37, using molecular proximity assays (Oostindie, S. C. et al, Haematologica, 2019). Nonbinding antibody IgG1-b12-P329R-E345R was used as a negative control.

As positive and negative controls for BRET signal induction, Daudi cells (high CD20 and CD37 expression) and huCD27-K562 cells (no CD20 and CD37 expression) were opsonized with antibody pair IgG1-CD20-11B8-E430G-LNLuc and IgG1-CD37-37.3-E430G-LHalo. BRET induction was detected only on Daudi cells, and not on huCD27-K562 cells lacking CD20 and CD37 (FIG. 24). Similarly, a non-binding control antibody pair (IgG1-b12-P329R-E345R-LNLuc+IgG1-b12-P329R-E345R-LHalo) did not induce BRET on either cell line. When huCD27-K562 cells were opsonized with a mixture of NanoLuc- and HaloTag-labeled CD27 antibodies bearing the hexamerization-enhancing mutation (IgG1-CD27-A-P329R-E345R-LNLuc+IgG1-CD27-A-P329R-E345R-LHalo), high BRET was detected, while BRET on Daudi cells did not exceed background levels (FIG. 24). A mixture of IgG1-CD27-A-LNLuc and IgG1-CD27-A-LHalo (WT) antibodies induced considerably lower BRET on huCD27-K562 cells compared to CD27 antibodies carrying the P329R and E345R mutations, and no BRET on Daudi cells. These results indicate that BRET signal was associated with higher target expression. CD27 expression on huCD27-K562 cells was found to be ~26 fold higher than on Daudi cells, while BRET levels for CD27-binding IgG1-CD27-A-P329R-E345R on huCD27-K562 cells were ~24 fold higher than on Daudi cells. Mixtures of NanoLuc- and HaloTag-labeled nonbinding and CD27-binding antibody pairs (IgG1-b12-P329R-E345R-LNLuc+IgG1-CD27-A-P329R-E345R-LHalo, and IgG1-CD27-A-P329R-E345R-LNLuc+IgG1-b12-P329R-E345R-LHalo respectively), did not induce BRET on either cell line. This confirms that observed BRET was dependent on simultaneous interaction of donor and acceptor antibodies bound to the cell-surface target.

In summary, IgG1-CD27-A-P329R-E345R induced high BRET on huCD27-K562 cells compared to its WT variant. This finding confirms enhanced proximity between membrane-bound IgG1-CD27-A-P329R-E345R molecules, compared to its WT variant, consistent with E345R-enhanced Fc-Fc interactions between cell surface-bound antibodies.

N.B. the experiment described in this example used a variant of IgG1-CD27-A carrying a F405L mutation, which is functionally irrelevant in the context of this experiment.

Example 27: Binding of IgG1-CD27-A-P329R-E345R to FcγRIa$^+$ M0 and M1 Macrophages Example 9 assessed binding of IgG1-CD27-A-P329R-E345R to human FcγR variants using surface plasmon resonance (SPR), showing minimal (FcγRIa) or no (FcγRIIa, FcγRIIb, and FcγRIIIa) binding to recombinant human IgG Fc receptor molecules. This residual FcγRIa binding was not sufficient to induce IgG1-CD27-A-P329R-E345R-dependent ADCP of CD27$^+$ cells (see Example 13). To further exclude interactions of IgG1-CD27-A-P329R-E345R with FcγRIa-positive macrophages, Fc-mediated binding of IgG1-CD27-A-P329R-E345R to M0 and M1 macrophages was determined.

Human CD14$^+$ monocytes were isolated from PBMCs from two healthy donors as described in Example 13, and differentiated into monocyte-derived macrophages by culturing the cells in medium (CellGenix, cat. no. 20801-0500) supplemented with 50 ng/mL M-CSF (Gibco, cat. no.

PHC9501) to obtain M0 macrophages, or 50 ng/mL GM-CSF (Immunotools, cat. no. 11343125) for differentiation into M1 macrophages. After 6 days of culture, M0 and M1 phenotypes were confirmed by FACS analysis according to expression of markers as defined in Table 8. Additionally, both macrophage subtypes were confirmed to express human Fc receptors FcγRIa, FcγRII and FcγRIIIa (Table 8).

TABLE 8

| | M0 | M1 |
|---|---|---|
| Phenotype markers | | |
| CD40 (BD Pharmingen, cat. no. 561211, 1:50 dilution) | + | + |
| CD86 (MACS, cat. no. 30-097-877, 1:50 dilution) | + | ++ |
| CD163 (Biolegend, cat. no. 333612, 1:200 dilution) | +/− | − |
| CD206 (Biolegend, cat. no. 321136, 1:200 dilution) | +/− | + |
| Fc receptors | | |
| FcγRIa (Biolegend, cat. no. 305006, 1:25 dilution) | ++ | ++ |
| FcγRII (BD Pharmingen, cat. no. 552883, 1:50 dilution) | ++ | ++ |
| FcγRIIIa (BD Pharmingen, cat. no. 555407, 1:50 dilution) | + | +/− |

Binding of IgG1-CD27-A-P329R-E345R to M0 and M1 macrophages was compared to binding of a WT IgG1 antibody (IgG1-b12) with an irrelevant antigen-binding region as a positive control for FcγRIa binding, and a variant of the same antibody also carrying the P329R mutation previously described to reduce interaction with FcγR (IgG1-b12-P329R-E345R). Since macrophages should not express CD27, any binding observed is hypothesized to occur via FcγRIa, which is the only FcγR that binds monovalent IgG. The differentiated macrophages were incubated with IgG1-CD27-A-P329R-E345R or control antibodies (30 μg/mL in DC medium) for 15 min, and PE-labeled polyclonal goat anti-human IgG (Jackson Immuno Research, cat. no. 109-116-097, dilution 1:200, 30 min at 4 °C). After incubation, cells were washed and resuspended in 100 μL FACS buffer containing nucleus-staining DAPI (BD Pharmingen, cat. no. 564907, 1:5000 dilution). Samples were measured on a FACSymphony flow cytometer (BD Biosciences) and analyzed using FlowJo software.

No binding above background (secondary antibody only) to M0 or M1 macrophages isolated from two independent donors was observed with either IgG1-CD27-A-P329R-E345R or control IgG1-b12-P329R-E345R (FIG. 25). WT IgG1-b12, which contains an active Fc region, consistently bound to both M0 and M1 macrophages.

In conclusion, the IgG1-CD27-A-P329R-E345R and control IgG1-b12-P329R-E345R do not bind M0 or M1 macrophages expressing FcγRIa, FcγRII and FcγRIIIa.

The invention claimed is:

1. An anti-CD27 antibody, or antigen binding fragment thereof, that specifically binds to human CD27, wherein the antibody or antigen binding fragment comprises a heavy chain variable (VH) region comprising a CDR1, CDR2, and CDR3 comprising the amino acid sequences as set forth in SEQ ID NOs: 5, 6, and 7, respectively, and wherein the antibody comprises a light chain variable (VL) region comprising a CDR1, CDR2, and CDR3 comprising the amino acid sequences as set forth in SEQ ID NO: 9, 10 and 11, respectively.

2. The antibody of claim 1, wherein the antibody further comprises a heavy chain constant region comprising a sequence selected from the group consisting of: SEQ ID NOs: 12, 13, 14, 15, 18, 19, 20, 21, 22, 23, 27, 28, 29, 30, 31, 32, 33, 34 and 36.

3. The antibody of claim 1, wherein the antibody further comprises a heavy chain constant region comprising the sequence as set forth in SEQ ID NO: 15.

4. A pharmaceutical composition comprising the anti-CD27 antibody or antigen binding fragment of claim 1 and a pharmaceutically acceptable carrier.

5. An anti-CD27 antibody, or antigen binding fragment thereof, that specifically binds to human CD27, wherein the antibody or antigen binding fragment thereof comprises a heavy chain variable (VH) region comprising the amino acid sequence as set forth in SEQ ID NO: 4 and a light chain variable (VL) region comprising the amino acid sequence as set forth in SEQ ID NO: 8.

6. The antibody of claim 5, wherein the antibody further comprises a IgG1 human heavy chain constant region.

7. The antibody of claim 5, wherein the antibody further comprises a heavy chain constant region comprising a sequence selected from the group consisting of SEQ ID NOs: 12, 13, 14, 15, 18, 19, 20, 21, 22, 23, 27, 28, 29, 30, 31, 32, 33, 34 and 36.

8. The antibody of claim 5, wherein the antibody further comprises:

a) a heavy chain constant region comprising the amino acid sequence set forth in SEQ ID NO: 15; and b) a light chain constant region comprising the amino acid sequence set forth in SEQ ID NO: 17.

9. A pharmaceutical composition comprising the anti-CD27 antibody of claim 5 and a pharmaceutically acceptable excipient, diluent, or carrier.

10. An anti-CD27 antibody that specifically binds to human CD27, wherein the antibody comprises a heavy chain comprising the amino acid sequence set forth in SEQ ID NO: 35 and a light chain comprising the amino acid sequence set forth in SEQ ID NO: 25.

11. A pharmaceutical composition comprising the anti-CD27 antibody of claim 10 and a pharmaceutically acceptable excipient, diluent, or carrier.

12. The antibody of claim 1, where the antibody further comprises a human IgG1 heavy chain constant region, wherein the amino acid residue in the heavy chain constant region at the positions corresponding to position E345 and P329 according to Eu numbering are both R.

13. A pharmaceutical composition comprising the anti-CD27 antibody of claim 12 and a pharmaceutically acceptable excipient, diluent, or carrier.

14. The antibody of claim 5, where the antibody further comprises a human IgG1 heavy chain constant region, wherein the amino acid residue in the heavy chain constant region at the positions corresponding to position E345 and P329 according to Eu numbering are both R.

15. A pharmaceutical composition comprising the anti-CD27 antibody of claim 14 and a pharmaceutically acceptable excipient, diluent, or carrier.

* * * * *